United States Patent
Heyes et al.

(10) Patent No.: US 11,896,672 B2
(45) Date of Patent: *Feb. 13, 2024

(54) TARGETED NUCLEIC ACID CONJUGATE COMPOSITIONS

(71) Applicant: ARBUTUS BIOPHARMA CORPORATION, Burnaby (CA)

(72) Inventors: James Heyes, Vancouver (CA);
Richard J. Holland, Vancouver (CA);
Alan D. Martin, Vancouver (CA);
Mark Wood, Port Moody (CA)

(73) Assignee: ARBUTUS BIOPHARMA CORPORATION, Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/092,685

(22) PCT Filed: Apr. 11, 2017

(86) PCT No.: PCT/CA2017/050447
§ 371 (c)(1),
(2) Date: Oct. 10, 2018

(87) PCT Pub. No.: WO2017/177326
PCT Pub. Date: Oct. 19, 2017

(65) Prior Publication Data
US 2019/0160176 A1    May 30, 2019

Related U.S. Application Data

(60) Provisional application No. 62/438,310, filed on Dec. 22, 2016, provisional application No. 62/417,156, (Continued)

(51) Int. Cl.
| | | |
|---|---|---|
| A61K 47/54 | (2017.01) | |
| A61K 31/713 | (2006.01) | |
| C12N 15/113 | (2010.01) | |
| A61K 47/60 | (2017.01) | |
| C07C 237/08 | (2006.01) | |
| C07H 15/18 | (2006.01) | |
| C07C 235/10 | (2006.01) | |
| C07H 15/26 | (2006.01) | |
| C07J 51/00 | (2006.01) | |
| C07H 15/08 | (2006.01) | |
| A61K 47/59 | (2017.01) | |
| C07J 63/00 | (2006.01) | |
(Continued)

(52) U.S. Cl.
CPC .......... *A61K 47/549* (2017.08); *A61K 31/713* (2013.01); *A61K 47/554* (2017.08); *A61K 47/59* (2017.08); *A61K 47/60* (2017.08); *C07C 235/10* (2013.01); *C07C 237/08* (2013.01); *C07H 15/08* (2013.01); *C07H 15/18* (2013.01); *C07H 15/26* (2013.01); *C07H 21/00* (2013.01); *C07J 51/00* (2013.01); *C07J 63/008* (2013.01); *C12N 15/113* (2013.01); *C07D 207/08* (2013.01); *C07D 207/12* (2013.01); *C07D 211/42* (2013.01); *C12N 15/111* (2013.01); *C12N 15/87* (2013.01); *C12N 2310/14* (2013.01); *C12N 2310/315* (2013.01); *C12N 2310/321* (2013.01); *C12N 2310/346* (2013.01); *C12N 2310/351* (2013.01); *C12N 2320/32* (2013.01)

(58) Field of Classification Search
CPC ..... C07C 235/10; C07C 237/08; A61K 47/60; A61K 47/59; A61K 47/554; A61K 47/549; A61K 31/7088; A61K 31/7105; A61K 31/711; A61K 31/7115; A61K 31/712; A61K 31/7125; A61K 31/713; C07H 15/08; C07H 15/26; C07H 21/00; C07H 15/18; C07J 51/00; C07J 63/008; C12N 15/113; C12N 2320/32; C12N 15/87; C12N 15/111; C12N 2310/321; C12N 2310/351; C12N 2310/315; C12N 2310/346; C12N 2310/14; C12N 2310/3521; C12N 2310/322; C12N 2310/3533; C07D 211/42; C07D 207/08; C07D 207/12

See application file for complete search history.

(56) References Cited

U.S. PATENT DOCUMENTS 7,833,992 B2 * 11/2010 Vargeese .............. A61K 47/544
   514/103
8,258,288 B2 *  9/2012 McSwiggen ............ A61P 37/00
   536/24.5
(Continued)

FOREIGN PATENT DOCUMENTS

WO   2003070918 A2   8/2003
WO   2005026165 A1   3/2005
(Continued)

OTHER PUBLICATIONS

U.S. Appl. No. 17/782,901, filed Jun. 2022, Heyes, James et al.*
(Continued)

*Primary Examiner* — Eric Olson
(74) *Attorney, Agent, or Firm* — Viksnins Harris Padys Malen LLP

(57) ABSTRACT

The invention provides conjugates that comprise a targeting moiety, a nucleic acid, and optional linking groups as well as synthetic intermediates and synthetic methods useful for preparing the conjugates. The conjugates are useful to target therapeutic nucleic acids to the liver and to treat liver diseases including hepatitis (e.g. hepatitis B and hepatitis D).

11 Claims, 8 Drawing Sheets

Specification includes a Sequence Listing.

Related U.S. Application Data filed on Nov. 3, 2016, provisional application No. 62/321,034, filed on Apr. 11, 2016.

(51) Int. Cl.

| | | |
|---|---|---|
| *C07H 21/00* | (2006.01) | |
| *C07D 211/42* | (2006.01) | |
| *C07D 207/08* | (2006.01) | |
| *C07D 207/12* | (2006.01) | |
| *C12N 15/11* | (2006.01) | |
| *C12N 15/87* | (2006.01) | |

(56) References Cited

U.S. PATENT DOCUMENTS

| | | | | |
|---|---|---|---|---|
| 8,313,772 | B2 * | 11/2012 | Rozema | A61P 3/10 |
| | | | | 424/486 |
| 8,450,467 | B2 * | 5/2013 | Manoharan | A61K 47/549 |
| | | | | 536/18.7 |
| 8,541,388 | B2 * | 9/2013 | Monia | A61P 3/04 |
| | | | | 514/44 A |
| 8,828,956 | B2 | 9/2014 | Manoharan et al. | |
| 8,956,825 | B2 * | 2/2015 | Weisbart | A61K 31/713 |
| | | | | 435/29 |
| 9,181,549 | B2 * | 11/2015 | Prakash | C12N 15/111 |
| 9,249,179 | B2 * | 2/2016 | Hadwiger | C07H 21/02 |
| 9,345,775 | B2 * | 5/2016 | Lewis | C12N 15/87 |
| 9,399,775 | B2 * | 7/2016 | Rajeev | C07H 21/02 |
| 9,796,974 | B2 * | 10/2017 | Rajeev | A61K 48/00 |
| 9,879,265 | B2 * | 1/2018 | Albæk | A61P 43/00 |
| 10,000,754 | B2 * | 6/2018 | Beigelman | C12N 15/1138 |
| 10,294,477 | B2 * | 5/2019 | Swayze | A61P 29/00 |
| 11,427,823 | B2 * | 8/2022 | Heyes | C12N 15/111 |
| 2009/0239814 | A1 * | 9/2009 | Manoharan | A61P 25/00 |
| | | | | 514/32 |
| 2012/0157509 | A1 | 6/2012 | Hadwiger et al. | |
| 2017/0253857 | A1 * | 9/2017 | Sentman | A61P 31/12 |
| 2017/0304459 | A1 * | 10/2017 | Jadhav | A61K 9/0075 |
| 2018/0193471 | A1 | 7/2018 | Nagatomo et al. | |
| 2019/0119676 | A1 * | 4/2019 | Frauendorf | A61K 47/56 |
| 2020/0407724 | A1 * | 12/2020 | Heyes | A61K 47/549 |
| 2022/0031847 | A1 * | 2/2022 | Heyes | C12N 15/111 |
| 2022/0288214 | A1 * | 9/2022 | Kondratowicz | A61P 5/00 |
| 2022/0387600 | A1 * | 12/2022 | Heyes | C12N 15/113 |
| 2023/0110295 | A1 * | 4/2023 | Heyes | A61K 47/549 |
| | | | | 514/44 A |

FOREIGN PATENT DOCUMENTS

| | | |
|---|---|---|
| WO | 2009073809 A2 | 6/2009 |
| WO | 2009082606 A2 | 7/2009 |
| WO | 2009082607 A2 | 7/2009 |
| WO | 2011056883 A1 | 5/2011 |
| WO | 2011104169 A1 | 9/2011 |
| WO | 2012083046 A2 | 6/2012 |
| WO | 2013033230 A1 | 3/2013 |
| WO | 2014179626 A2 | 11/2014 |
| WO | 2014179627 A2 | 11/2014 |
| WO | 2014205451 A2 | 12/2014 |
| WO | 2014207232 A1 | 12/2014 |
| WO | 2015042564 A1 | 3/2015 |
| WO | 2015168532 A2 | 11/2015 |
| WO | 2016055601 A1 | 4/2016 |
| WO | 2016077349 A1 | 5/2016 |
| WO | 2018191278 A2 | 10/2018 |

OTHER PUBLICATIONS

U.S. Appl. No. 17/854,575, filed Jun. 2022, Heyes, James et al.*
Das, et al., "A Peptide Nucleic Acid-Aminosugar Conjugate Targeting Transactivation Response Element of HIV-1 RNA Genome Shows a High Bioavailability in Human Cells and Strongly Inhibits Tat-mediated Transactivation of HIV-1 Transcription", J Med Chem 55(13), 6021-6032 (2012).
Database, "Hepatitis B virus mRNA-targeted antisense oligonucleotide, SEQ 1309", EBI assession No. GSN: BEP71596, Database accession No. BEP71596 sequence, (Mar. 30, 2017).
Database, "Hepatitis B virus X ORF targeted siRNA sense strand, SEQ ID 1793", EBI accession No. GSN: BDA34147, Databse accession No. BDA34147, Jun. 30, 2016.
Huang, Y, "Preclinical and Clinical Advances of GalNAc-Decorated Nucleic Acid Therapeutics", Molecular Therapy—Nucleic Acids 6, 116-132 (2017).
Kinberger, G, et al., "Conjugation of mono and di-GalNAc sugars enhances the potency of antisense oligonucleotides via ASGR mediated delivery to hepatocytes", Bioorganic & Medicinal Chemistry Letters 26(15), 3690-3693 (2016).
Nair, J, et al., "Multivalent N-acetylgalactosamine-conjugated siRNA localizes in hepatocytes and elicits robust RNAi-mediated gene silencing", J Am Chem Soc 136(49), 16958-16961 (2014).
National Center, for Biotechnology Information, "SCHEMBL4352939", PubChem Compound Database, Dec. 4, 2011, vol. CID=54474605, retrieved on Jul. 18, 2017.
Patent Cooperation Treaty, International Searching Authority, Search Report and Written Opinion for PCT/CA2017/050447, 26 pages, dated Aug. 9, 2017.
Prakash, T, et al., "Targeted delivery of antisense oligonucleotides to hepatocytes using triantennary N-acetyl galactosamine improves potency 10-fold in mice", Nucleic Acids Research 42(13), 8796-8807 (2014).
Winkler, J, "Oligonucleotide conjugates for therapeutic applications", Ther Deliv 4(7), 791-809 (2013).
Zimmermann, T, et al., "Clinical Proof of Concept for a Novel Hepatocyte-Targeting GalNAc-siRNA Conjugate", Molecular Therapy: The Journal of the American Society of Gene Therapy 25(1), 71-78 (2017).
Jadhav, S, et al., "Solid-Supported Porphyrins Useful for the Synthesis of Conjugates with Oligomeric Biomolecules" Bioconjugate Chem 27, 1023-1029 (2016).
Holland, R, et al., "Ligand conjugate SAR and enhanced delivery in NHP", Molecular Therapy 29 (10), 2910-2919 (2021).

* cited by examiner

Figure 7

Table 1: Efficacy of subcutaneously administered siRNA (TTR) – Conjugates (1mg/kg). (% of Plasma TTR Relative to PBS Control)

| Conjugates # | Day 2 | Day 4 | Day 5 | Day 7 | Day 8 | Day 9 | Day 11 | Day 14 | Day 21 | Day 28 |
|---|---|---|---|---|---|---|---|---|---|---|
| 1 | 37.7 | 37.2 | ND | 45.6 | ND | ND | 55.0 | 75.4 | 76.5 | ND |
| 34 | 58.1 | 56.5 | ND | 84.5 | ND | ND | 90.2 | ND | ND | ND |
| 36 | 55.1 | 54.1 | ND | 69.9 | ND | ND | 97.8 | 104.3 | 95.6 | ND |
| 42 | 100.9 | 112.8 | ND | 119.1 | ND | ND | 118.8 | ND | ND | ND |
| 43 | 63.3 | 68.5 | ND | 83.8 | ND | ND | 98.4 | 94.8 | 112.8 | ND |
| 142 | 61.6 | ND | 65.1 | 64.9 | ND | 73.5 | ND | 88.6 | 99.3 | ND |
| 145 | 34.1 | ND | 16.9 | 19.8 | ND | 25.2 | ND | 45.1 | 74.3 | ND |
| 153 | 42.0 | ND | 26.3 | 25.3 | ND | 31.2 | ND | 50.3 | 70.7 | ND |
| 158 | 43.4 | ND | 41.6 | 53.5 | 50.1 | ND | ND | 82.6 | 103.2 | ND |
| 168 | 56.6 | ND | 50.7 | 63.8 | 60.0 | ND | ND | 92.7 | 104.9 | ND |
| 173 | 48.5 | ND | 56.9 | 55.4 | 56.6 | ND | ND | 87.4 | 84.2 | ND |
| 176 | 29.6 | ND | 12.3 | 14.5 | ND | 20.5 | ND | ND | ND | ND |
| 179 | 56.9 | 63.9 | ND | 72.9 | ND | ND | 75.1 | ND | 91.3 | 100.9 |
| 182 | 61.8 | ND | 57.2 | 64.9 | ND | 65.4 | ND | 89.0 | 100.1 | ND |
| 185 | 64.1 | ND | 67.7 | 67.7 | ND | 68.9 | ND | 89.6 | 83.3 | ND |
| 191 | 35.8 | ND | ND | 26.4 | ND | 32.0 | ND | 44.9 | 73.1 | ND |
| 194 | 40.6 | ND | 17.6 | 18.6 | ND | 20.3 | ND | ND | ND | ND |
| 197 | 41.6 | ND | 24.4 | 27.1 | ND | 31.9 | ND | ND | ND | ND |
| 200 | 41.5 | ND | 24.4 | 31.0 | ND | 33.5 | ND | ND | ND | ND |
| 203 | 53.6 | ND | 34.1 | 46.0 | ND | 47.3 | ND | ND | ND | ND |
| 206 | 41.6 | ND | 41.7 | 50.8 | ND | 50.9 | ND | 67.8 | 84.3 | ND |
| 212 | 44.6 | ND | 23.3 | 29.7 | ND | 28.2 | ND | ND | ND | ND |
| 215 | 42.1 | ND | 22.3 | 27.7 | ND | 29.5 | ND | ND | ND | ND |
| 231 | 42.9 | ND | ND | 37.6 | ND | 46.5 | ND | 53.0 | 76.1 | ND |

Figure 8

Table 2: Efficacy of subcutaneously administered siRNA (TTR) – Conjugates (2mg/kg). (% of Plasma TTR Relative to PBS Control)

| Compound # | Day 2 | Day 4 | Day 5 | Day 7 | Day 8 | Day 9 | Day 11 | Day 14 | Day 21 | Day 28 |
|---|---|---|---|---|---|---|---|---|---|---|
| 1 | 21.2 | 13.9 | ND | 24.5 | ND | ND | 36.5 | 54.3 | 71.5 | ND |
| 34 | 48.9 | 45.3 | ND | 59.2 | ND | ND | 87.9 | ND | ND | ND |
| 36 | 34.4 | 33.3 | ND | 40.2 | ND | ND | 66.4 | 78.0 | 84.4 | ND |
| 42 | 103.9 | 106.5 | ND | 131.6 | ND | ND | 130.9 | ND | ND | ND |
| 43 | 31.6 | 32.2 | ND | 40.6 | ND | ND | 65.3 | 69.6 | 98.3 | ND |
| 142 | 41.1 | ND | 39.1 | 43.0 | ND | 53.3 | ND | 84.5 | 95.6 | ND |
| 145 | 13.5 | ND | 4.7 | 5.7 | ND | 6.2 | ND | 14.7 | 42.2 | ND |
| 153 | 22.5 | ND | 8.7 | 8.7 | ND | 11.1 | ND | 23.2 | 46.8 | ND |
| 158 | 29.1 | ND | 21.4 | 27.5 | 27.8 | ND | ND | 56.5 | 79.4 | ND |
| 168 | 32.4 | ND | 22.6 | 33.6 | 28.7 | ND | ND | 56.3 | 83.7 | ND |
| 173 | 28.7 | ND | 22.6 | 23.5 | 22.8 | ND | ND | 54.8 | 82.2 | ND |
| 176 | 17.0 | ND | 4.4 | 5.3 | ND | 6.2 | ND | ND | ND | ND |
| 179 | 48.0 | 34.9 | ND | 39.7 | ND | ND | 58.9 | ND | 89.1 | 101.6 |
| 182 | 40.4 | ND | 36.7 | 38.5 | ND | 47.7 | ND | 64.9 | 87.7 | ND |
| 185 | 38.4 | ND | 46.3 | 51.1 | ND | 52.1 | ND | 69.4 | 85.8 | 90.5 |
| 191 | 19.2 | ND | ND | 10.2 | ND | 11.8 | ND | 21.4 | 45.3 | ND |
| 194 | 20.3 | ND | 5.9 | 6.5 | ND | 6.2 | ND | ND | ND | ND |
| 197 | 24.6 | ND | 9.3 | 8.6 | ND | 10.1 | ND | ND | ND | ND |
| 200 | 31.6 | ND | 10.9 | 14.2 | ND | 12.6 | ND | ND | ND | ND |
| 203 | 28.7 | ND | 17.6 | 21.3 | ND | 26.3 | ND | ND | ND | ND |
| 206 | 24.0 | ND | 21.3 | 19.0 | ND | 21.1 | ND | 45.1 | 65.2 | 90.6 |
| 212 | 30.5 | ND | 10.4 | 10.8 | ND | 11.0 | ND | ND | ND | ND |
| 215 | 24.2 | ND | 9.5 | 10.9 | ND | 10.4 | ND | ND | ND | ND |

SEQUENCE LISTING

```
<160> NUMBER OF SEQ ID NOS: 32

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
agguauguug cccguuuguu u                                               21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
acaaacgggc aacauaccuu u                                               21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcucaguuua cuagugccau u                                               21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 4
uggcacuagu aaacugagcu u                                          21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccgugugcac uucgcuucau u                                          21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugaagcgaag ugcacacggu u                                          21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcucaguuua cuagugccau u                                          21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uggcacuagu aaacugagcu u                                          21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ccgugugcac uucgcuucau u                                          21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 10
ugaagcgaag ugcacacggu u                                             21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cuggcucagu uuacuagugu u                                             21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cacuaguaaa cugagccagu u                                             21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgugugcac uucgcuucau u                                             21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugaagcgaag ugcacacggu u                                             21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcucaguuua cuagugccau u                                             21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 16
uggcacuagu aaacugagcu u                    21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agguauguug cccguuuguu u                    21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
acaaacgggc aacauaccuu u                    21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gccgauccau acugcggaau u                    21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuccgcagua uggaucggcu u                    21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gccgauccau acugcggaau u                    21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uuccgcagua uggaucggcu u							21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gccgauccau acugcggaau u							21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuccgcagua uggaucggcu u							21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gccgauccau acugcggaau u							21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuccgcagua uggaucggcu u							21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gcucaguuua cuagugccau u							21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28

```
uggcacuagu aaacugagcu u                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cuggcucagu uuacuagugu u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cacuaguaaa cugagccagu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aacaguguuc uugcucuaua a                                              21

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uuauagagca agaacacugu uuu                                            23
```

TARGETED NUCLEIC ACID CONJUGATE COMPOSITIONS

CROSS-REFERENCE TO RELATED APPLICATIONS

This patent application is a 35 U.S.C. § 371 application of International Application Number PCT/CA2017/050447, filed Apr. 11, 2017; and claims the benefit of U.S. Provisional Application Ser. No. 62/438,310, filed Dec. 22, 2016, U.S. Provisional Application Ser. No. 62/417,156, filed Nov. 3, 2016 and U.S. Provisional Application Ser. No. 62/321,034, filed Apr. 11, 2016, which applications are herein incorporated by reference.

SEQUENCE LISTING

The instant application contains a Sequence Listing which has been submitted electronically in ASCII format and is hereby incorporated by reference in its entirety. Said ASCII copy, created on Apr. 7, 2017, is named 08155_056WO1_SL.txt and is 7,824 bytes in size.

BACKGROUND

A number of diseases are specific to the liver, for example Hepatitis B and nonalcoholic steatohepatitis (NASH). Accordingly, it would be beneficial to have therapeutic compositions that can be targeted primarily to the liver, kidney, heart, pancreas or other organs in living subjects.

Nucleic acids, including siRNA are useful as therapeutic agents.

Currently there is a need for compositions and methods that can be used to deliver (e.g. target) therapeutic nucleic acids in living subjects.

BRIEF SUMMARY

The invention provides compounds, compositions and methods that can be used to target therapeutic nucleic acids (e.g. to the liver).

Accordingly, in one aspect this invention provides a compound of formula I

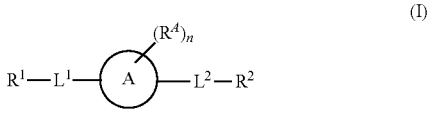

(I)

wherein:
R$^1$ a is targeting ligand;
L$^1$ is absent or a linking group;
L$^2$ is absent or a linking group;
R$^2$ is a nucleic acid;
the ring A is absent, a 3-20 membered cycloalkyl, a 5-20 membered aryl, a 5-20 membered heteroaryl, or a 3-20 membered heterocycloalkyl;
each R$^A$ is independently selected from the group consisting of hydrogen, hydroxy, CN, F, Cl, Br, I, —C$_{1-2}$ alkyl-OR$^B$, C$_{1-10}$ alkyl C$_{2-10}$ alkenyl, and C$_{2-10}$ alkynyl; wherein the C$_{1-10}$ alkyl C$_{2-10}$ alkenyl, and C$_{2-10}$ alkynyl are optionally substituted with one or more groups independently selected from halo, hydroxy, and C$_{1-3}$ alkoxy;

R$^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

Diseases and conditions which can be treated with the siRNA molecules, including combinations thereof, include liver diseases, e.g., liver diseases associated with or caused by fat accumulation, such as liver steatosis, non-alcoholic fatty liver disease (NAFLD), non-alcoholic steatohepatitis (NASH), steatotic liver transplant, hepatitis (e.g. B or D) and/or acute liver damage, including fulminant and subfulminant hepatic failure, and hypertriglyceridemia.

The invention also provides synthetic intermediates and methods disclosed herein that are useful to prepare compounds of formula I.

Other objects, features, and advantages of the present invention will be apparent to one of skill in the art from the following detailed description and figures.

BRIEF DESCRIPTION OF THE FIGURES

FIG. 7: Shows data from Example 25 for representative compounds.

FIG. 8: Shows data from Example 25 for representative compounds.

DETAILED DESCRIPTION

Figure 1:
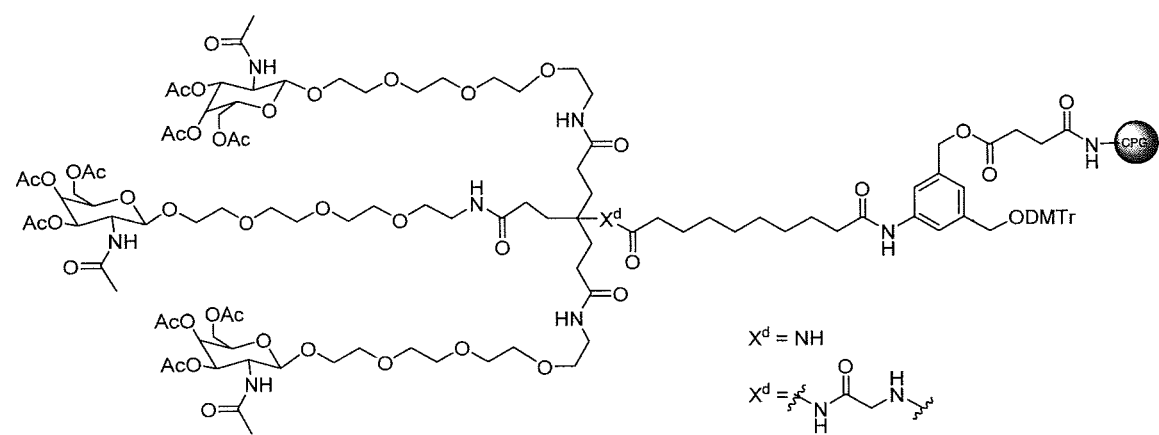
FIG. 1: Illustrates an intermediate compound of formula Ie, wherein a targeting ligand/linker is bound to a solid phase support, and wherein Pg$^1$ is the protecting group DMTr.
Figure 2:
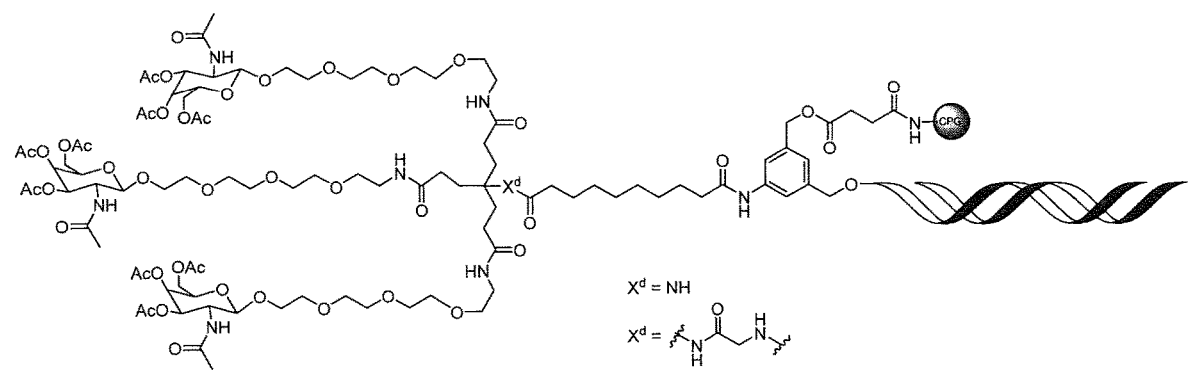
FIG. 2: Illustrates a representative compound of formula Id wherein a targeting ligand is bound to a solid phase support, with a nucleic acid covalently bound.
Figure 3:
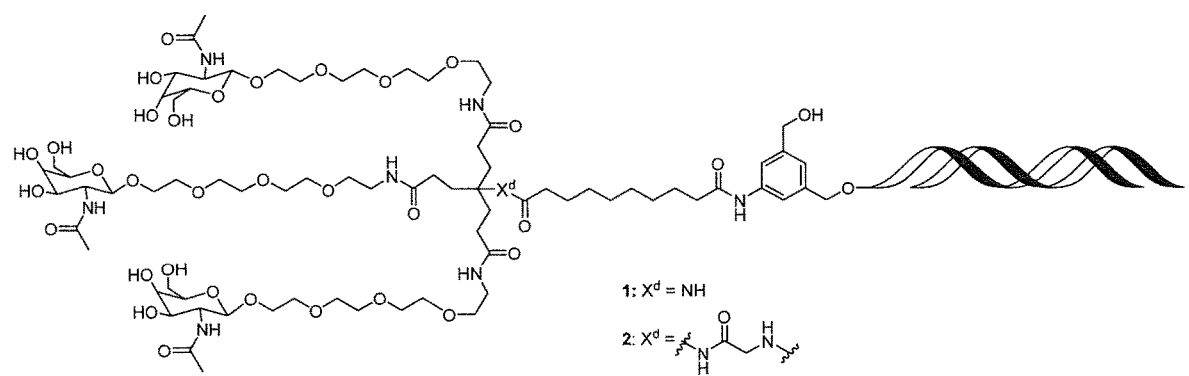
FIG. 3: Illustrates a representative compound of formula Id, wherein a targeting ligand-nucleic acid conjugate has been cleaved from a solid phase support and deprotected to provide the compound of formula I.
Figure 4:
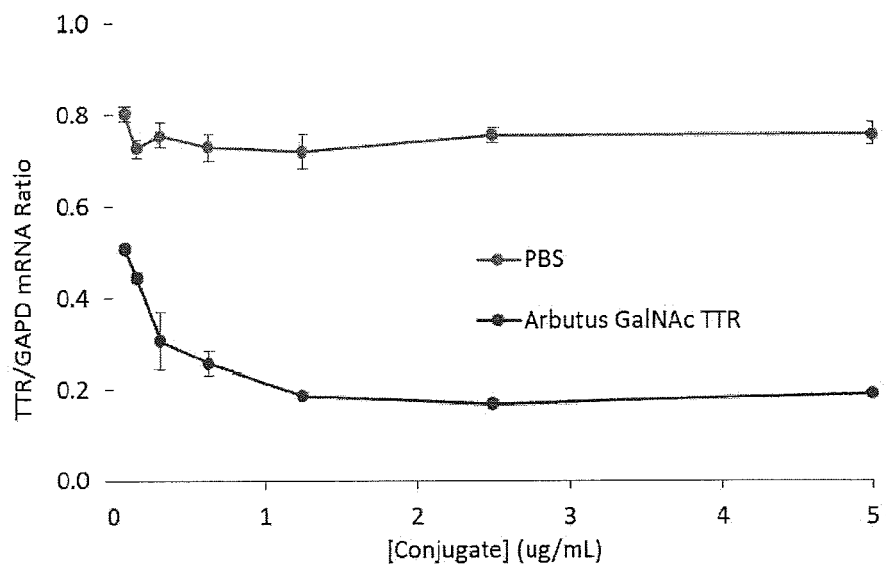
FIG. 4: Illustrates TTR mRNA gene knockdown experiment, following a 24 hours transfection of GalNAc conjugate at various doses on C57 primary hepatocytes.
Figure 5:
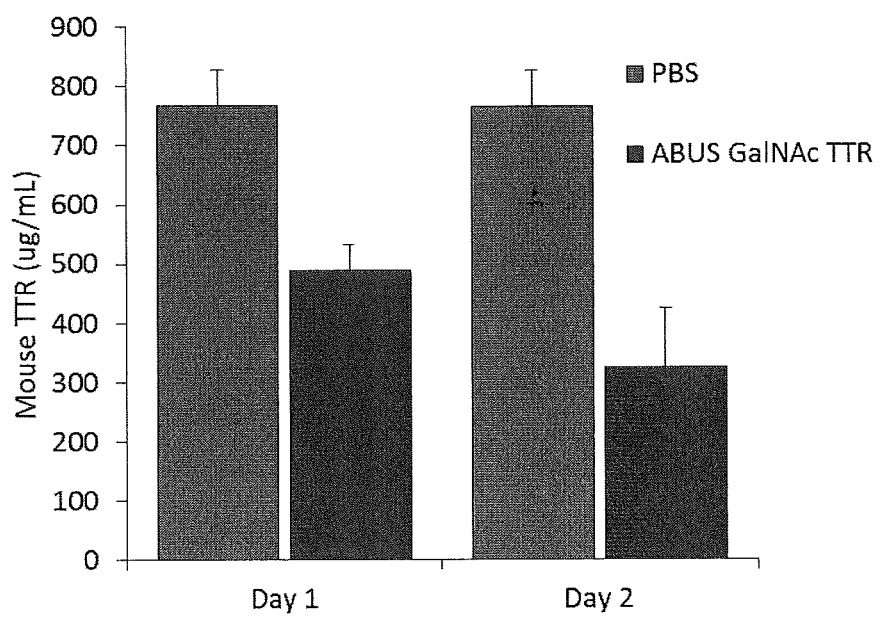
FIG. 5: Illustrates knockdown of TTR protein after a single, 1 mg/kg, SubQ dose of TTR siRNA-GalNAc Conjugate; C57 Mice (n=4).
Figure 6:
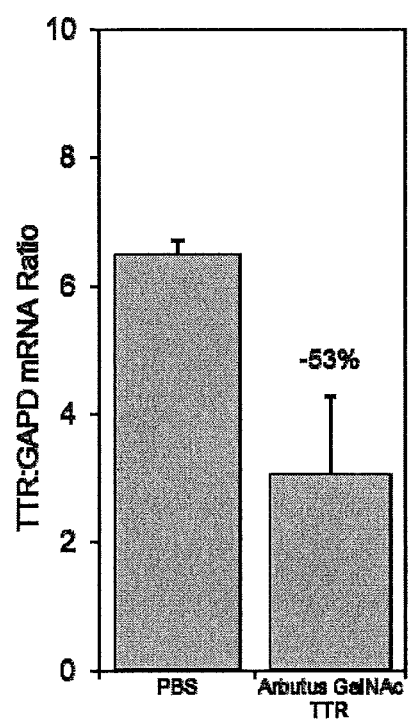
FIG. 6: Illustrates knockdown of TTR mRNA in the liver after a single, 1 mg/kg, SubQ dose of TTR siRNA-GalNAc Conjugate; C57 Mice (n=4).

As used herein, the following terms have the meanings ascribed to them unless specified otherwise.

The term "small-interfering RNA" or "siRNA" as used herein refers to double stranded RNA (i.e., duplex RNA) that is capable of reducing or inhibiting the expression of a target gene or sequence (e.g., by mediating the degradation or inhibiting the translation of mRNAs which are complementary to the siRNA sequence) when the siRNA is in the same cell as the target gene or sequence. The siRNA may have substantial or complete identity to the target gene or sequence, or may comprise a region of mismatch (i.e., a mismatch motif). In certain embodiments, the siRNAs may be about 19-25 (duplex) nucleotides in length, and is preferably about 20-24, 21-22, or 21-23 (duplex) nucleotides in length. siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand.

In certain embodiments, the 5' and/or 3' overhang on one or both strands of the siRNA comprises 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence (e.g., 3'overhang in the antisense strand) or the complementary strand thereof (e.g., 3' overhang in the sense strand).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad Sci. USA*, 99:9942-9947 (2002); Calegari et al., *Proc. Natl. Acad Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

The phrase "inhibiting expression of a target gene" refers to the ability of a siRNA of the invention to silence, reduce, or inhibit expression of a target gene (e.g., DGAT2 and optionally ANGPTL3 expression). To examine the extent of gene silencing, a test sample (e.g., a biological sample from an organism of interest expressing the target gene or a sample of cells in culture expressing the target gene) is contacted with a siRNA that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the siRNA. Control samples (e.g., samples expressing the target gene) may be assigned a value of 100%. In particular embodiments, silencing, inhibition, or reduction of expression of a target gene is achieved when the value of the test sample relative to the control sample (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "synthetic activating group" refers to a group that can be attached to an atom to activate that atom to allow it to form a covalent bond with another reactive group. It is understood that the nature of the synthetic activating group may depend on the atom that it is activating. For example, when the synthetic activating group is attached to an oxygen atom, the synthetic activating group is a group that will activate that oxygen atom to form a bond (e.g. an ester, carbamate, or ether bond) with another reactive group. Such synthetic activating groups are known. Examples of synthetic activating groups that can be attached to an oxygen atom include, but are not limited to, acetate, succinate, triflate, and mesylate. When the synthetic activating group is attached to an oxygen atom of a carboxylic acid, the synthetic activating group can be a group that is derivable from a known coupling reagent (e.g. a known amide coupling reagent). Such coupling reagents are known. Examples of such coupling reagents include, but are not limited to, N,N'-Dicyclohexylcarbodimide (DCC), hydroxybenzotriazole (HOBt), N-(3-Dimethylaminopropyl)-N'-ethylcarbonate (EDC), (Benzotriazol-1-yloxy)tris(dimethylamino)phosphonium hexafluorophosphate (BOP), benzotriazol-1-yl-oxytripyrrolidinophosphonium hexafluorophosphate (PyBOP) or O-benzotriazol-1-yl-N,N,N',N'-tetramethyluronium hexafluorophosphate (HBTU).

An "effective amount" or "therapeutically effective amount" of a therapeutic nucleic acid such as siRNA is an amount sufficient to produce the desired effect, e.g., an inhibition of expression of a target sequence in comparison to the normal expression level detected in the absence of a siRNA. In particular embodiments, inhibition of expression of a target gene or target sequence is achieved when the value obtained with a siRNA relative to the control (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "nucleic acid" as used herein refers to a polymer containing at least two nucleotides (i.e., deoxyribonucleotides or ribonucleotides) in either single- or double-stranded form and includes DNA and RNA. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphoramidates, methyl phosphonates, chiral-methyl phosphonates, 2'-O-methyl ribonucleotides, and peptide-nucleic acids (PNAs). Additionally, nucleic acids can include one or more UNA moieties.

The term "nucleic acid" includes any oligonucleotide or polynucleotide, with fragments containing up to 60 nucleotides generally termed oligonucleotides, and longer fragments termed polynucleotides. A deoxyribooligonucleotide consists of a 5-carbon sugar called deoxyribose joined covalently to phosphate at the 5' and 3' carbons of this sugar to form an alternating, unbranched polymer. DNA may be in the form of, e.g., antisense molecules, plasmid DNA, pre-condensed DNA, a PCR product, vectors, expression cassettes, chimeric sequences, chromosomal DNA, or derivatives and combinations of these groups. A ribooligonucleotide consists of a similar repeating structure where the 5-carbon sugar is ribose. RNA may be in the form, for example, of small interfering RNA (siRNA), Dicer-substrate dsRNA, small hairpin RNA (shRNA), asymmetrical interfering RNA (aiRNA), microRNA (miRNA), mRNA, tRNA, rRNA, viral RNA (vRNA), and combinations thereof. Accordingly, in the context of this invention, the terms "polynucleotide" and "oligonucleotide" refer to a polymer or oligomer of nucleotide or nucleoside monomers consisting of naturally-occurring bases, sugars and inter-sugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260: 2605-2608 (1985); Rossolini et al., *Mol. Cell. Probes,* 8:91-98 (1994)).

In one embodiment, the nucleic acid can be an siRNA. Suitable siRNA, as well as method and intermediates useful for their preparation are reported in International Patent Application Publication Number WO2016/054421. In one embodiment, the siRNA can be selected from the siRNA shown in the following table.

| Name | Duplex Sequences | |
|---|---|---|
| 1m | 5' A g G u A U g u U G C C C g U u U G U U U 3' | (SEQ ID NO: 1) |
| | 3' U U U C C A u A C A A C G G g C A A A C A 5' | (SEQ ID NO: 2) |
| 2m | 5' G C u c A g U U U A C U A G U G C c A U U 3' | (SEQ ID NO: 3) |
| | 3' U U C g A G U C A A A u G A U C A C G G U 5' | (SEQ ID NO: 4) |
| 3m | 5' C C G U g u G C A C U u C G C u u C A U U 3' | (SEQ ID NO: 5) |
| | 3' U U G g C A C A C g U G A A G C G A A G U 5' | (SEQ ID NO: 6) |
| 4m | 5' G C u c A g U U U A C U A G U G C c A U U 3' | (SEQ ID NO: 7) |
| | 3' U U C g A G U C A A A u G A U C A C G G U 5' | (SEQ ID NO: 8) |
| 5m | 5' C C G U g u G C A C U u C G C u U C A U U 3' | (SEQ ID NO: 9) |
| | 3' U U G g C A C A C g U G A A G C G A A G U 5' | (SEQ ID NO: 10) |
| 6m | 5' C u g g C U C A G U U U A C u A g U G U U 3' | (SEQ ID NO: 11) |
| | 3' U U G A C C g A g U C A A A U g A U C A C 5' | (SEQ ID NO: 12) |
| 7m | 5' C C G U g u G C A C U u C G C u U C A U U 3' | (SEQ ID NO: 13) |
| | 3' U U G g C A C A C g U G A A G C G A A G U 5' | (SEQ ID NO: 14) |
| 8m | 5' G C u c A g U U U A C u A g U G C C A U U 3' | (SEQ ID NO: 15) |
| | 3' U U C G A G u C A A A U G A U C A C G G U 5' | (SEQ ID NO: 16) |
| 9m | 5' A g G u A U G u U G C C C g U u U G U U U 3' | (SEQ ID NO: 17) |
| | 3' U U u C C A u A C A A C G G g C A A A C A 5' | (SEQ ID NO: 18) |
| 10m | 5' G C C g A u C C A U A C u g C g g A A U U 3' | (SEQ ID NO: 19) |
| | 3' U U C g G C U A g G U A U g A C G C C U U 5' | (SEQ ID NO: 20) |
| 11m | 5' G C C g A u C C A U A C u g C g g A A U U 3' | (SEQ ID NO: 21) |
| | 3' U U C g G C U A g G U A U g A C G C C U U 5' | (SEQ ID NO: 22) |
| 12m | 5' G C C g A u C C A U A C u g C g g A A U U 3' | (SEQ ID NO: 23) |
| | 3' U U C g G C U A g G U A U g A C G C C U U 5' | (SEQ ID NO: 24) |
| 13m | 5' G C C g A u C C A U A C u g C g g A A U U 3' | (SEQ ID NO: 25) |
| | 3' U U C g G C U A g G U A U g A C G C C U U 5' | (SEQ ID NO: 26) |
| 14m | 5' G C u c A g U U U A C u A g U G C C A U U 3' | (SEQ ID NO: 27) |
| | 3' U U C G A G u C A A A U G A U C A C G G U 5' | (SEQ ID NO: 28) |
| 15m | 5' C u g G C u C A G U U u A C U A G U G U U 3' | (SEQ ID NO: 29) |
| | 3' U U G A C C g A G U C A A A U G A U C A C 5' | (SEQ ID NO: 30) |

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane (including straight and branched alkanes), as exemplified by —$CH_2CH_2CH_2CH_2$— and —$CH(CH_3)CH_2CH_2$—.

The term "cycloalkyl," "carbocyclic," or "carbocycle" refers to hydrocarbon ringsystem having 3 to 20 overall number of ring atoms (e.g., 3-20 membered cycloalkyl is a cycloalkyl with 3 to 20 ring atoms, or $C_{3-20}$ cycloalkyl is a cycloalkyl with 3-20 carbon ring atoms) and for a 3-5 membered cycloalkyl being fully saturated or having no more than one double bond between ring vertices and for a 6 membered cycloalkyl or larger being fully saturated or having no more than two double bonds between ring vertices. As used herein, "cycloalkyl," "carbocyclic," or "carbocycle" is also meant to refer to bicyclic, polycyclic and spirocyclic hydrocarbon ring system, such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heterocycloalkyl," "heterocyclic," or "heterocycle" refers to a saturated or partially unsaturated ring system radical having the overall having from 3-20 ring atoms (e.g., 3-20 membered heterocycloalkyl is a heterocycloalkyl radical with 3-20 ring atoms, a $C_{2-19}$ heterocycloalkyl is a heterocycloalkyl having 3-10 ring atoms with between 2-19 ring atoms being carbon) that contain from one to ten heteroatoms selected from N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring can be a monocyclic, a bicyclic, spirocyclic or a polycylic ring system. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and poly-halogenated variants thereof.

The terms "alkoxy," and "alkylthio", are used in their conventional sense, and refer to those alkyl groups attached to the remainder of the molecule via an oxygen atom ("oxy") or thio group, and further include mono- and poly-halogenated variants thereof.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent. Additionally, the term "haloalkyl," is meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means a carbocyclic aromatic group having 6-14 carbon atoms, whether or not fused to one or more groups. Examples of aryl groups include phenyl, naphthyl, biphenyl and the like unless otherwise stated.

The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

The term saccharide includes monosaccharides, disaccharides and trisaccharides. The term includes glucose, sucrose fructose, galactose and ribose, as well as deoxy sugars such as deoxyribose and amino sugar such as galactosamine. Saccharide derivatives can conveniently be prepared as described in International Patent Applications Publication Numbers WO 96/34005 and 97/03995. A saccharide can conveniently be linked to the remainder of a compound of formula I through an ether bond, a thioether bond (e.g. an S-glycoside), an amine nitrogen (e.g., an N-glycoside), or a carbon-carbon bond (e.g. a C-glycoside). In one embodiment the saccharide can conveniently be linked to the remainder of a compound of formula I through an ether bond. In one embodiment the term saccharide includes a group of the formula:

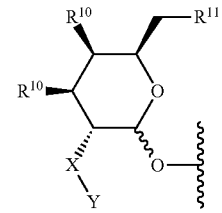

wherein:

X is $NR^3$, and Y is selected from —(C=O)$R^4$, —$SO_2R^5$, and —(C=O)$NR^6R^7$; or X is —(C=O)— and Y is $NR^8R^9$;

$R^3$ is hydrogen or ($C_1$-$C_4$)alkyl;

$R^4$, $R^5$, $R^6$, $R^7$, $R^8$ and $R^9$ are each independently selected from the group consisting of hydrogen, ($C_1$-$C_8$)alkyl, ($C_1$-$C_8$)haloalkyl, ($C_1$-$C_8$)alkoxy and ($C_3$-$C_6$)cycloalkyl that is optionally substituted with one or more groups independently selected from the group consisting of halo, $(C_1-C_4)$alkyl, $(C_1-C_4)$haloalkyl, $(C_1-C_4)$ alkoxy and $(C_1-C_4)$haloalkoxy;

$R^{10}$ is —OH, —$NR^8R^9$ or —F; and $R^{11}$ is —OH, —$NR^8R^9$, —F or 5 membered heterocycle that is optionally substituted with one or more groups independently selected from the group consisting of halo, hydroxyl, carboxyl, amino, $(C_1-C_4)$alkyl, $(C_1-C_4)$ haloalkyl, $(C_1-C_4)$alkoxy and $(C_1-C_4)$haloalkoxy. In another embodiment the saccharide can be selected from the group consisting of:

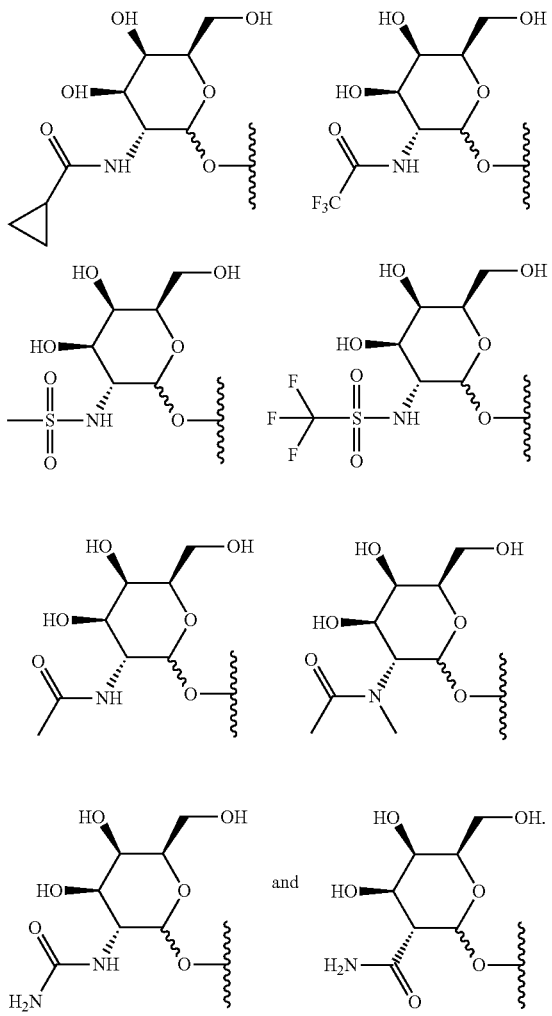

In another embodiment the saccharide can be:

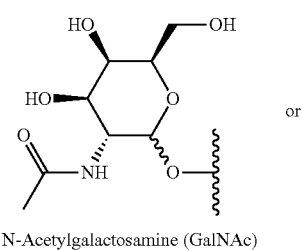

N-Acetylgalactosamine (GalNAc)

or

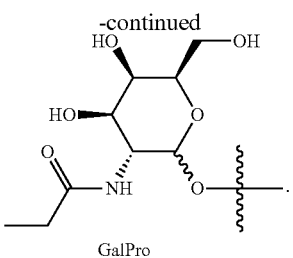

GalPro

The term "animal" includes mammalian species, such as a human, mouse, rat, dog, cat, hamster, guinea pig, rabbit, livestock, and the like.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

Methods for isolating RNA, synthesizing RNA, hybridizing nucleic acids, making and screening cDNA libraries, and performing PCR are well known in the art (see, e.g., Gubler and Hoffman, *Gene*, 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Typically, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art. siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection.

Embodiments of the Invention

One aspect of the invention is a compound of formula I, as set forth about in the Summary of the Invention, or a salt thereof.

In one embodiment of the compound of formula I, $R^1$ a is targeting ligand;

$L^1$ is absent or a linking group;

$L^2$ is absent or a linking group;

$R^2$ is a nucleic acid;

the ring A is absent, a 3-20 membered cycloalkyl, a 5-20 membered aryl, a 5-20 membered heteroaryl, or a 3-20 membered heterocycloalkyl;

each $R^A$ is independently selected from the group consisting of hydrogen, hydroxy, CN, F, Cl, Br, I, —$C_{1-2}$ alkyl-$OR^B$ and $C_{1-8}$ alkyl that is optionally substituted with one or more groups independently selected from halo, hydroxy, and $C_{1-3}$ alkoxy;

$R^B$ is hydrogen, a protecting group, a covalent bond to a solid support, or a bond to a linking group that is bound to a solid support; and n is 0, 1, 2, 3, 4, 5, 6, 7, 8, 9, or 10.

In one embodiment $R^1$ is —$C(H)_{(3-p)}(L^3\text{-saccharide})_p$, wherein each $L^3$ is independently a linking group; p is 1, 2, or 3; and saccharide is a monosaccharide or disaccharide.

In one embodiment the saccharide is:

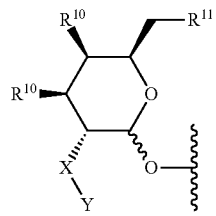

wherein:

X is $NR^3$, and Y is selected from —(C=O)$R^4$, —$SO_2R^5$, and —(C=O)$NR^6R^7$; or X is —(C=O)— and Y is $NR^8R^9$;

$R^3$ is hydrogen or $(C_1\text{-}C_4)$alkyl;

$R^4$, $R^5$, $R^6$, $R^7$, $R^8$ and $R^9$ are each independently selected from the group consisting of hydrogen, $(C_1\text{-}C_8)$alkyl, $(C_1\text{-}C_8)$haloalkyl, $(C_1\text{-}C_8)$alkoxy and $(C_3\text{-}C_6)$cycloalkyl that is optionally substituted with one or more groups independently selected from the group consisting of halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^{10}$ is —OH, —$NR^8R^9$ or —F; and $R^{11}$ is —OH, —$NR^8R^9$, —F or 5 membered heterocycle that is optionally substituted with one or more groups independently selected from the group consisting of halo, hydroxyl, carboxyl, amino, $(C_1\text{-}C_4)$alkyl, $(C_1\text{-}C_4)$ haloalkyl, $(C_1\text{-}C_4)$alkoxy and $(C_1\text{-}C_4)$haloalkoxy; or a salt thereof.

In one embodiment the saccharide is selected from the group consisting of:

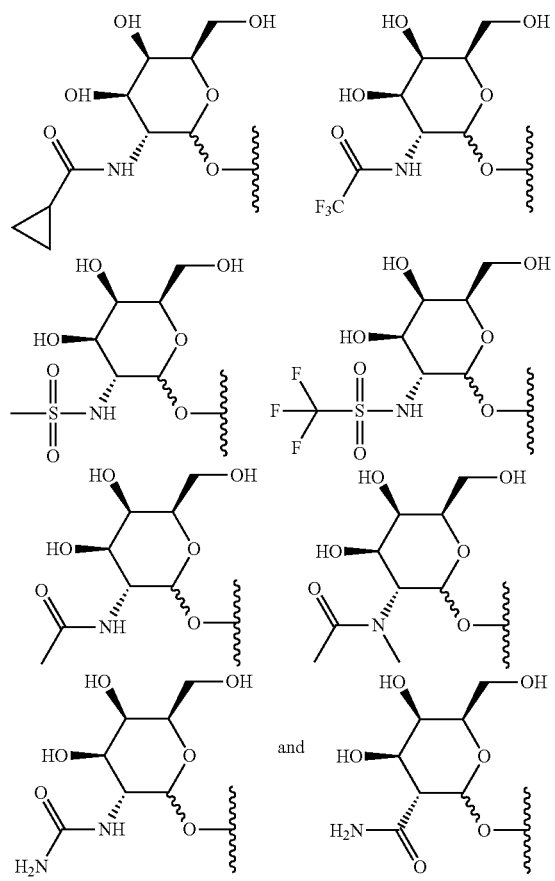

and salts thereof.

In one embodiment the saccharide is:

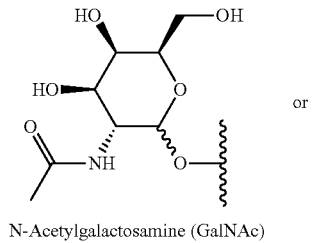

N-Acetylgalactosamine (GalNAc)

or

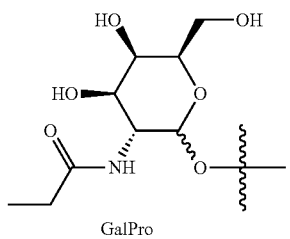

GalPro

In one embodiment each L is independently a divalent, branched or unbranched, saturated or unsaturated, hydrocarbon chain, having from 0 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or (C$_1$-C$_6$)alkyl, and wherein the hydrocarbon chain, is optionally substituted with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In one embodiment each L$^3$ is independently a divalent, branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or (C$_1$-C$_6$)alkyl, and wherein the hydrocarbon chain, is optionally substituted with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C1-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In one embodiment L$^3$ is:

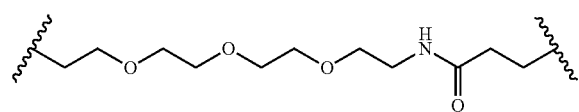 [SMILES: *CCOCCOCCOCCNC(=O)CC*]

or a salt thereof.

In one embodiment R$^1$ is:

In one embodiment R$^1$ is:

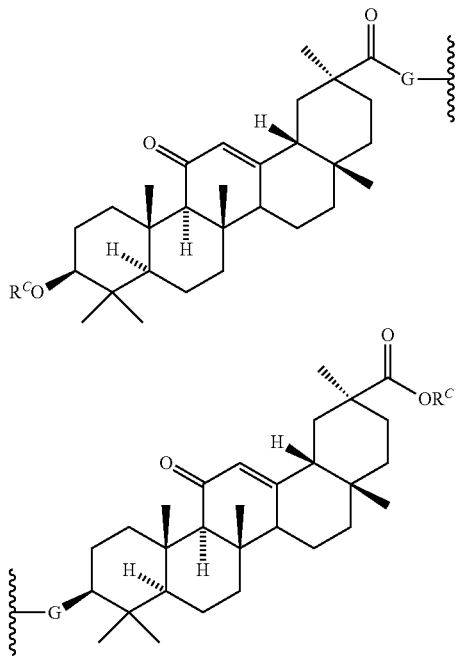

wherein G is —NH— or —O—;

R$^C$ is hydrogen, (C$_1$-C$_8$)alkyl, (C$_1$-C$_8$)haloalkyl, (C$_1$-C$_8$) alkoxy, (C$_1$-C$_6$)alkanoyl, (C$_3$-C$_{20}$)cycloalkyl, (C$_3$-C$_{20}$) heterocycle, aryl, heteroaryl, monosaccharide, disaccharide or trisaccharide; and wherein the cycloalkyl, heterocycle, ary, heteroaryl and saccharide are optionally substituted with one or more groups independently selected from the group consisting of halo, carboxyl,

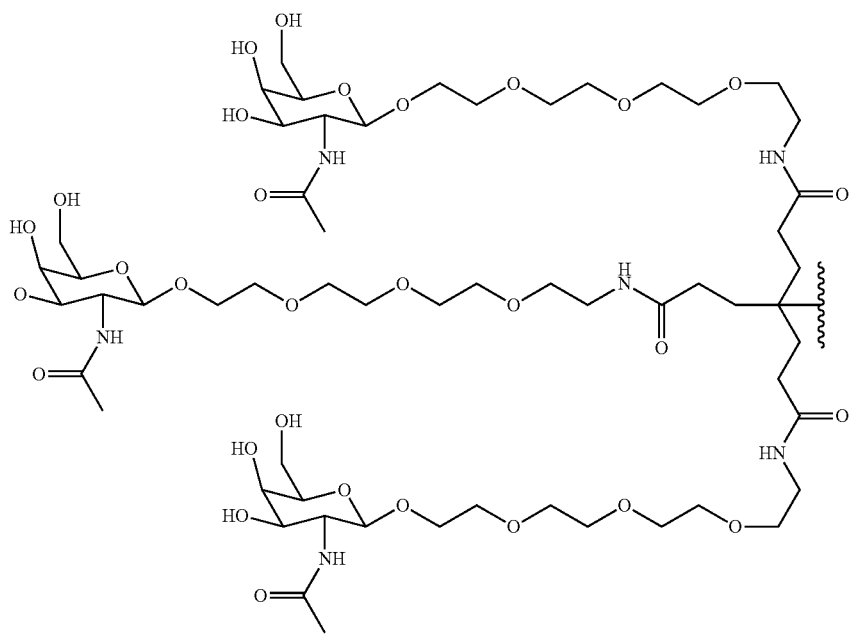 [SMILES: *C(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]

or a salt thereof.

hydroxyl, amino, $(C_1-C_4)$alkyl, $(C_1-C_4)$haloalkyl, $(C_1-C_4)$alkoxy and $(C_1-C_4)$haloalkoxy;
or a salt thereof.

In one embodiment $R^C$ is:

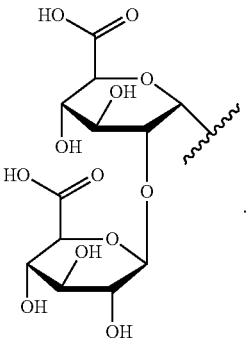

In one embodiment $R^1$ is:

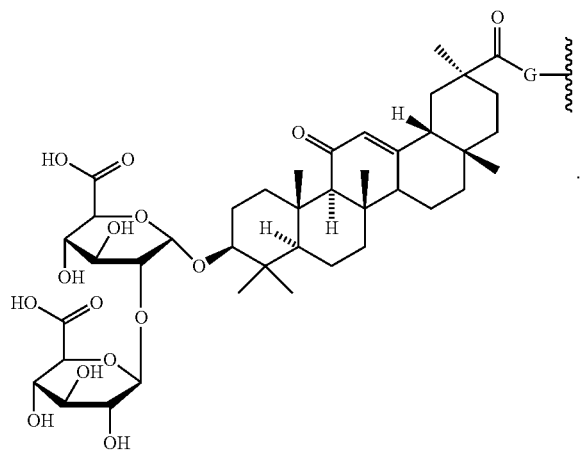

In one embodiment $R^C$ is:

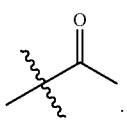 [SMILES: *C(C)=O]

In one embodiment G is —NH—.
In one embodiment $R^1$ is:

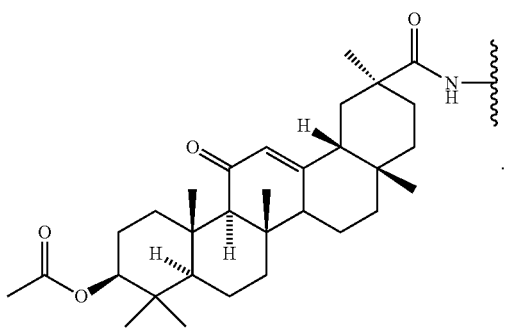

In one embodiment $R^1$ is:

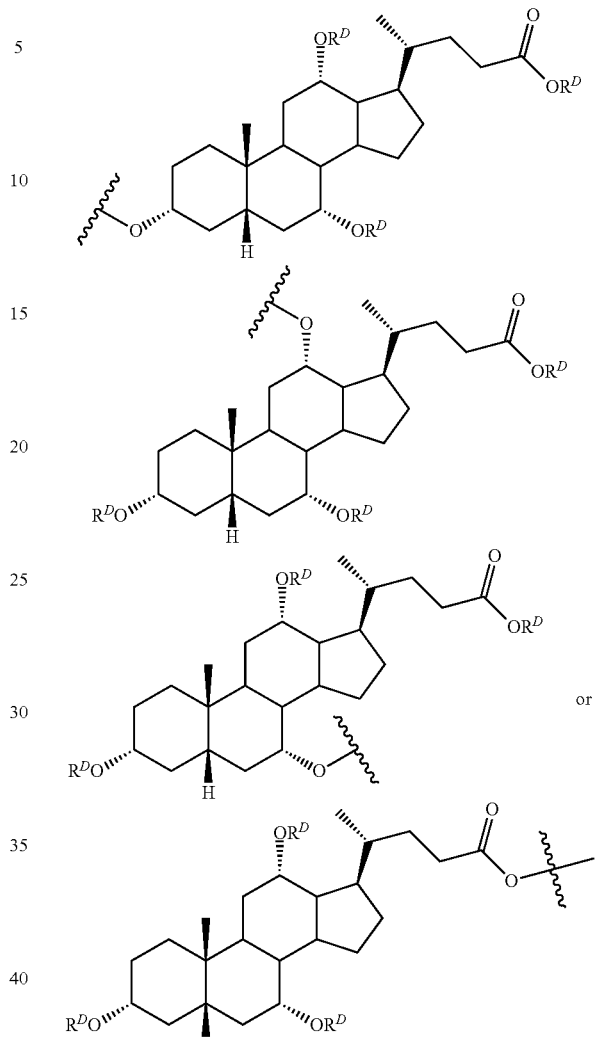

wherein each $R^D$ is independently selected from the group consisting of hydrogen, $(C_1-C_6)$alkyl, $(C_9-C_{20})$alkylsilyl, $(R^W)_3Si$—, $(C_2-C_6)$alkenyl, tetrahydropyranyl, $(C_1-C_6)$alkanoyl, benzoyl, aryl$(C_1-C_3)$alkyl, TMTr (Trimethoxytrityl), DMTr (Dimethoxytrityl), MMTr (Monomethoxytrityl), and Tr (Trityl); and
each $R^W$ is independently selected from the group consisting of $(C_1-C_4)$alkyl and aryl.

In one embodiment linking groups $L^1$ and $L^2$ are independently a divalent, branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —$NR^X$—, —$NR^X$—C(=O)—, —C(=O)—$NR^X$— or —S—, and wherein $R^X$ is hydrogen or $(C_1-C_6)$alkyl, and wherein the hydrocarbon chain, is optionally substituted with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $L^1$ and $L^2$ are independently a divalent, branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or (C$_1$-C$_6$)alkyl, and wherein the hydrocarbon chain, is optionally substituted with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In one embodiment L$^1$ and L$^2$ are independently, a divalent, branched or unbranched, saturated or unsaturated, hydrocarbon chain, having from 1 to 14 carbon atoms, wherein one or more (e.g. 1, 2, 3, or 4) of the carbon atoms in the hydrocarbon chain is optionally replaced —O—, —NR$^X$—, —NR$^X$—C(=O)—, —C(=O)—NR$^X$— or —S—, and wherein R$^X$ is hydrogen or (C$_1$-C$_6$)alkyl, and wherein the hydrocarbon chain, is optionally substituted with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In one embodiment L$^1$ is connected to R$^1$ through —NH—, —O—, —S—, —(C=O)—, —(C=O)—NH—, —NH—(C=O)—, —(C=O)—O—, —NH—(C=O)—NH—, or —NH—(SO$_2$)—.

In one embodiment L$^2$ is connected to R$^2$ through —O—.

In one embodiment L$^1$ is selected from the group consisting of:

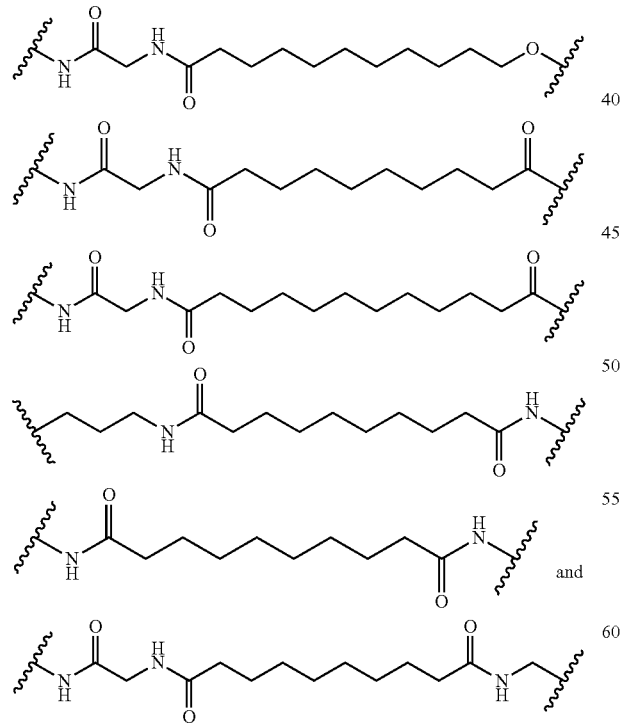

In one embodiment L$^1$ is selected from the group consisting of:

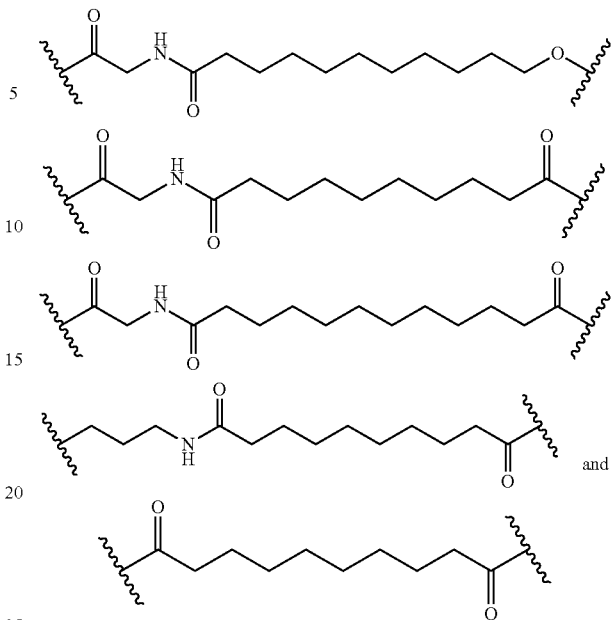

and salts thereof.

In one embodiment L$^2$ is —CH$_2$—O— or —CH$_2$—CH$_2$—O—.

In one embodiment a compound of formula I has the following formula Ia:

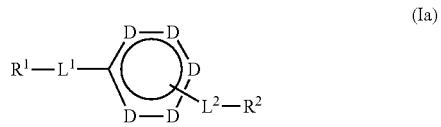

wherein:

each D is independently selected from the group consisting of

and —N=;

or a salt thereof.

In one embodiment a compound of formula Ia is selected from the group consisting of:

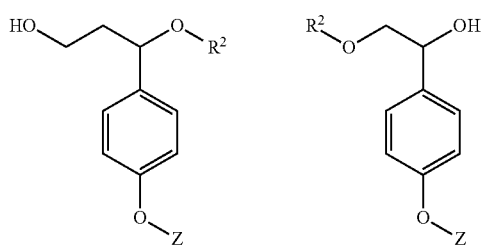

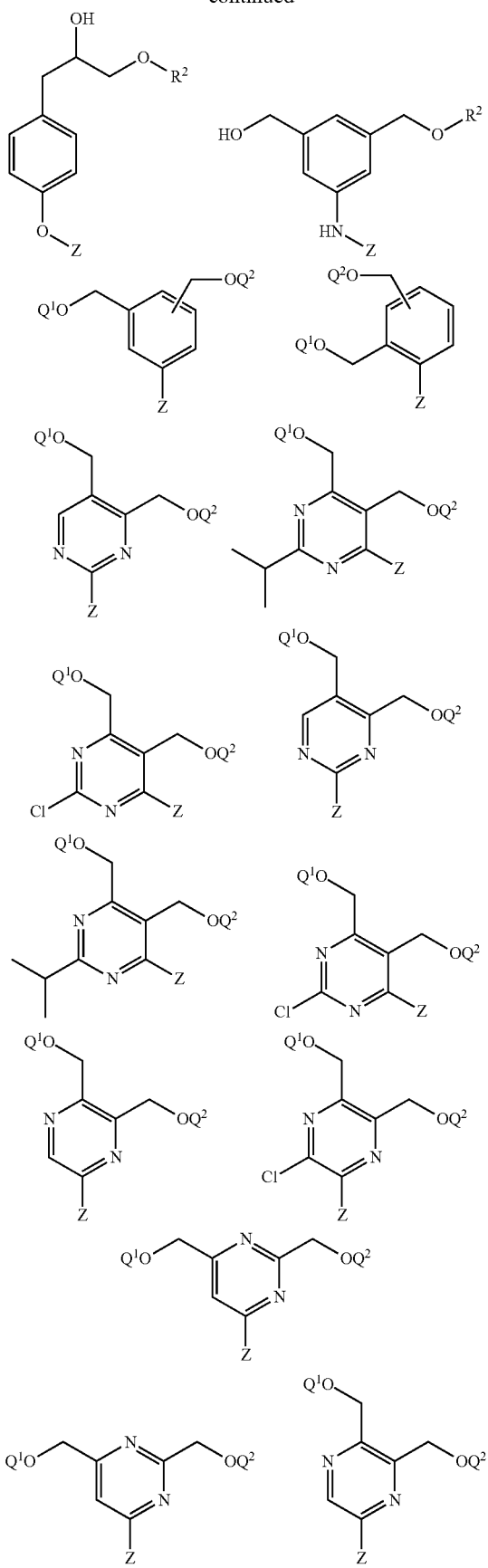
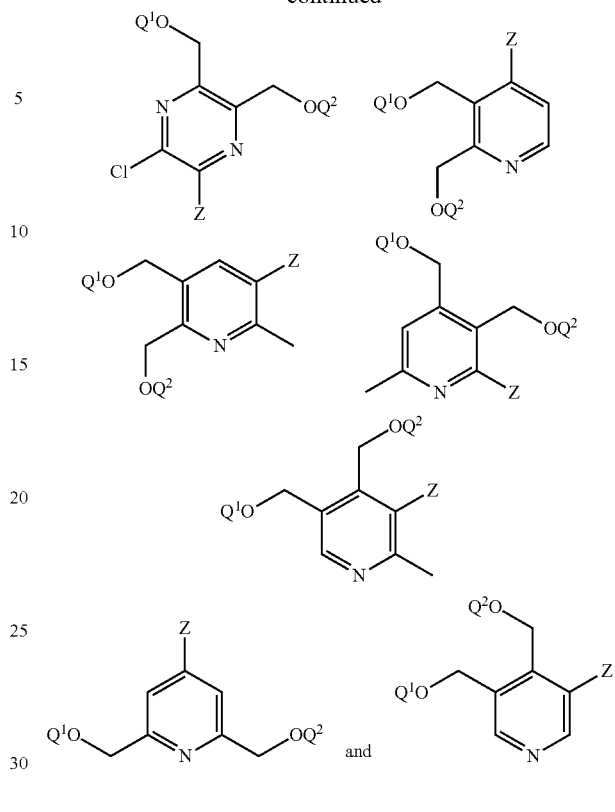

wherein:

Q$^1$ is hydrogen and Q$^2$ is R$^2$; or Q$^1$ is R$^2$ and Q$^2$ is hydrogen;

Z is -L$^1$-R$^1$;

and salts thereof.

In one embodiment a compound of formula I has the following formula Ib:

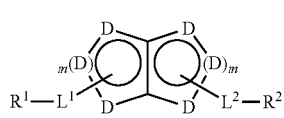
(Ib)

wherein:

each D is independently selected from the group consisting of

and —N=;

each m is independently 1 or 2;

or a salt thereof.

In one embodiment a compound of formula Ib is selected from the group consisting of:

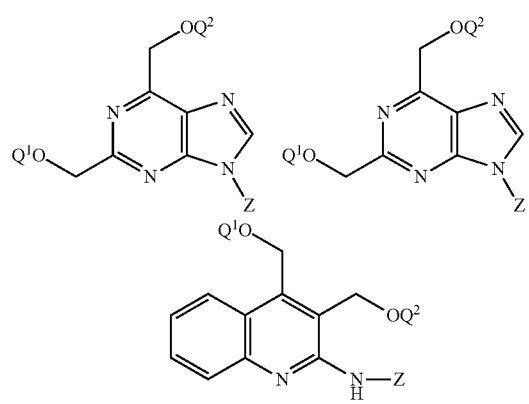

wherein:
$Q^1$ is hydrogen and $Q^2$ is $R^2$; or $Q^1$ is $R^2$ and $Q^2$ is hydrogen;
Z is $-L^1-R^1$;
and salts thereof.

In one embodiment a compound of formula I has the following formula (Ic):

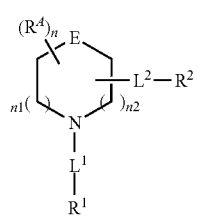

Wherein E is —O— or —CH$_2$—;
n is selected from the group consisting of 0, 1, 2, 3, and 4; and
n1 and n2 are each independently selected from the group consisting of 0, 1, 2, and 3;
or a salt thereof.

In certain embodiments a compound of formula (Ic) is selected from the group consisting of:

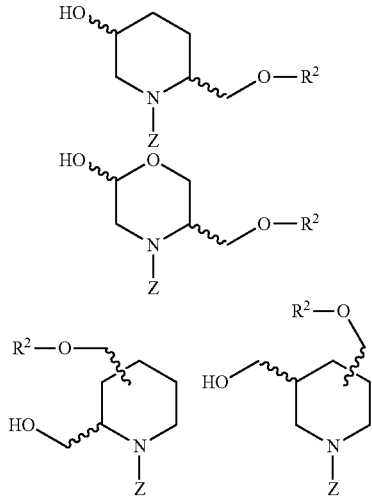

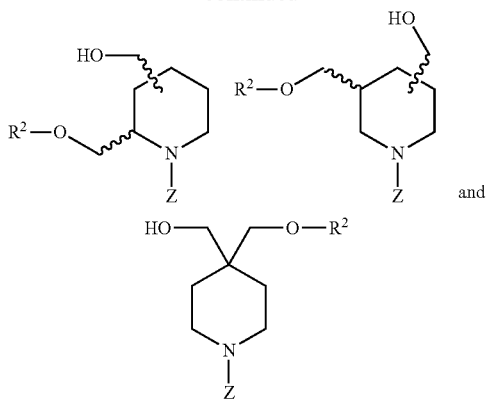

wherein Z is $-L^1-R^1$;
and salts thereof.

In one embodiment the $-A-L^2-R^2$ moiety is:

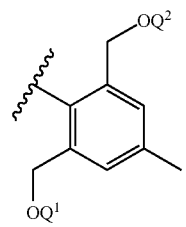

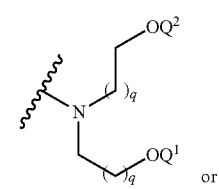

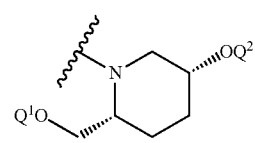

wherein:
$Q^1$ is hydrogen and $Q^2$ is $R^2$; or $Q^1$ is $R^2$ and $Q^2$ is hydrogen; and
each q is independently 0, 1, 2, 3, 4 or 5;
or a salt thereof.

In one embodiment $R^2$ is an oligonucleotide.
In one embodiment $R^2$ is an siRNA.
In one embodiment a compound of formula (I) is selected from the group consisting of:

23
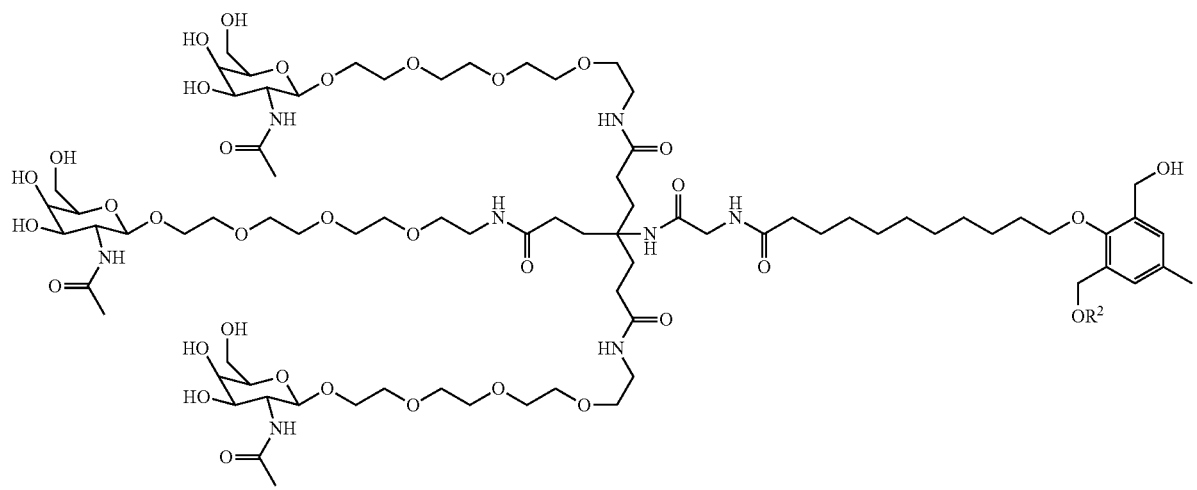
24
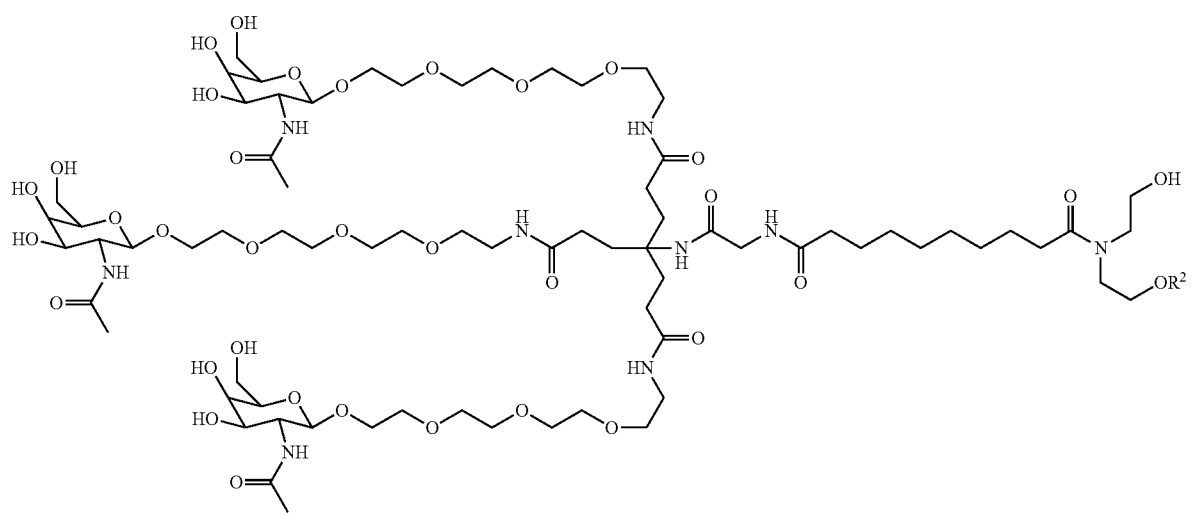
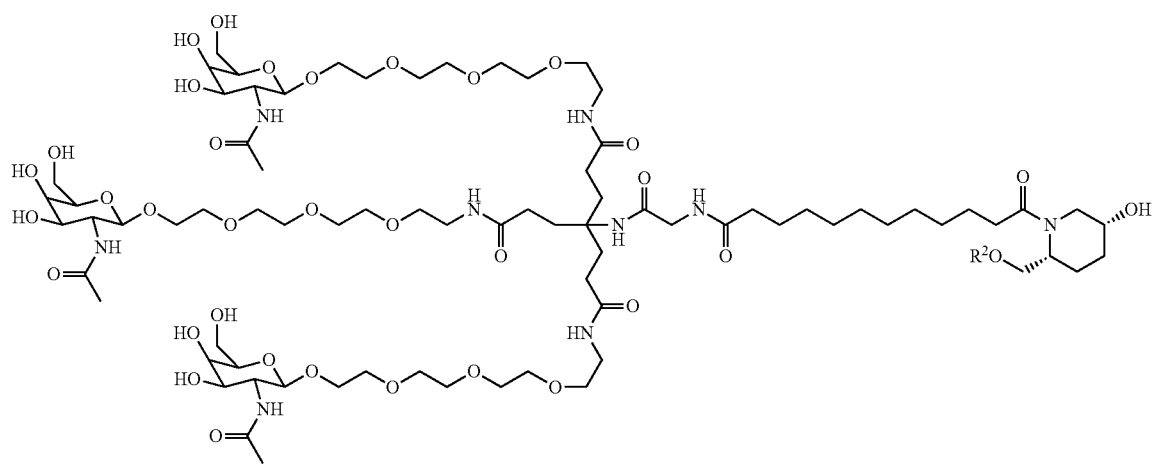
and

-continued
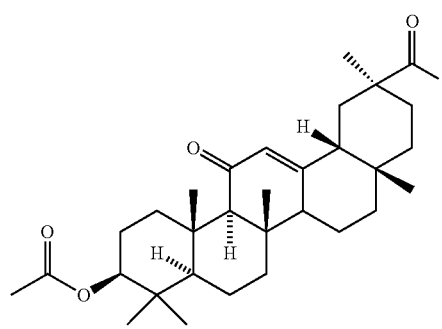
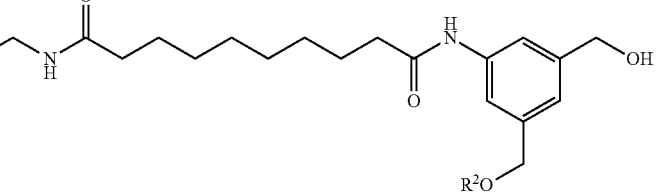
and salts thereof.
In one embodiment $R^1$ is selected from the group consisting of:
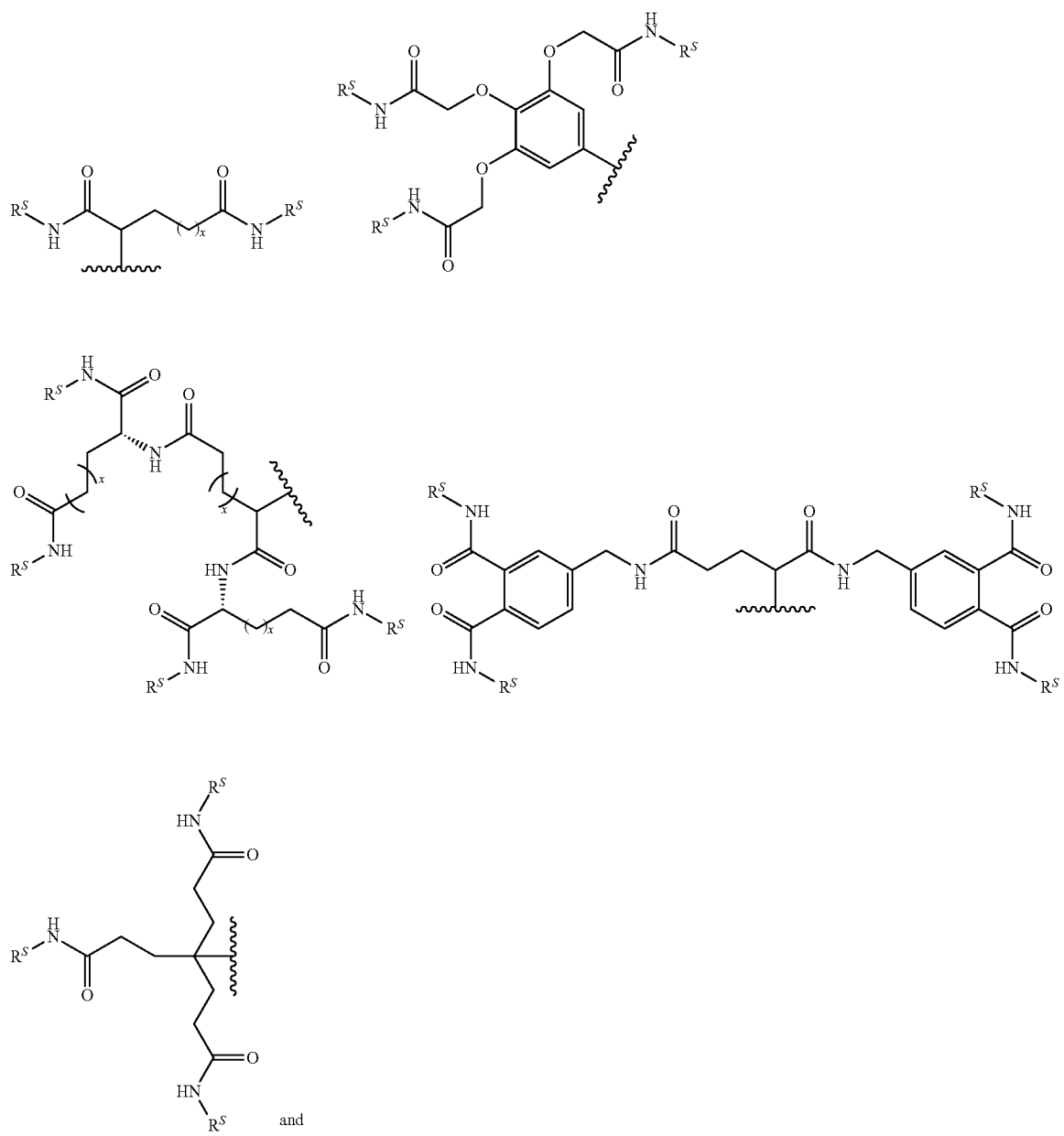
and

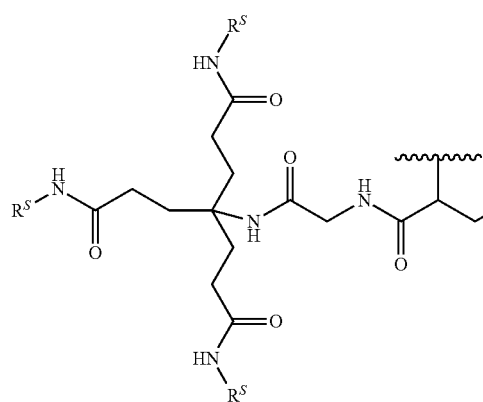
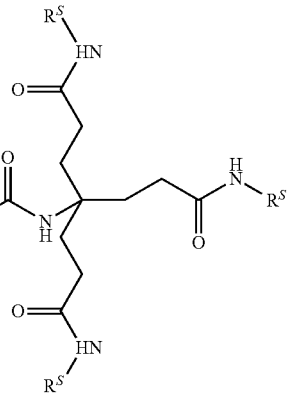
wherein $R^S$ is
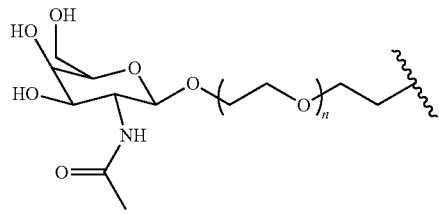
n is 2, 3, or 4;
x is 1 or 2.
In one embodiment $L^1$ is selected from the group consisting of:
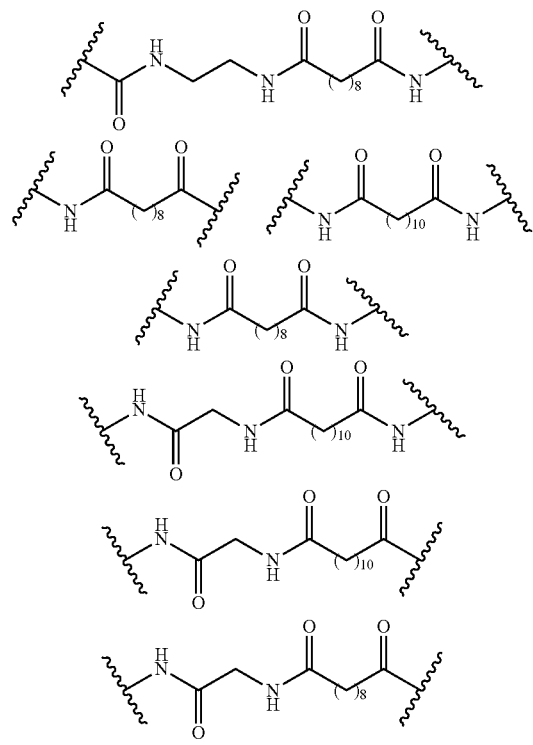
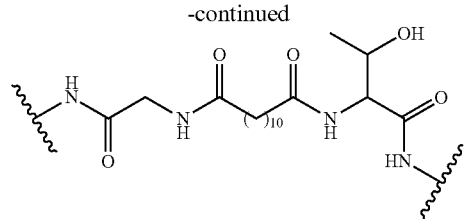
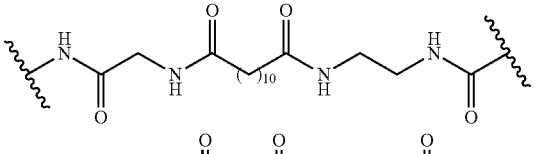
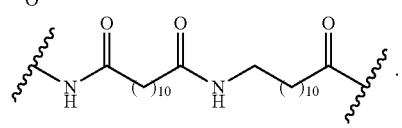
and
In one embodiment $L^1$ is selected from the group consisting of:
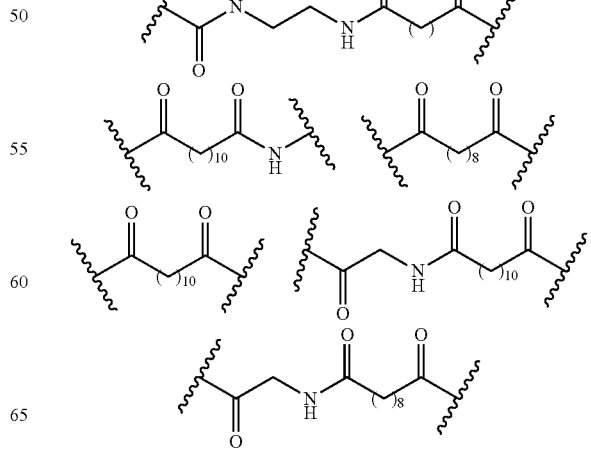

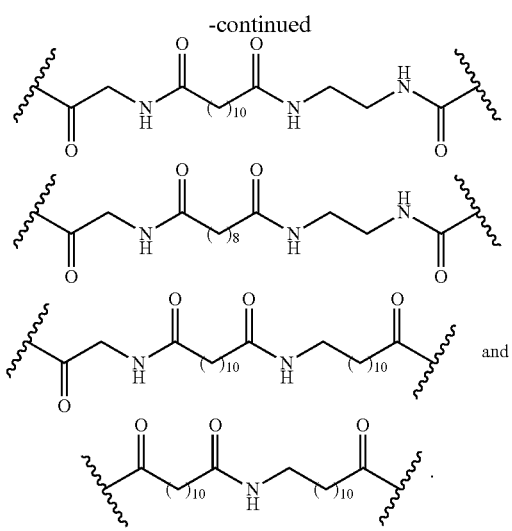

In one embodiment A is absent, phenyl, pyrrolidinyl, or cyclopentyl.

In one embodiment $L^2$ is $C_{1-4}$ alkylene-O— that is optionally substituted with hydroxy.

In one embodiment $L^2$ is —CH$_2$O—, —CH$_2$CH$_2$O—, or —CH(OH)CH$_2$O—.

In one embodiment each $R^4$ is independently hydroxy or $C_{1-8}$ alkyl that is optionally substituted with hydroxyl.

In one embodiment each $R_A$ is independently selected from the group consisting of hydroxy, methyl and —CH$_2$OH.

In one embodiment a compound of formula I has the following formula (Ig):

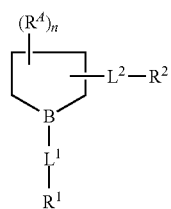

(Ig)

wherein B is —N— or —CH—;
$L^1$ is absent or —NH—;
$L^2$ is $C_{1-4}$ alkylene-O— that is optionally substituted with hydroxyl or halo;
n is 0, 1, or 2;
or a salt thereof.

In one embodiment a compound of formula I has the following formula (Ig):

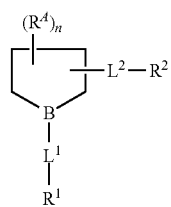

(Ig)

wherein B is —N— or —CH—;
$L^1$ is absent or —NH—;
$L^2$ is $C_{1-4}$ alkylene-O— that is optionally substituted with hydroxyl or halo;
n is 0, 1, 2, 3, 4, 5, 6, or 7;
or a salt thereof.

In one embodiment a compound of formula I has the following formula (Ig):

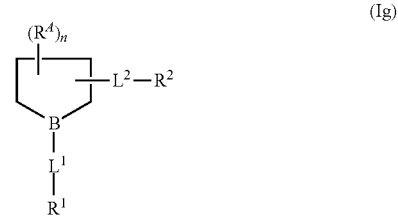

(Ig)

wherein B is —N— or —CH—;
$L^1$ is absent or —NH—;
$L^2$ is $C_{1-4}$ alkylene-O— that is optionally substituted with hydroxyl or halo;
n is 0, 1, 2, 3, or 4;
or a salt thereof.

In one embodiment a compound of formula Ig is selected from the group consisting of:

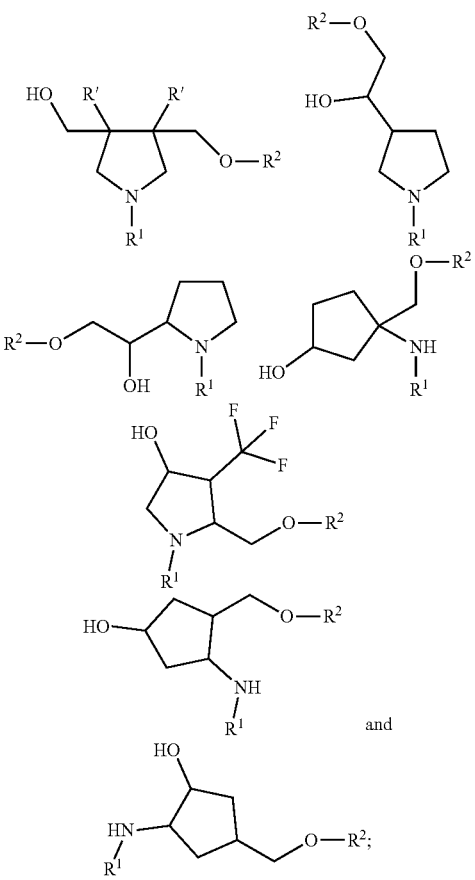

wherein R' is $C_{1-9}$ alkyl, $C_{2-9}$ alkenyl or $C_{2-9}$ alkynyl;
wherein the $C_{1-9}$ alkyl, $C_{2-9}$ alkenyl or $C_{2-9}$ alkynyl are optionally substituted with halo or hydroxyl;
and salts thereof.

In one embodiment a compound of formula I is selected from the group consisting of:
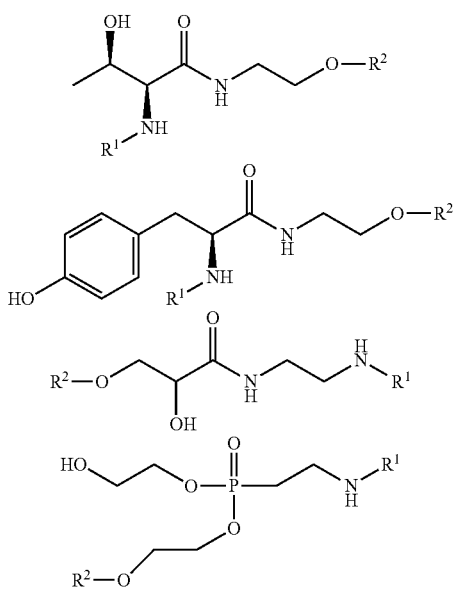
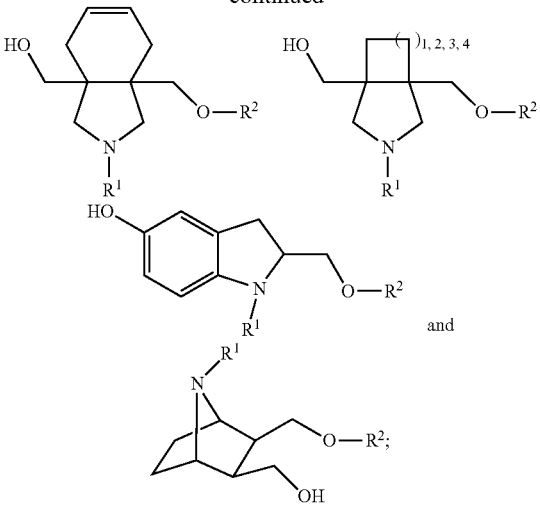
and salts thereof.
In one embodiment the compound of formula I or the salt thereof is selected from the group consisting of:
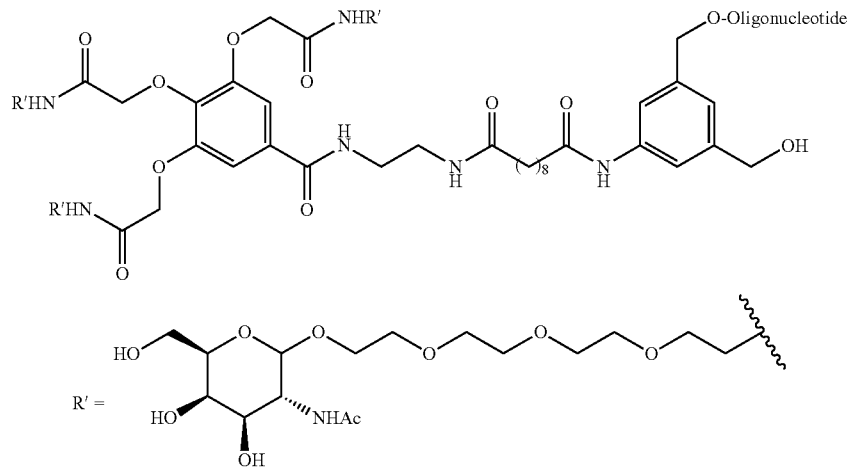
142
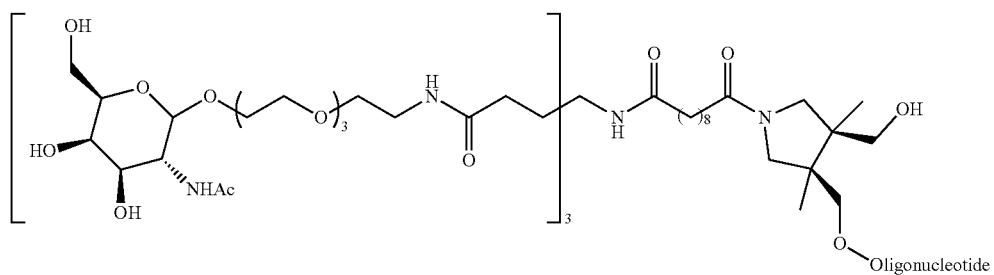
145

-continued
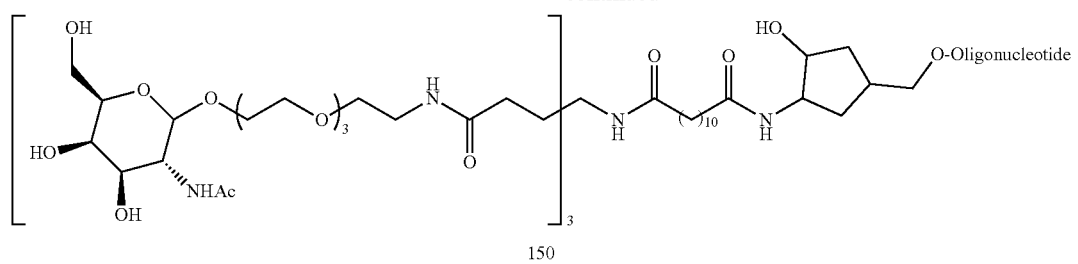
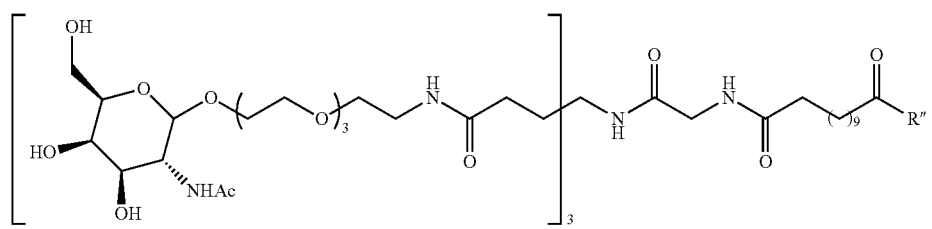
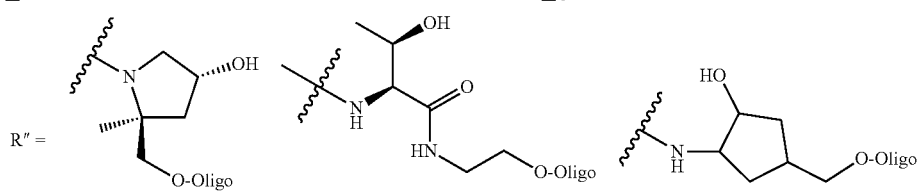
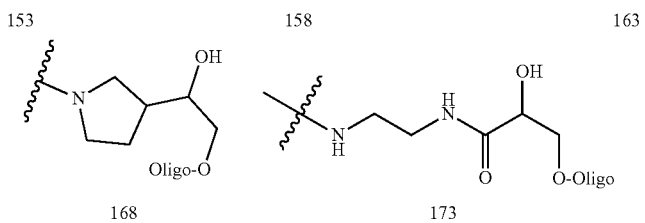
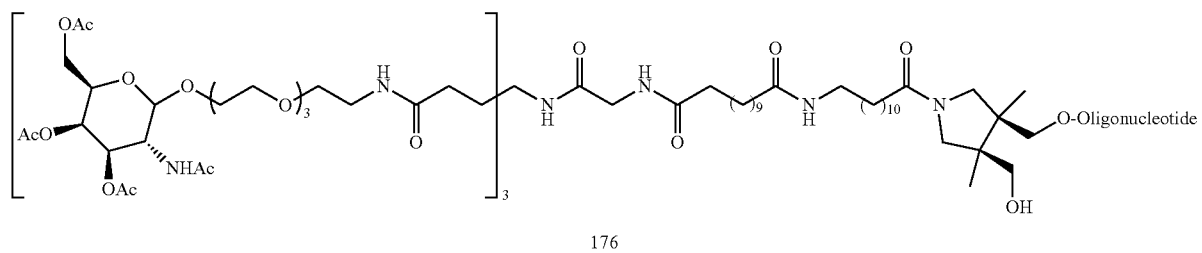
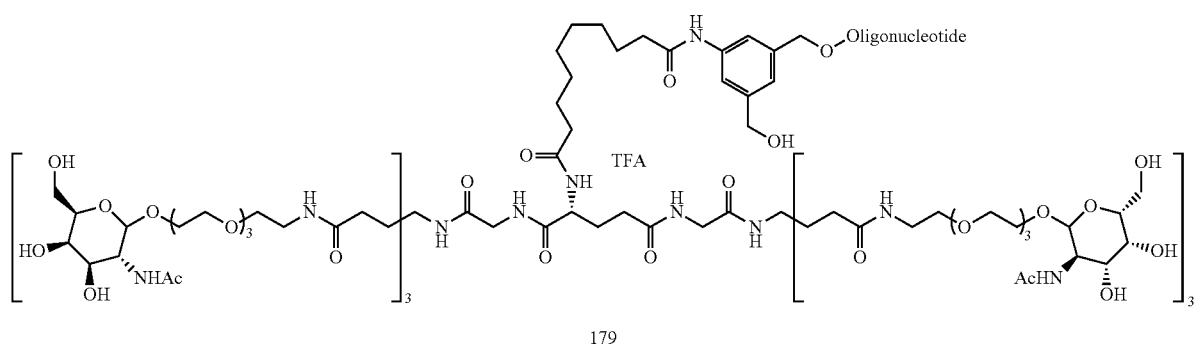

-continued
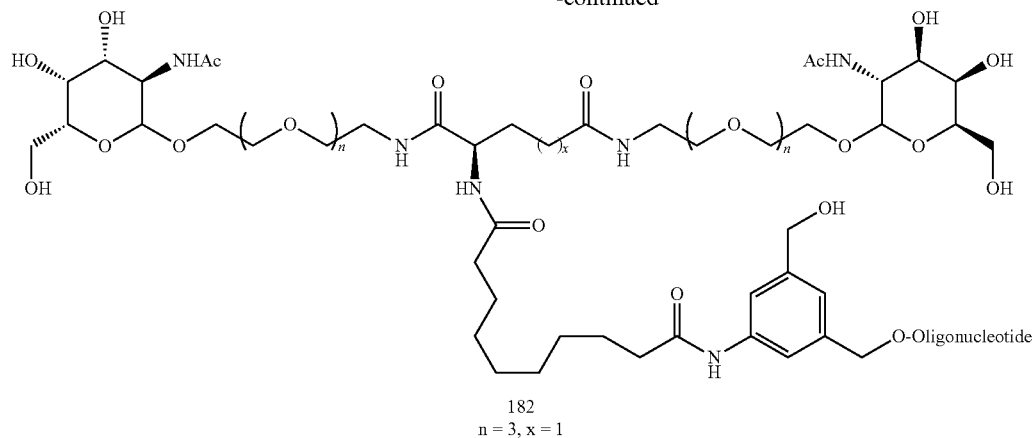
182
n = 3, x = 1
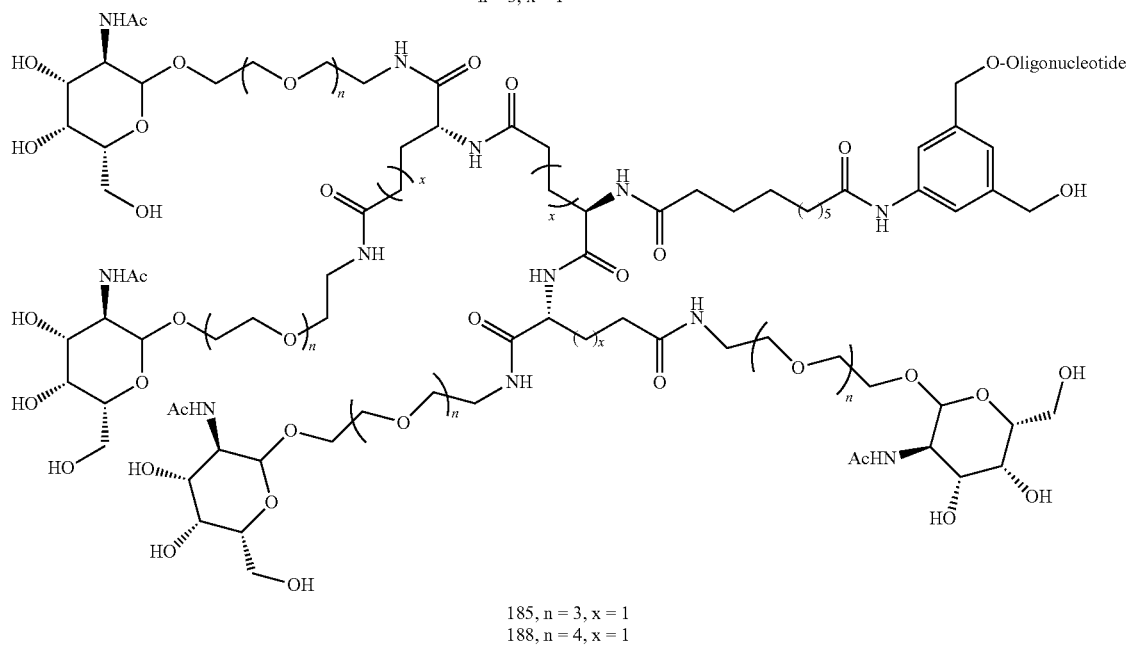
185, n = 3, x = 1
188, n = 4, x = 1
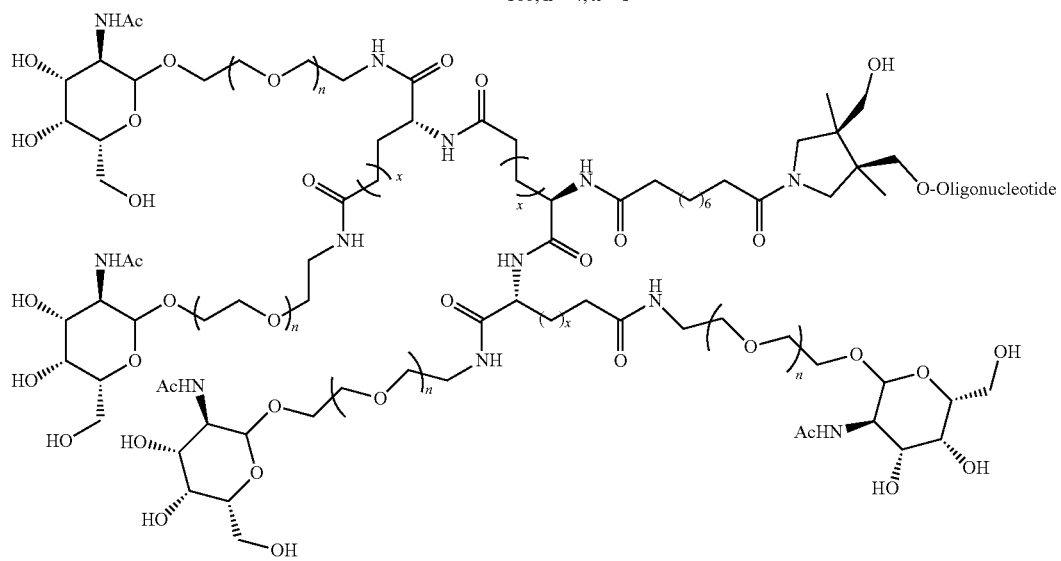
191, n = 2, x = 1
194, n = 3, x = 1
197, n = 4, x = 1
200, n = 3, x = 2

-continued
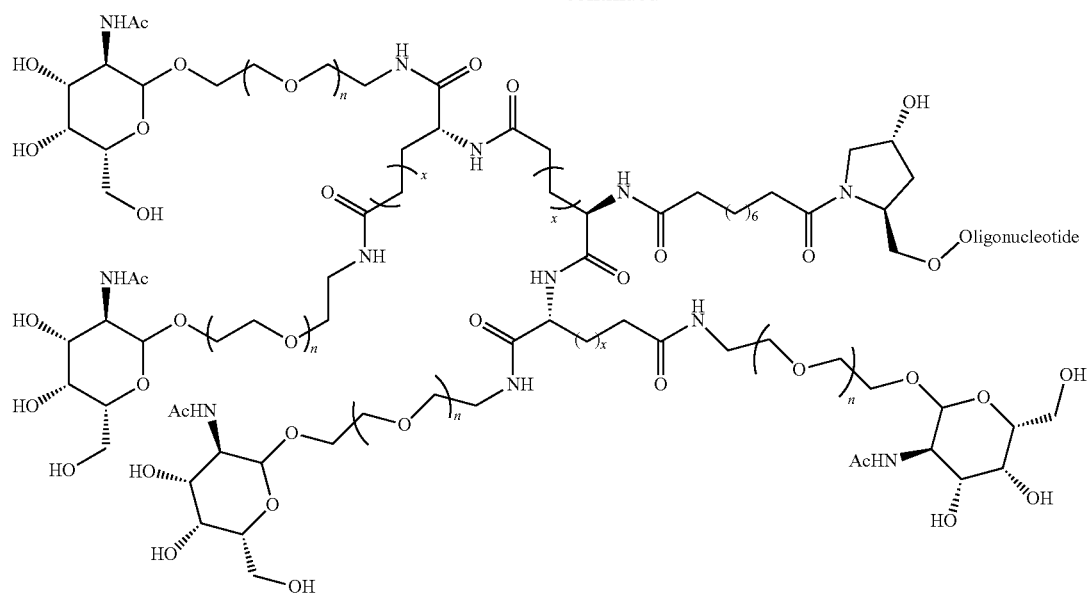
203, n = 3, x = 1
206, n = 4, x = 1
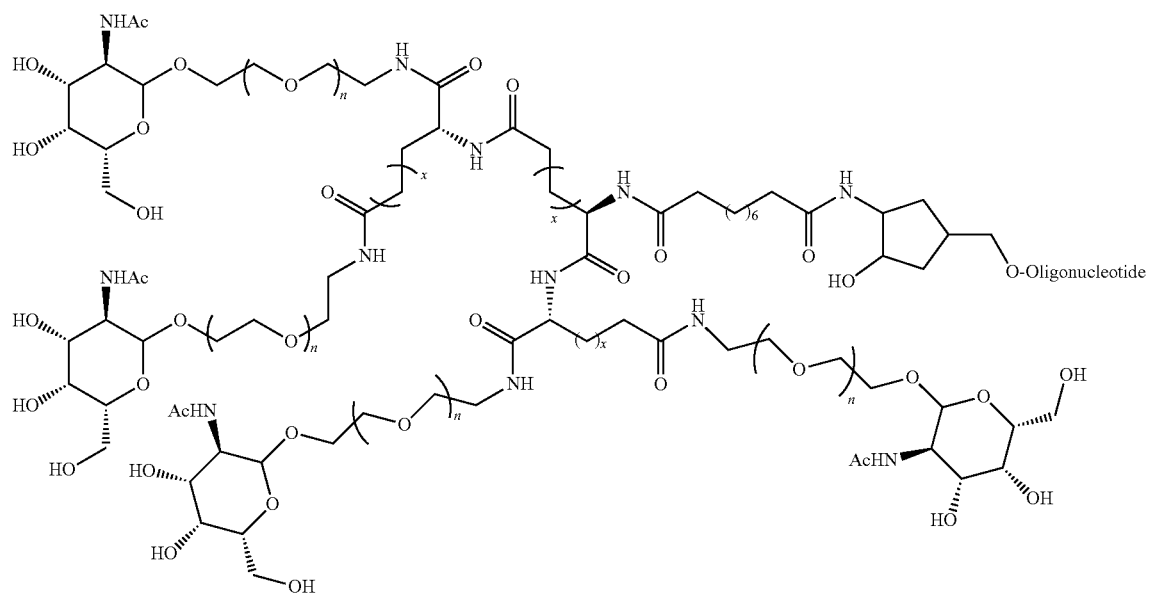
209, n = 3, x = 1

-continued
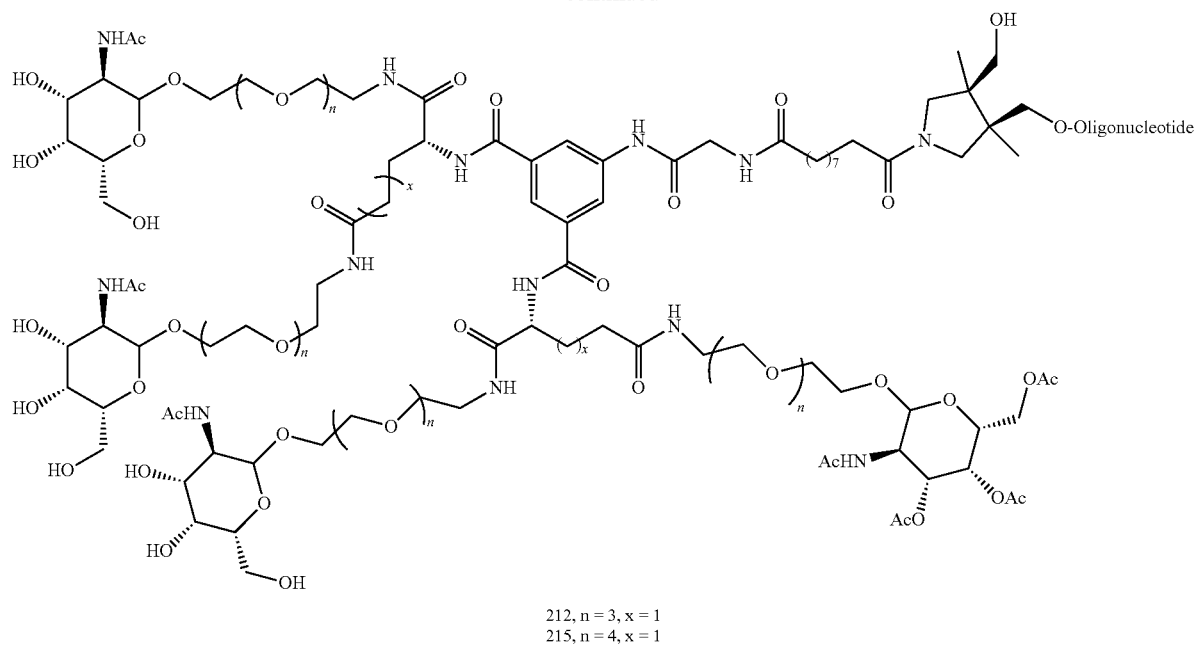
212, n = 3, x = 1
215, n = 4, x = 1
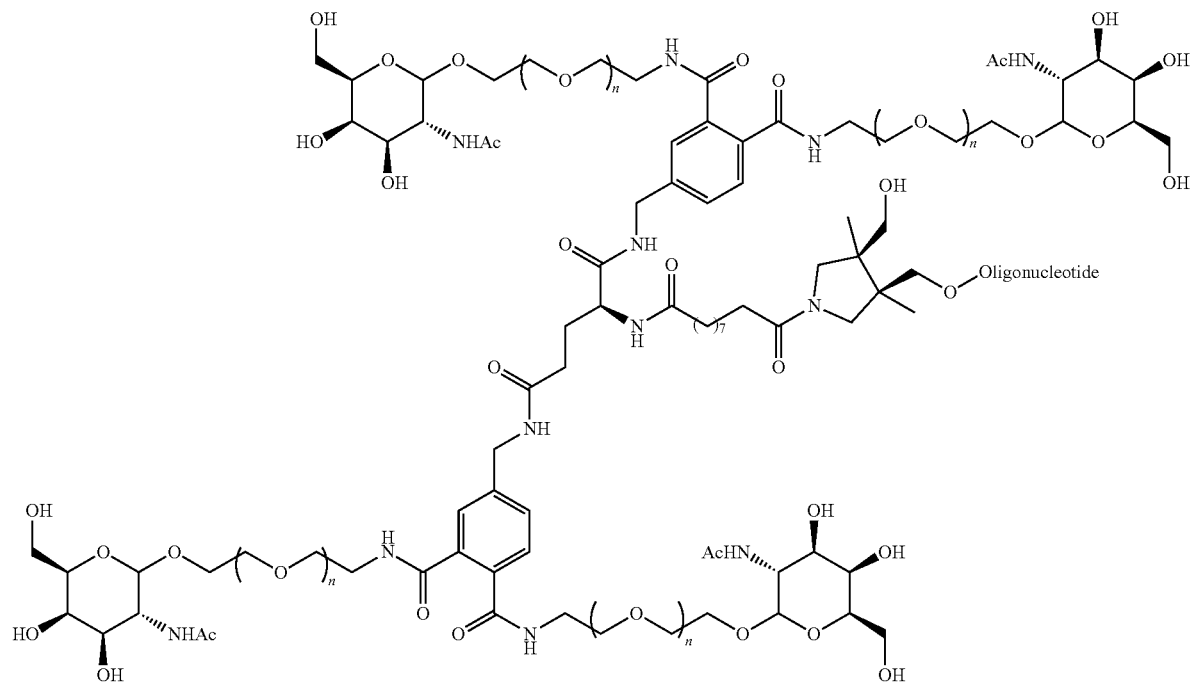
218, n = 2
221, n = 3

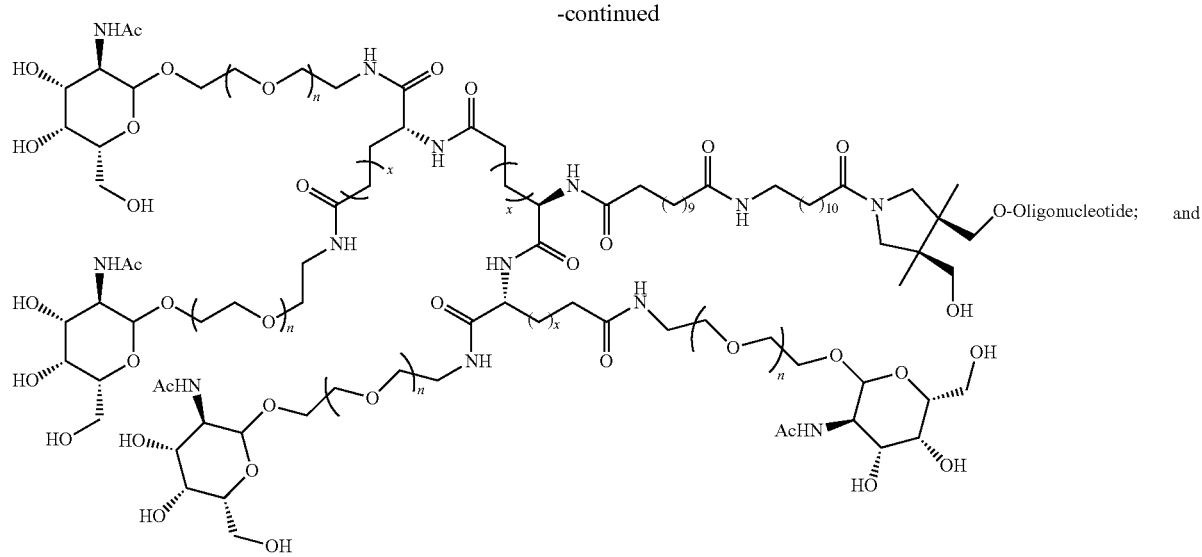

224, n = 3, x = 1

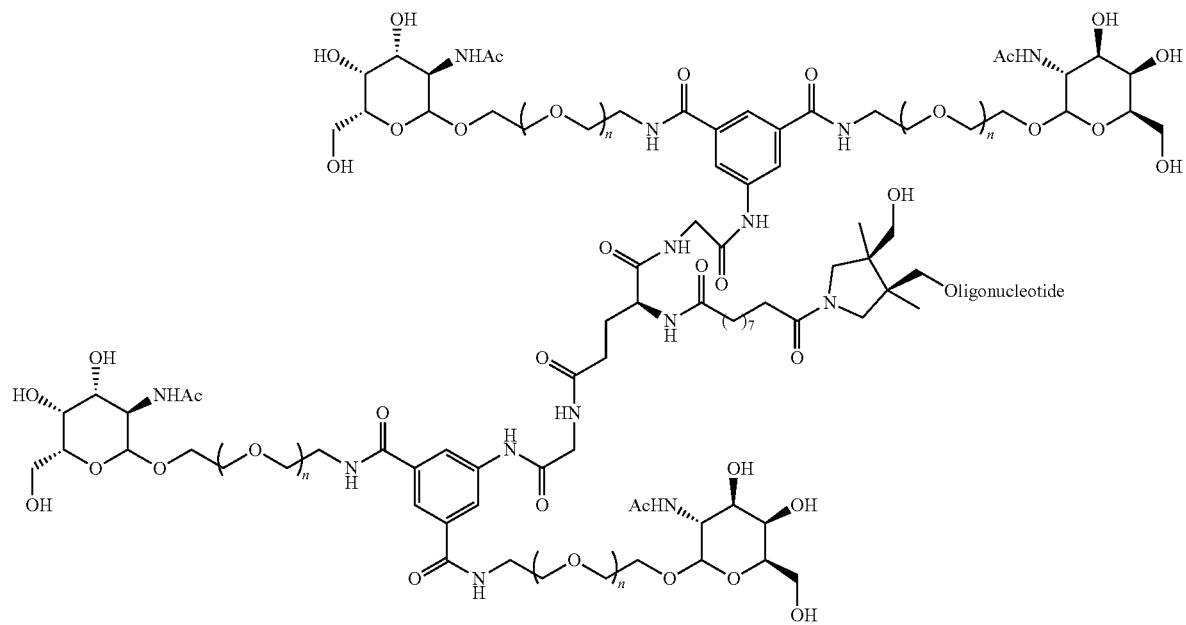

231, n = 3 or pharmaceutically acceptable salts thereof.

One aspect of this invention is pharmaceutical composition comprising a compound of formula I, and a pharmaceutically acceptable carrier.

Another aspect of this invention is a method to deliver a nucleic acid to the liver of an animal comprising administering a compound of formula I or a pharmaceutically acceptable salt thereof, to the animal.

In one embodiment a compound of formula I has the following formula (Id):

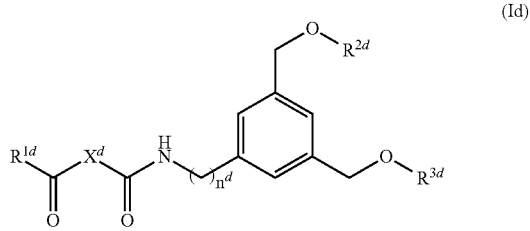

wherein:
R$^{1d}$ is selected from:

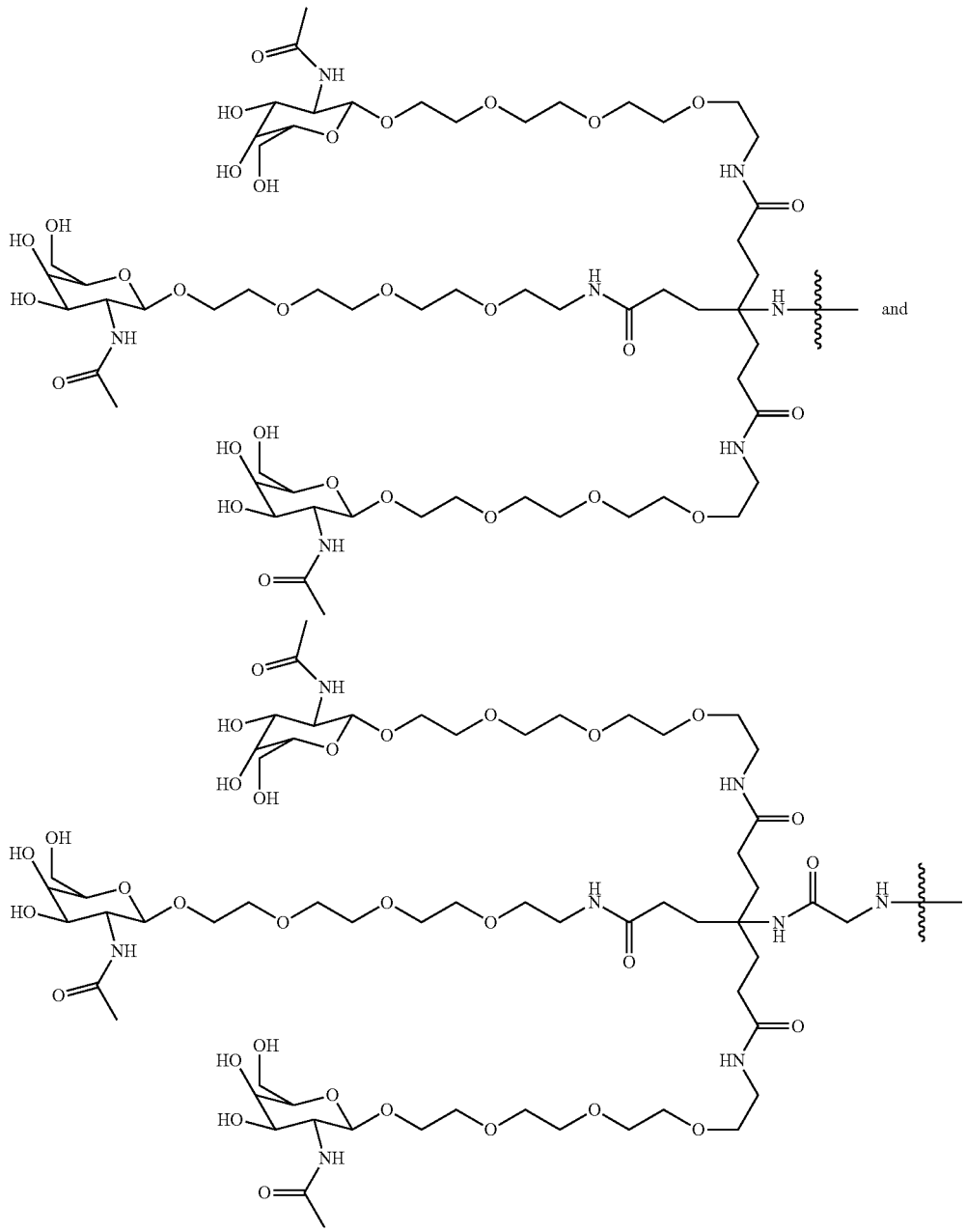

X$^d$ is C$_{2-10}$ alkylene;
N$^d$ is 0 or 1;
R$^2$ is a nucleic acid; and
R$^{3d}$ is H, a protecting group, a covalent bond to a solid support, or a bond to a linking group that is bound to a solid support.

In one embodiment R$^{3d}$ includes a linking group that joins the remainder of the compound of formula Id to a solid support. The nature of the linking group is not critical provided the compound is a suitable intermediate for preparing a compound of formula Id wherein R$^{2d}$ is a nucleic acid.

In one embodiment the linker in R$^{3d}$ has a molecular weight of from about 20 daltons to about 1,000 daltons.

In one embodiment the linker in R$^{3d}$ has a molecular weight of from about 20 daltons to about 500 daltons.

In one embodiment the linker in R$^{3d}$ separates the solid support from the remainder of the compound of formula I by about 5 angstroms to about 40 angstroms, inclusive, in length.

In one embodiment the linker in R$^{3d}$ is a divalent, branched or unbranched, saturated or unsaturated, hydrocarbon chain, having from 2 to 15 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from (C$_1$-C$_6$)alkoxy, (C$_3$-

$C_6$)cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$alkylthio, azido, cyano, nitro, halo, hydroxy, oxo (=O), carboxy, aryl, aryloxy, heteroaryl, and heteroaryloxy.

In one embodiment the linker in $R^{3d}$ is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$alkylthio, azido, cyano, nitro, halo, hydroxy, oxo (=O), carboxy, aryl, aryloxy, heteroaryl, and heteroaryloxy.

In one embodiment the linker in $R^{3d}$ is —C(=O)CH$_2$CH$_2$C(=O)N(H)—.

In one embodiment $R^{1d}$ is:

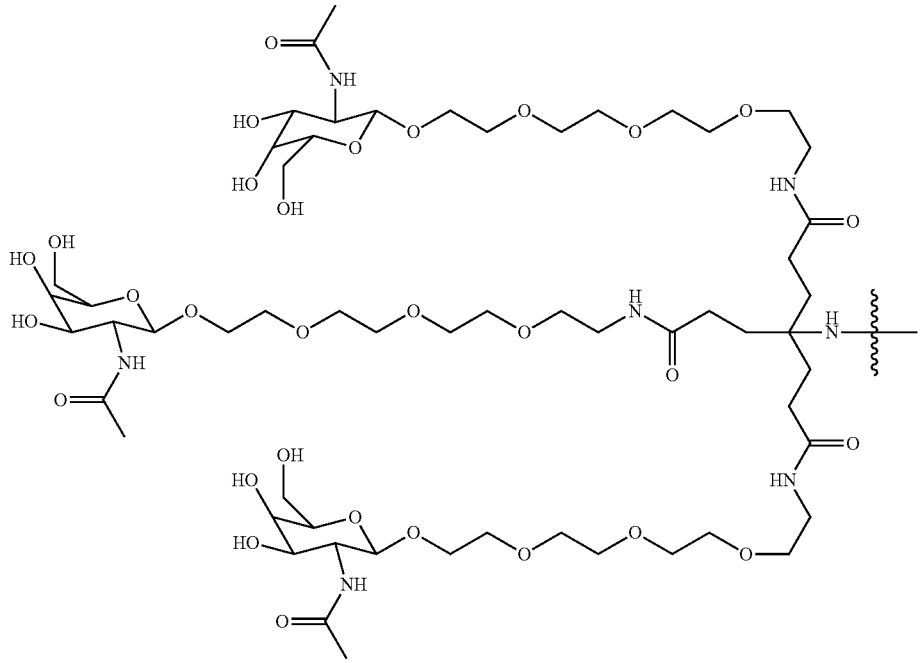 [SMILES: *NC(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]

In one embodiment $R^{1d}$ is:

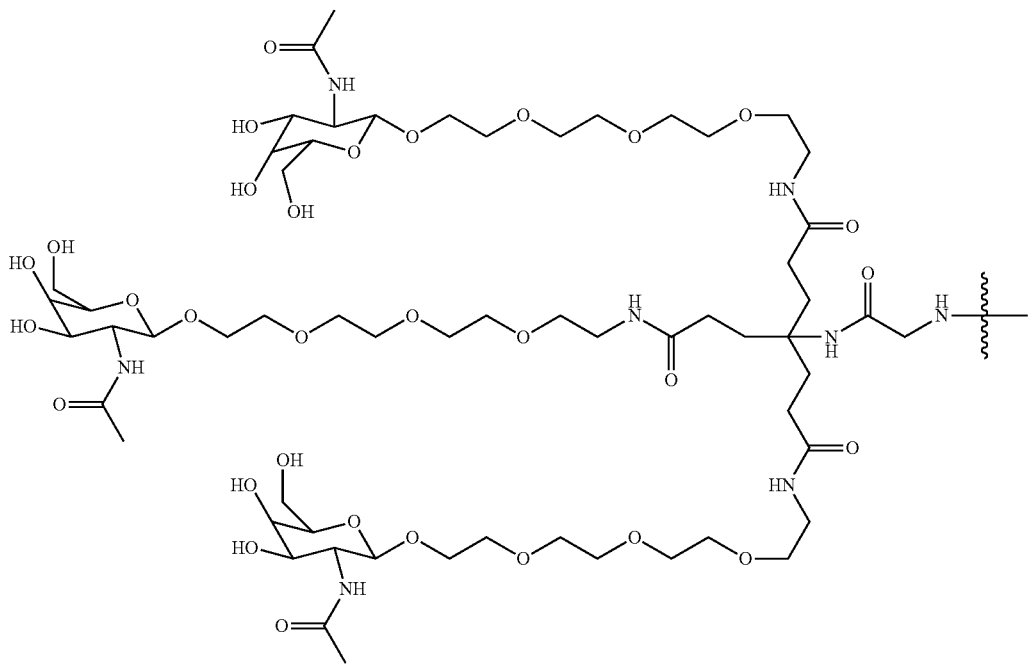 [SMILES: *NCC(=O)NC(CCC(=O)NCCOCCOCCOCCOC1OC(CO)C(O)C(O)C1NC(C)=O)(CCC(=O)NCCOCCOCCOCCOC1OC(CO)C(O)C(O)C1NC(C)=O)CCC(=O)NCCOCCOCCOCCOC1OC(CO)C(O)C(O)C1NC(C)=O]

In one embodiment $X^d$ is $C_8$alkylene.
In one embodiment $n^d$ is 0.
In one embodiment $R^{2d}$ is an siRNA.

In one embodiment $R^{3d}$ is H.

In another embodiment a compound of (Id) or the salt thereof is selected from the group consisting of:

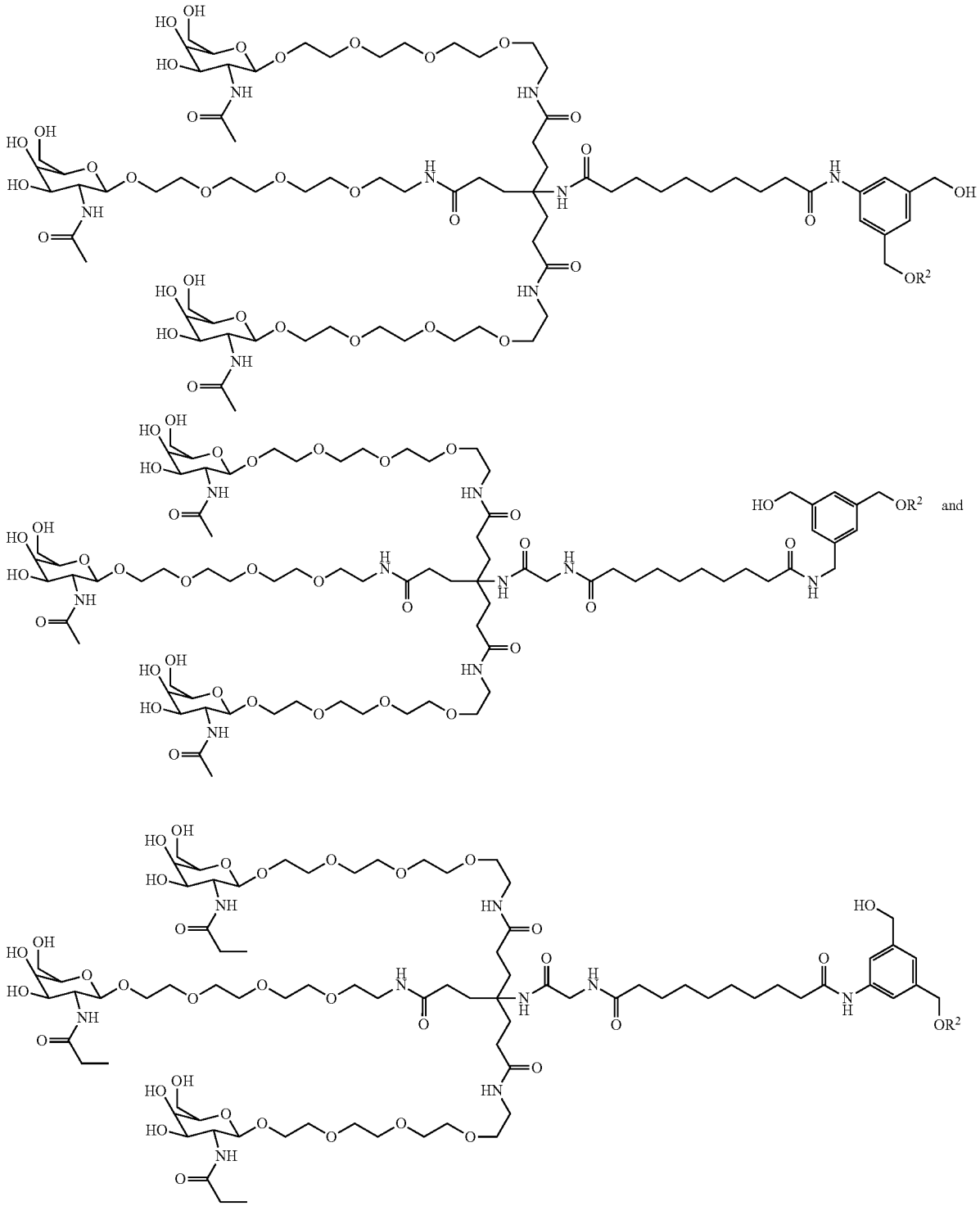

and salts thereof.

One aspect of this invention is a pharmaceutical composition comprising a compound of formula (Id), and a pharmaceutically acceptable carrier.

One aspect of this invention is a nucleic acid to the liver of an animal comprising administering a compound of formula (Id) or a pharmaceutically acceptable salt thereof, to the animal.

The invention also provides synthetic intermediates and methods disclosed herein that are useful to prepare compounds of formula (Id). For example, the invention includes an intermediate compound of formula Ie:

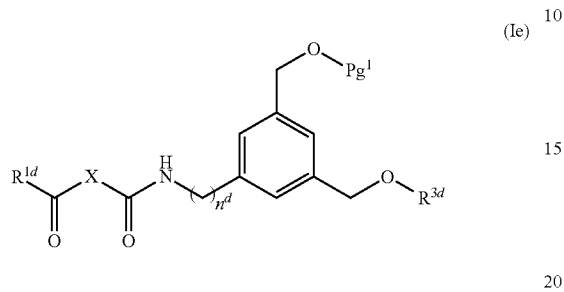

(Ie)

or a salt thereof, wherein:
$R^{1d}$ is selected from:

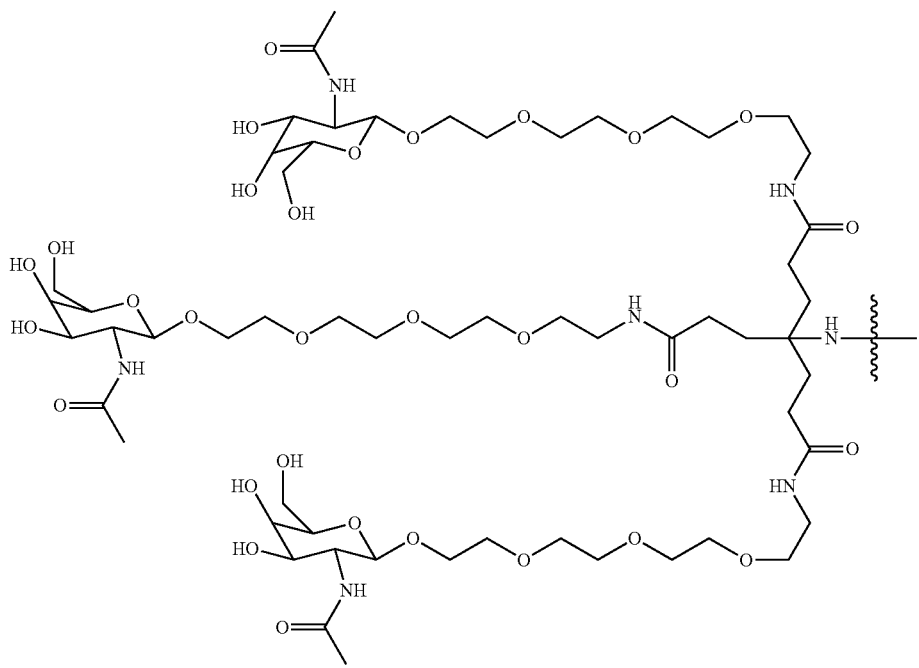

and

-continued

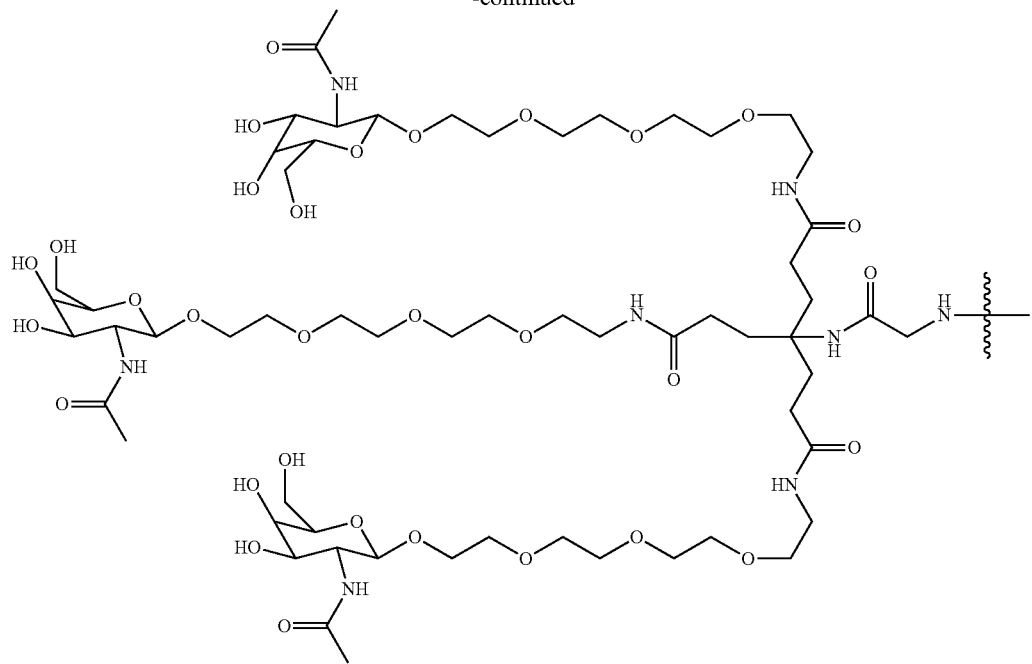

$X^d$ is $C_{2-8}$ alkylene;
$n^d$ is 0 or 1;
$Pg^1$ is H or a suitable protecting group; and
$R^{3d}$ is H, a protecting group, a covalent bond to a solid support, or a bond to a linking group that is bound to a solid support. FIG. 1 illustrates a representative intermediate compound of formula (Ie), wherein a targeting ligand/linker is bound to a solid phase support, and wherein $Pg^1$ is the protecting group DMTr.

In one embodiment $Pg^1$ is TMTr (Trimethoxytrityl), DMTr (Dimethoxytrityl), MMTr (Monomethoxytrityl), or Tr (Trityl).

The invention also provides a method to prepare a compound of formula (Id) as described herein comprising subjecting a corresponding compound of formula (Ie):

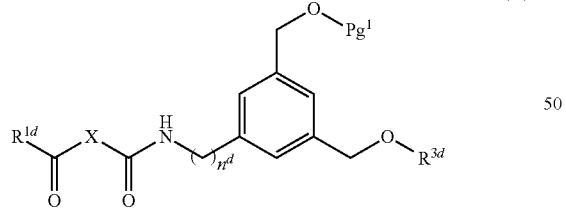

(Ie)

wherein:
$X^d$ is $C_{2-8}$ alkylene;
$n^d$ is 0 or 1;
$Pg^1$ is H; and
$R^3$ is a covalent bond to a solid support or a bond to a linking group that is bound to a solid support, to solid phase nucleic acid synthesis conditions to provide a corresponding compound of formula Id wherein $R^{2d}$ is a nucleic acid.

In one embodiment the method further comprises removing the compound from the solid support to provide the corresponding compound of formula Id wherein $R^{3d}$ is H.

In one embodiment the compound is not:
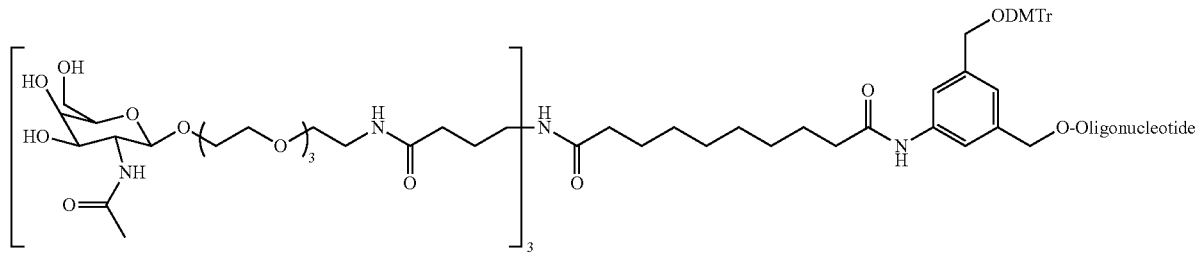
In one embodiment the compound is not a compound formula Id:
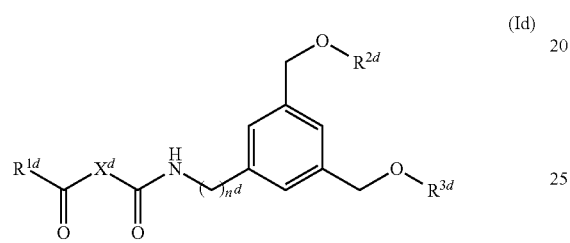
or a salt thereof, wherein:
$R^{1d}$ is selected from:
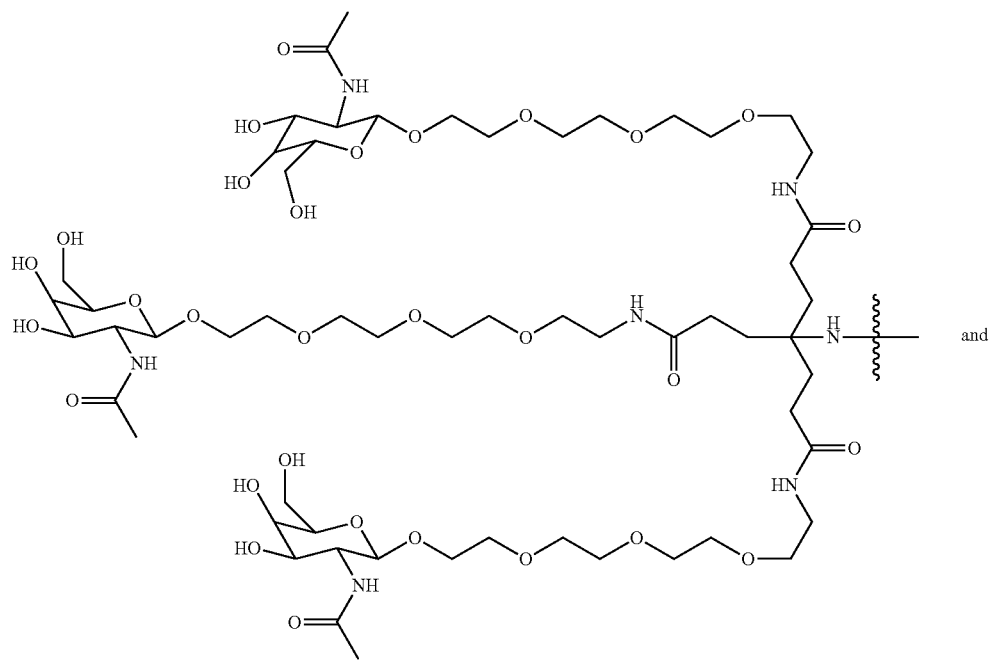
and -continued
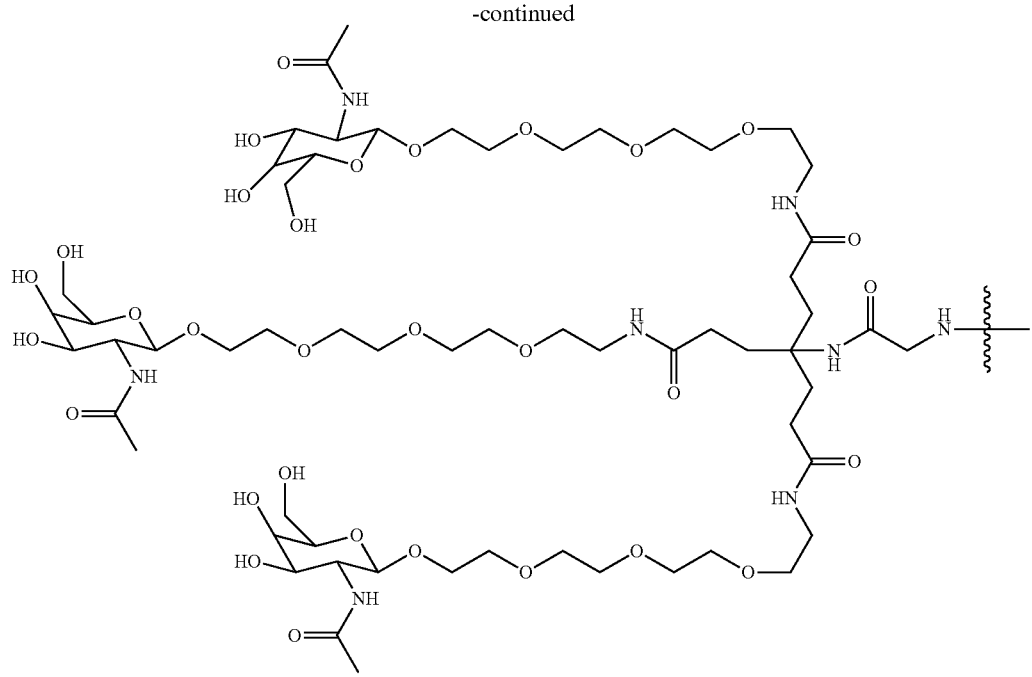
$X^d$ is $C_{2-10}$ alkylene;
$N^d$ is 0 or 1;
$R^{2d}$ is a nucleic acid; and
$R^{3d}$ is H, a protecting group, a covalent bond to a solid support, or a bond to a linking group that is bound to a solid support.
In one embodiment the compound is not a compound formula Ie:
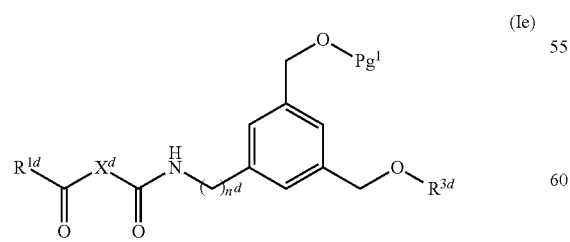
(Ie)

or a salt thereof, wherein:
$R^{1d}$ is selected from:

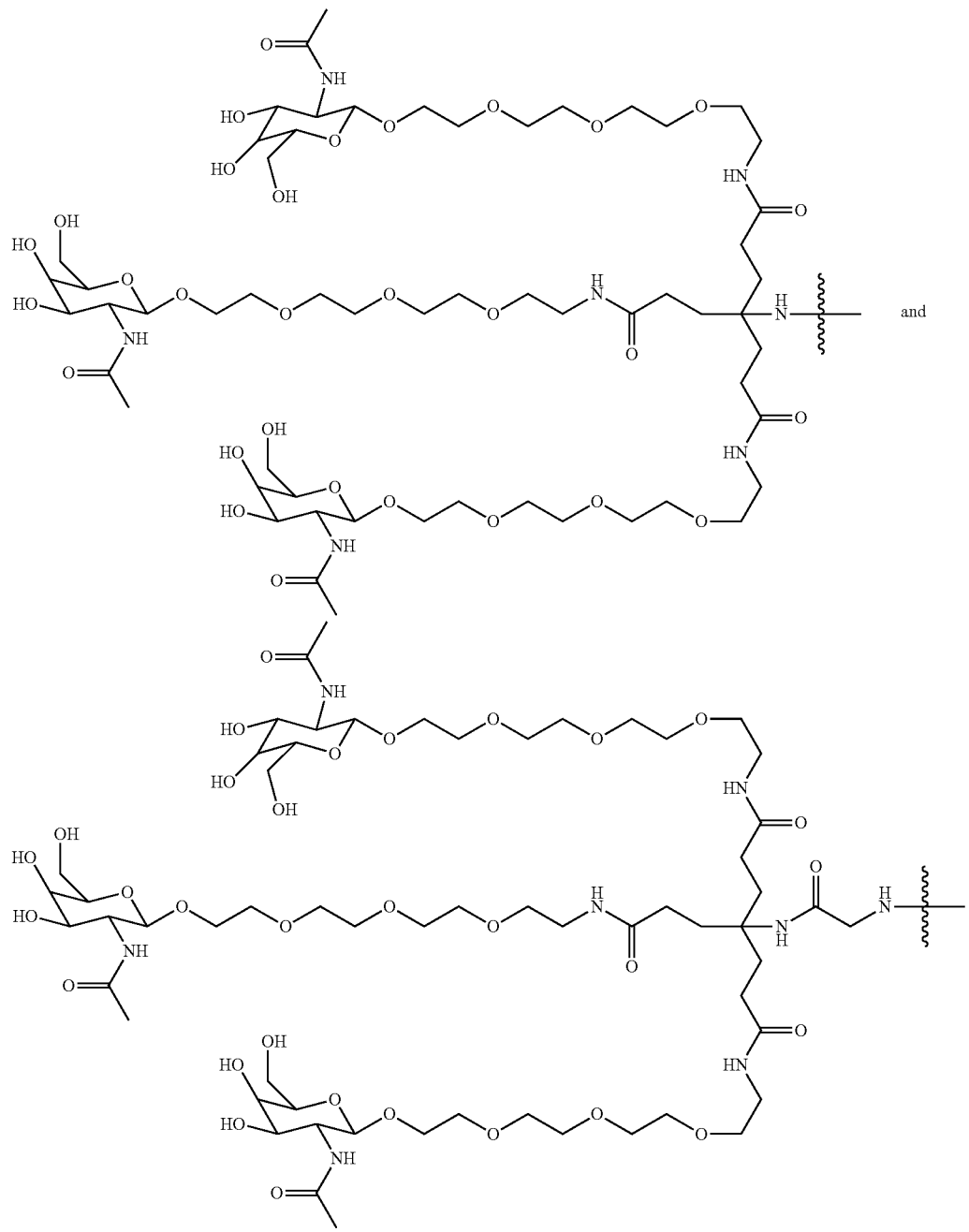

$X^d$ is $C_{2-8}$ alkylene;
$n^d$ is 0 or 1;
$Pg^1$ is H or a suitable protecting group; and
$R^{3d}$ is H, a protecting group, a covalent bond to a solid support, or a bond to a linking group that is bound to a solid support.

In one embodiment $R^{3d}$ is H.

In one embodiment $R^{3d}$ is a covalent bond to a solid support.

In one embodiment $R^{3d}$ is a bond to a linking group that is bound to a solid support, wherein the linking group is a divalent, branched or unbranched, saturated or unsaturated, hydrocarbon chain, having from 2 to 15 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In one embodiment $R^{3d}$ is a bond to a linking group that is bound to a solid support, wherein the linking group is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—) or (—N(H)—), and wherein the chain is optionally substituted on carbon with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In one embodiment R$^{3d}$ is a bond to a linking group that is bound to a solid support, wherein the linking group is —C(=O)CH$_2$CH$_2$C(=O)N(H)—.

In one embodiment the invention provides a compound of formula (I):

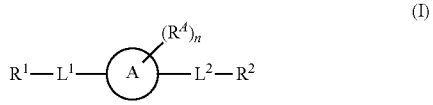

(I)

wherein:
R$^1$ is H or a synthetic activating group;
L$^1$ is absent or a linking group;
L$^2$ is absent or a linking group;
R$^2$ is a nucleic acid;
the ring A is absent, a 3-20 membered cycloalkyl, a 5-20 membered aryl, a 5-20 membered heteroaryl, or a 3-20 membered heterocycloalkyl;
each R$^4$ is independently selected from the group consisting of hydrogen, hydroxy, CN, F, Cl, Br, I, —C$_{1-2}$ alkyl-OR$^B$, C$_{1-10}$ alkyl C$_{2-10}$ alkenyl, and C$_{2-10}$ alkynyl; wherein the C$_{1-10}$ alkyl C$_{2-10}$ alkenyl, and C$_{2-10}$ alkynyl are optionally substituted with one or more groups independently selected from halo, hydroxy, and C$_{1-3}$ alkoxy;
R$^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

In one embodiment the invention provides a compound of formula (I):

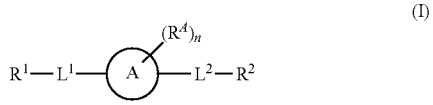

(I)

wherein:
R$^1$ a is targeting ligand;
L$^1$ is absent or a linking group;
L$^2$ is absent or a linking group;
R$^2$ is H or a synthetic activating group;
the ring A is absent, a 3-20 membered cycloalkyl, a 5-20 membered aryl, a 5-20 membered heteroaryl, or a 3-20 membered heterocycloalkyl;
each R$^4$ is independently selected from the group consisting of hydrogen, hydroxy, CN, F, Cl, Br, I, —C$_{1-2}$ alkyl-OR$^B$, C$_{1-10}$ alkyl C$_{2-10}$ alkenyl, and C$_{2-10}$ alkynyl; wherein the C$_{1-10}$ alkyl C$_{2-10}$ alkenyl, and C$_{2-10}$ alkynyl are optionally substituted with one or more groups independently selected from halo, hydroxy, and C$_{1-3}$ alkoxy;
R$^B$ is hydrogen, a protecting group, a covalent bond to a solid support, or a bond to a linking group that is bound to a solid support; and
n is 0, 1, 2, 3, 4, 5, 6, 7, 8, 9, or 10;
or a salt thereof.

In one embodiment the invention provides a compound of formula (Ig):

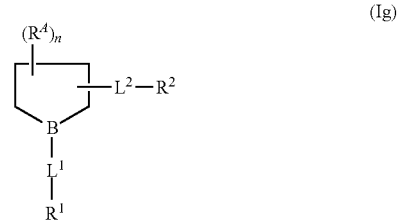

(Ig)

wherein:
B is —N— or —CH—;
L$^2$ is C$_{1-4}$ alkylene-O— that is optionally substituted with hydroxyl or halo; and
n is 0, 1, 2, 3, 4, 5, 6, or 7;
or a salt thereof.

In one embodiment the invention provides a compound selected from the group consisting of:

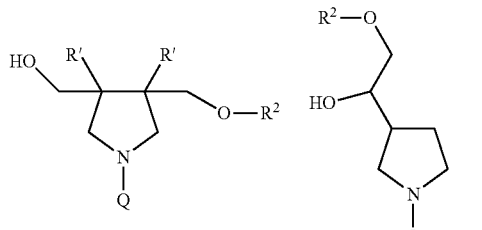

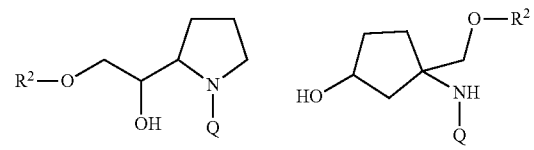

and

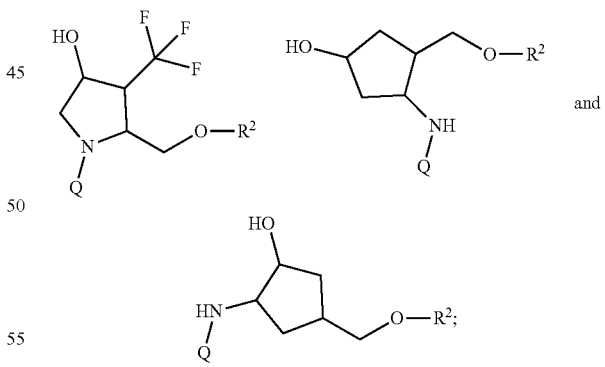

wherein:
Q is -L$^1$-R$^1$; and
R$^1$ is C$_{1-9}$ alkyl, C$_{2-9}$ alkenyl or C$_{2-9}$ alkynyl; wherein the C$_{1-9}$ alkyl, C$_{2-9}$ alkenyl or C$_{2-9}$ alkynyl are optionally substituted with halo or hydroxyl;
and salts thereof.

In one embodiment the invention provides a compound selected from the group consisting of:

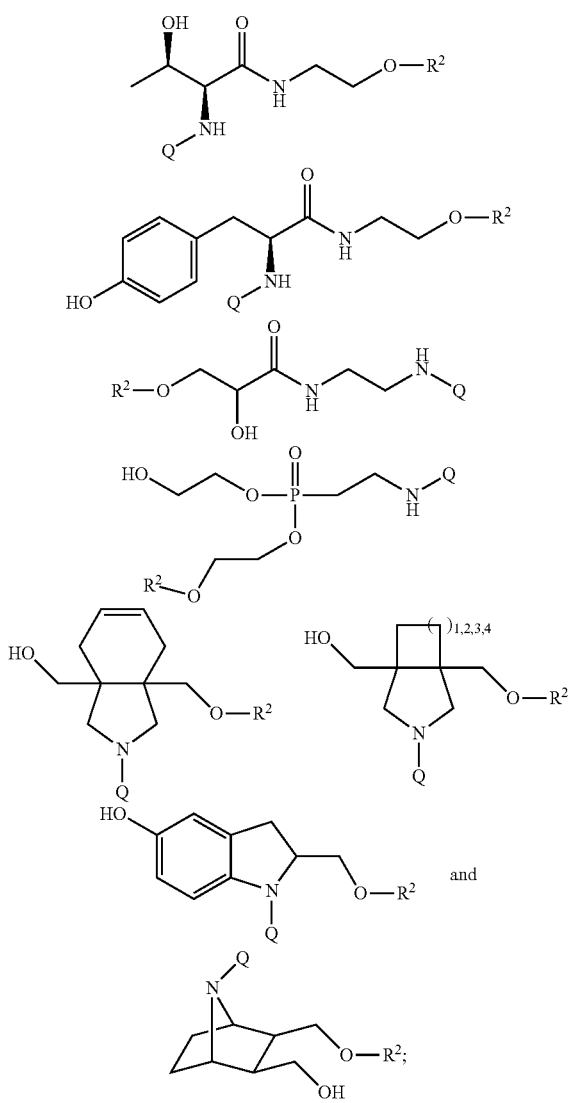

wherein: Q is -L¹-R¹; and salts thereof.

In one embodiment the invention provides a compound of formula (Ig):

$$\text{(Ig)}$$

wherein:
B is —N— or —CH—;
L¹ is absent or a linking group;
L² is $C_{1-4}$ alkylene-O— that is optionally substituted with hydroxyl or halo;
n is 0, 1, 2, 3, 4, 5, 6, or 7;
R¹ is H or a synthetic activating group; and
R² is H or a synthetic activating group;
or a salt thereof.

In one embodiment the invention provides a compound selected from the group consisting of:

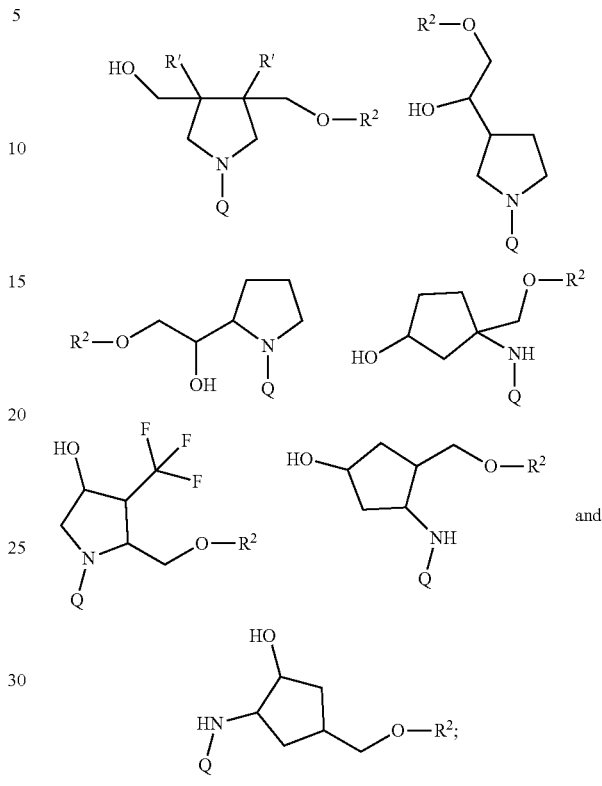

wherein Q is -L¹-R¹;
L¹ is absent or a linking group;
R¹ is $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;
R¹ is H or a synthetic activating group; and
R² is H or a synthetic activating group;
or a salt thereof.

In one embodiment the invention provides a compound selected from the group consisting of:

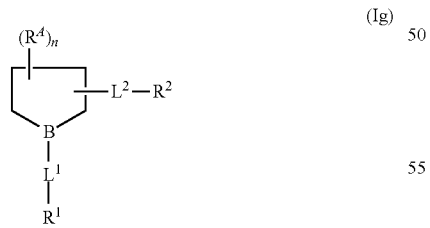

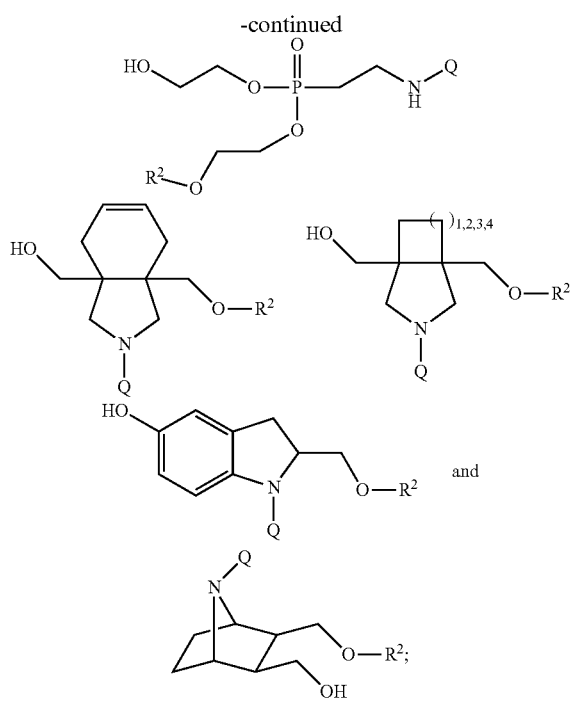

wherein:

Q is -L$^1$-R$^1$;

L$^1$ is absent or a linking group;

R$^1$ is H or a synthetic activating group; and

R$^2$ is H or a synthetic activating group;

or a salt thereof.

In one embodiment R$^1$ is H or a synthetic activating group derivable from DCC, HOBt, EDC, BOP, PyBOP or HBTU.

In one embodiment R$^2$ is H, acetate, triflate, mesylate or succinate.

In one embodiment R$^1$ is a synthetic activating group derivable from DCC, HOBt, EDC, BOP, PyBOP or HBTU.

In one embodiment R$^2$ is acetate, triflate, mesylate or succinate.

In one embodiment L$^1$ is a divalent, branched or unbranched, saturated or unsaturated, hydrocarbon chain, having from 5 to 20 carbon atoms, wherein one or more (e.g. 1, 2, 3, or 4) of the carbon atoms in the hydrocarbon chain is optionally replaced —O—, —NH—, —NH—C(=O)—, —C(=O)—NH— or —S—.

In one embodiment the invention provides a compound of formula (XX):

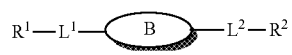

(XX)

wherein:

R$^1$ a is targeting ligand;

L$^1$ is absent or a linking group;

L$^2$ is absent or a linking group;

R$^2$ is a nucleic acid;

B is divalent and is selected from the group consisting of:

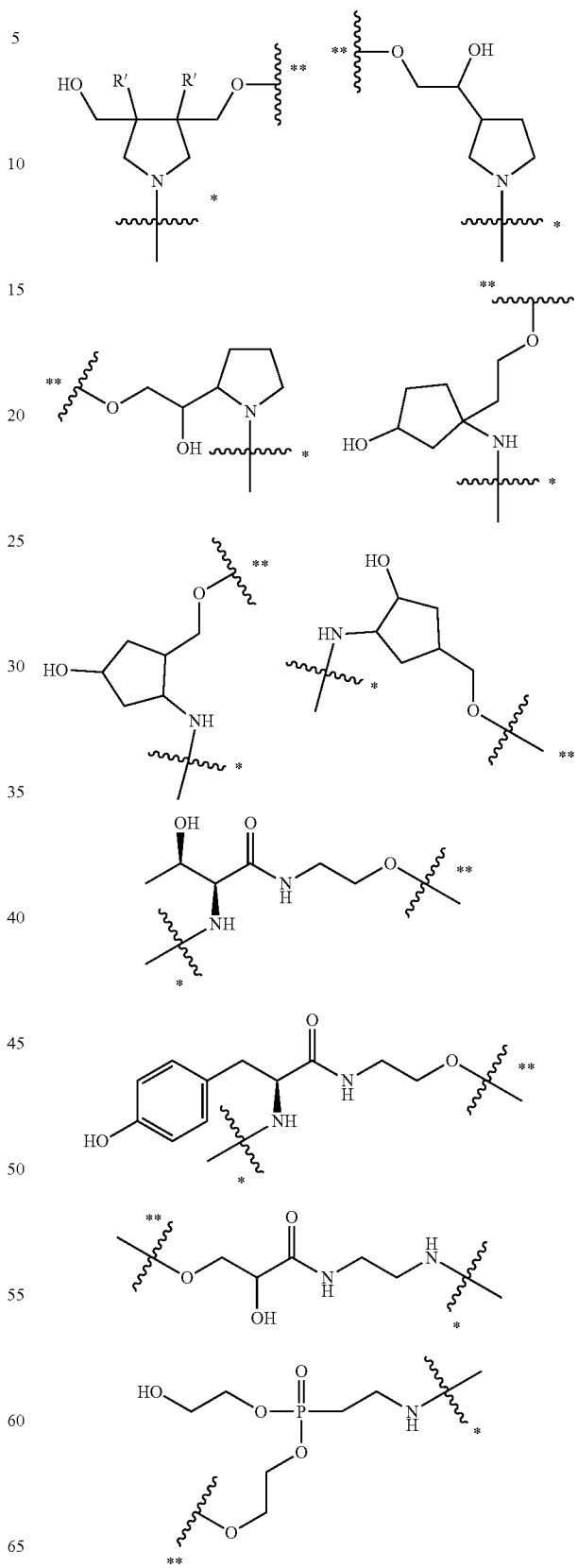

-continued

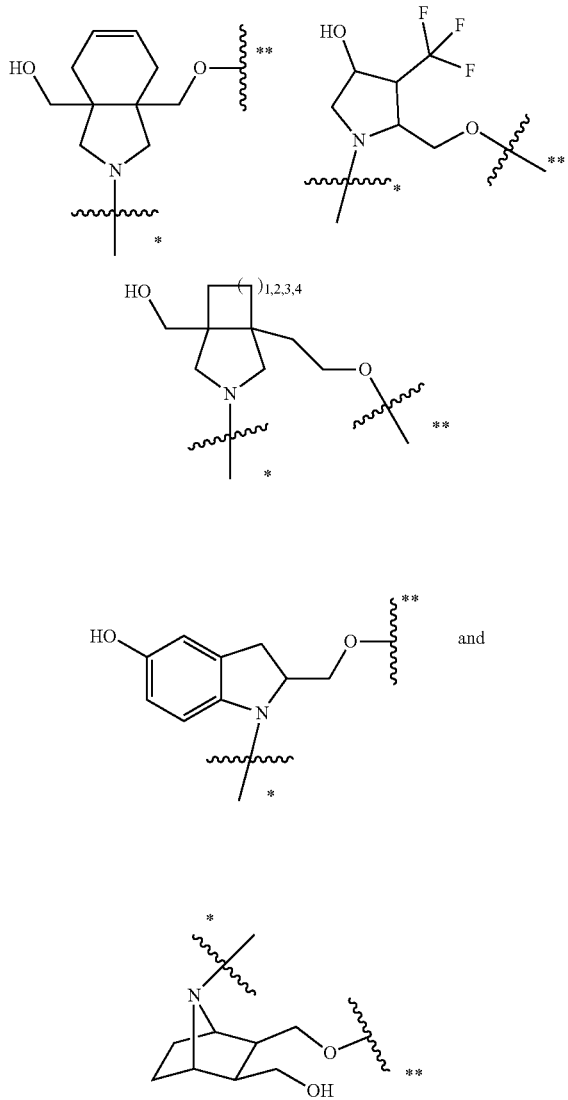

wherein:
  each $R^1$ is independently $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl;
  the valence marked with * is attached to $L^1$ or is attached to $R^1$ if $L^1$ is absent; and
  the valence marked with ** is attached to $L^2$ or is attached to $R^2$ if $L^2$ is absent;
  or a salt thereof.

In one embodiment $R^1$ comprises 2-8 saccharides.
In one embodiment $R^1$ comprises 2-6 saccharides.
In one embodiment $R^1$ comprises 2-4 saccharides.
In one embodiment $R^1$ comprises 3-8 saccharides.
In one embodiment $R^1$ comprises 3-6 saccharides.
In one embodiment $R^1$ comprises 3-4 saccharides.
In one embodiment $R^1$ comprises 3 saccharides.
In one embodiment $R^1$ comprises 4 saccharides.

In one embodiment $R^1$ has the following formula:

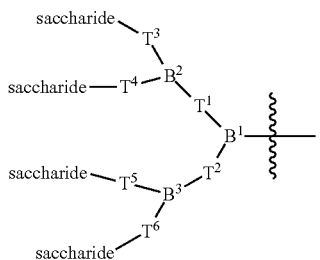

wherein:
  $B^1$ is a trivalent group comprising about 1 to about 20 atoms and is covalently bonded to $L^1$, $T^1$, and $T^2$.
  $B^2$ is a trivalent group comprising about 1 to about 20 atoms and is covalently bonded to $T^1$, $T^3$, and $T^4$;
  $B^3$ is a trivalent group comprising about 1 to about 20 atoms and is covalently bonded to $T^2$, $T^5$, and $T^6$;
  $T^1$ is absent or a linking group;
  $T^2$ is absent or a linking group;
  $T^3$ is absent or a linking group;
  $T^4$ is absent or a linking group;
  $T^5$ is absent or a linking group; and
  $T^6$ is absent or a linking group In one embodiment each saccharide is independently selected from:

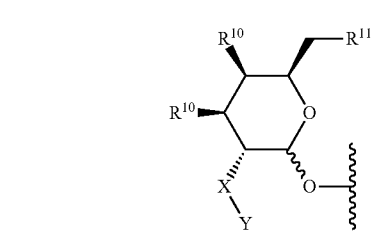

wherein:
  X is $NR^3$, and Y is selected from $-(C=O)R^4$, $-SO_2R^5$, and $-(C=O)NR^6R^7$; or X is $-(C=O)-$ and Y is $NR^8R^9$;
  $R^3$ is hydrogen or $(C_1-C_4)$alkyl;
  $R^4$, $R^5$, $R^6$, $R^7$, $R^8$ and $R^9$ are each independently selected from the group consisting of hydrogen, $(C_1-C_8)$alkyl, $(C_1-C_8)$haloalkyl, $(C_1-C_8)$alkoxy and $(C_3-C_6)$cycloalkyl that is optionally substituted with one or more groups independently selected from the group consisting of halo, $(C_1-C_4)$alkyl, $(C_1-C_4)$haloalkyl, $(C_1-C_4)$alkoxy and $(C_1-C_4)$haloalkoxy;
  $R^{10}$ is $-OH$, $-NR^8R^9$ or $-F$; and
  $R^{11}$ is $-OH$, $-NR^8R^9$, $-F$ or 5 membered heterocycle that is optionally substituted with one or more groups independently selected from the group consisting of halo, hydroxyl, carboxyl, amino, $(C_1-C_4)$alkyl, $(C_1-C_4)$haloalkyl, $(C_1-C_4)$alkoxy and $(C_1-C_4)$haloalkoxy.

In one embodiment each saccharide is independently selected from the group consisting of:

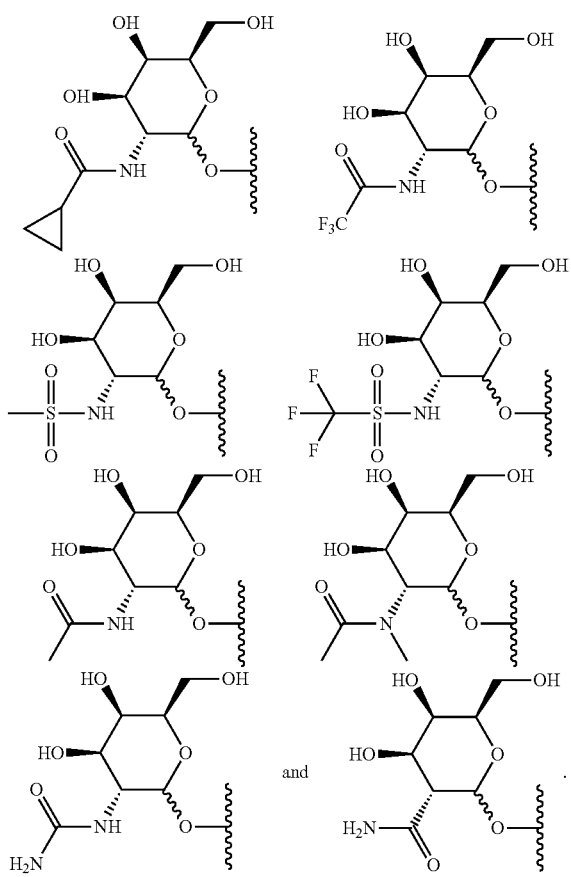

In one embodiment each saccharide is independently:

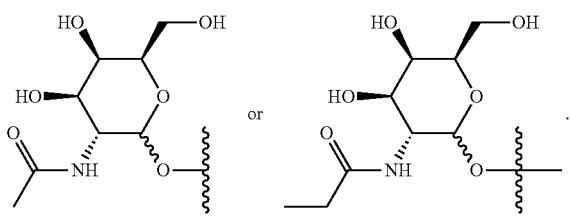 [SMILES: *OC1O[C@H](CO)[C@H](O)[C@H](O)[C@H]1NC(C)=O ; *OC1O[C@H](CO)[C@H](O)[C@H](O)[C@H]1NC(=O)CC]

In one embodiment one of $T^1$ and $T^2$ is absent.

In one embodiment both $T^1$ and $T^2$ are absent.

In one embodiment each of $T^1$, $T^2$, $T^3$, $T^4$, $T^5$, and $T^6$ is independently absent or a branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or (C1-C6)alkyl, and wherein the hydrocarbon chain, is optionally substituted with one or more (e.g. 1, 2, 3, or 4) substituents selected from (C1-C6)alkoxy, (C3-C6)cycloalkyl, (C1-C6)alkanoyl, (C1-C6)alkanoyloxy, (C1-C6)alkoxycarbonyl, (C1-C6)alkylthio, azido, cyano, nitro, halo, hydroxy, oxo (=O), carboxy, aryl, aryloxy, heteroaryl, and heteroaryloxy.

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O—, —NR$^X$—, —NR$^X$—C(=O)—, —C(=O)—NR$^X$— or —S—, and wherein R$^X$ is hydrogen or (C1-C6)alkyl, and wherein the hydrocarbon chain, is optionally substituted with one or more (e.g. 1, 2, 3, or 4) substituents selected from (C1-C6)alkoxy, (C3-C6)cycloalkyl, (C1-C6)alkanoyl, (C1-C6)alkanoyloxy, (C11-C6) alkoxycarbonyl, (C1-C6)alkylthio, azido, cyano, nitro, halo, hydroxy, oxo (=O), carboxy, aryl, aryloxy, heteroaryl, and heteroaryloxy.

In one embodiment each of $T^1$, $T^2$, $T^3$, $T^4$, $T^5$, and $T^6$ is independently absent or a branched or unbranched, saturated or unsaturated, hydrocarbon chain, having from 1 to 50 carbon atoms, or a salt thereof, wherein one or more (e.g. 1, 2, 3, or 4) of the carbon atoms in the hydrocarbon chain is optionally replaced by —O— or —NR$^X$—, and wherein R$^X$ is hydrogen or (C$_1$-C$_6$)alkyl, and wherein the hydrocarbon chain, is optionally substituted with one or more (e.g. 1, 2, 3, or 4) substituents selected from halo, hydroxy, and oxo (=O).

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O— and wherein the hydrocarbon chain, is optionally substituted with one or more (e.g. 1, 2, 3, or 4) substituents selected from halo, hydroxy, and oxo (=O).

In one embodiment each of $T^1$, $T^2$, $T^3$, $T^4$, $T^5$, and $T^6$ is independently absent or a branched or unbranched, saturated or unsaturated, hydrocarbon chain, having from 1 to 20 carbon atoms, wherein one or more (e.g. 1, 2, 3, or 4) of the carbon atoms in the hydrocarbon chain is optionally replaced by —O— and wherein the hydrocarbon chain, is optionally substituted with one or more (e.g. 1, 2, 3, or 4) substituents selected from halo, hydroxy, and oxo (0).

In one embodiment at least one of $T^3$, $T^4$, $T^5$, and $T^6$ is:

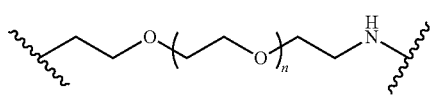

wherein:
n=1, 2, 3.

In one embodiment each of $T^3$, $T^4$, $T^5$, and $T^6$ is independently selected from the group consisting of:

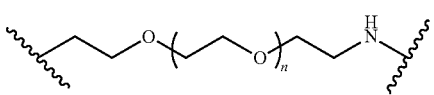

wherein:
n=1, 2, 3.

In one embodiment at least one of $T^1$ and $T^2$ is glycine

In one embodiment each of $T^1$ and $T^2$ is glycine.

In one embodiment $B^1$ is a trivalent group comprising 1 to 15 atoms and is covalently bonded to $L^1$, $T^1$, and $T^2$.

In one embodiment $B^1$ is a trivalent group comprising 1 to 10 atoms and is covalently bonded to $L^1$, $T^1$, and $T^2$.

In one embodiment $B^1$ comprises a (C$_1$-C$_6$)alkyl.

In one embodiment $B^1$ comprises a C$_{3-8}$ cycloalkyl.

In one embodiment $B^1$ comprises a silyl group.

In one embodiment B¹ comprises a D- or L-amino acid.
In one embodiment B¹ comprises a saccharide.
In one embodiment B¹ comprises a phosphate group.
In one embodiment B¹ comprises a phosphonate group.
In one embodiment B¹ comprises an aryl.
In one embodiment B¹ comprises a phenyl ring.
In one embodiment B¹ is a phenyl ring.
In one embodiment B¹ is CH.
In one embodiment B¹ comprises a heteroaryl.
In one embodiment B¹ is selected from the group consisting of:

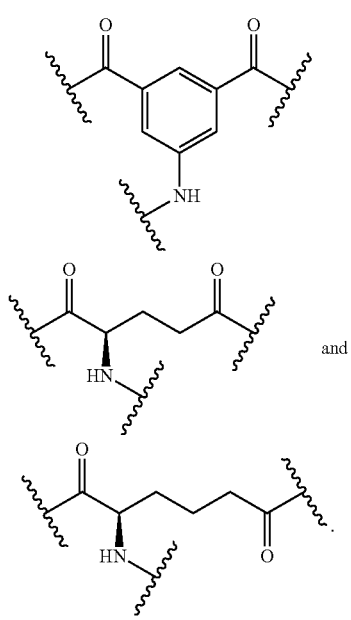

In one embodiment B² is a trivalent group comprising 1 to 15 atoms and is covalently bonded to $L^1$, $T^1$, and $T^2$.

In one embodiment B² is a trivalent group comprising 1 to 10 atoms and is covalently bonded to $L^1$, $T^1$, and $T^2$.

In one embodiment B² comprises a $(C_1-C_6)$alkyl
In one embodiment B² comprises a $C_{3-8}$ cycloalkyl.
In one embodiment B² comprises a silyl group.
In one embodiment B² comprises a D- or L-amino acid.
In one embodiment B² comprises a saccharide.
In one embodiment B² comprises a phosphate group.
In one embodiment B² comprises a phosphonate group.
In one embodiment B² comprises an aryl.
In one embodiment B² comprises a phenyl ring.
In one embodiment B² is a phenyl ring.
In one embodiment B² is CH.
In one embodiment B² comprises a heteroaryl.
In one embodiment B² is selected from the group consisting of:

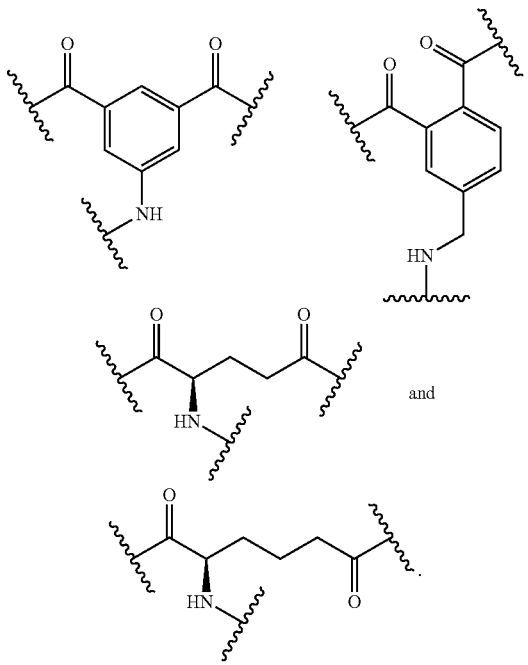

In one embodiment B³ is a trivalent group comprising 1 to 15 atoms and is covalently bonded to $L^1$, $T^1$, and $T^2$.
In one embodiment B³ is a trivalent group comprising 1 to 10 atoms and is covalently bonded to $L^1$, $T^1$, and $T^2$.
In one embodiment B¹ comprises a $(C_1-C_6)$alkyl.
In one embodiment B³ comprises a $C_{3-8}$ cycloalkyl.
In one embodiment B³ comprises a silyl group.
In one embodiment B³ comprises a D- or L-amino acid.
In one embodiment B³ comprises a saccharide.
In one embodiment B³ comprises a phosphate group.
In one embodiment B³ comprises a phosphonate group.
In one embodiment B³ comprises an aryl.
In one embodiment B³ comprises a phenyl ring.
In one embodiment B³ is a phenyl ring.
In one embodiment B³ is CH.
In one embodiment B³ comprises a heteroaryl.
In one embodiment B³ is selected from the group consisting of:

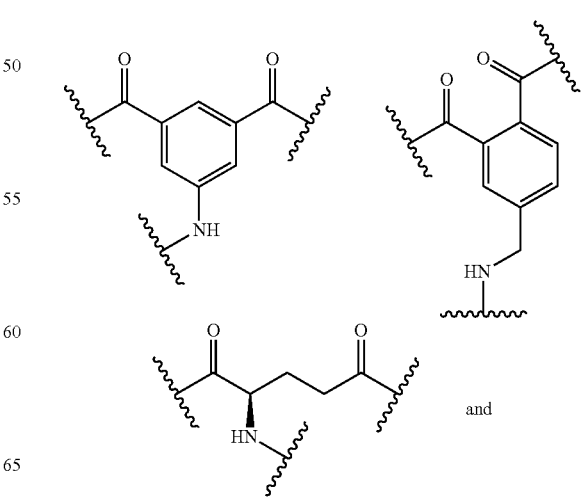

71

-continued

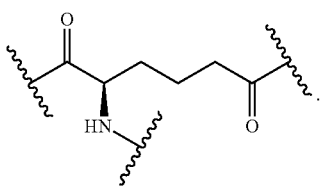

or a salt thereof.

In one embodiment $L^1$ and $L^2$ are independently a divalent, branched or unbranched, saturated or unsaturated, hydrocarbon chain, having from 1 to 50 carbon atoms, wherein one or more (e.g. 1, 2, 3, or 4) of the carbon atoms in the hydrocarbon chain is optionally replaced by —O—, —$NR^x$—, —$NR^x$—C(=O)—, —C(=O)—$NR^x$— or —S—, and wherein $R^x$ is hydrogen or (C1-C6)alkyl, and wherein the hydrocarbon chain, is optionally substituted with one or more (e.g. 1, 2, 3, or 4) substituents selected from (C1-C6)alkoxy, (C3-C6)cycloalkyl, (C1-C6)alkanoyl, (C1-C6)alkanoyloxy, (C1-C6)alkoxycarbonyl, (C1-C6)alkylthio, azido, cyano, nitro, halo, hydroxy, oxo (=O), carboxy, aryl, aryloxy, heteroaryl, and heteroaryloxy.

In one embodiment $L^1$ is selected from the group consisting of:

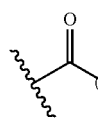 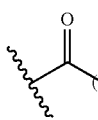 and

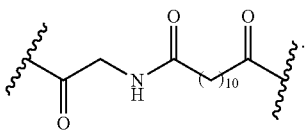

or a salt thereof.

In one embodiment $L^1$ is connected to $B^1$ through a linkage selected from the group consisting of: —O—, —S—, —(C=O)—, —(C=O)—NH—, —NH—(C=O), —(C=O)—O—, —NH—(C=O)—NH—, or —NH—($SO_2$)—.

In one embodiment $L^1$ is selected from the group consisting of:

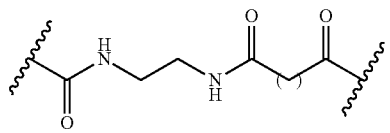

72

-continued

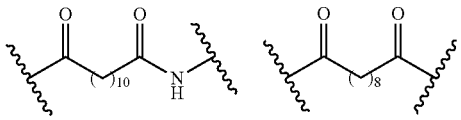

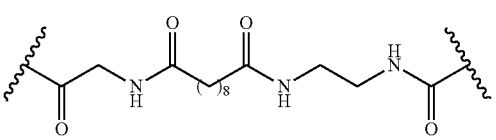

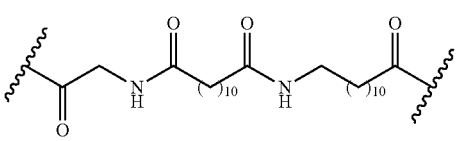

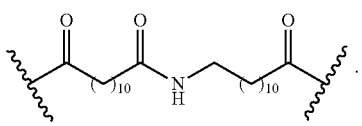

In one embodiment $L^2$ is connected to $R^2$ through —O—.

In one embodiment $L^2$ is $C_{1-4}$ alkylene-O— that is optionally substituted with hydroxy.

In one embodiment $L^2$ is connected to $R^2$ through —O—.

In one embodiment $L^2$ is absent.

In one embodiment the invention provides a compound or salt selected from the group consisting of:

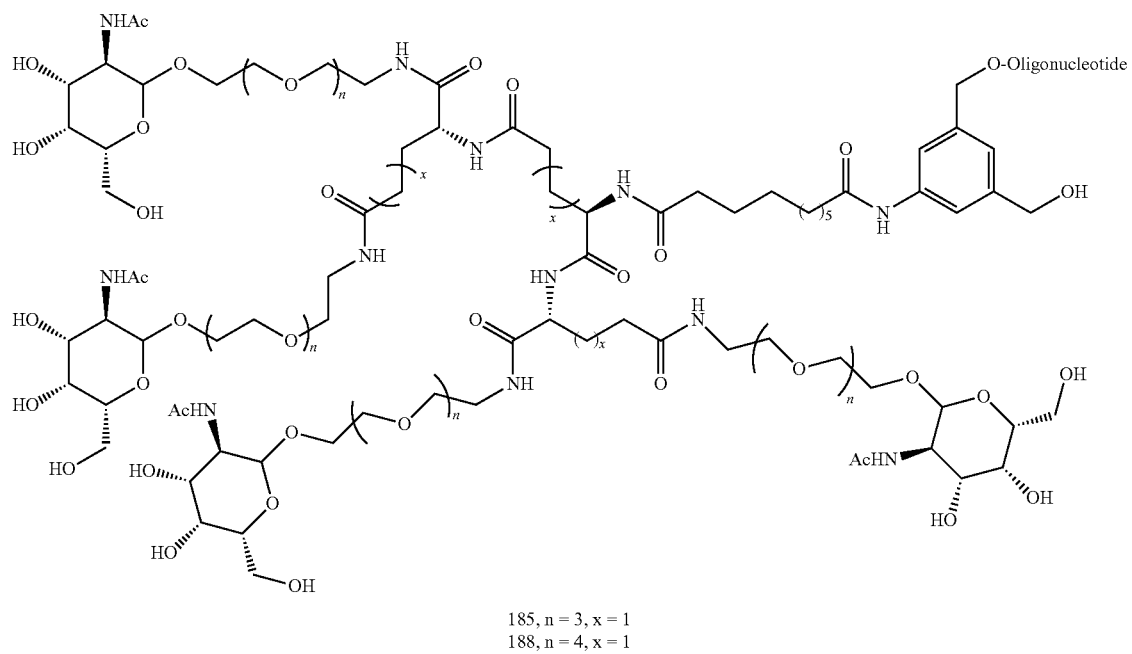
185, n = 3, x = 1
188, n = 4, x = 1
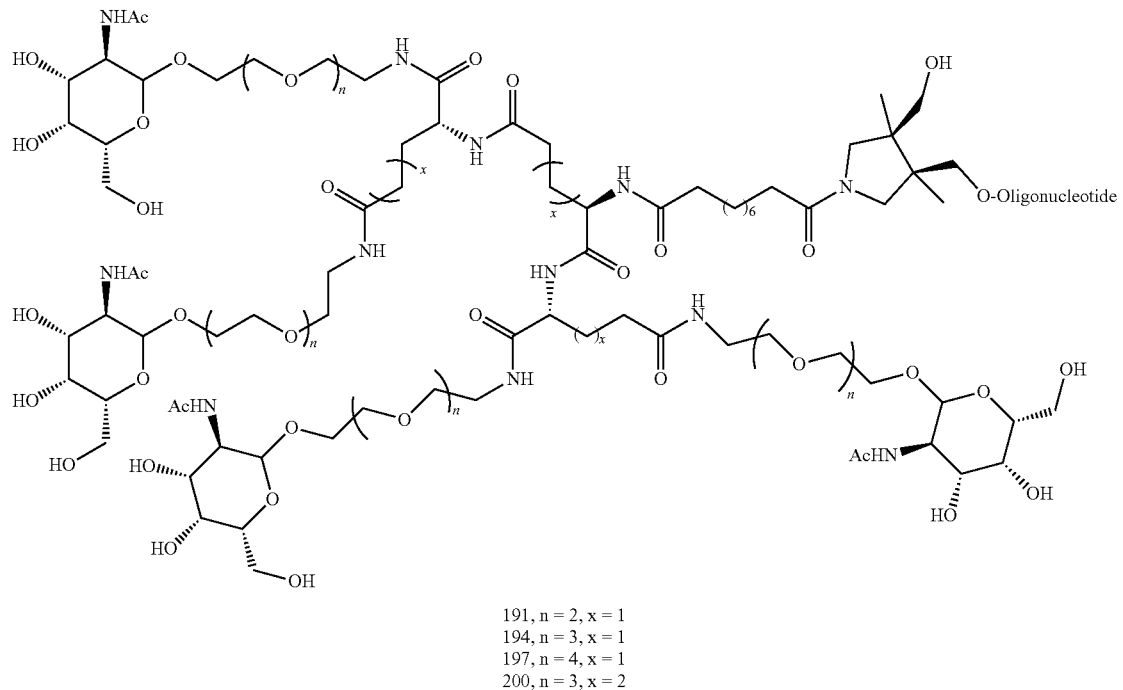
191, n = 2, x = 1
194, n = 3, x = 1
197, n = 4, x = 1
200, n = 3, x = 2

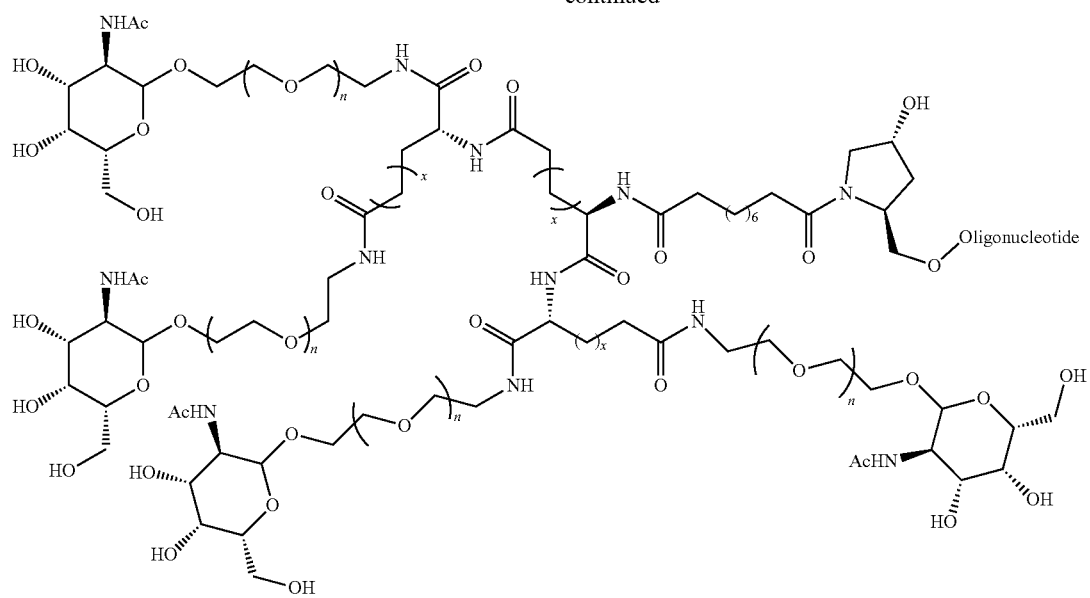
203, n = 3, x = 1
206, n = 4, x = 1
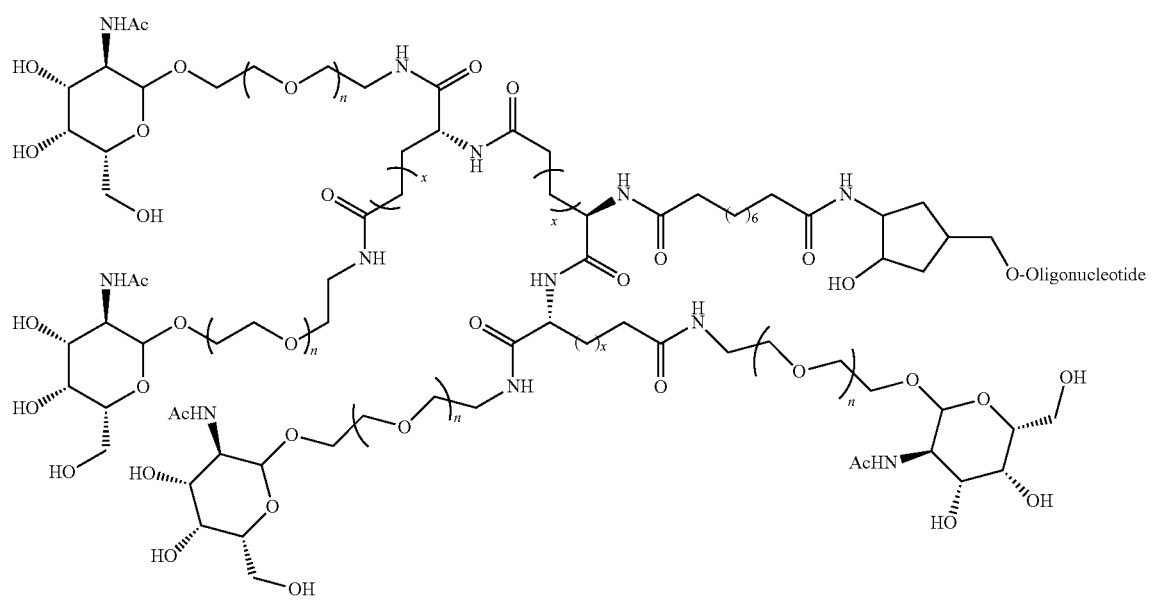
209, n = 3, x = 1

-continued
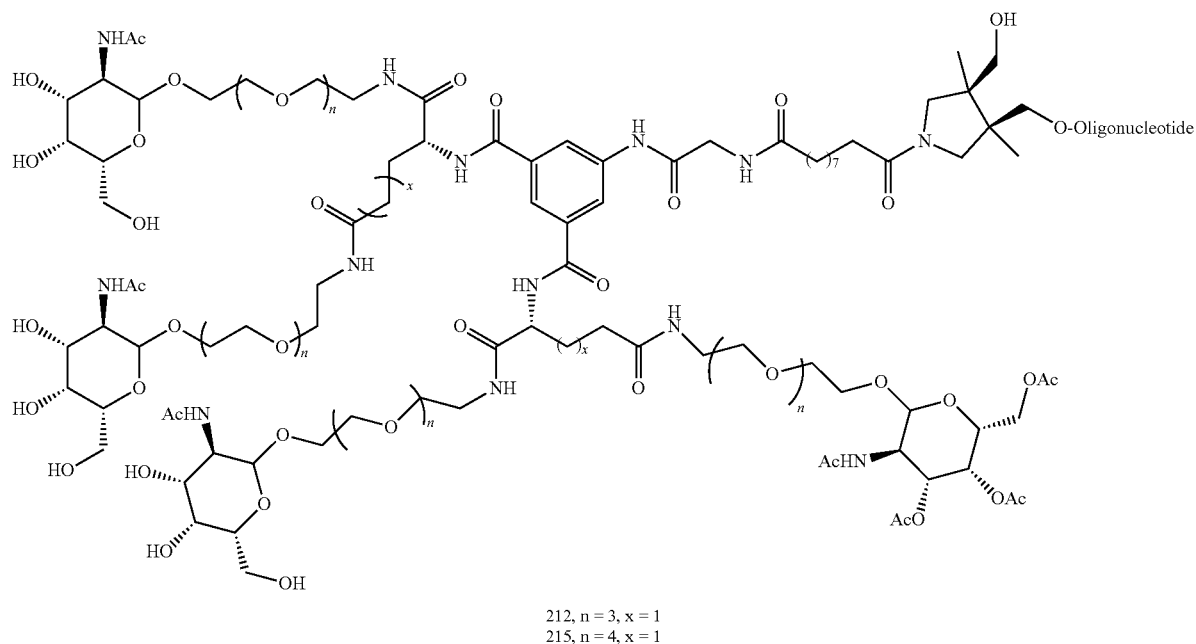
212, n = 3, x = 1
215, n = 4, x = 1
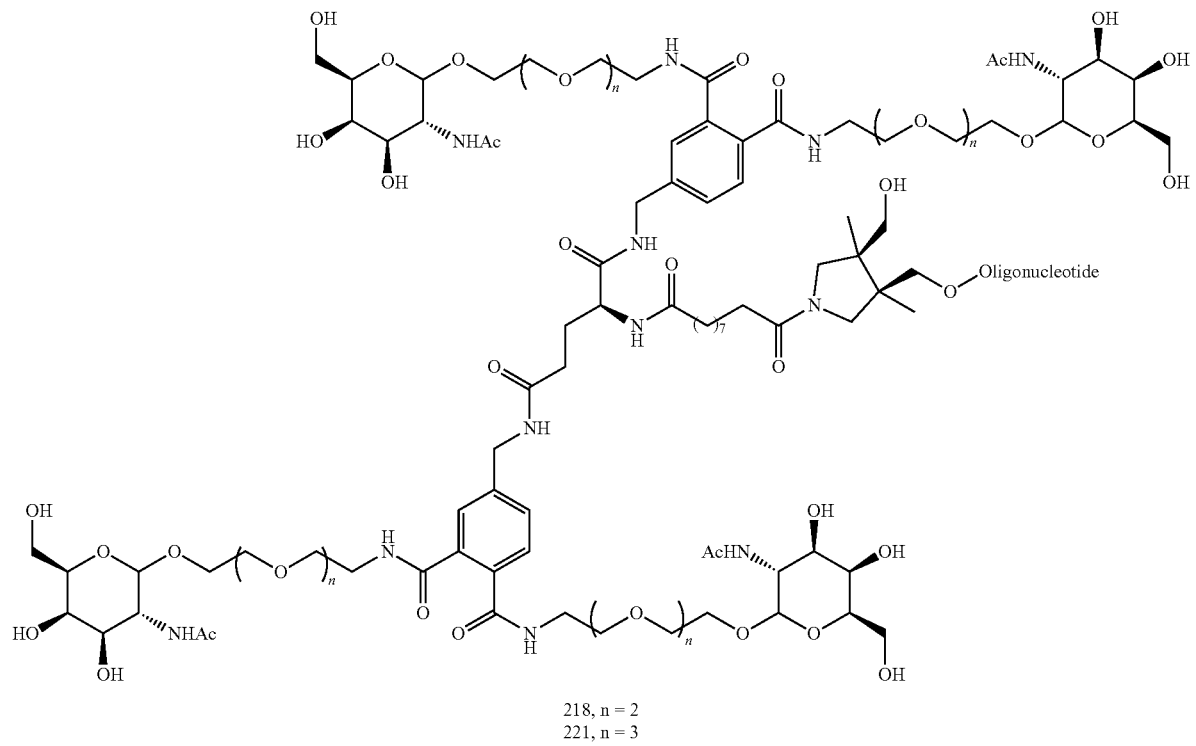
218, n = 2
221, n = 3

-continued

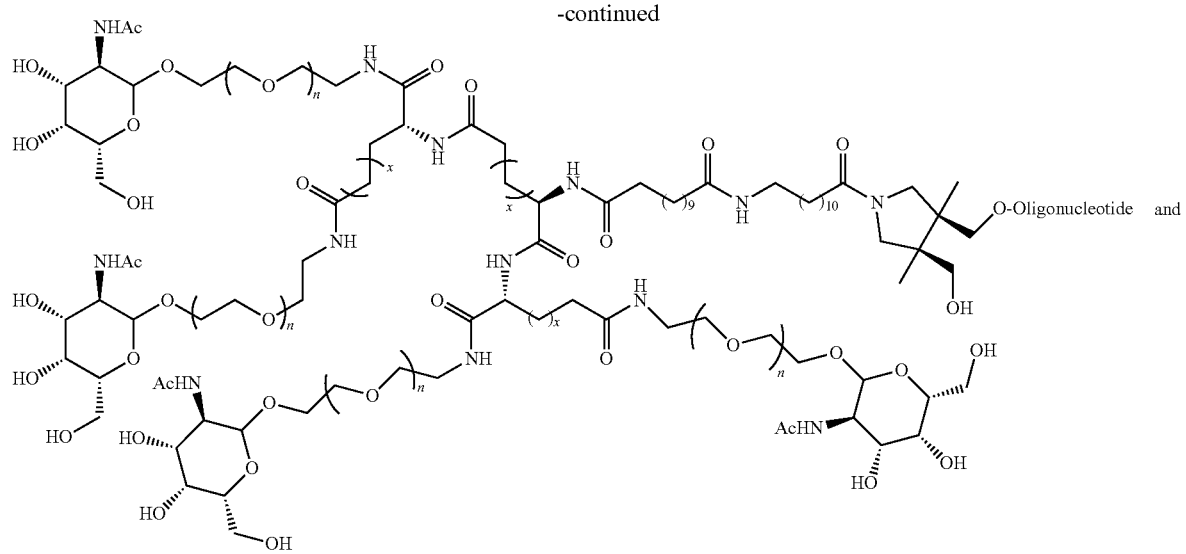

224, n = 3, x = 1

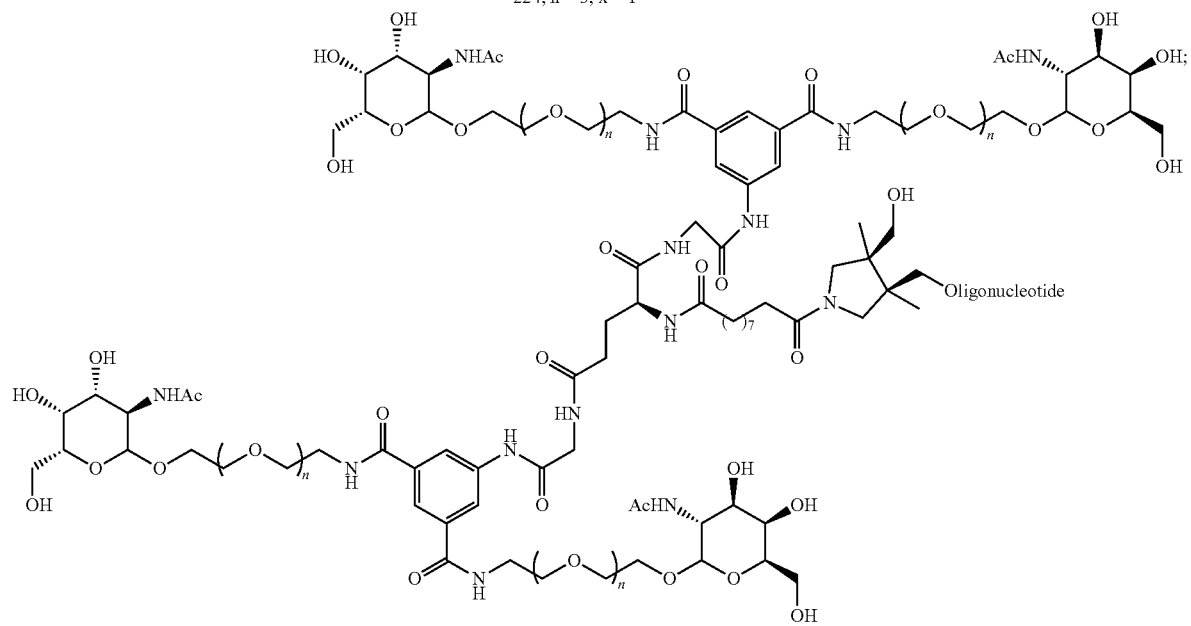

231, n = 3 and pharmaceutically acceptable salts thereof.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Synthesis of Conjugate 1

Scheme 1.

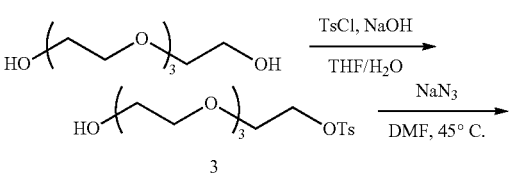

81
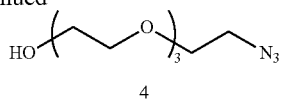
4
Scheme 2.
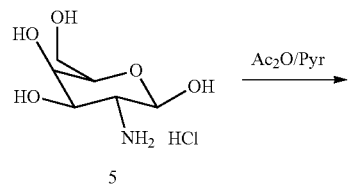
5
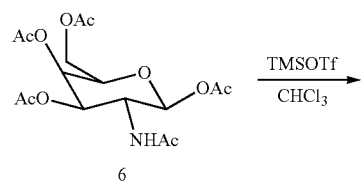
6
82
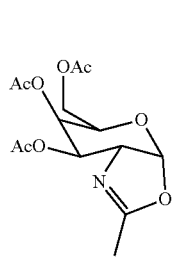
7
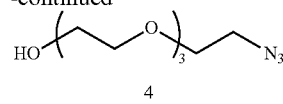
4
TMSOTf
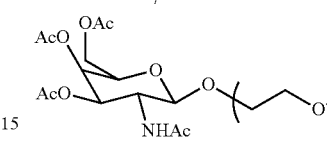
8
H₂(g), Pd—C
TFA
EtOAc
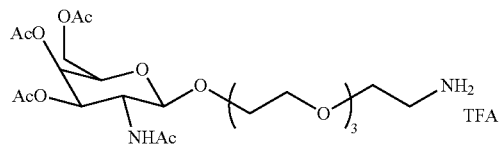
9
Scheme 3.
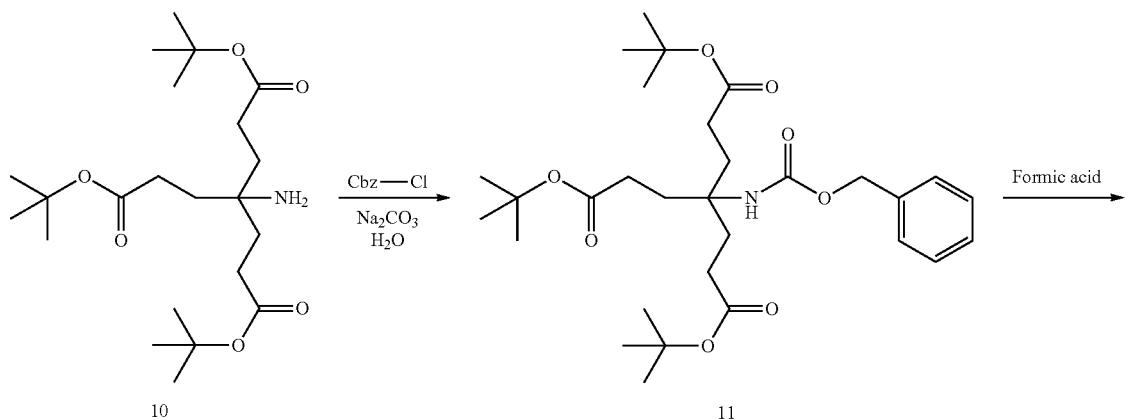
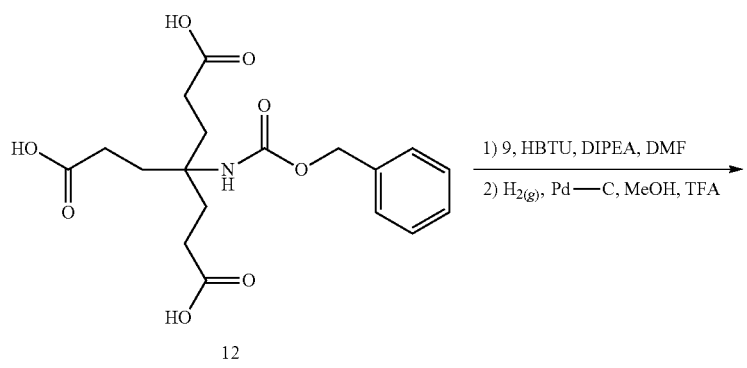

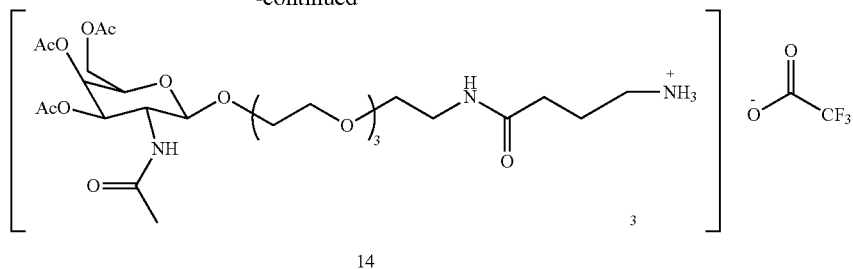
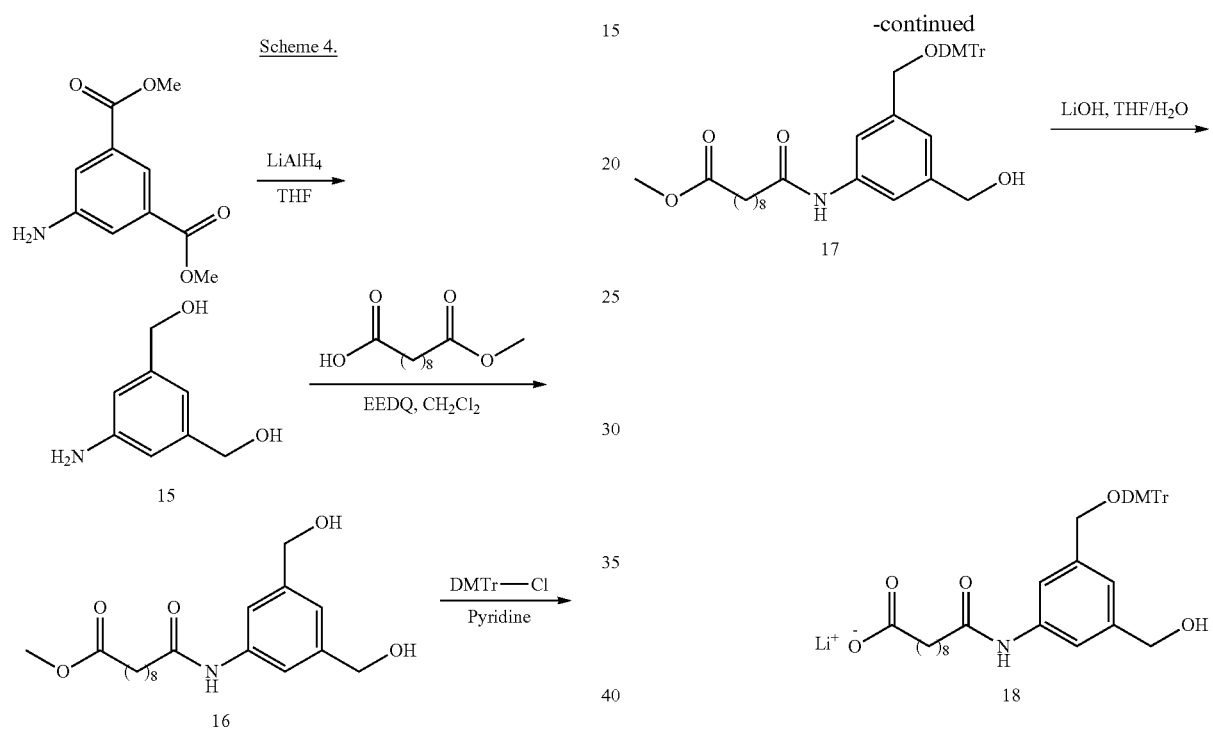
Scheme 4.
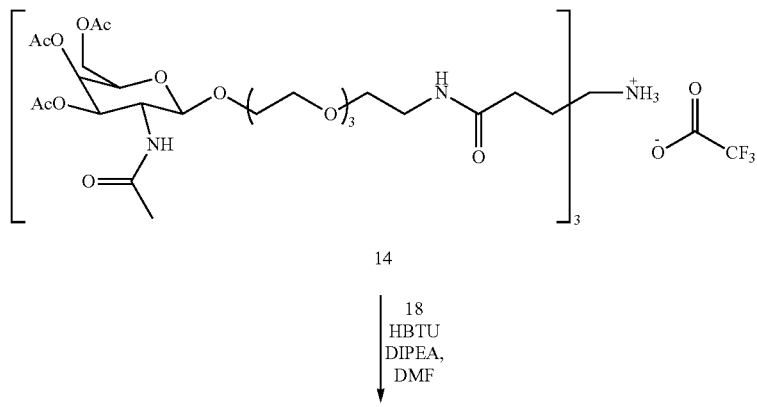
Scheme 5.

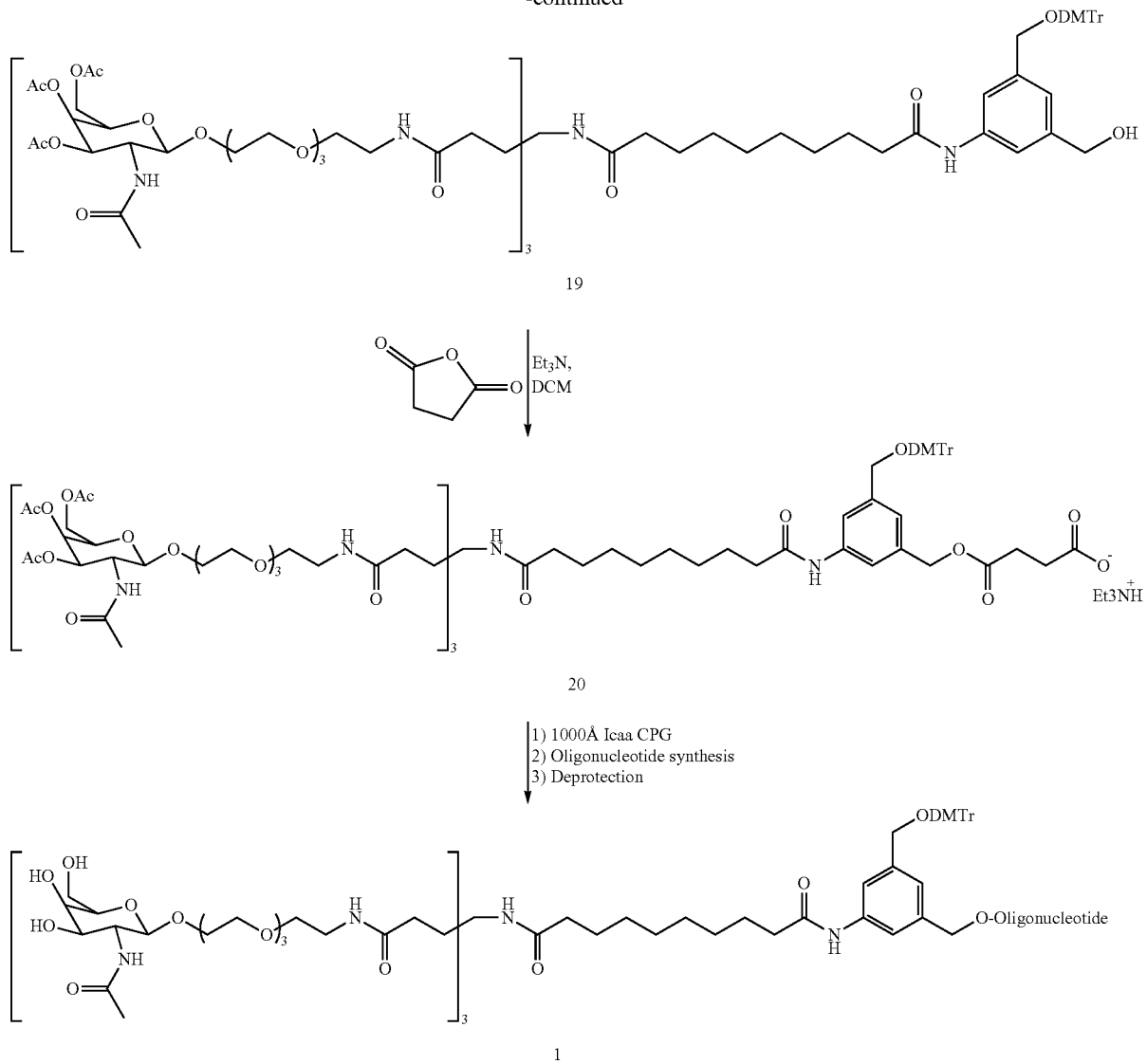

Step 1. Preparation of 2-(2-(2-(2-hydroxyethoxy)ethoxy)ethoxy)ethyl 4-methylbenzenesulfonate 3

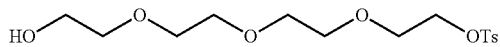 [SMILES: Cc1ccc(S(=O)(=O)OCCOCCOCCOCCO)cc1]

A solution of tetraethylene glycol (934 g, 4.8 mol) in THF (175 mL) and aqueous NaOH (5M, 145 mL) was cooled (0° C.) and treated with p-Toluensulfonyl chloride (91.4 g, 480 mmol) dissolved in THF (605 mL) and then stirred for two hours (0° C.). The reaction mixture was diluted with water (3 L) and extracted (3×500 mL) with CH$_2$Cl$_2$. The combined extracts were washed with water and brine then dried (MgSO$_4$), filtered and concentrated to afford 2-(2-(2-(2-hydroxyethoxy)ethoxy)ethoxy)ethyl 4-methylbenzenesulfonate 3 (140 g, 84%) as a pale yellow oil. R$_f$ (0.57, 10% MeOH—CH$_2$Cl$_2$).

Step 2. Preparation of 2-(2-(2-(2-azidoethoxy)ethoxy)ethoxy)ethan-1-ol 4

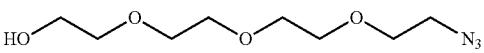 [SMILES: [N-]=[N+]=NCCOCCOCCOCCO]

A solution of 3 (140 g, 403 mmol) in DMF (880 mL) was treated with sodium azide (131 g, 2.02 mol) and heated (45° C.) overnight. A majority of the DMF was removed under reduced pressure and the residue was dissolved in CH$_2$Cl$_2$ (500 mL) and washed (3×500 mL) with brine then dried (MgSO$_4$), filtered and concentrated. The residue was passed through a short bed of silica (5% MeOH—CH$_2$Cl$_2$) and concentrated to yield 2-(2-(2-(2-azidoethoxy)ethoxy)ethoxy)ethan-1-ol 4 (65 g, 74%) as a yellow oil. R$_f$ (0.56, 10% MeOH—CH$_2$Cl$_2$).

Step 3. Preparation of Peracetylated Galactosamine 6

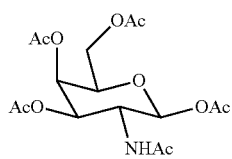

D-Galactosamine hydrochloride 5 (250 g, 1.16 mol) in pyridine (1.5 L) was treated with acetic anhydride (1.25 L, 13.2 mol) over 45 minutes. After stirring overnight the reaction mixture was divided into three 1 L portions. Each 1 L portion was poured into 3 L of ice water and mixed for one hour. After mixing the solids were filtered off, combined, frozen over liquid nitrogen and then lyophilized for five days to yield peracetylated galactosamine 6 (369.4 g, 82%) as a white solid. Rf (0.58, 10% MeOH—$CH_2Cl_2$).

Step 4. Preparation of (3aR,5R,6R,7R,7aR)-5-(acetoxymethyl)-2-methyl-3a,6,7,7a-tetrahydro-5H-pyrano[3,2-d]oxazole-6,7-diyl diacetate 7

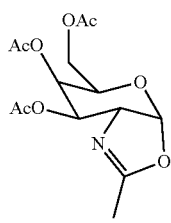

A solution of per-acetylated galactosamine 6 (8.45 g, 21.7 mmol) in $CHCl_3$ (320 mL) was treated dropwise with TMSOTf (4.32 mL, 23.9 mmol). After stirring (1.5 hr, 40° C.) the reaction was quenched by the addition of triethylamine (5 mL) and concentrated to dryness to afford compound 7 as a pale yellow glass (7.2 g, Quant.). The product was used without further purification. Rf (0.59, 10% MeOH—$CH_2Cl_2$).

Step 5. Preparation of (2R,3R,4R,5R,6R)-5-acetamido-2-(acetoxymethyl)-6-(2-(2-(2-(2-azidoethoxy)ethoxy)ethoxy)ethoxy)tetrahydro-2H-pyran-3,4-diyl diacetate 8

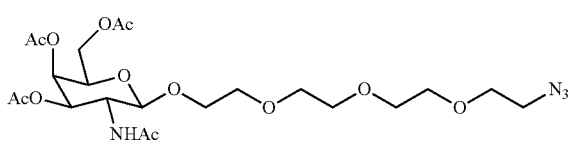 [SMILES: CC(=O)NC1C(OCCOCCOCCOCCN=[N+]=[N-])OC(COC(C)=O)C(OC(C)=O)C1OC(C)=O]

Compound 7 (7.2 g, 21.7 mmol) and 2-(2-(2-(2-azidoethoxy)ethoxy)ethoxy)ethan-1-ol 4 (2.65 g, 15.2 mmol) were azeotroped (3×) from toluene (150 mL) to remove traces of water. The dried material was dissolved in 1,2-dichloroethane (150 mL), cooled (~5° C.) and treated with TMSOTf (784 µL, 4.34 mmol). After stirring overnight the reaction was quenched by the addition of triethylamine (5 mL) and concentrated. The residue was purified by chromatography (1%→5% MeOH—$CH_2Cl_2$) to afford 8 (7.12 g, 85%) as a brown oil. Rf (0.3, 10% MeOH—$CH_2Cl_2$).

Step 6. Preparation of 2-(2-(2-(2-(((2R,3R,4R,5R,6R)-3-acetamido-4,5-diacetoxy-6-(acetoxymethyl)tetrahydro-2H-pyran-2-yl)oxy)ethoxy)ethoxy)ethoxy)ethan-1-aminium 2,2,2-trifluoroacetate 9

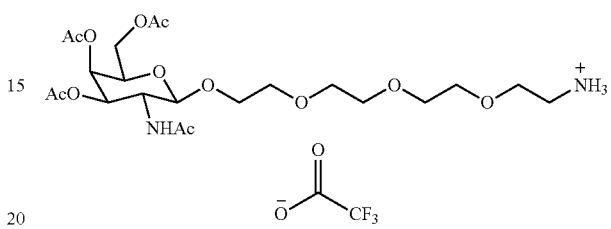

A solution of the azide 8 (7.12 g, 13 mmol) in EtOAc (150 mL) and trifluoroacetic acid (2 mL) was treated with palladium on charcoal (1.5 g, 10% w/w wet basis). The reaction mixture was then purged with hydrogen and stirred vigorously overnight. After purging with nitrogen, the mixture was filtered through Celite, rinsing with MeOH. The filtrate was concentrated and purified via chromatography (5%→10%→20% MeOH—$CH_2Cl_2$) to afford 9 (5.8 g, 72%) as a brown oil. Rf (0.34, 15% MeOH—$CH_2C2$).

Step 7. Preparation of di-tert-butyl 4-(((benzyloxy)carbonyl)amino)-4-(3-(tert-butoxy)-3-oxopropyl)heptanedioate 11

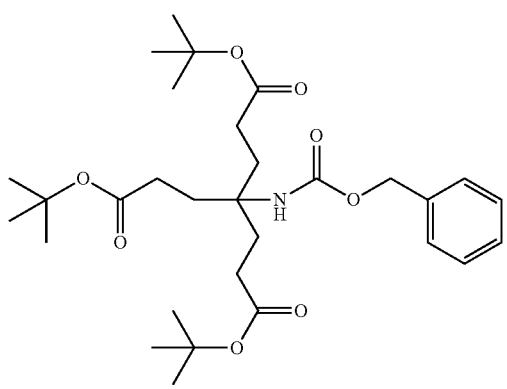 [SMILES: CC(C)(C)OC(=O)CCC(CCC(=O)OC(C)(C)C)(CCC(=O)OC(C)(C)C)NC(=O)OCc1ccccc1]

To a solution of di-tert-butyl 4-amino-4-(3-(tert-butoxy)-3-oxopropyl)heptanedioate 10 (13.5 g, 33 mmol), 25% $Na_2CO_3$ $_{(aq)}$ (150 mL) and dichloromethane (300 mL) was added slowly benzyl chloroformate (14 mL, 98 mmol). The solution was stirred vigorously overnight (16 h) at room temperature. Upon completion, additional dichloromethane (100 mL) was added and the dichloromethane layer was separated. The aqueous layer was extracted with dichloromethane (2×100 mL). The combine dichloromethane extracts were dried on magnesium sulfate, filtered and concentrated to dryness. The product 11 was isolated as a colorless oil that required no further purification (15.8 g, 88%). Rf (0.7, 1:1 EtOAc-Hexane).

Step 8. Preparation of 4-(((benzyloxy)carbonyl) amino)-4-(2-carboxyethyl)heptanedioic acid 12

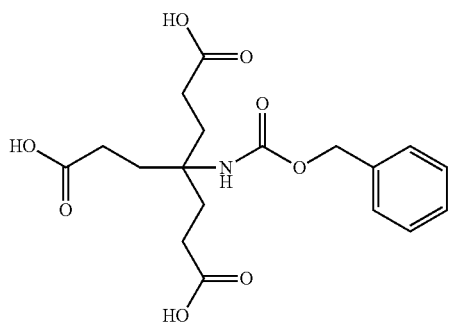

A solution of 11 (15.6 g, 28.8 mmol) in formic acid (50 mL) was stirred at room temperature for 2 hours. The solution was concentrated to dryness and dissolved in ethyl acetate (~25 mL). Upon standing, the product crystallized as a colorless solid. The solid was filtered, washed with ethyl acetate and air dried to afford 12 as a colorless solid (10.2 g, 93%). Rf (0.1, 10% MeOH—$CH_2Cl_2$).

Step 9. Preparation of Compound 13

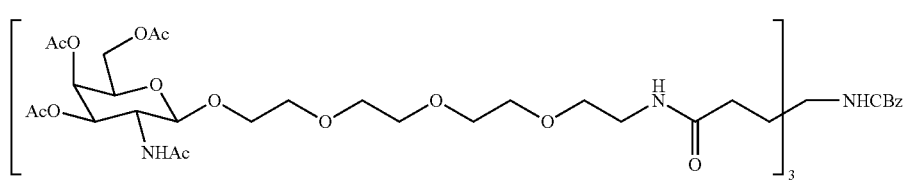

A solution of 12 (793 mg, 2.08 mmol) and 9 (5.8 g, 9.36 mmol) in DMF (50 mL) was treated with BOP (3.67 g, 8.32 mmol) then N,N-diisopropylethylamine (4.31 mL, 25 mmol). After stirring overnight the mixture was concentrated to dryness and subjected to chromatography (1%→2%→5%→10%→15% MeOH—$CH_2Cl_2$) to afford 13 (5.71 g [crude], >100%—contained coupling by-products that did not affect the next step). Rf (0.45, 10% MeOH—$CH_2Cl_2$).

Step 10. Preparation of Compound 14

Compound 13 (5.7 g) was dissolved in MeOH (150 mL) and TFA (1.5 mL) and treated with palladium on charcoal (1 g, 10% w/w wet basis). The reaction mixture was then purged with hydrogen and stirred vigorously overnight. After purging with nitrogen, the mixture was filtered through Celite, rinsing with MeOH. The filtrate was concentrated and purified via chromatography (5%→10%→20% MeOH—$CH_2Cl_2$) to afford 14 as a brown oil (2.15 g, 56% over two steps). Rf (0.32, 10% MeOH—$CH_2Cl_2$).

Step 11. Preparation of (5-amino-1,3-phenylene)dimethanol 15

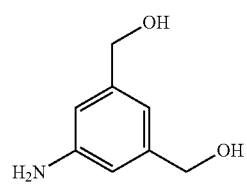

A solution of dimethyl 5-aminoisophthalate (20.0 g, 96 mmol) in THF (350 mL) was added, dropwise, to a refluxing mixture of 3.75 eq $LiAlH_4$ (13.6 g, 358 mmol) in THF (440 mL) over one hour. The mixture was stirred at reflux for a further two hours, then cooled to room temperature and quenched by the careful addition of MeOH (27 mL) then water (40 mL). After stirring the quenched mixture for two hours it was filtered and concentrated to dryness. The residue was recrystallized (2×) from EtOAc to afford 15 as brownish-yellow crystals (10.2 g, 70%).

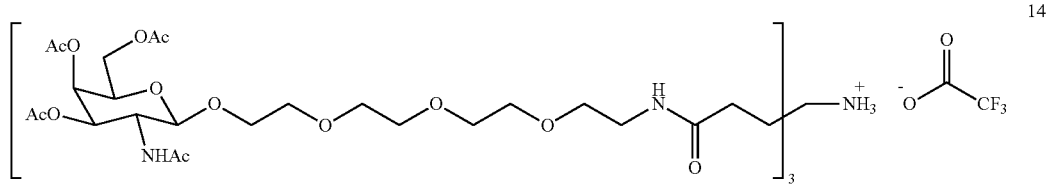

Step 12. Preparation of methyl 10-((3,5-bis(hydroxymethyl)phenyl)amino)-10-oxodecanoate 16

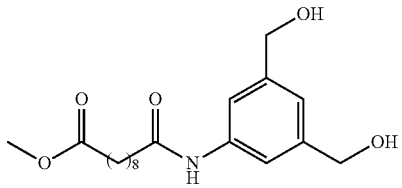

A solution of methyl sebacate (3.8 g, 17 mmol), 15 (2.5 g, 17 mmol) and EEDQ (8.1 g, 33 mmol) in 2:1 dichloromethane/methanol (200 mL) was stirred at room temperature for 2 hours. Upon completion the solution was concentrated to dryness. The solid obtained was triturated with dichloromethane (50 mL) and filtered. The solid was rinsed with cold dichloromethane and air dried to afford 16 as a colorless solid (4.3 g, 72%). Rf (0.33, EtOAc).

Step 13. Preparation of methyl 10-((3-((bis(4-methoxyphenyl)(phenyl)methoxy)methyl)-5-(hydroxymethyl)phenyl)amino)-10-oxodecanoate 17

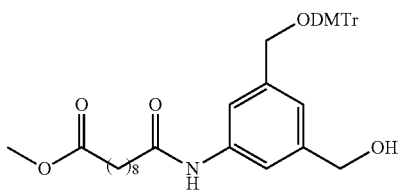

To a solution of 16 (4.3 g, 12 mmol) in pyridine (50 mL) was added 4,4'-(chloro(phenyl)methylene)bis(methoxybenzene) (4.1 g, 12 mmol). The solution was stirred under nitrogen overnight at room temperature. Upon completion the solution was concentrated to dryness and the residue was purified by column chromatography (0.5%→0.75%→1%→1.5% MeOH—CH$_2$Cl$_2$) to afford 17 as a yellow solid (2.9 g, 35%). Rf (0.6, 10% MeOH—CH$_2$Cl$_2$).

Step 14. Preparation of lithium 10-((3-((bis(4-methoxyphenyl)(phenyl)methoxy)methyl)-5-(hydroxymethyl)phenyl)amino)-10-oxodecanoate 18

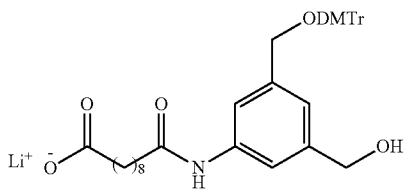

To a solution of 17 (2.9 g, 4.3 mmol) in THF (60 mL) was added water (15 mL) and lithium hydroxide (112 mg, 4.7 mmol). The solution was stirred overnight at room temperature. Upon completion the solution was concentrated to remove the THF. The remaining aqueous solution was flash frozen on liquid nitrogen and lyophilized overnight to afford a colorless solid (2.9 g, quant.). Rf (0.3, 10% MeOH—CH$_2$Cl$_2$).

Step 15. Preparation of Compound 19

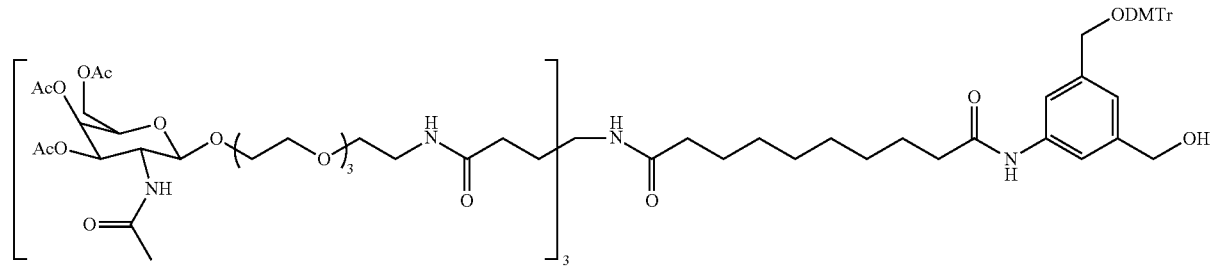

To a solution 14 (454 mg, 0.67 mmol), 18 (1.25 g, 0.67 mmol) and HBTU (381 mg, 1.0 mmol) in anhydrous DMF (25 mL) was added N,N-diisopropylethylamine (0.35 mL, 2.0 mmol). The solution was stirred overnight at room temperature. Upon completion, the solution was poured into ethyl acetate (250 mL) and washed with brine (3×200 mL). The ethyl acetate layer was dried on magnesium sulfate, filtered and concentration to dryness. Purification by column chromatography (5%→7.5%→10%→15% MeOH in CH$_2$Cl$_2$) afforded 19 as a pale orange foam (1.5 g, 94%). Rf (0.25, 10% MeOH—CH$_2$Cl$_2$).

Step 16. Preparation of Compound 20

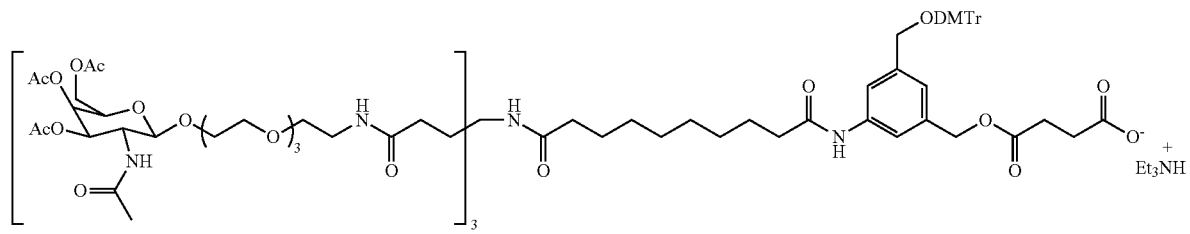

A solution of compound 19 (1.5 g, 0.6 mmol), succinic anhydride (120 mg, 1.2 mmol), DMAP (220 mg, 1.8 mmol) and trimethylamine (250 μL, 1.8 mmol) in anhydrous CH$_2$Cl$_2$ (50 mL) was stirred overnight at room temperature. Upon completion, the solution was concentrated to dryness and filtered through a short plug of silica (100% CH$_2$Cl$_2$→15% MeOH in CH$_2$Cl$_2$) to afford the product 20 as a light beige foam (1.1 g, 70%). Mass m/z (ES-TOF MS) 727.7 [M+3H−DMTr]$^+$, 1091.1 [M+2H−DMTr]. $^1$H NMR (400 MHz, CDCl$_3$) 8.92 (br s, 1H), 7.78 (s, 1H), 7.49-7.47 (m, 3H), 7.41 (br s, 1H), 7.38-7.34 (m, 5H), 7.32-7.26 (m, 4H), 7.24-7.08 (br s, 3H), 7.08 (s, 1H), 6.90-6.80 (m, 7H), 5.31 (d, 3H, J=2.7 Hz), 5.12 (s, 2H), 5.06 (dd, 3H, J=11.2, 3.2 Hz), 4.78 (d, 3H, J=8.5 Hz), 4.24-4.08 (m, 12H), 3.95-3.88 (m, 7H), 3.85-3.76 (m, 4H), 3.78 (s, 6H), 3.68-3.56 (m, 34H), 3.54-3.44 (m, 8H), 3.41-3.33 (m, 6H), 2.70-2.60 (m, 4H), 2.52-2.30 (m, 30H), 2.24-2.16 (m, 8H), 2.14 (s, 9H), 2.04 (s, 9H), 2.02-1.96 (m, 6H), 1.98 (s, 9H), 1.96 (s, 9H), 1.74-1.52 (m, 4H), 1.36-1.24 (m, 12H).

Step 17. Preparation of Conjugate 1

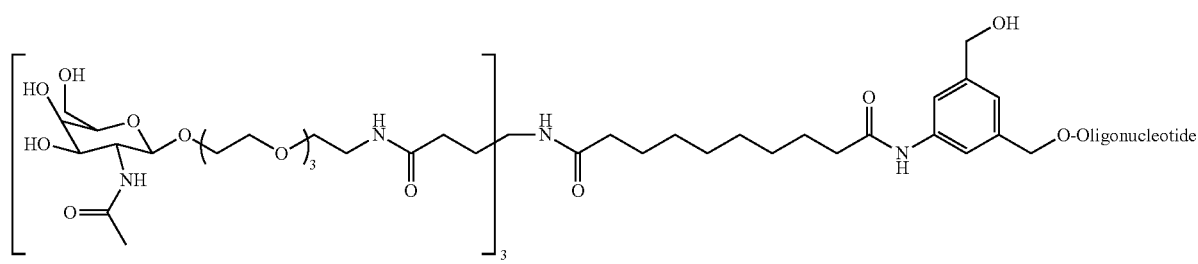

The succinate 20 was loaded onto 1000 Å LCAA (long chain aminoalkyl) CPG (control pore glass) using standard amide coupling chemistry. A solution of diisopropylcarbodiimide (52.6 μmol), N-hydroxy succinimide (0.3 mg, 2.6 μmol) and pyridine (10 μL) in anhydrous acetonitrile (0.3 mL) was added to 20 (20.6 mg, 8 μmol) in anhydrous dichloromethane (0.2 mL). This mixture was added to LCAA CPG (183 mg). The suspension was gently mixed overnight at room temperature. Upon disappearance of 20 (HPLC), the reaction mixture was filtered and the CPG was washed with 1 mL of each dichloromethane, acetonitrile, a solution of 5% acetic anhydride/5% N-methylimidazole/5% pyridine in THF, then THF, acetonitrile and dichloromethane. The CPG was then dried overnight under high vacuum. Loading was determined by standard DMTr assay by UV/Vis (504 nm) to be 25 μmol/g. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 1 as a representative example.

Example 2: Synthesis of Conjugate 34
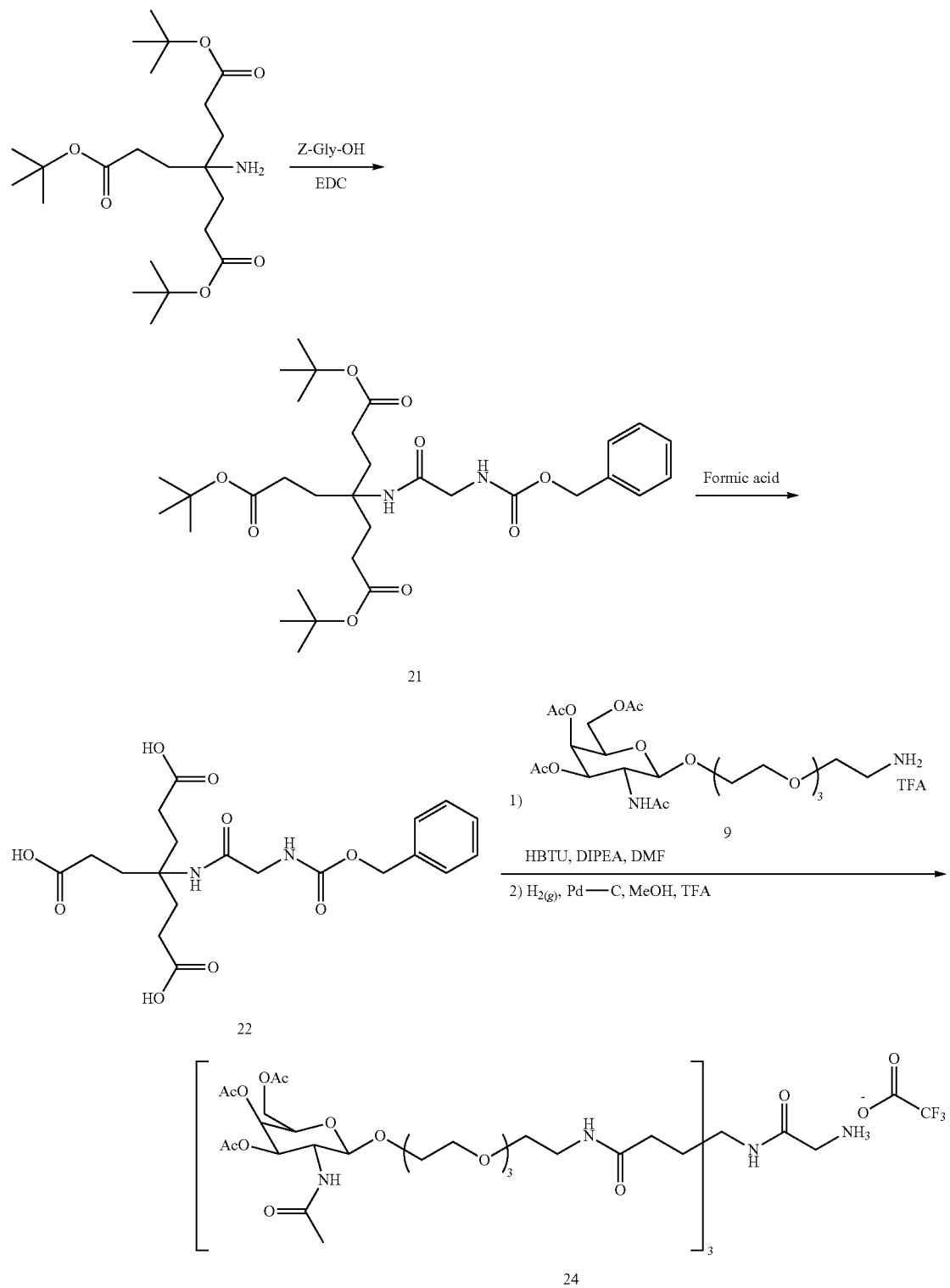
Scheme 6.

Scheme 7.
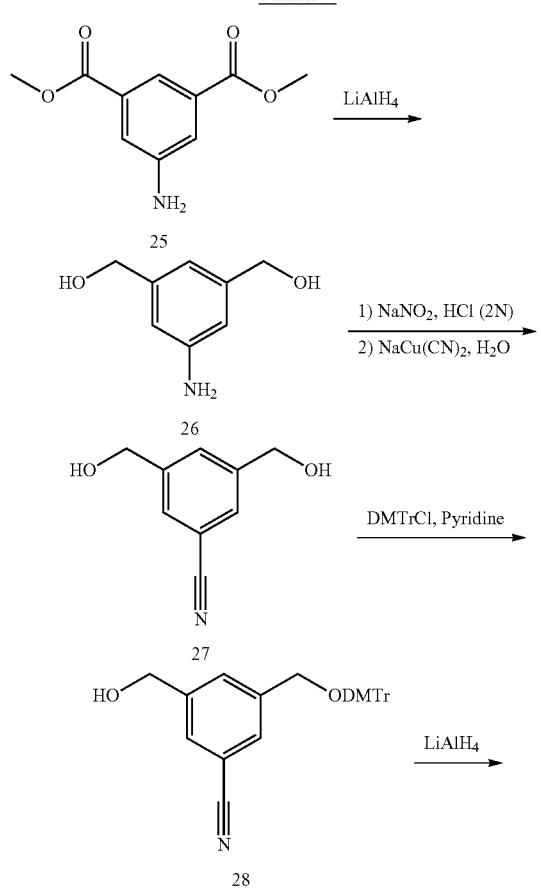
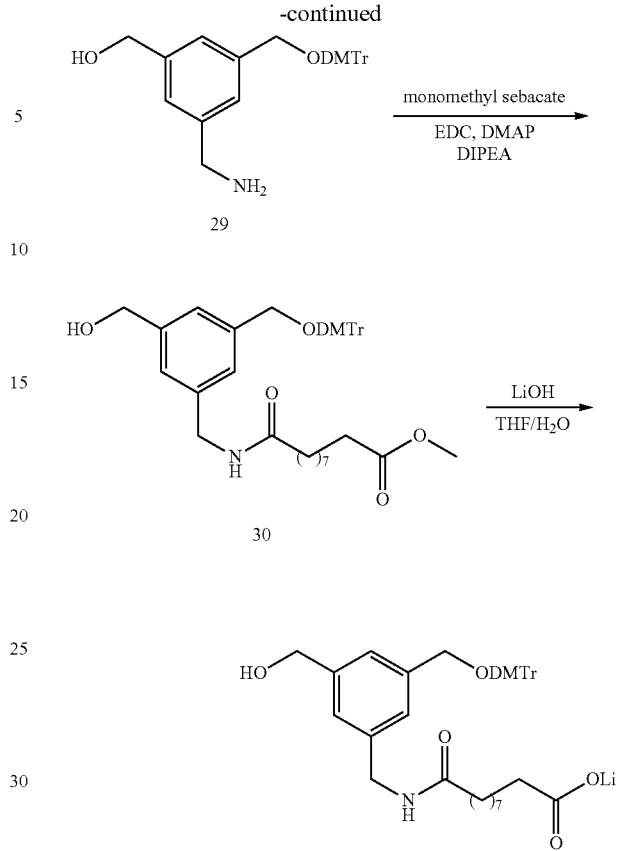
Scheme 8.
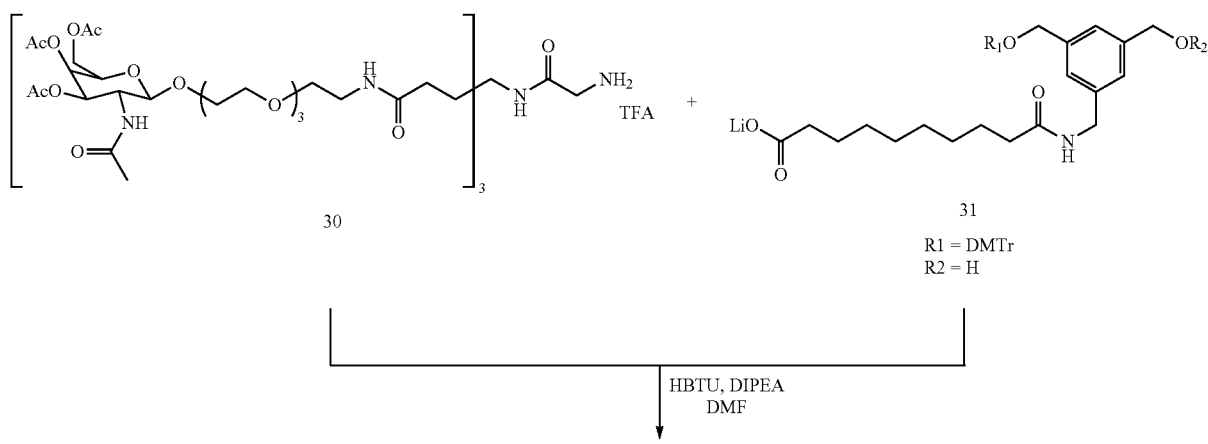

-continued

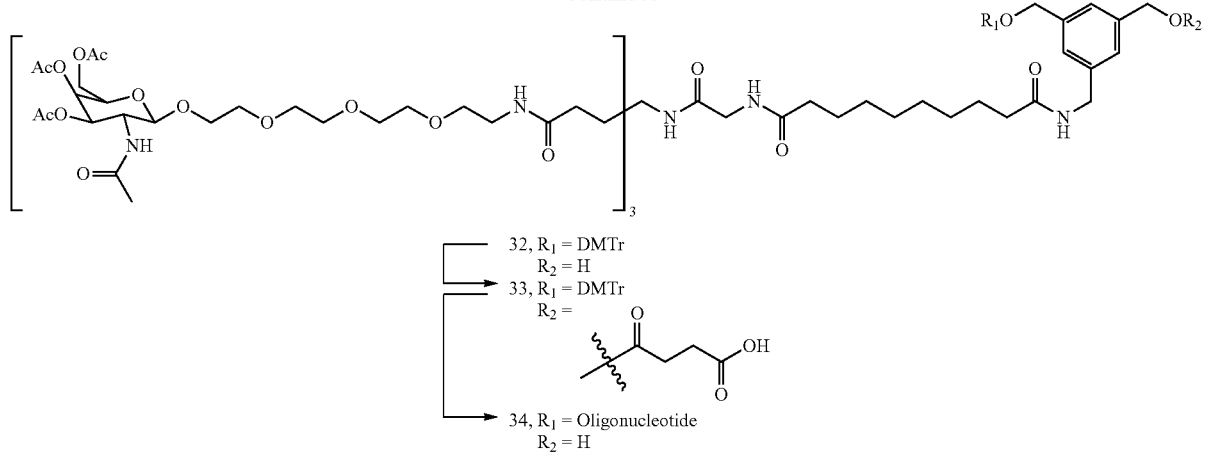

32, R₁ = DMTr, R₂ = H
33, R₁ = DMTr, R₂ = [levulinyl group]
34, R₁ = Oligonucleotide, R₂ = H Step 1. Preparation of di-tert-butyl 4-(2-(((benzyloxy)carbonyl)amino)acetamido)-4-(3-(tert-butoxy)-3-oxopropyl)heptanedioate 21

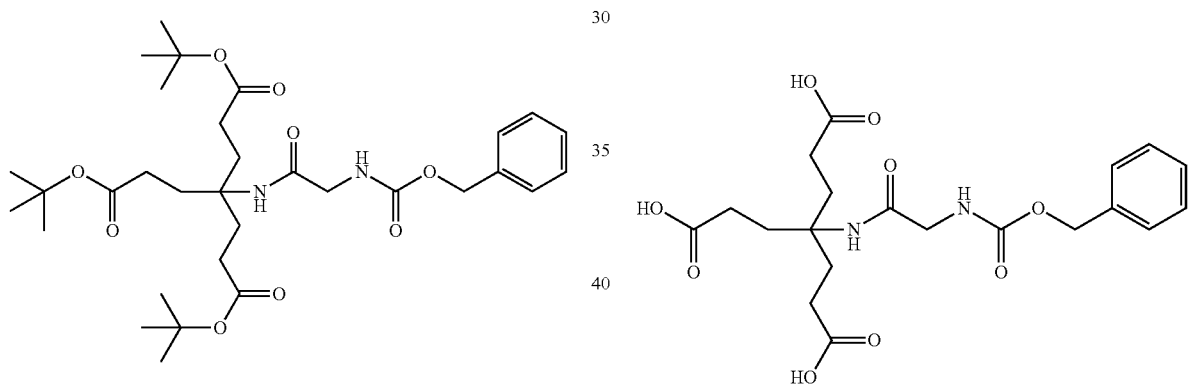

A solution of di-tert-butyl 4-amino-4-(3-(tert-butoxy)-3-oxopropyl)heptanedioate (25 g, 60 mmol) and Z-glycine (18.9 g, 90.2 mmol) in CH₂Cl₂ (300 mL) was treated successively with EDC (23 g, 120 mmol), Diisopropylethylamine (32 mL, 180 mmol) and DMAP (Cat. 17 mg). After stirring (16 h) the reaction mixture was poured into NaHCO₃ (Sat. Aq.), extracted with CH₂Cl₂, washed with brine, dried (MgSO₄), filtered and concentrated to afford di-tert-butyl 4-(2-(((benzyloxy)carbonyl)amino)acetamido)-4-(3-(tert-butoxy)-3-oxopropyl)heptanedioate 21 as an amorphous solid and was used without further processing (36 g, quant.). Rf (0.85, 10% MeOH—CH₂Cl₂).

Step 2. Preparation of 4-(2-(((benzyloxy)carbonyl)amino)acetamido)-4-(2-carboxyethyl)heptanedioic acid 22

A solution of di-tert-butyl 4-(2-(((benzyloxy)carbonyl)amino)acetamido)-4-(3-(tert-butoxy)-3-oxopropyl)heptanedioate 21 (59.3 mmol, 36 g) was stirred in neat formic acid (150 mL) for 72 hours. Upon completion, the formic acid was removed under reduced pressure and the crude solid was dried overnight on high-vacuum to yield 22 as a colorless solid (15.9 g, 61%). Rf (0.15, 10% MeOH—CH₂Cl₂).

Step 3. Preparation of Compound 23

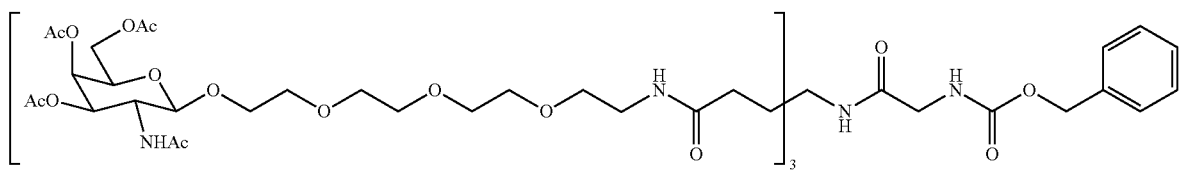

A solution of 22 (6.2 g, 14.1 mmol) and 2-(2-(2-(2-(((2R,3R,4R,5R,6R)-3-acetamido-4,5-diacetoxy-6-(acetoxymethyl)tetrahydro-2H-pyran-2-yl)oxy)ethoxy)ethoxy)ethoxy)ethan-1-aminium 2,2,2-trifluoroacetate (35 g, 56.5 mmol) in DMF (250 mL) was treated with BOP (25 g, 56.5 mmol) then N,N-diisopropylethylamine (29 mL, 170 mmol). After stirring overnight the mixture was concentrated to dryness and subjected to chromatography (100% $CH_2Cl_2$ to 15% MeOH—$CH_2Cl_2$) to afford compound 23 (24.6 g, 89%). Rf (0.55, 15% MeOH—$CH_2Cl_2$).

Step 4. Preparation of Compound 24

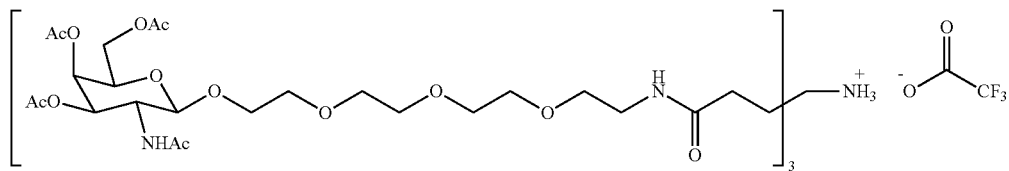

24

Compound 23 (24.6 g) was dissolved in MeOH (200 mL) and TFA (1.5 mL) and purged with nitrogen. Palladium on charcoal (1 g, 10% w/w wet basis) was added and then the reaction mixture was purged with hydrogen and stirred vigorously overnight. Upon completion, the reaction was purged with nitrogen, filtered through Celite and rinsed with MeOH. The filtrate was concentrated and purified by column chromatography on silica gel 60 (gradient: 5%→10%→20% MeOH—$CH_2Cl_2$) to afford 24 as a pale brown viscous oil (23 g). Rf (0.32, 10% MeOH—$CH_2Cl_2$).

Step 5. Preparation of (5-amino-1,3-phenylene)dimethanol 26

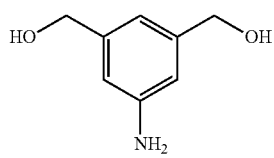 [SMILES: Nc1cc(CO)cc(CO)c1]

A suspension of lithium aluminum hydride (13.6 g, 358 mmol) in anhydrous tetrahydrofuran (450 mL) was brought to reflux under a nitrogen atmosphere and treated, dropwise, with a solution of dimethyl-5-aminoisophthalte 25 (20 g, 96 mmol) in anhydrous tetrahydrofuran (350 mL). After the addition was complete the mixture was heated to reflux for an additional 2 hours. Upon completion, the solution was cooled to room temperature and quenched by the slow addition of MeOH (27 mL) then water (40 mL). After stirring for 2 hours the mixture was filtered, concentrated and recrystallized from EtOAc to yield (5-amino-1,3-phenylene)dimethanol 26 as off-white crystals (10.2 g, 70%). Rf 0.5 (15% MeOH—$CH_2Cl_2$).

Step 6. Preparation of 3,5-bis(hydroxymethyl)benzonitrile 27

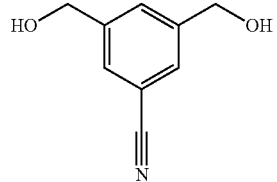 [SMILES: N#Cc1cc(CO)cc(CO)c1]

A solution of 26 (5 g, 33 mmol) in 2N hydrochloric acid (100 mL) was cooled to 0° C. and treated with a cold solution of sodium nitrite (3.53 g, 36 mmol) in water (50 mL). The reaction mixture was maintained at a temperature ≤5° C. for 30 min then treated with a solution of copper(I) cyanide (3.19 g, 35.6 mmol) and sodium cyanide (3.53 g, 72 mmol) in water (50 mL) in a single portion. After stirring overnight at room temperature the mixture was filtered, extracted with dichloromethane (3×100 mL), concentrated and used without further purification. The diol, 3,5-bis(hydroxymethyl)benzonitrile 27 was obtained as a yellow solid (2.19 g, 41%). Rf 0.75 (15% MeOH—$CH_2Cl_2$).

Step 7. Preparation of 3-((bis(4-methoxyphenyl)(phenyl)methoxy)methyl)-5-(hydroxymethyl)benzonitrile 28

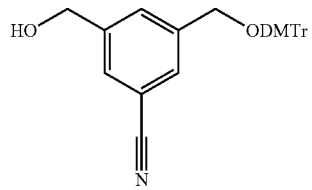

A solution of 3,5-bis(hydroxymethyl)benzonitrile 27 (538 mg, 3.3 mmol) in pyridine (14 mL) was treated with 4,4'-Dimethoxytrityl chloride (1.17 g, 3.46 mmol) and stirred overnight at room temperature. Once complete, the mixture was concentrated and dispersed in diethyl ether (25 mL), filtered and concentrated. The crude product was purified by column chromatography of silica gel 60 (gradient: 10% to 50% EtOAc-Hexane) to yield the 28 as a yellow solid (725 mg, 47%). Rf 0.5 (1:1 EtOAc-hexane).

Step 8. Preparation of (3-(aminomethyl)-5-((bis(4-methoxyphenyl)(phenyl)methoxy)methyl)phenyl) methano 29

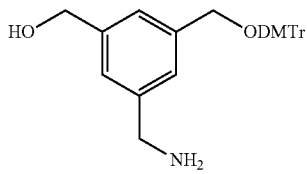

A solution of the 28 (100 mg, 0.22 mmol) in methyl tetrahydrofuran (5 mL) was cooled to 0° C. and treated slowly with lithium aluminum hydride (0.64 mmol=0.28 mL of a 2.3M solution in MeTHF). After stirring for one hour the reaction was quenched by the addition of methanol (1 mL) then water (0.3 mL) and stirred for 30 min. The mixture was filtered and concentrated, to yield (3-(aminomethyl)-5-((bis(4-methoxyphenyl)(phenyl)methoxy)methyl)phenyl) methanol 29 (78 mg, 77%). Rf 0.15 (10% MeOH—$CH_2Cl_2$).

Step 9. Preparation of methyl 10-((3-((bis(4-methoxyphenyl)(phenyl)methoxy)methyl)-5-(hydroxymethyl)benzyl)amino)-10-oxodecanoate 30

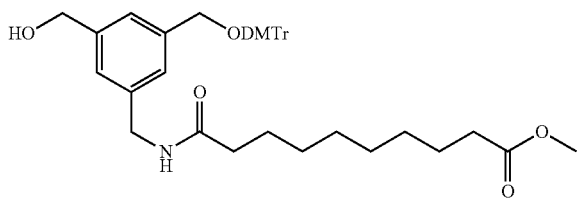

A solution of (3-(aminomethyl)-5-((bis(4-methoxyphenyl)(phenyl)methoxy)-methyl)phenyl)methanol 29 (78 mg, 0.17 mmol) and monomethyl sebacate (38 mg, 0.17 mmol) in dichloromethane (5 mL) were treated successively with EDC (48 mg, 0.25 mmol), DMAP (cat., 5 mg) and diisopropylethylamine (57 µL, 0.33 mmol). After stirring (3.5 hr) the reaction mixture was poured into saturated sodium bicarbonate solution (50 mL). The sodium bicarbonate solution was extracted with dichloromethane (3×50 mL), washed with brine (50 mL), dried on magnesium sulfate, filtered and concentrated to dryness. The crude material was purified by column chromatography on silica gel 60 (gradient: 2% to 5% MeOH—$CH_2Cl_2$) to afford methyl 10-((3-((bis(4-methoxyphenyl)(phenyl)methoxy)methyl)-5-(hydroxymethyl)benzyl)amino)-10-oxodecanoate 30 as a yellow oil (57 mg, 53%). Rf 0.45 (10% MeOH—$CH_2Cl_2$).

Step 10. Preparation of lithium 10-((3-((bis(4-methoxyphenyl)(phenyl)methoxy)methyl)-5-(hydroxymethyl)benzyl)amino)-10-oxodecanoate 31

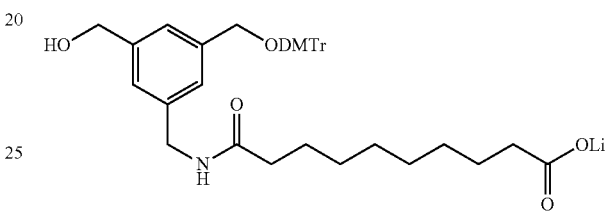

Compound 30 (188 mg, 0.28 mmol) was dissolved in tetrahydrofuran (5 mL) and treated with a solution of LiOH (7 mg, 0.30 mmol) in water (1 mL). Upon completion, the tetrahydrofuran was removed in vacuo and the remaining aqueous mixture was frozen and lyophilized to afford lithium 10-((3-((bis(4-methoxyphenyl)(phenyl)methoxy)methyl)-5-(hydroxymethyl)benzyl)amino)-10-oxodecanoate 31 as a colorless solid (180 mg, 99%). Rf 0.45 (10% MeOH—$CH_2Cl_2$).

Step 11. Preparation of Compounds 32, 33, and 34

Compounds 32, 33 and 34 were prepared according to same procedure used to synthesize compounds 19, 20, and 1 respectfully.

Example 3. Synthesis of Conjugate 36

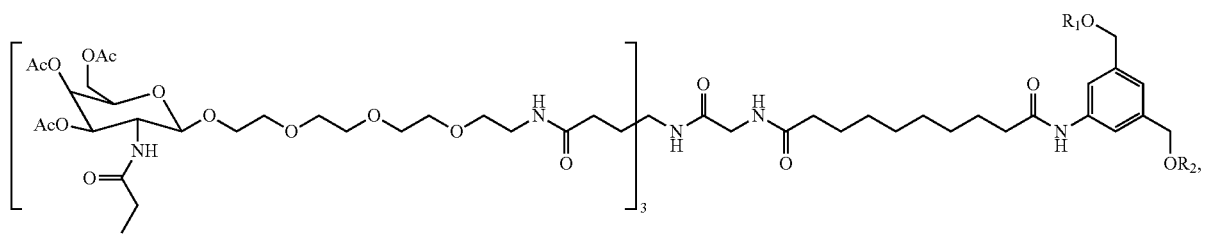

36

$R_1$ = Oligonucleotide
$R_2$ = H

Step 1. Preparation of Conjugate 36
Conjugate 36 was prepared using identical procedures as used to synthesize compound 34 and all corresponding intermediates. The only exception being the synthesis of compound 6 where propanoic anhydride was used in place of acetic anhydride.
Example 4. Synthesis of Conjugate 42
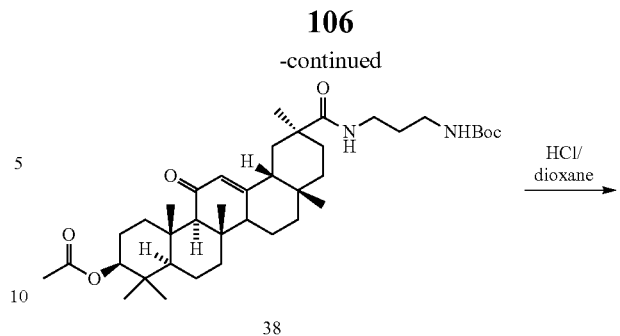
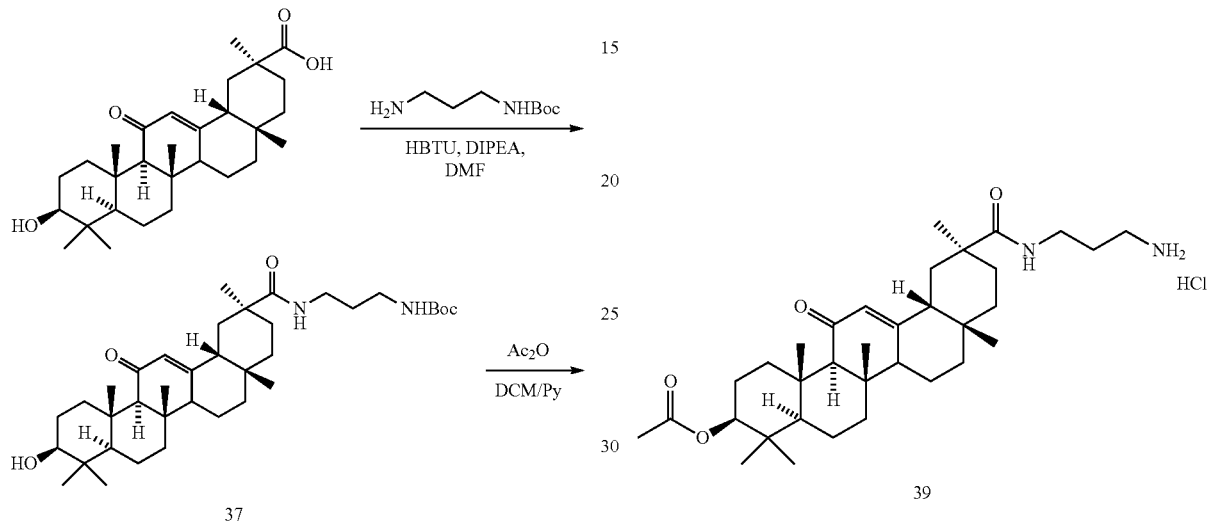
Scheme 9.
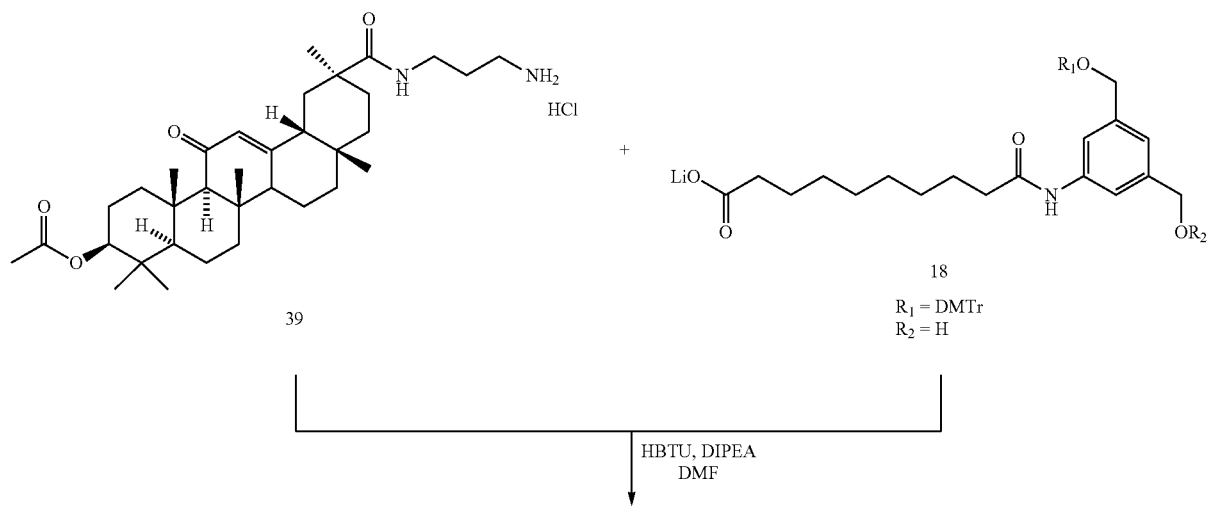
Scheme 10.

-continued

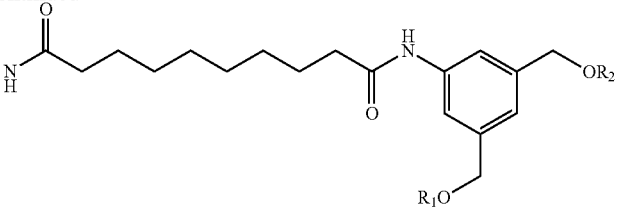

40, R₁ = DMTr
R₂ = H

41, R₁ = DMTr
R₂ = 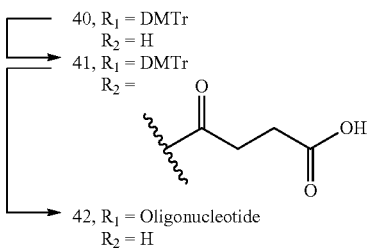

42, R₁ = Oligonucleotide
R₂ = H

Step 1. Preparation of Compound 37

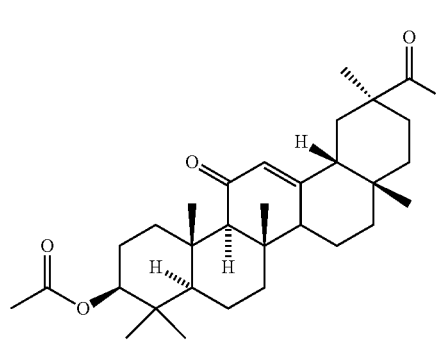

A solution of 18β-glycyrrhetinic acid (2.5 g, 5.3 mmol), tert-butyl (3-aminopropyl)carbamate (1.1 g, 6.4 mmol) and HBTU (3.0 g, 8.0 mmol) in N,N-dimethylformamide (20 mL) was added diisopropylethylamine (2.75 mL, 15.9 mmol). The solution was stirred overnight at room temperature. Upon completion, the solution was concentrated in vacuo to dryness. The residue was purified by column chromatography on silica gel 60 (gradient: 2% to 5% MeOH/CH₂Cl₂) to afford the product as a colorless solid (2.1 g, 63%).

Step 2. Preparation of Compound 38

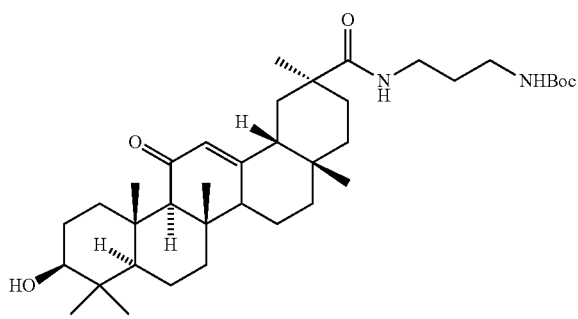

To a solution of 37 (2.1 g, 3.3 mmol) and triethylamine (3.5 mL, 10 mmol) in dichloromethane (25 mL) was added acetic anhydride (850 μL, 5.3 mmol) and DMAP (5 mg). The solution was stirred overnight at room temperature. Upon completion, the solution was concentrated to dryness and dissolved in ethyl acetate (100 mL), washed with water (100 mL), dried on magnesium sulfate, filtered and concentrated to dryness to afford a pale brown foam (1.9 g, 85%).

Step 3. Preparation of Compound 39

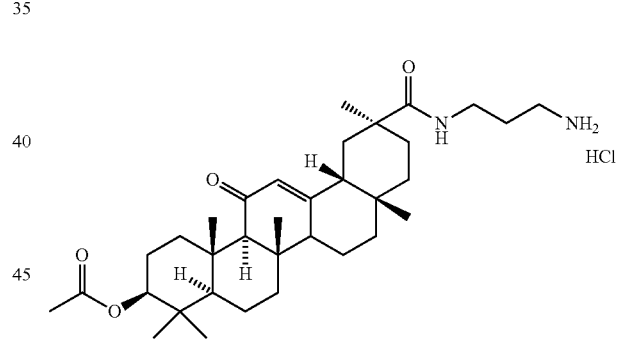

To a solution of 38 (1.5 g, 2.3 mmol) in anhydrous dioxane (25 mL) was added 2M Hydrogen chloride in dioxane (25 mL). The solution was stirred overnight at room temperature then concentrated in vacuo to dryness to afford a light brown solid (1.3 g, 96%).

Step 4. Preparation of Compounds 40, 41 and 42

Compounds 40, 41 and 42 were prepared according to the same procedure used to synthesize compounds 19, 20, and 1 respectfully.

Example 5. Synthesis of Conjugate 43
Scheme 11.
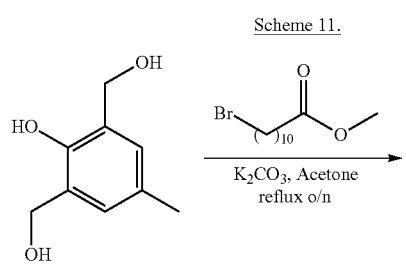
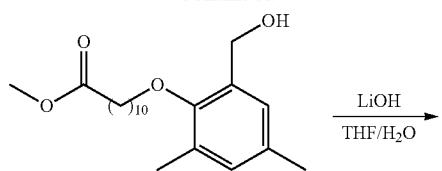
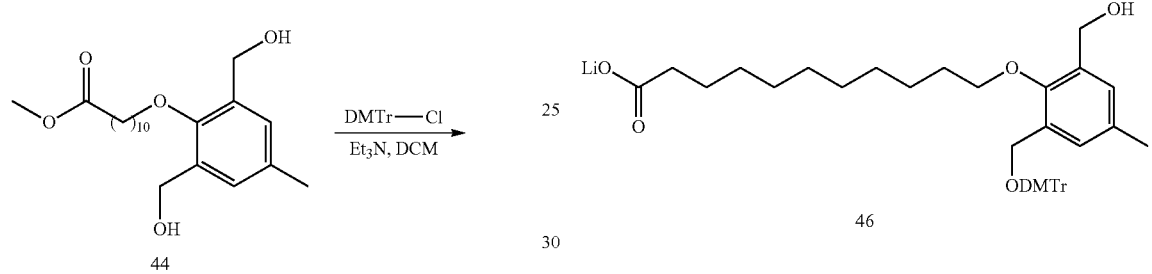
Scheme 12.
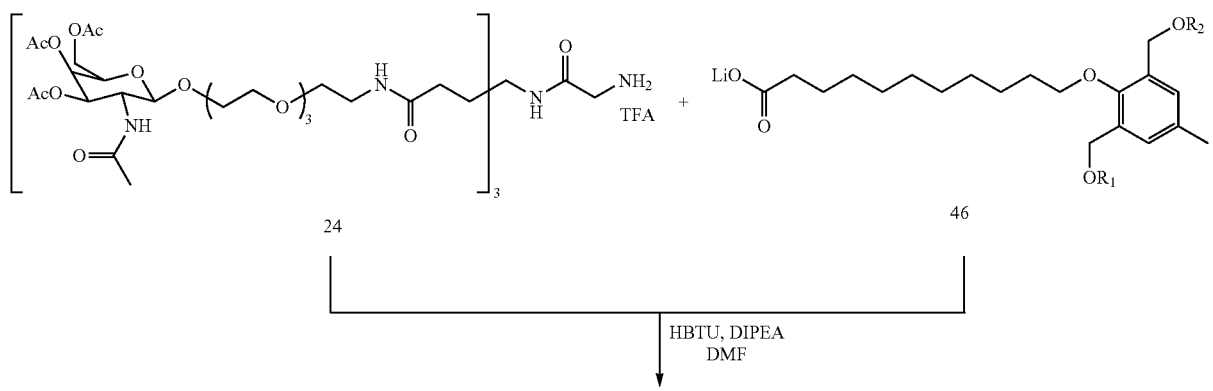

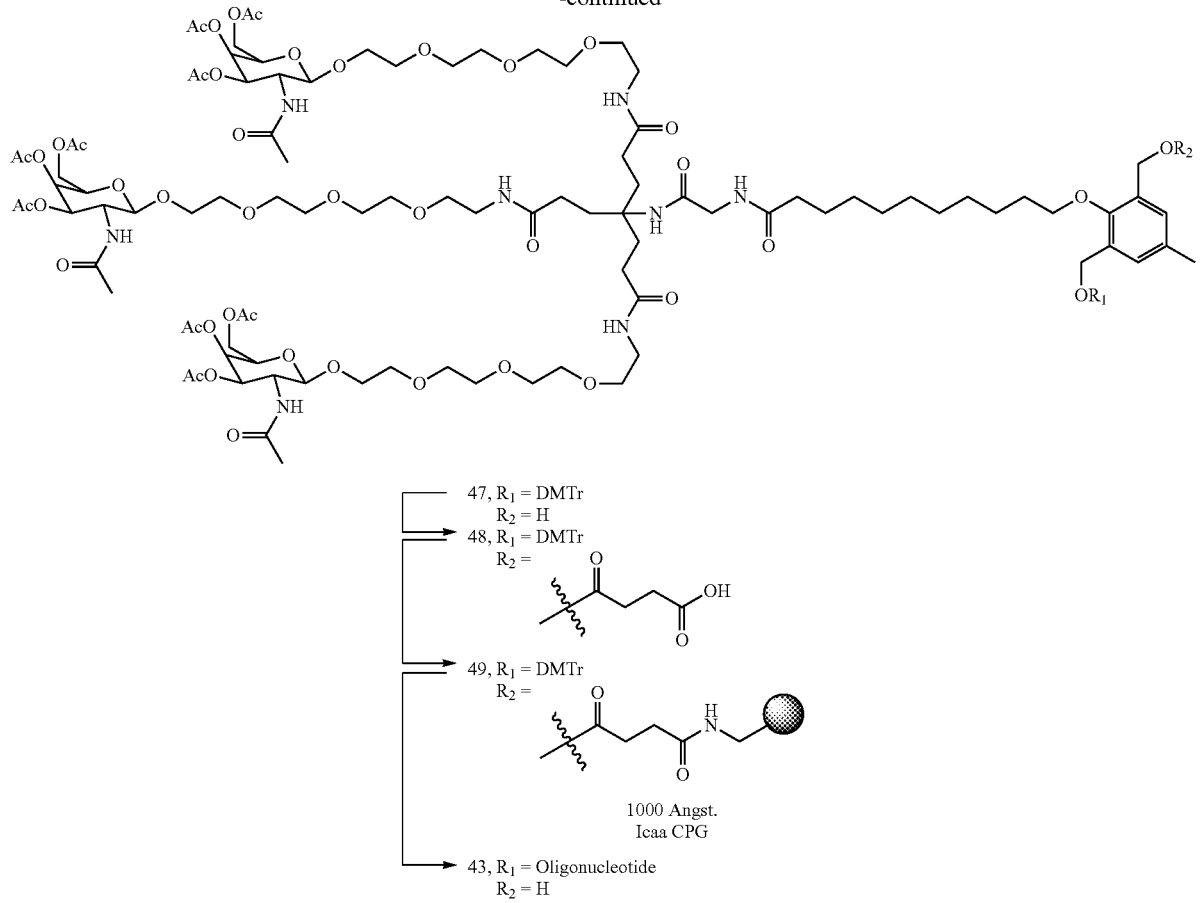

- 47, R₁ = DMTr, R₂ = H
- 48, R₁ = DMTr, R₂ = 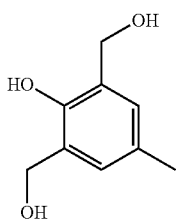
- 49, R₁ = DMTr, R₂ = 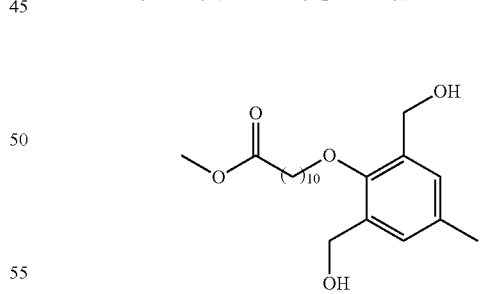

1000 Angst. lcaa CPG

- 43, R₁ = Oligonucleotide, R₂ = H

Step 1. Preparation of methyl 11-(2,6-bis(hydroxymethyl)-4-methylphenoxy)undecanoate To a solution of 2,6-bis(hydroxymethyl)-p-cresol (2.7 g, 16.3 mmol), methyl 11-bromoundecanoate (5.0 g, 17.9 mmol) and potassium carbonate (4.5 g, 32.6 mmol) in acetone (100 mL) was refluxed for 16 hours. Upon completion the solution was concentrated in vacuo to dryness, suspended in ethyl acetate (150 mL) and washed with water (2×100 mL) and brine (100 mL). The ethyl acetate layer was dried on magnesium sulfate, filtered and concentrated in vacuo to dryness. The residue was purified by column chromatography on silica gel 60 (gradient 100% Hex→50% EtOAc/Hex) to afford methyl 11-(2,6-bis(hydroxymethyl)-4-methylphenoxy)undecanoate 44 as a colorless oil (1.6 g, 27%).

Step 2. Preparation of methyl 11-(2-((bis(4-methoxyphenyl)(phenyl)methoxy)methyl)-6-(hydroxymethyl)-4-methylphenoxy)undecanoate 45

To a solution of methyl 11-(2,6-bis(hydroxymethyl)-4-methylphenoxy)undecanoate 44 (1.5 g, 4.1 mmol) in anhydrous pyridine (20 mL) was added 4,4'-Dimethoxytrityl chloride (1.4 g, 4.1 mmol). The solution was stirred overnight at room temperature. Upon completion the solution was concentrated in vacuo to dryness and purified by column chromatography on silica gel 60 (0.5 to 1% MeOH in CH₂Cl₂) to afford Methyl 11-(2-((bis(4-methoxyphenyl)(phenyl)methoxy)methyl)-6-(hydroxymethyl)-4-methylphenoxy)undecanoate 45 as a pale yellow solid (1.1 g, 40%).

Step 3. Preparation of lithium 11-(2-((bis(4-methoxyphenyl)(phenyl)methoxy)methyl)-6-(hydroxymethyl)-4-methylphenoxy)undecanoate 46

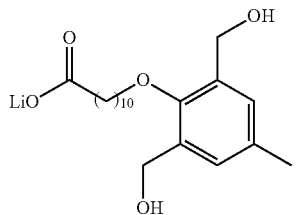

To a solution of Methyl 11-(2-((bis(4-methoxyphenyl)(phenyl)methoxy)methyl)-6-(hydroxymethyl)-4-methylphenoxy)undecanoate 45 (1.1 g, 1.7 mmol) in anhydrous tetrahydrofuran (40 mL) and water (10 mL) was added lithium hydroxide (44 mg, 1.8 mmol).

The solution was concentrated in vacuo to remove all tetrahydrofuran. The remaining aqueous solution was flash frozen on liquid nitrogen then lyophilized overnight to afford lithium 11-(2-((bis(4-methoxyphenyl)(phenyl)methoxy)methyl)-6-(hydroxymethyl)-4-methylphenoxy)undecanoate 46 as a pale pink solid (1.1 g, 94%).

Step 4. Preparation of Compound 47

A solution of 10 (1.33 g, 0.66 mmol), 46 (0.5 g, 0.73 mmol), HBTU (400 mg, 1 mmol) in N,N-dimethylformamide (25 mL) was added diisopropylethylamine (0.35 mL, 2 mmol). The solution was stirred overnight (18 hours) at room temperature. Upon completion, the solvent was remove in vacuo and the residue was purified by column chromatography on silica gel (gradient: 100% $CH_2Cl_2$—5%→10%→15% MeOH in $CH_2Cl_2$) to afford 47 as a colorless solid (710 mg, 41%).

Step 5. Preparation of Compound 48

To a solution of 47 (0.71 g, 0.3 mmol), triethylamine (0.4 mL, 3.0 mmol) and polystyrene-DMAP (3 mmol/g loading, 200 mg, 0.6 mmol) in dichloromethane (15 mL) was added succinic anhydride (60 mg, 0.6 mmol). The solution was stirred overnight at room temperature and upon completion filtered and concentrated in vacuo to dryness. The residue was purified by column chromatography on silica gel 60 (gradient 5% to 20% MeOH in $CH_2Cl_2$) to afford the 48 as a pale yellow solid (570 mg, 70%). $^1$H NMR (DMSO-$d_6$, 400 MHz) δ 7.91 (m, 1H), 7.86-7.76 (m, 6H), 7.45-7.40 (m, 2H), 7.36-7.14 (m, 10H), 7.10 (s, 1H), 6.91 (d, J=8.9 Hz, 4H), 5.21 (d, J=3.3 Hz, 3H), 5.01 (s, 2H), 4.97 (dd, J=11.2, 3.4 Hz, 3H), 4.56 (d, J=8.5 Hz, 3H), 4.06-3.98 (m, 11H), 3.93-3.84 (m, 3H), 3.81-3.72 (m, 3H), 3.74 (s, 6H), 3.65-3.46 (m, 38H), 3.40-3.35 (m, 6H), 3.20-3.16 (m, 6H), 2.56-2.44 (m, 4H), 2.33 (s, 3H), 2.15-2.08 (m, 2H), 2.10 (s, 9H), 2.04-1.96 (m, 6H), 1.89 (s, 9H), 1.82-1.76 (m, 4H), 1.77 (s, 9H), 1.54-1.34 (m, 4H), 1.28-1.10 (m, 12H).

Step 6. Preparation of Compound 49

To a solution of 48 (100 mg, 40 μmol), N-Hydroxysuccinimide (30 mg/mL soln in acetonitrile, 50 μL, 13 μmol), N,N-Diisopropylcarbodiimide (40 μL, 264 μmol) and pyridine (50 μL) in dichloromethane (2 mL) and acetonitrile (3 mL) was added 1000 Å lcaa CPG (prime synthesis, 920 mg). The solution was stirred overnight at room temperature on an orbital shaker. TLC analysis of the reaction solution showed only partial consumption of the activated N-Hydroxysuccinic ester so additional CPG (500 mg) was added. The solution was stirred again overnight. Upon completion, the CPG was filtered and washed with dichloromethane (25 mL), acetonitrile (25 mL) and tetrahydrofuran (25 mL). The unreacted amine residues on the CPG were acetylated (capped) by adding a 1:1 solution of acetic anhydride in acetonitrile (3 mL) and 10% N-methylimidazole/10% pryridine in tetrahydrofuran (3 mL). The suspension was left for 2 hours then filtered and rinsed with equal parts tetrahydrofuran (25 mL), acetonitrile (25 mL) and dichloromethane (25 mL). The loaded CPG 49 was dried under high vacuum overnight. The ligand loading efficiency was determined to be 22 μmole/g using a standard DMT loading assay (3% trichloroacetic acid in $CH_2Cl_2$, UV-VIS, $A_{504}$).

Step 7. Preparation of Conjugate 43

The resulting GalNAc loaded CPG solid support 49 was employed in automated oligonucleotide synthesis using standard procedures. Nucleotide deprotection followed by removal from the solid support (with concurrent galactosamine acetate deprotection) afforded a GalNAc-oligonucleotide conjugate 43.

Example 6. Synthesis of Conjugate 50

Scheme 13.

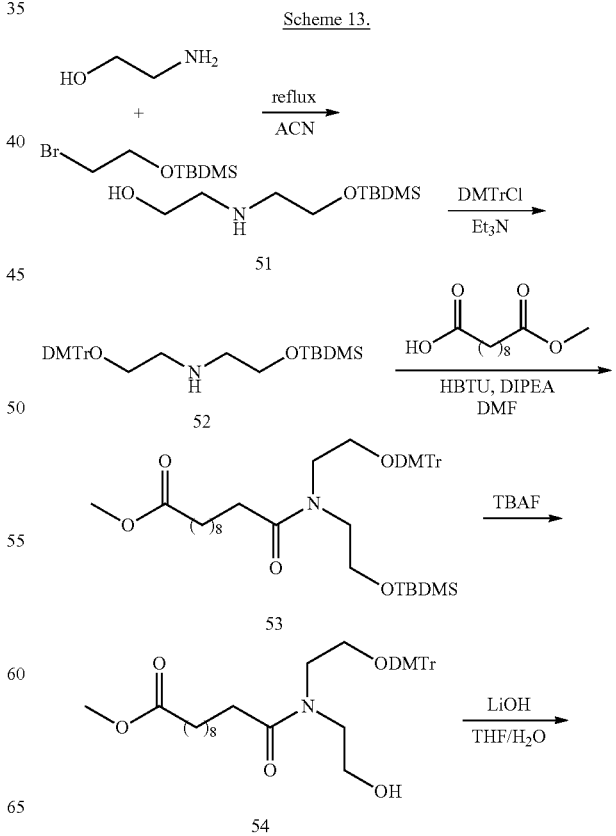

115
-continued
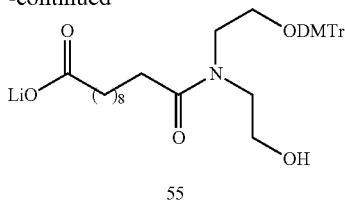
55
116
Step 1. Preparation of 2-((2-((tert-butyldimethylsi-lyl)oxy)ethyl)amino)ethan-1-ol 51
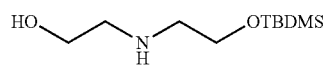
A solution of ethanolamine (77 mL, 1.25 mol) and (2-bromoethoxy)-tert-butyl dimethylsilane (15 g, 62.7 mmol) in
Scheme 14.
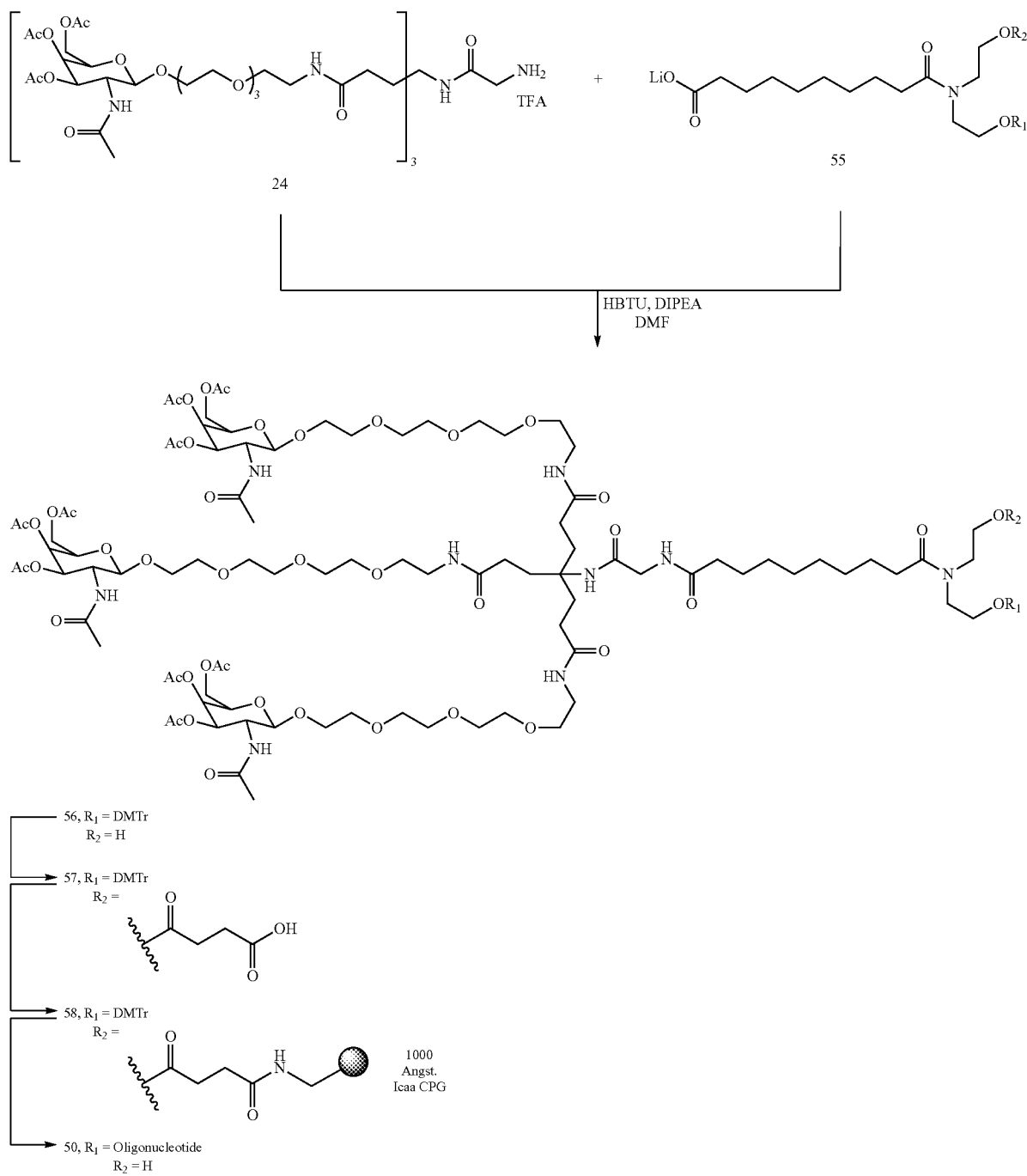

anhydrous acetonitrile (200 mL) was refluxed for 3 hours. Upon completion the reaction was cooled to room temperature, diluted with water (400 mL) and extracted with ethyl acetate (3×150 mL). The combined ethyl acetate extracts were dried on magnesium sulfate, filtered and concentrated in vacuo to dryness. The residue was purified by filtration through a pad of silica first with 50% ethyl acetate/hexanes then 50% MeOH/EtOAc to afford 51 as a pale yellow oil (14 g, 100%).

Step 2. Preparation of 2-(bis(4-methoxyphenyl) (phenyl)methoxy)-N-(2-((tert-butyldimethylsilyl) oxy)ethyl)ethan-1-amine 52

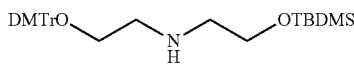

To a solution of 2-((2-((tert-butyldimethylsilyl)oxy)ethyl) amino)ethan-1-ol 51 (14 g, 64 mmol) and triethylamine (17.5 mL, 128 mmol) in anhydrous dichloromethane (250 mL) was added 4,4'-Dimethoxytrityl chloride (24 g, 70 mmol). The solution was stirred overnight at room temperature then concentrated in vacuo to dryness. The residue was dissolved in ethyl acetate (300 mL) and washed with water (250 mL) and brine (250 mL). The ethyl acetate was dried on magnesium sulfate, filtered and concentrated in vacuo to dryness. Purification by column chromatography on silica gel 60 (1% to 5% MeOH in CH$_2$Cl$_2$) afforded 52 as a pale yellow viscous oil (13 g, 39%/).

Step 3. Preparation of methyl 10-((2-(bis(4-methoxyphenyl)(phenyl)methoxy)ethyl)(2-((tert-butyldimethylsilyl)oxy)ethyl)amino)-10-oxodecanoate 53

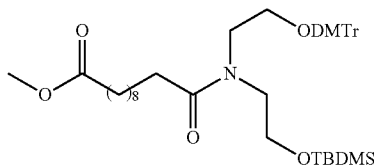

A solution of 2-(bis(4-methoxyphenyl)(phenyl)methoxy)-N-(2-((tert-butyldimethylsilyl)oxy)ethyl)ethan-1-amine 52 (5.4 g, 10.3 mmol), monomethyl sebacate (2.2 g, 10.3 g), HBTU (4.9 g, 12.9 mmol), DIPEA (5.3 mL, 30.9 mmol) in N,N-dimethylformamide (100 mL) was stirred for 3 hours at room temperature. Upon completion, the solution was poured into water (400 mL) and extracted with ethyl acetate (1×500 mL). The ethyl acetate extract was washed with brine (2×250 mL), dried on magnesium sulfate, filtered and concentrated in vacuo to dryness. Purification by column chromatography on silica gel 60 (10% to 25% ethyl acetate in hexanes) afforded 53 as a viscous yellow oil (6.5 g, 87%).

Step 4. Preparation of methyl 10-((2-(bis(4-methoxyphenyl)(phenyl)methoxy)ethyl)(2-hydroxyethyl)amino)-10-oxodecanoate 54

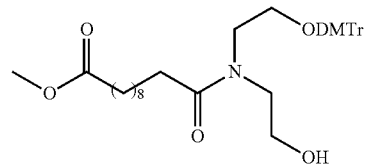

To a solution of methyl 10-((2-(bis(4-methoxyphenyl) (phenyl)methoxy)ethyl)(2-((tert-butyldimethylsilyl)oxy) ethyl)amino)-10-oxodecanoate 53 (2.0 g, 2.8 mmol) and triethylamine (1 mL) in anhydrous tetrahydrofuran (20 mL) was added TBAF (1M in THF, 3.4 mL, 3.3 mmol). The solution was stirred for 6 h, but only partial conversion observed by TLC (5% MeOH in CH$_2$Cl$_2$). Additional 1.7 mL TBAF added and the solution was stirred overnight at room temperature. Upon completion, the solution was concentrated in vacuo and purified by column chromatography on silica gel 60 (10% to 50% EtOAc in hexanes then 100%/EtOAc) to afford 54 as a viscous colorless oil (0.5 g, 29%).

Step 5. Preparation of lithium 10-((2-(bis(4-methoxyphenyl)(phenyl)methoxy)ethyl)(2-hydroxyethyl)amino)-10-oxodecanoate 55

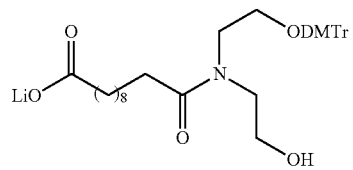

To a solution of methyl 10-((2-(bis(4-methoxyphenyl) (phenyl)methoxy)ethyl)(2-hydroxyethyl)amino)-10-oxodecanoate 54 (0.5 g, 0.83 mmol) in THF (40 mL) was added water (10 mL) and lithium hydroxide (24 mg, 1.0 mmol). The solution was stirred overnight at room temperature then concentrated in vacuo to remove the THF. The remaining aqueous solution was flash frozen on liquid nitrogen and lyophilized to afford 55 as a colorless solid (485 mg, 95%).

Step 6. Preparation of Compounds 56, 57, 58 and 50

Compounds 56, 57, 58 and 50 were prepared using the identical procedures to those used to synthesize compounds 47, 48, 49 and 43 respectfully.

Example 7. Synthesis of Conjugate 59

Scheme 15.

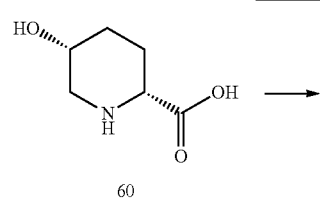

60

119
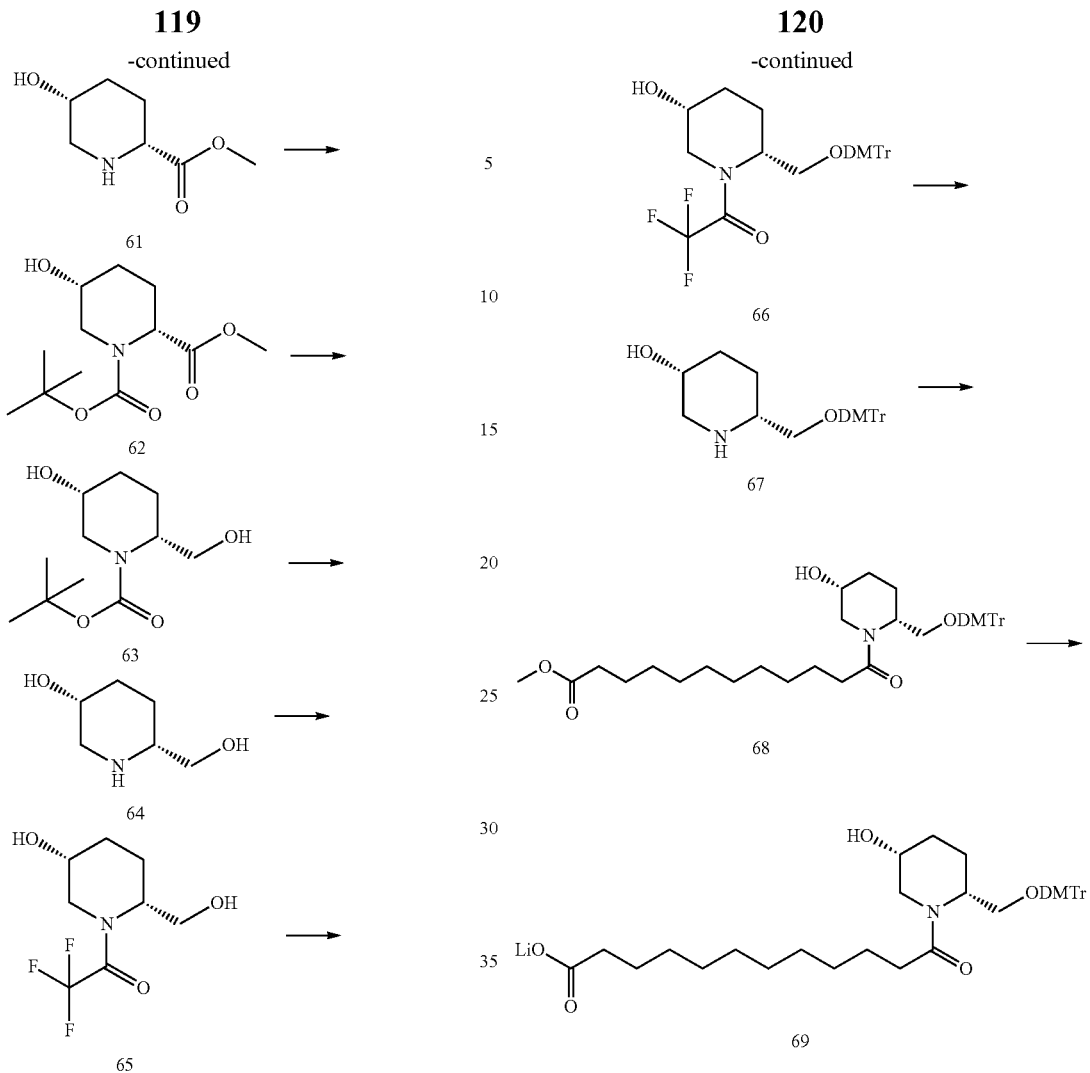
Scheme 16.
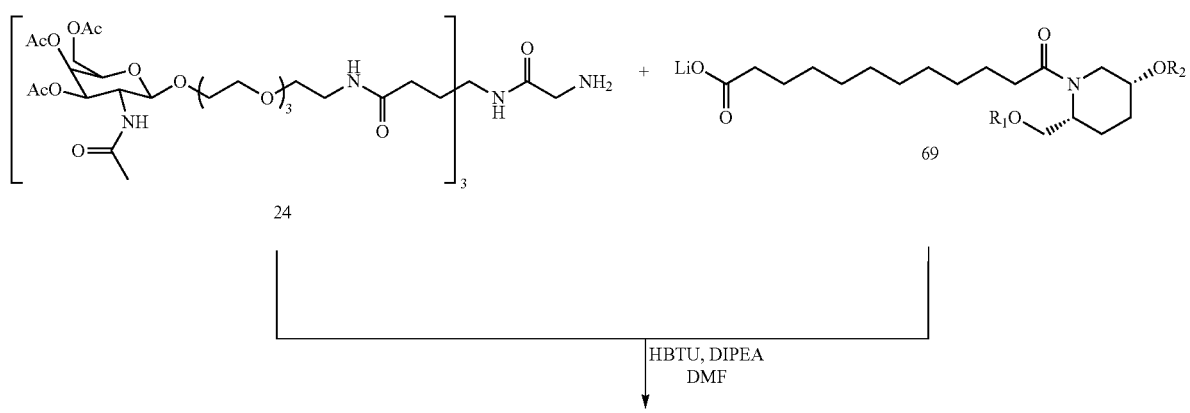

-continued

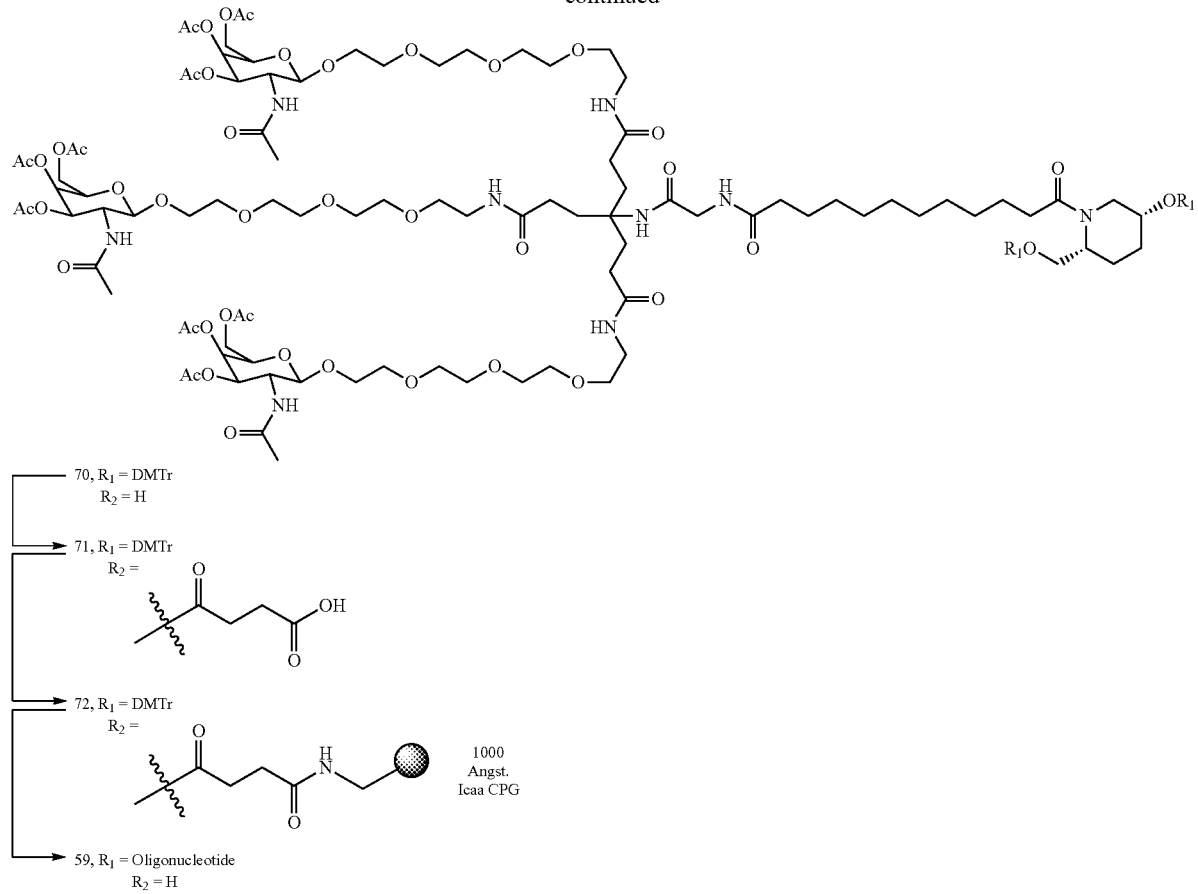

70, R₁ = DMTr
    R₂ = H

71, R₁ = DMTr
    R₂ = 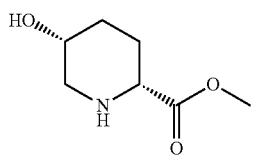

72, R₁ = DMTr
    R₂ = 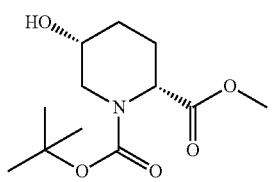 [SMILES: COC(=O)[C@H]1CC[C@@H](O)CN1C(=O)OC(C)(C)C]
    1000 Angst. lcaa CPG

59, R₁ = Oligonucleotide
    R₂ = H

Step 1. Preparation of methyl (2R,5R)-5-hydroxypiperidine-2-carboxylate 61

(2R,5R)-5-hydroxypiperidine-2-carboxylic acid 60 (3.5 g, 24.1 mmol) was stirred in MeOH (50 mL). HCl (g) was bubbled through the solution for 2 mins and the reaction stirred at reflux for 1.5 h. The reaction was concentrated in-vacuo to give methyl (2R,5R)-5-hydroxypiperidine-2-carboxylate 61 in quantitative yield which was used without further purification.

Step 2. Preparation of 1-(tert-butyl) 2-methyl (2R,5R)-5-hydroxypiperidine-1,2-dicarboxylate 62

Methyl (2R,5R)-5-hydroxypiperidine-2-carboxylate 61 (24.1 mmol) and TEA (7.2 mL, 53.02 mmol) were stirred in DCM (100 mL) at RT. Di-tert-butyl-di-carbonate (5.7 g, 26.5 mmol) was added in portions and the reaction stirred for 2 h. The reaction was diluted with DCM (100 mL) and washed sequentially with 1M HCl (2×75 mL), saturated NaHCO₃ (2×75 mL), H₂O (2×75 mL) and saturated NaCl solution (2×75 mL). The organics were separated, dried (Na₂SO₄) and concentrated in-vacuo to give 1-(tert-butyl) 2-methyl (2R,5R)-5-hydroxypiperidine-1,2-dicarboxylate 62 (5.53 g, 88%) which was used without further purification.

Step 3. Preparation of tert-butyl (2R,5R)-5-hydroxy-2-(hydroxymethyl)piperidine-1-carboxylate 63

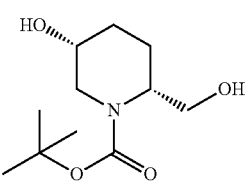 [SMILES: CC(C)(C)OC(=O)N1C[C@H](O)CC[C@@H]1CO]

(2R,5R)-1-(tert-Butoxycarbonyl)-5-hydroxypiperidine-2-carboxylic acid 62 (5.53 g, 21.4 mmol) was stirred in THF at 0° C. LiBH₄ (3.0 M solution in THF) (8.9 mL, 27.7 mmol)

was added dropwise over 1 hr. The reaction was allowed to warm to RT and stirring continued for 16 h. Reaction was quenched with 1M NaOH, THF removed in-vacuo and the aqueous exhaustively extracted with EtOAc (10×100 mL). The combined organics were washed with H$_2$O (50 mL), saturated NaCl solution (2×50 mL), dried (Na$_2$SO$_4$) and concentrated in-vacuo to give tert-butyl (2R,5R)-5-hydroxy-2-(hydroxymethyl)piperidine-1-carboxylate 63 (2.4 g, 49.0%) which was used without further purification.

Step 4. Preparation of (3R,6R)-6-(hydroxymethyl)piperidin-3-ol 64

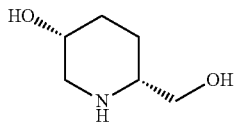

tert-Butyl (2R,5R)-5-hydroxy-2-(hydroxymethyl)piperidine-1-carboxylate 63 (2.4 g, 10.4 mmol) was stirred in Et$_2$O at RT. HCl (g) was bubbled through for 45 secs and the reaction stirred at RT for 45 mins. The reaction was concentrated in-vacuo and dried under hi-vac to afford (3R,6R)-6-(hydroxymethyl)piperidin-3-ol 64. The product was used without further purification.

Step 5. Preparation of 2,2,2-trifluoro-1-((2R,5R)-5-hydroxy-2-(hydroxymethyl)piperidin-1-yl)ethan-1-one 65

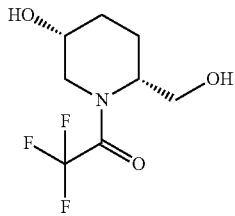

Crude (3R,6R)-6-(hydroxymethyl)piperidin-3-ol 64 from the previous reaction was stirred in MeCN (50 mL) with TEA (3.5 mL, 25.2 mmol) at RT. Ethyl trifluoroacetate (3 mL, 25.2 mmol) was added and the reaction stirred at RT for 16 hr, then concentrated in-vacuo to give 2,2,2-trifluoro-1-((2R,5R)-5-hydroxy-2-(hydroxymethyl)piperidin-1-yl)ethan-1-one 65. The product was used without further purification.

Step 6. Preparation of 1-((2R,5R)-2-((bis(4-methoxyphenyl)(phenyl)methoxy)methyl)-5-hydroxypiperidin-1-yl)-2,2,2-trifluoroethan-1-one 66

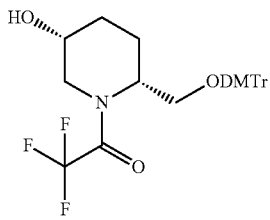

Crude 2,2,2-trifluoro-1-((2R,5R)-5-hydroxy-2-(hydroxymethyl)piperidin-1-yl)ethan-1-one 65 from the previous reaction was stirred in DCM with TEA (50 mL) at RT. 4,4'-Dimethoxytrityl chloride (DMTrCl) (3.87 g, 11.44 mmol) was added in one portion and the reaction stirred at RT for 3 hours. The reaction was diluted with DCM (50 mL) and washed sequentially with saturated NaHCO$_3$ (2×75 mL), H$_2$O (2×75 mL) and saturated NaCl solution (2×75 mL). The organics were separated, dried (Na$_2$SO$_4$), concentrated in-vacuo and purified by column chromatography (100% hexanes-60% EtOAc/Hexanes) (0.1% TEA) to give 1-((2R,5R)-2-((bis(4-methoxyphenyl)(phenyl)methoxy)methyl)-5-hydroxypiperidin-1-yl)-2,2,2-trifluoroethan-1-one 66 (3.14 g, 57%).

Step 7. Preparation of (3R,6R)-6-((bis(4-methoxyphenyl)(phenyl)methoxy)methyl)-piperidin-3-ol 67

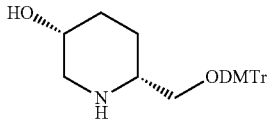

1-((2R,5R)-2-((bis(4-methoxyphenyl)(phenyl)methoxy)methyl)-5-hydroxypiperidin-1-yl)-2,2,2-trifluoroethan-1-one 66 (3.14 g, 6.0 mmol) was stirred in MeOH (50 mL) at RT. KOH (672 mg, 12 mmol) was added and the reaction stirred at RT for 16 hours. Additional KOH (300 mg, 6 mmol) was added and stirring continued for an additional 24 h. The reaction was concentrated in-vacuo, taken up in DCM (150 mL), washed with H$_2$O (4×50 mL), dried (Na$_2$SO$_4$) and concentrated in-vacuo to give (3R,6R)-6-((bis(4-methoxyphenyl)(phenyl)methoxy)methyl)piperidin-3-ol 67 (2.34 g, 90%) which was used without further purification.

Step 8. Preparation of methyl 12-((2R,5R)-2-((bis(4-methoxyphenyl)(phenyl)-methoxy)methyl)-5-hydroxypiperidin-1-yl)-12-oxododecanoate 68

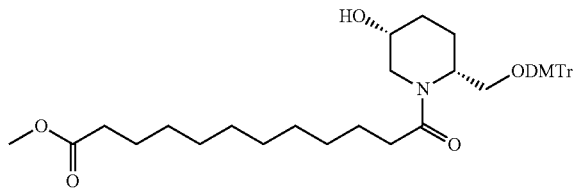

(3R,6R)-6-((Bis(4-methoxyphenyl)(phenyl)methoxy)methyl)piperidin-3-ol 67 (2.34 g, 5.34 mmol) was stirred in DCM (75 mL) at RT. Triethylamine (2.2 mL, 16.2 mmol), HATU (3.5 g, 9.2 mmol) and 12-methoxy-12-oxododecanoic acid (1.32 g, 5.4 mmol) were added and the reaction stirred at RT for 3 h. The resultant solid precipitate was removed by filtration, the filtrate concentrated in-vacuo and the residue purified by column chromatography (2.5% MeOH/DCM, 0.1% TEA) to give methyl 12-((2R,5R)-2-((bis(4-methoxyphenyl)(phenyl)methoxy)methyl)-5-hydroxypiperidin-1-yl)-12-oxododecanoate 68 in quantitative yield.

Step 9. Preparation of lithium 12-((2R,5R)-2-((bis(4-methoxyphenyl)(phenyl)methoxy)-methyl)-5-hydroxypiperidin-1-yl)-12-oxododecanoate 69

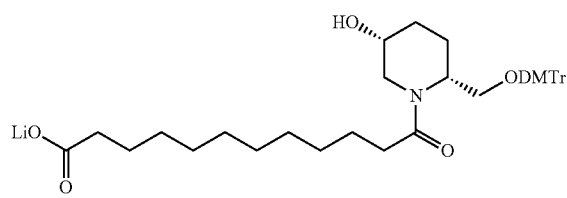

Methyl 12-((2R,5R)-2-((bis(4-methoxyphenyl)(phenyl)methoxy)methyl)-5-hydroxypiperidin-1-yl)-12-oxododecanoate 68 (5.4 mmol) and LiOH (140 mg, 5.94 mmol) were stirred in THF:H$_2$O (1:1, 100 mL) at RT for 48 h. The THF was removed in-vacuo, the aqueous frozen and lyophilized to give lithium 12-((2R,5R)-2-((bis(4-methoxyphenyl)(phenyl)methoxy)methyl)-5-hydroxypiperidin-1-yl)-12-oxododecanoate 69 (3.2 g, 91%). Which was used in subsequent reactions without additional purification.

Step 10. Preparation of Compounds 70, 71, 72, and 59

Compounds 70, 71, 72 and 59 were prepared using the identical procedures to those used to synthesize compounds 47, 48, 49 and 43 respectfully.

Example 8. Synthesis of Conjugate 142

Scheme 17.

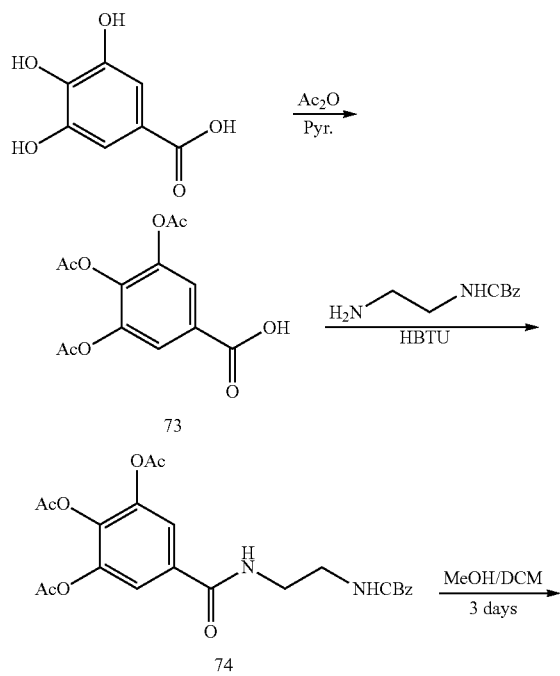

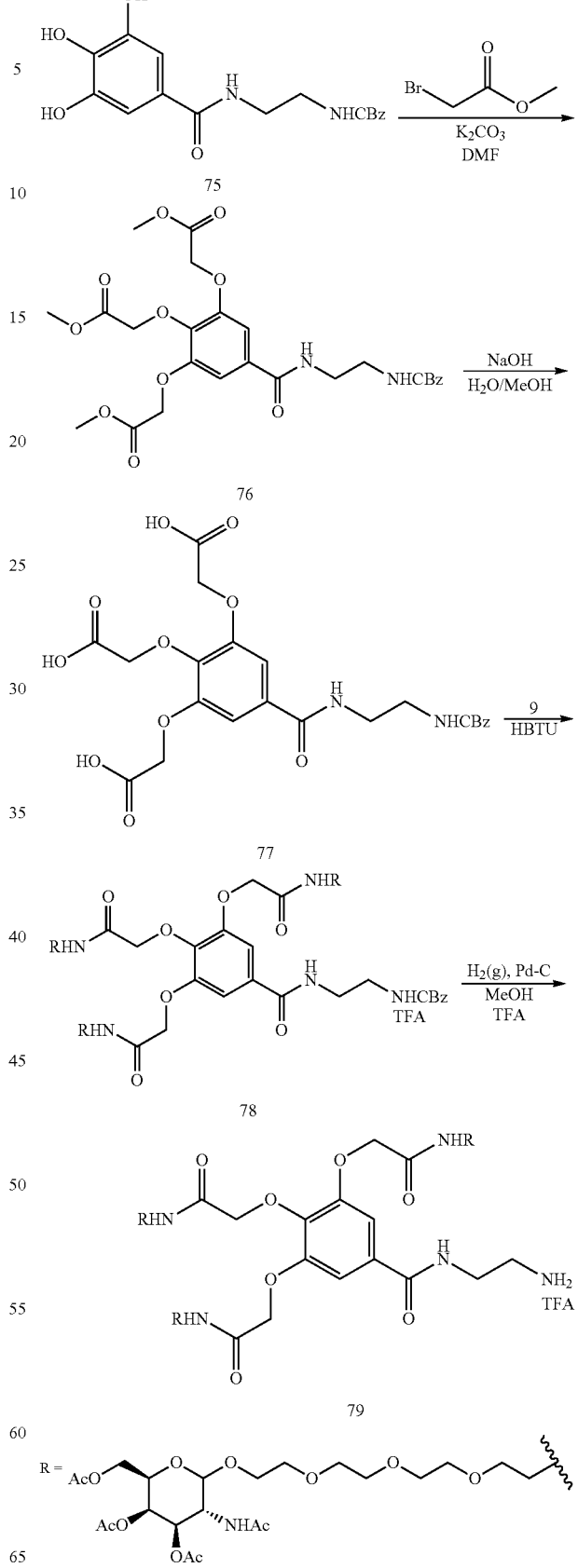

Scheme 18.

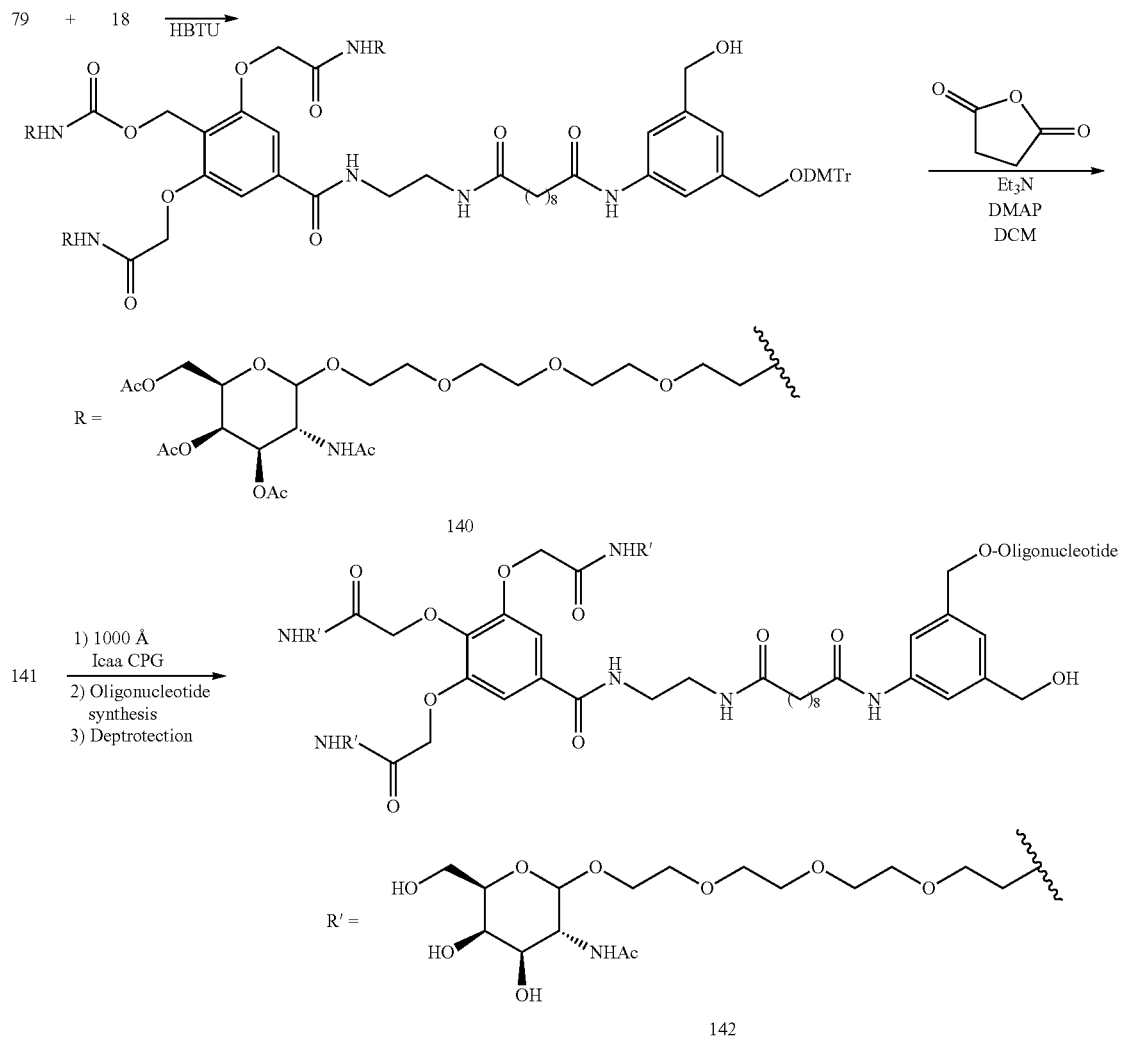

Step 1. Preparation of 3,4,5-Triacetoxybenzoic acid 73

To a solution of Gallic acid (20 g) in pyridine (50 mL) and acetic anhydride (50 mL). The solution was stirred overnight at room temperature then poured into ice water (1 L). The solution was made acidic with concentrated hydrochloric acid where upon a colorless solid precipitated. The solid was collected via filtration and washed with water (5×100 mL). The wet solid was frozen on liquid nitrogen and freeze dried to afford 3,4,5-triacetoxybenzoic acid (26 g, 75%).

Step 2. Preparation of 5-((2-((2-Oxo-2-phenyl-1λ²-ethyl)amino)ethyl)carbamoyl)benzene-1,2,3-triyl triacetate 74

To a solution of 3,4,5-triacetoxybenzoic acid (10 g, 33.8 mmol), N-carbobenzoxy-1,2-diaminoethane hydrochloride (5.3 g, 33.8 mmol) and HBTU (13.5 g, 35.5 mmol) in DMF (200 mL) was added DIPEA (17.5 mL, 101 mmol). The solution was stirred for 16 hours then diluted with ethyl acetate (250 mL), washed with brine (3×200 mL), dried on magnesium sulfate, filtered and concentrated in vacuo to dryness. The crude product was purified by column chromatography on silica gel (Gradient 1% to 5% MeOH in DCM) to afford 5-((2-((2-Oxo-2-phenyl-1λ²-ethyl)amino)ethyl)carbamoyl)benzene-1,2,3-triyl triacetate as an off white solid (5.5 g).

Step 3. Preparation of 3,4,5-Trihydroxy-N-(2-((2-oxo-2-phenyl-1λ²-ethyl)amino)ethyl)benzamide 75

A solution of 5-((2-((2-Oxo-2-phenyl-1λ²-ethyl)amino) ethyl)carbamoyl)benzene-1,2,3-triyl triacetate (5 g, 1.1 mmol) in 1:1 MeOH/CH₂Cl₂ (100 mL) was stirred for 3 days at room temperature. Upon completion the solvent was removed to afford 3,4,5-Trihydroxy-N-(2-((2-oxo-2-phenyl-1λ²-ethyl)amino)ethyl)benzamide as a colorless solid (4 g, quantitative).

Step 4. Preparation of Trimethyl 2,2',2''-((5-((2-((2-oxo-2-phenyl-1λ²-ethyl)amino)ethyl)carbamoyl) benzene-1,2,3-triyl)tris(oxy))triacetate 76

A solution of 3,4,5-Trihydroxy-N-(2-((2-oxo-2-phenyl-1λ²-ethyl)amino)ethyl)benzamide (4 g, 11.6 mmol), methyl bromoacetate (7.7 g, 46.4 mmol) and potassium carbonate (9.6 g, 69.4 mmol) in DMF (100 mL) was stirred overnight at 60° C. Upon completion the solution was cooled to room temperature, diluted with ethyl acetate (200 mL), washed with water (200 mL), brine (3×100 mL), dried on magnesium sulfate, filtered and concentrated in vacuo to dryness. The crude product was purified by column chromatography on silica gel (Gradient 2% to 10%/o MeOH in DCM) to afford trimethyl 2,2',2"-((5-((2-((2-oxo-2-phenyl-1$\lambda^2$-ethyl)amino)ethyl)carbamoyl)benzene-1,2,3-triyl)tris(oxy))-triacetate as a beige solid (5 g, 79%)

Step 5. Preparation of 2,2',2"-((5-((2-((2-Oxo-2-phenyl-1$\lambda^2$-ethyl)amino)ethyl)-carbamoyl)benzene-1,2,3-triyl)tris(oxy))triacetic acid 77

A solution of trimethyl 2,2',2"-((5-((2-((2-oxo-2-phenyl-1$\lambda^2$-ethyl)amino)ethyl)-carbamoyl)benzene-1,2,3-triyl)tris(oxy))triacetate (5 g, 9.2 mmol) and 1M NaOH (30 mL) in methanol (100 mL) was stirred for 2 hours at room temperature. Upon completion the reaction was concentrated to remove the methanol and diluted with water (75 mL). The mixture was cooled to 0° C., acidified with 2M HCl and extracted with ethyl acetate (5×150 mL). The combined ethyl acetate extracts were dried on magnesium sulfate, filtered and concentrated in vacuo to dryness to afford 2,2',2"-((5-((2-((2-Oxo-2-phenyl-1$\lambda^2$-ethyl)amino)ethyl)carbamoyl)benzene-1,2,3-triyl)tris(oxy))triacetic acid as a colorless solid (2.3 g, 50%).

Step 6. Preparation of Compound 78

Compound 78 was prepared from compounds 9 (2.75 g, 4.3 mmol) and 77 (0.5 g, 0.96 mmol) using an identical procedure to that used for compound 13. Yield: 600 mg.

Step 7. Preparation of Compound 79

Compound 79 was prepared from compounds 78 (0.6 g) using an identical procedure to that used for compound 14. Yield: 500 mg.

Step 8. Preparation of Compound 140

Compound 140 was prepared from compound 79 (500 mg, 0.25 mmol) and compound 18 (175 mg, 0.25 mmol) using an identical procedure to that used for compound 19. Yield: 250 mg, 44%.

Step 9. Preparation of Compound 141

Compound 141 was prepared from compound 140 (250 mg, 0.11 mmol) using an identical procedure to that used for compound 20. Yield: 200 mg.

Step 10. Preparation of Conjugate 142

Conjugate 142 was prepared from compound 141 (200 mg) and 1000 A lcaa CPG (1.8 g) using an identical procedure to that used for compound 1. Yield: 1.9 g, 22 µmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 142.

Example 9. Synthesis of Conjugate 145

Scheme 19.

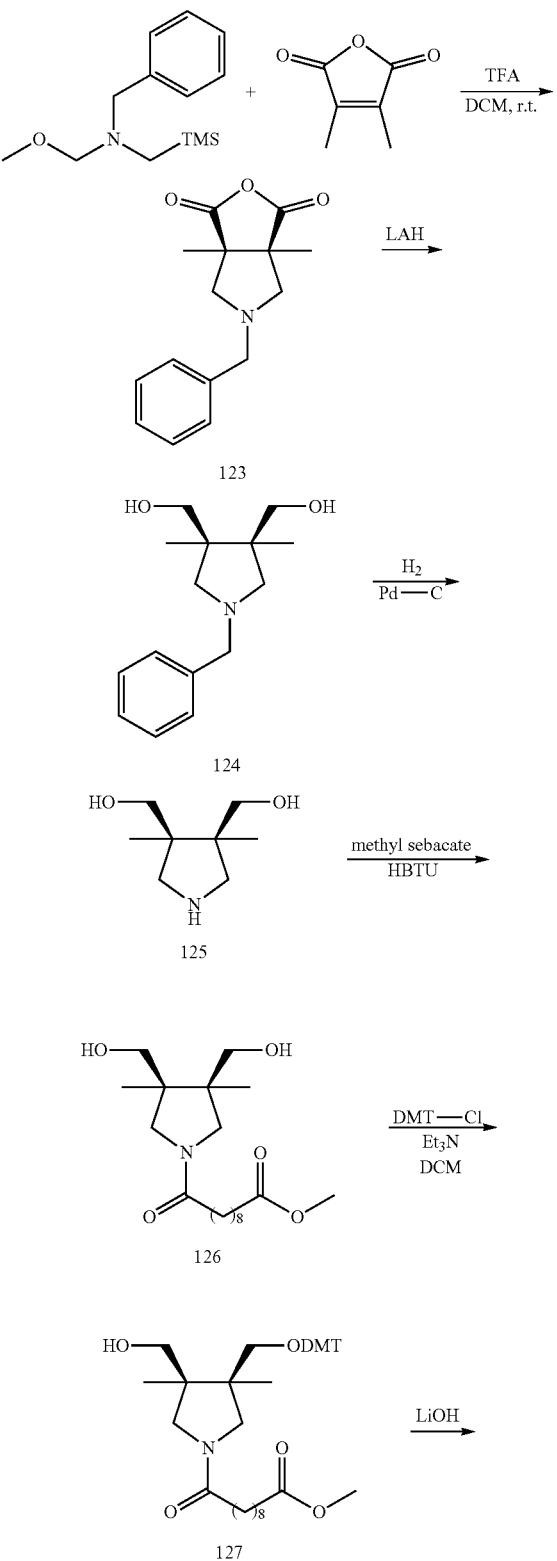

-continued

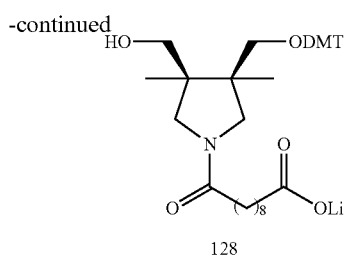

128 one (3.5 g, 13.4 mmol) in anhydrous diethyl ether (50 mL) was added slowly lithium aluminum hydride pellets (1.5 g, 40 mmol) over three portions. The solution was stirred overnight warming to room temperature as the ice water bath melted. Upon completion, the reaction was cooled to 0° C. and very slowly quenched with 1.5 mL of 5M NaOH followed by 1.5 mL of water. Stir for 30 minutes then add magnesium sulfate and filter. The filtrate was concentrated to afford ((3R,4S)-1-Benzyl-3,4-dimethylpyrrolidine-3,4-diyl) dimethanol as a colorless oil (2.7 g).

Scheme 20.

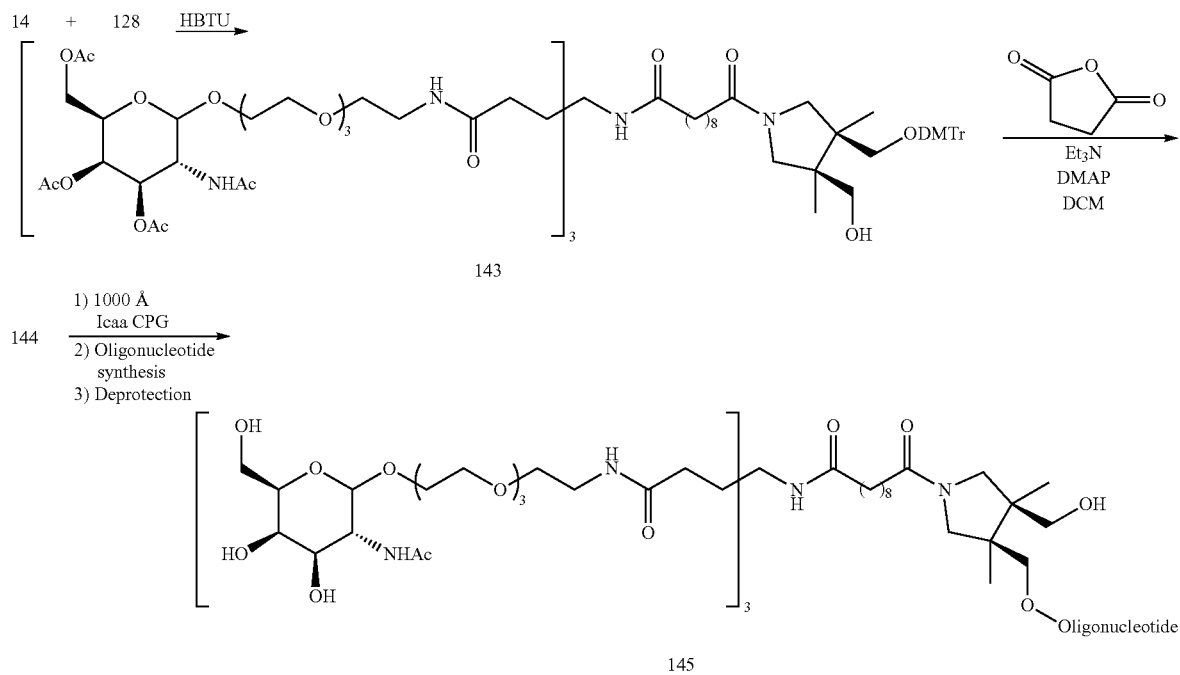

Step 1. Preparation of (3aR,6aS)-5-Benzyl-3a,6a-dimethyltetrahydro-H-furo[3,4-c]pyrrole-1,3(3aH)-dione 123

To a cooled solution (0° C.) of 3,4-dimethylfuran-2,5-dione (3 g, 24 mmol) and N-benzyl-1-methoxy-N-((trimethylsilyl)methyl)methanamine (7 g, 29.8 mmol) in dichloromethane (75 mL) was slowly added trifluoroacetic acid (75 μL). Stir overnight allowing the solution to slowly warm to room temperature as the ice bath melted. The reaction mixture was concentrated to dryness, dissolved in ethyl acetate (100 mL), washed with saturated sodium bicarbonate (2×100 mL), dried on magnesium sulfate, filtered and concentrated to dryness. Purification by column chromatography on silica gel (gradient: 20% ethyl acetate in hexanes to 100% ethyl acetate) afforded (3aR,6aS)-5-Benzyl-3a,6a-dimethyltetrahydro-1H-furo[3,4-c]pyrrole-1,3(3aH)-dione as a yellow oil (3.5 g, 56%).

Step 2. Preparation of ((3R,4S)-1-Benzyl-3,4-dimethylpyrrolidine-3,4-diyl)dimethanol 124

To a cooled (0° C.) solution of (3aR,6aS)-5-Benzyl-3a,6a-dimethyltetrahydro-1H-furo[3,4-c]pyrrole-1,3(3aH)-di-

Step 3. Preparation of ((3R,4S)-3,4-Dimethylpyrrolidine-3,4-diyl)dimethanol 125

To a solution of ((3R,4S)-1-Benzyl-3,4-dimethylpyrrolidine-3,4-diyl)dimethanol (10 g, 40 mmol) in methanol (10 mL) was added 10% palladium on activated charcoal wet (1 g). The solution was stirred vigorously under a hydrogen atmosphere for 16 hours. Upon completion the solution was filtered through Celite, and concentrated to dryness to afford ((3R,4S)-3,4-Dimethylpyrrolidine-3,4-diyl)dimethanol as a colorless solid (5.5 g, 86%).

Step 4. Preparation of Methyl 10-((3R,4S)-3,4-bis(hydroxymethyl)-3,4-dimethylpyrrolidin-1-yl)-10-oxodecanoate 126

Compound 126 was prepared from compound 125 (1.3 g, 8.2 mmol) and monomethyl sebacate (1.8 g, 8.2 mmol) using an identical procedure to that used for compound 17. Yield: 1.8 g, 61%.

Step 5. Preparation of Methyl 10-((3R,4S)-3-((bis(4-methoxyphenyl)(phenyl)methoxy)methyl)-4-(hydroxymethyl)-3,4-dimethylpyrrolidin-1-yl)-10-oxodecanoate 127

Compound 127 was prepared from compound 126 (1.8 g, 5.0 mmol) and 4,4'-Dimethoxytrityl chloride (1.7 g, 5.0 mmol) using an identical procedure to that used for compound 18. Yield: 1.4 g, 42%.

Step 6. Preparation of Lithium 10-((3R,4S)-3-((bis(4-methoxyphenyl)(phenyl)methoxy)methyl)-4-(hydroxymethyl)-3,4-dimethylpyrrolidin-1-yl)-10-oxodecanoate 128

To a solution of compound 127 (3.0 g, 4.6 mmol) in THF (50 mL) and water (50 mL) was added lithium hydroxide (121 mg, 5.0 mmol). The solution was stirred for 4 hours at room temperature then concentrated to remove the THF. The remaining aqueous solution was freeze dried overnight to afford a pale pink solid (2.9 g, quantitative).

Step 7. Preparation of Compound 143

Compound 143 was prepared from compound 128 (270 mg, 0.42 mmol) and compound 14 (800 mg, 0.42 mmol) using an identical procedure to that used for compound 19. Yield: 900 mg, 87%.

Step 8. Preparation of Compound 144

Compound 144 was prepared from compound 143 (500 mg, 0.2 mmol) using an identical procedure to that used for compound 20. Yield: 200 mg.

Step 9. Preparation of Conjugate 145

Conjugate 145 was prepared from compound 144 (200 mg) and 1000 A lcaa CPG (1.8 g) using an identical procedure to that used for compound 1. Yield: 1.9 g, 20 μmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 145.

Example 10. Synthesis of Conjugate 150

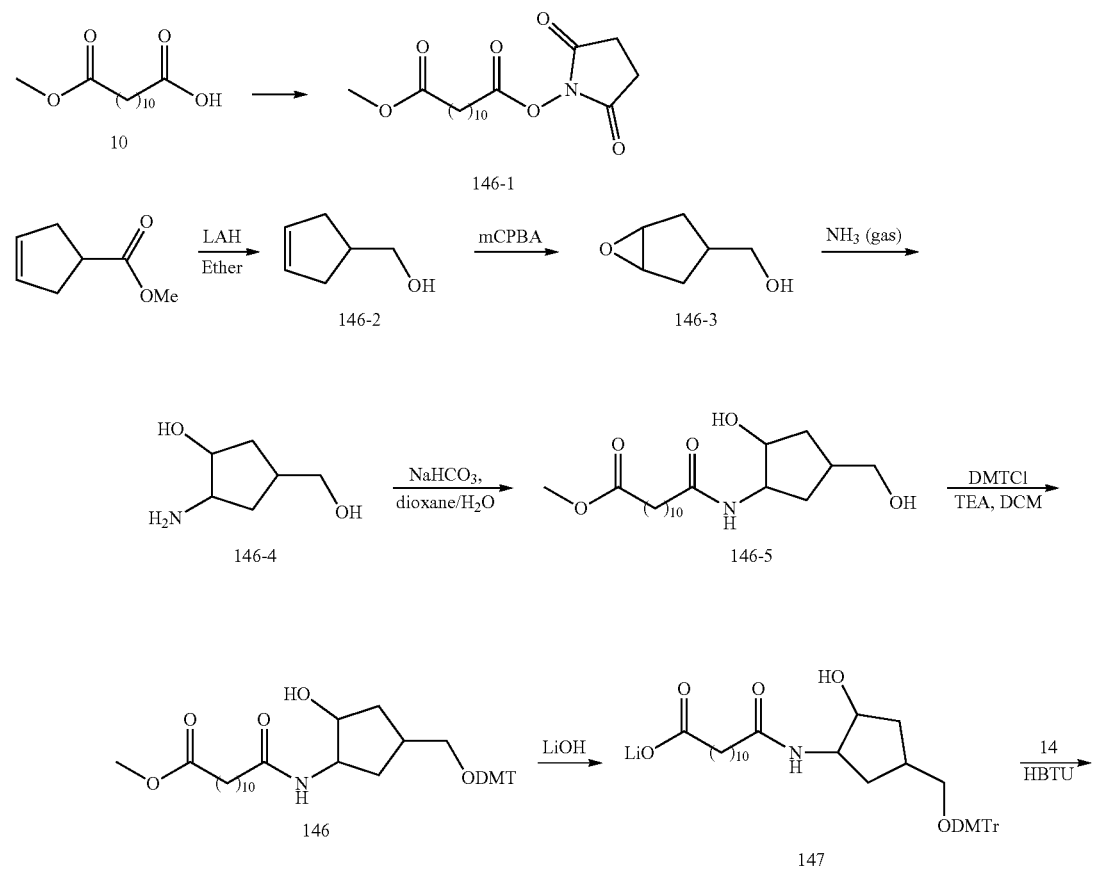

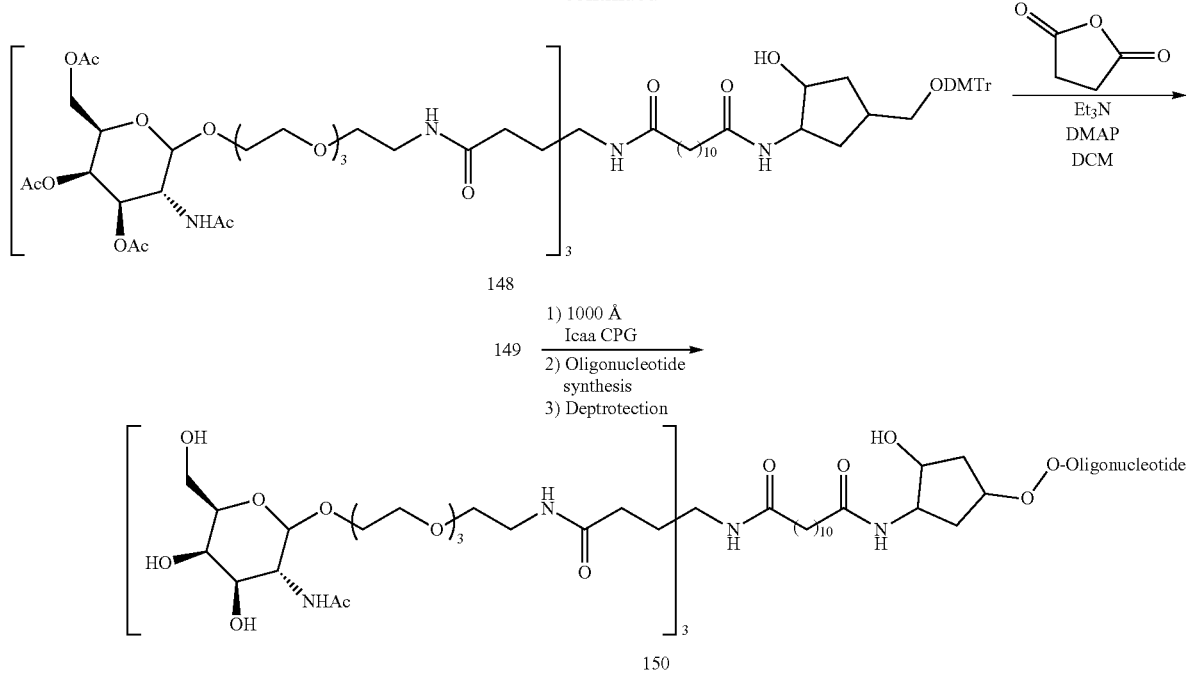

Step 1. Preparation of 146-1

To a solution of mono methyl ester of dodecanedioic acid (12.2 g, 50.0 mmol) in dichloromethane (300 mL) was added N-hydroxysuccinimide (6.10 g, 53.0 mmol) and 1-ethyl-3-(3-dimethylaminopropyl)carbodiimide hydrochloride (EDC) (10.52 g, 55.0 mmol). The cloudy mixture was stirred overnight at room temperature and the reaction became a clear solution. TLC indicated the reaction was completed. The organics were washed with saturated $NH_4Cl$ (300 mL) and brine (100 mL). The organic layer was separated, dried over $MgSO_4$ and concentrated to dryness to pure 1-(2,5-dioxopyrrolidin-1-yl) 12-methyl dodecanedioate 146-1 as a white solid (16.7 g, 97.8%).

Step 2. Preparation of cyclopent-3-en-1-ylmethanol 146-2

To a suspension of lithium aluminum hydride (15.2 g, 0.40 mol) in anhydrous ether (1 L) at 0° C. under nitrogen, was added the solution of methyl cyclopent-3-enecarboxylate (50 g, 0.40 mol) in ether (300 mL) dropwise over 5 hrs. The suspension was stirred at room temperature overnight. TLC indicated the completion of the reaction. The reaction was re-cooled to 0° C. Saturated solution of $Na_2SO_4$ (32 mL) was added dropwise to quench the reaction. After the addition was complete, the mixture was stirred for another 3 hrs and was filtered through a pad of celite. Evaporation of solvent afforded cyclopent-3-enylmethanol 146-2 (37.3 g, 95%) as a colorless liquid.

Step 3. Preparation of (6-oxabicyclo[3.1.0]hexan-3-yl)methanol 146-3

To a solution of cyclopent-3-enylmethanol 146-2 (4.0 g, 41 mmol) in dichloromethane (150 mL) at 0° C. was added 3-chloroperbenzoic acid (10 g, 45 mmol, 77% purity) by portion. The reaction was stirred overnight. Dichloromethane (150 mL) was added. The organics was washed with sodium thiosulfate (12 g in 10 mL water), followed by saturated $NaHCO_3$ (40 mL). This was repeated till all the remaining 3-chloroperbenzoic acid was washed away. The organic was dried over $MgSO_4$. Evaporation of solvent gave a mixture of cis- and trans-6-oxabicyclo[3.1.0]hexan-3-ylmethanol 146-3 (2.6 g, 57%) as a yellow oil. GC-MS: m/z 114 (5) (M+), 95 (15), 88 (100), 81 (15).

Step 4. Preparation of 2-amino-4-(hydroxymethyl)cyclopentan-1-ol 146-4

To a solution of 6-oxabicyclo[3.1.0]hexan-3-ylmethanol 146-3 (2.0 g, 17.6 mmol) in methanol (20 mL) at 0° C. was purged ammonia gas for 10 min. The reaction was stirred at room temperature overnight. TLC indicated the incompletion of the reaction. Methanol was removed and $NH_3 \cdot H_2O$ (50 mL) was added and this was stirred at room temperature over a week. TLC confirmed the completion of the reaction. Water was removed by azeotropically with ethanol to afford 2-amino-4-(hydroxymethyl)cyclopentanol 146-4 (2.1 g, 91%) as a yellow oil.

Step 5. Preparation of Methyl 12-(2-hydroxy-4-(hydroxymethyl)cyclopentylamino)-12-oxododecanoate 146-5

Compound 146-5 was prepared from 2-amino-4-(hydroxymethyl)cyclopentanol 146-4 and 1-(2,5-dioxopyrrolidin-1-yl) 12-methyl dodecanedioate 146-1, using the same procedure as described in the synthesis of 12-(2-(tert-butoxycarbonylamino)ethylamino)-12-oxododecanoate (3-2). Methyl 12-(2-hydroxy-4-(hydroxymethyl)cyclopentylamino)-12-oxododecanoate 146-5 was obtained in 87.4% yield as an off-white solid.

Step 6. Preparation of Compound 147

Compound 147 was prepared quantitatively from compound 146 (1.4 g, 2.33 mmol) using an identical procedure to that used for compound 18.

Step 7. Preparation of Compound 148

Compound 148 was prepared from compound 147 (150 mg, 0.23 mmol) and compound 14 (431 mg, 0.23 mmol) using an identical procedure to that used for compound 19. Yield: 460 mg, 84%.

Step 8. Preparation of Compound 149

Compound 149 was prepared from compound 148 (460 mg, 0.19 mmol) using an identical procedure to that used for compound 20. Yield: 436 mg, 91%.

Step 9. Preparation of Conjugate 150

Compound 150 was prepared from compound 149 (436 mg) and 1000 A lcaa CPG (2.62 g) using an identical procedure to that used for compound 1. Yield: 2.7 g, 21.3 µmol/g CPG loading. The resulting GalNAc loaded CPG solid support was employed in automated oligonucleotide synthesis using standard procedures. Nucleotide deprotection followed by removal from the solid support (with concurrent galactosamine acetate deprotection) afforded the GalNAc-oligonucleotide conjugate 150.

Example 11. Synthesis of Conjugates 153, 158, 163, 168 and 173

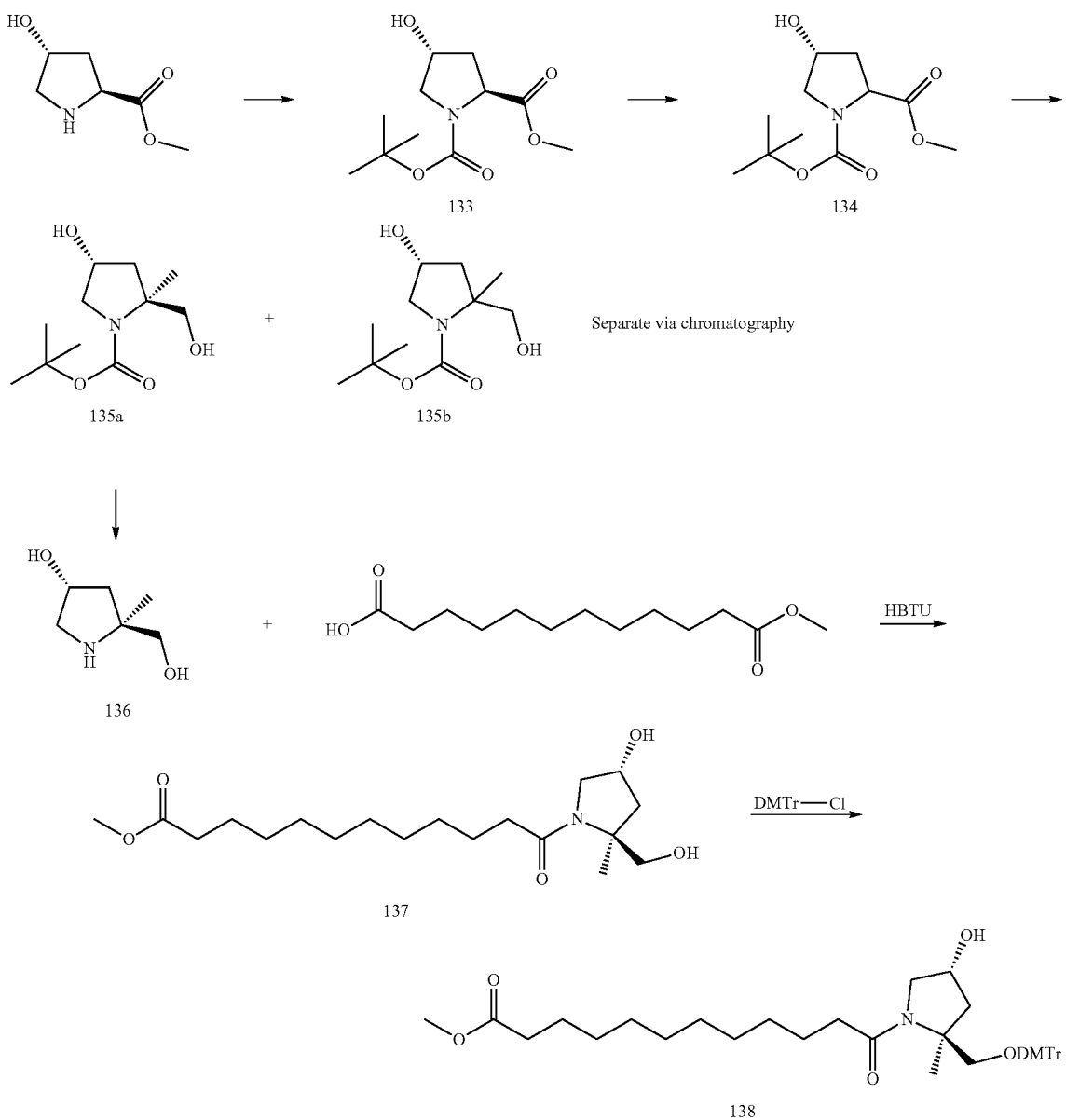

Scheme 22.

Step 1. Preparation of 1-(tert-butyl) 2-methyl (2S, 4R)-4-hydroxypyrrolidine-1,2-dicarboxylate (133)

Methyl (2S,4R)-4-hydroxypyrrolidine-2-carboxylate (25.9 g, 46 mmol), BOC anhydride (65.9 g, 302.5 mmol) and TEA (42 ml, 302.5 mmol) were stirred in DCM at RT for 16 h. The organics were washed sequentially with 1M HCl (×2), saturated NaHCO₃ (×2), H₂O and brine, dried and concentrated in-vacuo to give 1-(tert-butyl) 2-methyl (2S, 4R)-4-hydroxypyrrolidine-1,2-dicarboxylate (133) (58.1 g, 85%).

Step 2. Preparation of 1-(tert-butyl) 2-methyl (4R)-4-hydroxy-2-methylpyrrolidine-1,2-dicarboxylate (134)

1-(tert-butyl) 2-methyl (2S,4R)-4-hydroxypyrrolidine-1,2-dicarboxylate (133) (5 g, 20.4 mmol) and MeI (12 g, 84.5 mmol) were stirred in anhydrous THF at −40° C. LDA (2.0 M solution in THF) (37.5 mL, 75 mmol) was added dropwise. The reaction was allowed to warm to RT and stirred for 4 h then quenched with saturated NH₄Cl. The reaction was extracted with EtOAc, washed with H₂O and brine, dried (Na₂SO₄) and concentrated in-vacuo. The residue was purified by column chromatography 50:50 EtOAc//hexanes to give 1-(tert-butyl) 2-methyl (4R)-4-hydroxy-2-methylpyrrolidine-1,2-dicarboxylate (134) as a racemic mixture (3.6 g, 68%)

Step 3. Preparation of tert-butyl (2S,4R)-4-hydroxy-2-(hydroxymethyl)-2-methylpyrrolidine-1-carboxylate (135a)

1-(Tert-butyl) 2-methyl (4R)-4-hydroxy-2-methylpyrrolidine-1,2-dicarboxylate (134) (19 g, 73.5 mmol) was stirred in anhydrous THF under N₂. LiBH₄ solution (48 ml, 96 mmol) was added dropwise and the reaction stirred at RT for 48 h. The reaction was quenched with 1M NaOH, the THF removed in-vacuo and the residual extracted with EtOAc (4×100 ml). The organics were washed with H₂O and brine, dried (Na₂SO₄) and concentrated in-vacuo. The residue was purified by column chromatography (5% MeOH/DCM) to give tert-butyl (2S,4R)-4-hydroxy-2-(hydroxymethyl)-2-methylpyrrolidine-1-carboxylate (135a) as the major product (8 g, 47%). Structure assigned according to literature references.

Step 4. Preparation of (3R,5S)-5-(hydroxymethyl)-5-methylpyrrolidin-3-ol hydrochloride (136)

tert-Butyl (2S,4R)-4-hydroxy-2-(hydroxymethyl)-2-methylpyrrolidine-1-carboxylate (135a) (8 g, 34.6 mmol) was stirred in EtOAc at RT and gaseous HCl applied for approximately two minutes. The reaction was stirred for one hour then concentrated in-vacuo and dried under high vacuum to give (3R,5S)-5-(hydroxymethyl)-5-methylpyrrolidin-3-ol hydrochloride (136) in quantitative fashion.

Step 5. Preparation of methyl 12-((2S,4R)-4-hydroxy-2-(hydroxymethyl)-2-methylpyrrolidin-1-yl)-12-oxododecanoate (137)

(3R,5S)-5-(Hydroxymethyl)-5-methylpyrrolidin-3-ol hydrochloride (136) (7.9 g, 47.4 mmol), 12-methoxy-12-oxododecanoic acid (11.5 g, 47.4 mmol), HBTU (36 g, 76 mmol) and TEA 20 mL, 142.2 mmol) were stirred in DCM at RT for 16 h. The precipitate was removed by filtration and the organics washed with 1M HCl (×2), saturated NaHCO₃ (×2), H₂O and brine. After drying the organics were concentrated in-vacuo and purified by column chromatography (5% MeOH/DCM) to give methyl 12-((2S,4R)-4-hydroxy-2-(hydroxymethyl)-2-methylpyrrolidin-1-yl)-12-oxododecanoate (137) (3.1 g, 18.3%).

Step 6. Preparation of methyl 12-((2S,4R)-2-((bis (4-methoxyphenyl)(phenyl)methoxy)methyl)-4-hydroxy-2-methylpyrrolidin-1-yl)-12-oxododecanoate (138)

Methyl 12-((2S,4R)-4-hydroxy-2-(hydroxymethyl)-2-methylpyrrolidin-1-yl)-12-oxododecanoate (137) (3.1 g, 9.0 mmol), DMTr-Cl (2.8 g, 8.2 mmol) and TEA (1.1 ml, 8.2 mmol) were stirred in DC<at RT for 16 h. The reaction was concentrated in-vacuo and the residue purified by column chromatography (5% MeOH/DCM, 0.1% TEA) to give methyl 12-((2S,4R)-2-((bis(4-methoxyphenyl)(phenyl) methoxy)methyl)-4-hydroxy-2-methylpyrrolidin-1-yl)-12-oxododecanoate (138) (2.7 g, 45.5 mmol).

Scheme 23

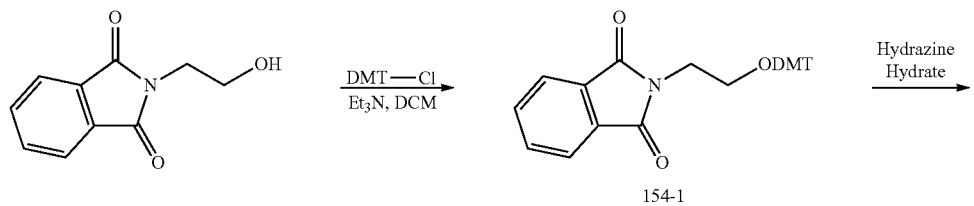

154-1

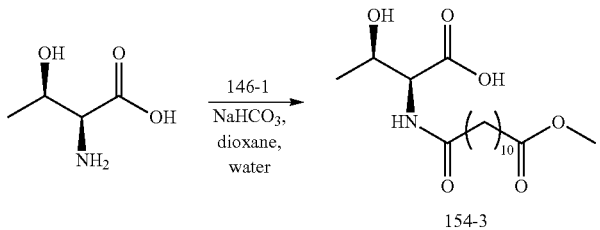
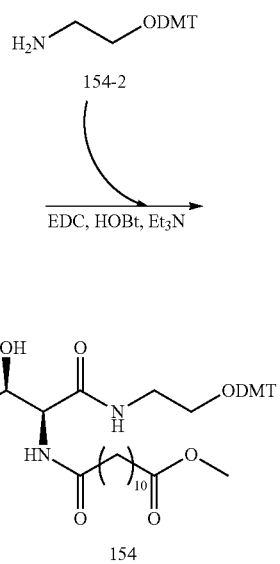

Step 7. Preparation of Compound 154-1

To a solution of N-(2-hydroxyethyl)phthalimide (4.80 g, 25.0 mmol) and 4,4'-dimethoxytrityl chloride (8.8 g, 26.0 mmol) in dichloromethane (200 mL) at 0° C. under nitrogen, was added triethylamine (10.4 mL, 74.6 mmol) dropwise. The reaction mixture was stirred at room temperature for 3 hrs. TLC indicated the completion of the reaction. The organic layer was washed with brine (100 mL), dried over MgSO$_4$, and concentrated to dryness. This was used directly for the next reaction without purification.

Step 8. Preparation of Compound 154-2

2-(2-(Bis(4-methoxyphenyl)(phenyl)methoxy)ethyl) isoindoline-1,3-dione (154-1) obtained above and hydrazine monohydrate (3.6 mL, 74 mmol) in ethanol (100 mL) was stirred overnight at room temperature. TLC indicated the completion of the reaction. The precipitate was filtered out. The filtrate was evaporated. The residue was taken up by ethyl acetate (100 mL). The organic solution was washed with 10% NaOH, water and brine, and dried over MgSO$_4$. Evaporation of solvent afforded 2-(bis(4-methoxyphenyl)(phenyl)methoxy)ethanamine (154-2) as a yellow liquid (8.11 g, 89.3% yield over two steps). This was used for the next reaction without further purification.

Step 9. Preparation of Compound 154-3

To a solution of L-threonine (1.19 g, 10.0 mmol) and NaHCO$_3$ (2.3 g, 27 mmol) in water (20 mL) and dioxane (10 mL), was added 1-(2,5-dioxopyrrolidin-1-yl) 12-methyl dodecanedioate 146-1 (3.1 g, 9.1 mmol) in dioxane (10 mL) dropwise. The reaction mixture was stirred at room temperature overnight. 4N HCl (10 mL) was added. The precipitate was collected by filtration and washed with water (3×10 mL). The solid was dried over P$_2$O$_5$ in a desiccator to afford (2S,3R)-3-hydroxy-2-(12-methoxy-12-oxododecanamido)butanoic acid 154-3 as an off-white solid (2.84 g, 82.2%). LC-MS (ESI): m/z: 346 (100), (M+H+).

Step 10. Preparation of Compound 154

(2S,3R)-3-hydroxy-2-(12-methoxy-12-oxododecanamido)butanoic acid 154-3 (2.47 g, 7.15 mmol), 2-(bis(4-methoxyphenyl)(phenyl)methoxy)ethanamine 154-2 (2.60 g, 7.15 mmol), EDC (1.64 g, 8.58 mmol), 1-hydroxybenzotriazole (HOBt) (1.16 g, 8.58 mmol) and TEA (2.4 mL, 17.2 mmol) were stirred in dichloromethane (72 mL) at room temperature for 2 hrs. Water (30 mL) was added. The organic layer was separated and washed with brine (2×30 mL). Evaporation of solvent followed by column chromatography (30% ethyl acetate/hexanes-50% ethyl acetate/hexanes) afforded methyl 12-((2S,3R)-1-(2-(bis(4-methoxyphenyl)(phenyl)methoxy)ethylamino)-3-hydroxy-1-oxobutan-2-ylamino)-12-oxododecanoate 154 as a waxy yellow semi-solid (2.60 g, 52.6%). $^1$HNMR (400 MHz, acetone-d6, ppm): δ 7.51 (t, J=5.5 Hz, 1H), 7.45-7.49 (m, 2H), 7.28-7.36 (m, 6H), 7.21 (tt, J=7.2, 1.2 Hz, 1H), 7.08 (d, J=8.1 Hz, 1H), 6.88 (dt, J=8.9, 2.5 Hz, 4H), 4.39 (dd, J=8.2, 3.0 Hz, 1H), 4.20-4.27 (m, 1H), 3.78 (s, 6H), 3.60 (s, 1H), 3.35-3.52 (m, 2H), 3.07-3.16 (m, 2H), 2.23-2.37 (m, 4H), 1.53-1.65 (m, 4H), 1.23-1.36 (m, 12H), 1.10 (d, J=6.4 Hz, 3H).

Scheme 24

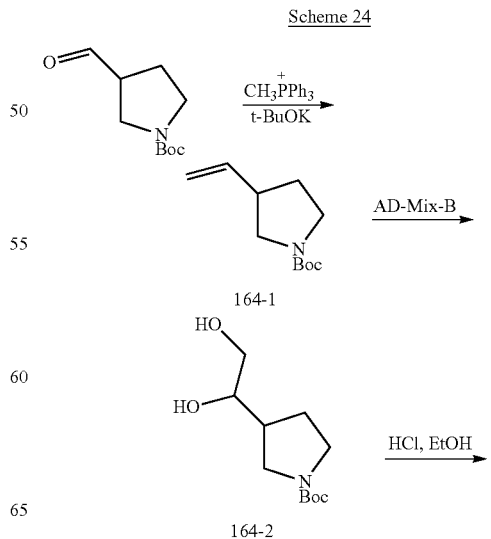

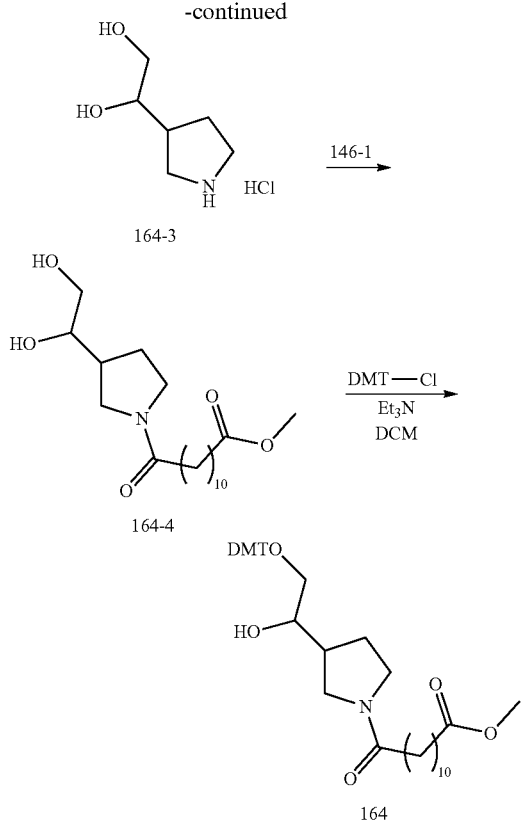

Step 11. Preparation of Compound 164-1

To a suspension of potassium t-butoxide (14.6 g, 130 mol) in THF (120 mL)/ether (360 mL) was added methyltriphenylphosphonium bromide (46.6 g, 130 mmol). The mixture was refluxed for 2 hrs and then cooled to 0° C. tert-butyl 2-formylpyrrolidine-1-carboxylate (13.0 g, 65.2 mmol) in ether (50 mL) was added dropwise. The reaction mixture was stirred at 0° C. and then quenched by the addition of water (250 mL). The organic layer was separated and the aqueous was extracted with ether (250 mL). The combined extract was dried over MgSO$_4$. Evaporation of solvent, followed by column chromatography purification (5% ethyl acetae/hexanes) gave tert-butyl 3-vinylpyrrolidine-1-carboxylate 164-1 (11.5 g, 89.4%) as a colorless liquid. GC-MS: m/z: 197 (2) (M+), 141 (40), 124 (30), 57 (100).

Step 12. Preparation of Compound 164-2

To a mixture of t-BuOH (140 mL) and water (70 mL), was charged AD-mix-3 (47.4 g) and methanesulfonamide (2.89 g, 30.4 mmol). The mixture was stirred at room temperature for 30 min and was then cooled to 0° C. tert-Butyl 3-vinylpyrrolidine-1-carboxylate 164-1 (6.00 g, 30.4 mmol) was added. The reaction was stirred at room temperature overnight. The reaction mixture was cooled to 0° C. Sodium thiosulfate pentahydrate (96 g, 387 mmol) was added and the temperature was allowed to warm to room temperature. Water (700 mL) was added and the mixture was extracted with ethyl acetate (500 mL). The extract was washed with water (2×50 mL) and brine (50 mL), and dried over MgSO$_4$. Evaporation of solvent, followed by column chromatography (2% methanol/dichloromethane-7% methanol/dichloromethane) gave tert-butyl 3-(1,2-dihydroxyethyl)pyrrolidine-1-carboxylate 164-2 (5.4 g, 77%) as a light brown oil.

Step 13. Preparation of Compound 164-3

To a solution of tert-butyl 3-(1,2-dihydroxyethyl)pyrrolidine-1-carboxylate 164-2 (3.1 g, 13.4 mmol) in ethanol (10 mL) was added 3N HCl (30 mL, 90 mmol). The reaction mixture was stirred at room temperature overnight. TLC indicated the completion of the reaction. Ethanol was evaporated. Toluene was added and evaporated. This was repeated three times to give 1-(pyrrolidin-3-yl)ethane-1,2-diol hydrochloride 164-3 (2.0 g, 89%) as a brown oil. LC-MS (ESI): m/z: 132 (100), (M+H$^+$, free amine).

Step 14 Preparation of Compound 164-4

To a solution of 1-(pyrrolidin-3-yl)ethane-1,2-diol hydrochloride 164-2 (2.0 g, 12 mmol) in water (30 mL) was added NaHCO$_3$ (3.7 g, 44 mmol) by portion. Dioxane (20 mL) was then added. To the above solution was added 1-(2,5-dioxopyrrolidin-1-yl) 12-methyl dodecanedioate 146-1 (3.7 g, 11 mmol) in dioxane (30 mL). The reaction mixture was stirred overnight. This was extracted with ethyl acetate (3×100 mL). The combined extract was washed with 0.5N HCl (50 mL) and brine (50 mL), and dried over MgSO$_4$.

Step 15. Preparation of Compound 164

This substance was prepared from methyl 12-(3-(1,2-dihydroxyethyl)pyrrolidin-1-yl)-12-oxododecanoate 164-4 and 4,4-dimethoxytrityl chloride (1 eq) using the same procedure as described in the synthesis of 2-(2-(bis(4-methoxyphenyl)(phenyl)methoxy)ethyl)isoindoline-1,3-dione 138. The product was purified by column chromatography (1.5% methanol/dichloromethane). Methyl 12-(3-(2-(bis(4-methoxyphenyl)(phenyl)methoxy)-1-hydroxyethyl)pyrrolidin-1-yl)-12-oxododecanoate 164 was obtained in 51% yield as a yellow oil. $^1$HNMR (400 MHz, acetone-d6, ppm): δ 7.49-7.54 (m, 2H), 7.35-7.40 (m, 4H), 7.28-7.34 (m, 2H), 7.19-7.25 (m, 1), 6.86-6.91 (m, 4H), 4.11-4.20 (m, 1H), 3.79 (s, 6H), 3.68-3.77 (m, 1H), 3.60 (s, 3H), 3.29-3.59 (m, 3H), 3.06-3.20 (m, 3H), 2.33-2.55 (m, 1H), 2.29 (t, J=7.4 Hz, 2H), 2.19 (t, J=7.6 Hz, 2H), 1.65-2.0 (m, 2H), 1.51-1.62 (m, 4H), 1.26-1.35 (m, 12H).

Scheme 25

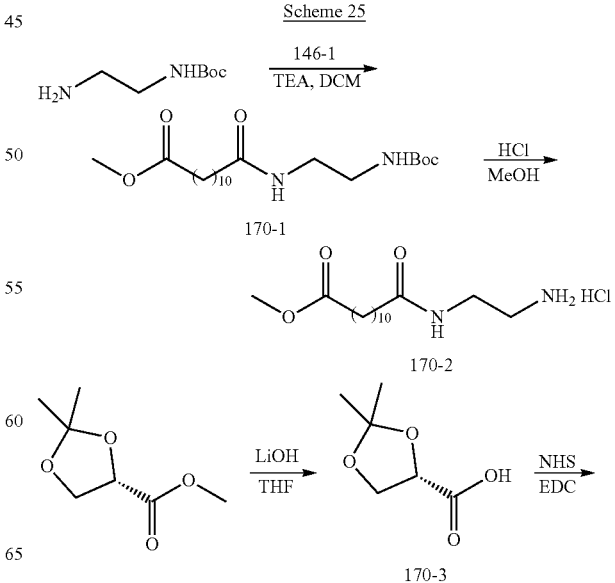

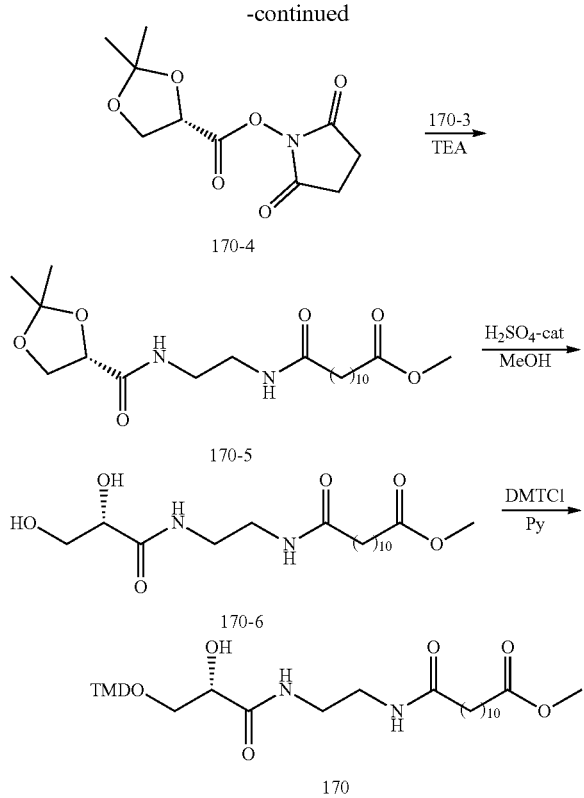

Step 16. Preparation of Compound 170-1

To a solution of tert-butyl 2-aminoethylcarbamate (2.88 g, 18.0 mmol) and triethylamine (2.98 g, 29.4 mmol) in dichloromethane (100 mL), was added 1-(2,5-dioxopyrrolidin-1-yl) 12-methyl dodecanedioate (146-1) (5.09 g, 14.9 mmol) in dichloromethane (50 mL) dropwise at room temperature. The reaction mixture was stirred overnight and TLC indicated the completion of the reaction. 100 mL brine was added and the organic layer was separated. The organic layer was washed with 0.5N HCl (150 mL), brine (2×100 mL) and dried over MgSO₄. Evaporation of solvent gave pure methyl 12-(2-(tert-butoxycarbonylamino)ethylamino)-12-oxododecanoate 170-1 (5.85 g 100%) as a white solid.

Step 17. Preparation of Compound 170-2

To a solution of 12-(2-(tert-butoxycarbonylamino)ethylamino)-12-oxododecanoate 170-1 (5.55 g, 14.4 mmol) in methanol (100 mL) at 0° C., was added thionyl chloride (3.3 mL, 45.5 mmol) dropwise. The reaction was then stirred at room temperature overnight. TLC indicated the completion of the reaction. The solvent and volatile organics were evaporated. The residue was then co-evaporated with heptanes twice to give methyl 12-(2-aminoethylamino)-12-oxododecanoate hydrochloride 170-2 quantitatively as a white solid. LC-MS (ESI): m/z: 287 (100), (M+H⁺, free amine).

Step 18. Preparation of Compound 170-3

(−)-Methyl (S)-2,2-dimethyl-1,3-dioxolane-4-carboxylate (5.01 g, 31.2 mmol) and LiOH·H₂O (2.55 g, 60.8 mmol) in THF (50 mL) and water (50 mL) was stirred overnight. TLC indicated the completion of the reaction. THF was evaporated and the aqueous was acidified with 1N HCl to pH=1. This was extracted with ethyl acetate (5×50 mL). The combined extract was dried over MgSO₄. Evaporation of solvent gave (S)-2,2-dimethyl-1,3-dioxolane-4-carboxylic acid 170-3 (2.93 g, 64.3%) as a light yellow liquid.

Step 19. Preparation of Compound 170-4

Compound 170-4 was synthesized from (S)-2,2-dimethyl-1,3-dioxolane-4-carboxylic acid 170-3 and N-hydroxysuccinimide in 86% yield, using the same procedure as described in the synthesis of 1-(2,5-dioxopyrrolidin-1-yl) 12-methyl dodecanedioate 146-1. (S)-2,5-Dioxopyrrolidin-1-yl 2,2-dimethyl-1,3-dioxolane-4-carboxylate 170-4 was obtained in 86% yield as a white solid.

Step 20. Preparation of Compound 170-5

To a suspension of methyl 12-(2-aminoethylamino)-12-oxododecanoate hydrochloride 170-2 (14.4 mmol) and (S)-2,5-dioxopyrrolidin-1-yl 2,2-dimethyl-1,3-dioxolane-4-carboxylate 170-4 (3.80 g, 15.6 mmol) in dichloromethane (100 mL) was added triethylamine (6 mL, 43.0 mmol) in dichloromethane (25 mL) over 4 hrs at 0° C. The reaction mixture was then stirred at room temperature overnight. LC-MS indicated that the starting material 170-2 was completely converted. The organic layer was washed with brine (50 mL), 1N HCl (50 mL), brine (50 mL), dried over MgSO₄ and concentrated to dryness to afford (S)-methyl 12-(2-(2,2-dimethyl-1,3-dioxolane-4-carboxamido)ethylamino)-12-oxododecanoate 170-5 (5.93 g, 99.3%) as a white solid.

Step 21. Preparation of Compound 170-6

To a solution of (S)-methyl 12-(2-(2,2-dimethyl-1,3-dioxolane-4-carboxamido)ethylamino)-12-oxododecanoate 170-5 (5.93 g, 14.3 mmol) was added one drop of concentrated sulfuric acid. This was refluxed for 6 hrs and then cooled to room temperature. The solid was collected through filtration and washed twice with cold methanol. The solid was dried in the air (3.32 g). The second crop (0.42 g) was obtained from the mother liquid to give (S)-methyl 12-(2-(2,3-dihydroxypropanamido)ethylamino)-12-oxododecanoate 170-6 (3.74 g in total, 69.4%) as a white crystal. LC-MS (ESI): m/z: 375 (100), (M+H). ¹HNMR (400 MHz, DMSO-d6, ppm): δ 7.79 (br, 2H), 5.49 (d, J=5.3 Hz, 1H), 4.66 (t, J=5.8 Hz, 1H), 3.83-3.88 (m, 1H), 3.55-3.61 (m, 4H), 3.41-3.47 (m, 1H), 3.05-3.15 (m, 4H), 2.29 (t, J=7.4 Hz, 2H), 2.03 (t, J=7.6 Hz, 2H), 1.42-1.52 (m, 4H), 1.18-1.29 (m, 12H).

Step 22. Preparation of Compound 170

To a solution of (S)-methyl 12-(2-(2,3-dihydroxypropanamido)ethylamino)-12-oxododecanoate 170-6 (2.99 g, 7.99 mmol) in dry pyridine (57.5 mL) under nitrogen, was added 4,4'-dimethoxytrityl chloride (2.84 g, 8.38 mmol) in one portion. The reaction was stirred at room temperature for two days. Methanol (5 mL) was added to quench the reaction. Pyridine was evaporated. Toluene was added and then evaporated. This was repeated three times. Water (100 mL) was added and this was extracted with ethyl acetate (5×250 mL). The extracts were combined and dried over MgSO4. Evaporation of solvent, followed by column chromatography (1% methanol/dichloromethane-3% methanol/dichloromethane) gave (S)-methyl 12-(2-(3-(bis(4-methoxyphenyl)(phenyl)methoxy)-2-hydroxypropanamido)ethylamino)-12-oxododecanoate 170 (1.70 g, 31.4%) as a viscous oil. ¹HNMR (400 MHz, acetone-d6, ppm): δ 7.64-7.70 (br, 1H), 7.47-7.51 (m, 2H), 7.33-7.37 (m, 4H), 7.26-7.32 (m, 2H), 7.20 (dt, J=7.3, 2.1 Hz, 1H), 7.11 (br, 1H), 6.86 (d, J=8.7 Hz, 4H), 4.84 (br, 1H), 4.21 (dd, J=5.1, 3.8 Hz, 1H), 3.78 (s, 6H), 3.60 (s, 1H), 3.25-3.42 (m, 6H), 2.28 (t, J=7.4 Hz, 2H), 1.48-1.62 (m, 4H), 1.21-1.34 (m, 12H).
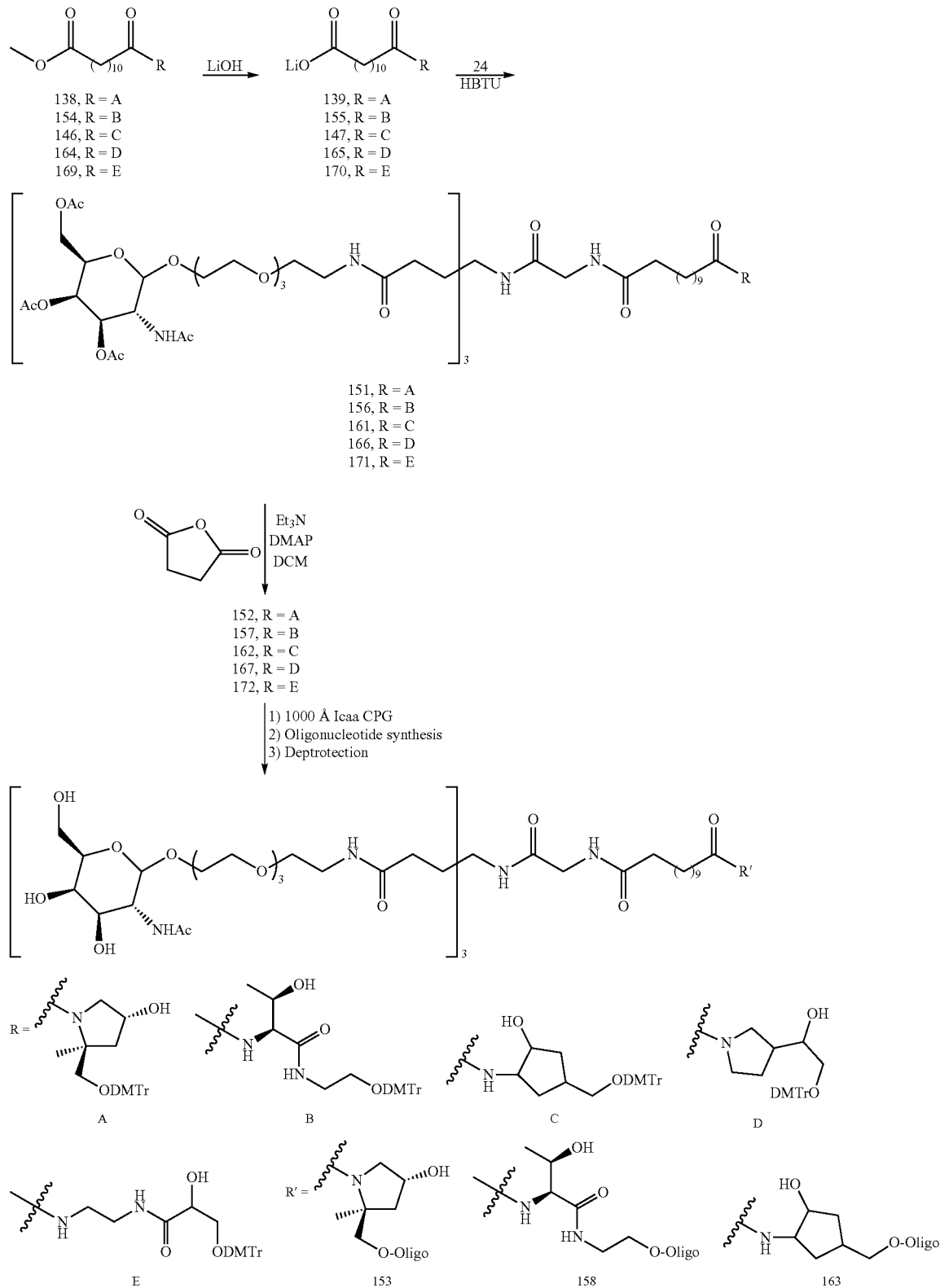

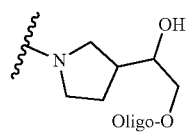
168
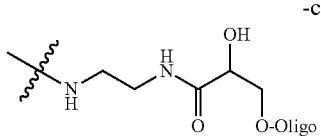
173
-continued
Step 23. Preparation of Compounds 139, 155, 160, 165 and 170
Compounds 139, 155, 160, 165 and 170 were prepared from compounds 138, 154, 159, 164 and 169 using an identical procedure to that used for compound 18.
Step 24. Preparation of Conjugates 153, 158, 163, 168 and 173
Conjugates 153, 158, 163, 168 and 173 were prepared from compound 139, 154, 159, 164 and 169 using an identical procedure to that used for compound 1.
Example 12. Synthesis of Conjugate 176
Scheme 27.
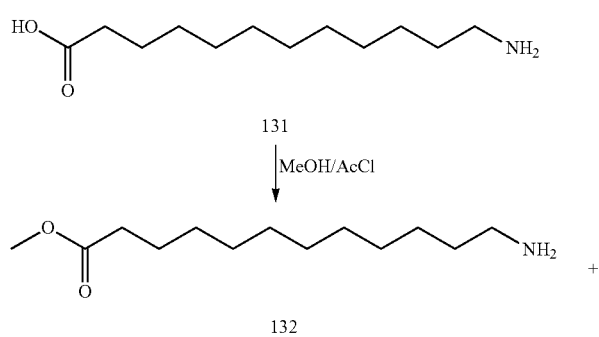
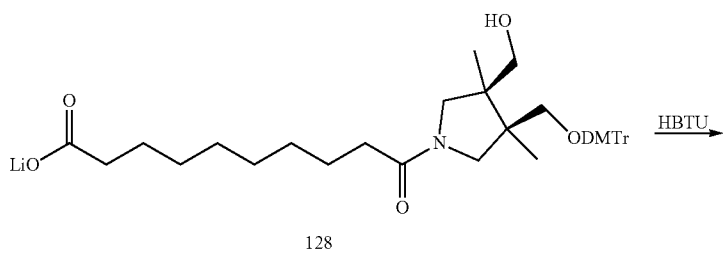
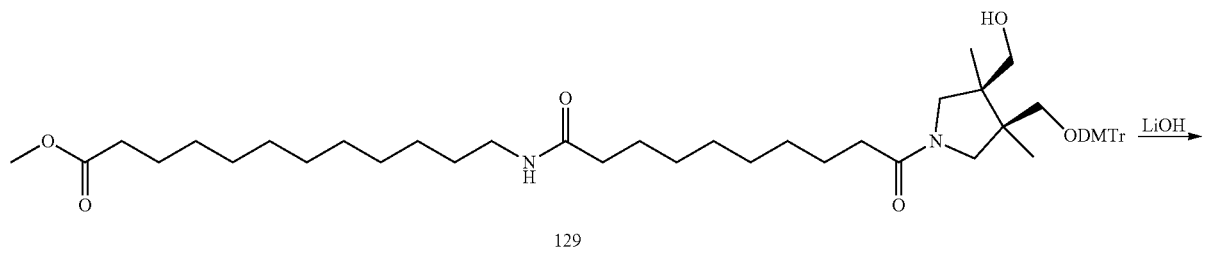

-continued

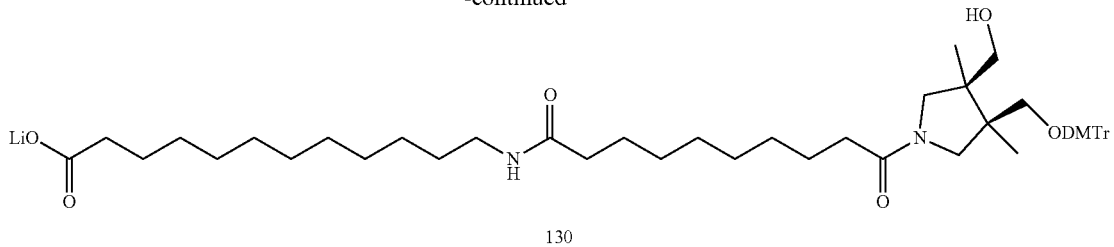

130

Scheme 28.

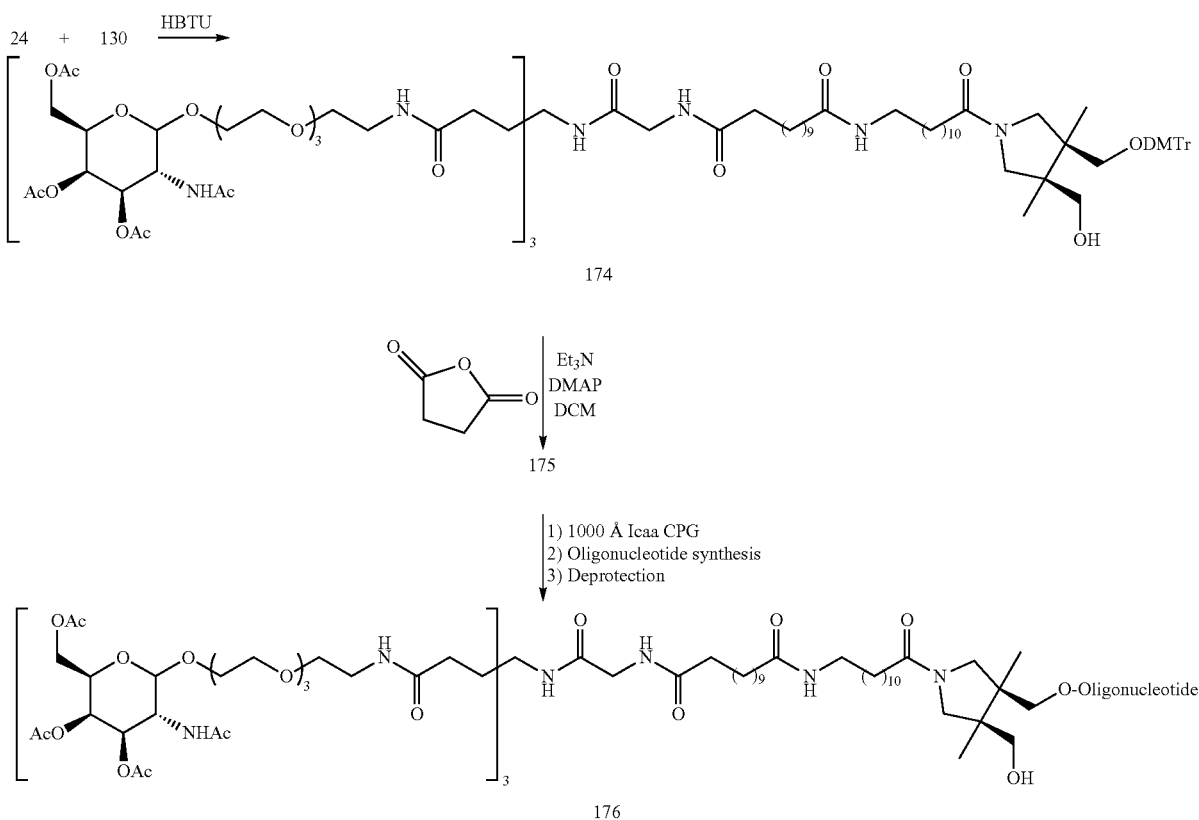

Step. 1. Preparation of methyl 12-aminododecanoate 132

12-aminoundecanoic acid (131) (10 g, 4.64 mmol) was stirred in MeOH at RT. Acetyl chloride (856 μL, 12 mmol) was added dropwise and the reaction stirred for 1.5 hr. The solvent was removed in-vacuo, the residue taken up in MTBE and chilled in the fridge overnight. The resultant precipitate was collected by filtration, washed with ice cold MTBE and dried under high vacuum to afford methyl 12-aminododecanoate 132.

Step 2. Preparation of Methyl 12-(12-(10-((3R,4S)-3-((bis(4-methoxyphenyl)-(phenyl)methoxy)methyl)-4-(hydroxymethyl)-3,4-dimethylpyrrolidin-1-yl)-10-oxodecanamido)dodecanamido)dodecanoate 129

Lithium 10-((3R,4S)-3-((bis(4-methoxyphenyl)(phenyl)methoxy)methyl)-4-(hydroxymethyl)-3,4-dimethylpyrrolidin-1-yl)-10-oxodecanoate (128) (2 g, 3.1 mmol), of methyl 12-aminododecanoate (132) (778 mg, 3.1 mmol), HBTU (1.2 g, 3.1 mmol) and TEA (1.4 mL, 10 mmol) were stirred in DCM at RT O/N. The precipitate was removed by filtration, the filtrate concentrated in-vacuo and the residue purified by column chromatography (5% MeOH, DCM). TLC showed two close running spots with identical mass that were assigned as geometric isomers and pooled together to give of Methyl 12-(12-(10-((3R,4S)-3-((bis(4-methoxyphenyl)(phenyl)methoxy)methyl)-4-(hydroxymethyl)-3,4-dimethylpyrrolidin-1-yl)-10-oxodecanamido)dodecanamido)dodecanoate (129) in quantitative fashion.

Step 3. Preparation of Lithium 12-(12-(10-((3R,4S)-3-((bis(4-methoxyphenyl)(phenyl)-methoxy)methyl)-4-(hydroxymethyl)-3,4-dimethylpyrrolidin-1-yl)-10-oxodecanamido)-dodecanamido) dodecanoate 130

Methyl 12-(12-(10-((3R,4S)-3-((bis(4-methoxyphenyl)(phenyl)methoxy)methyl)-4-(hydroxymethyl)-3,4-dimethylpyrrolidin-1-yl)-10-oxodecanamido)dodecanamido)dodecanoate (129) (3.1 mmol) was stirred in THF:H$_2$O (50:50) with LiOH (88 mg, 3.7 mmol) at RT O/N. Reaction was confirmed by TLC and the THF removed in-vacuo. The aqueous solution was frozen in liquid N$_2$ and lyophilized for 48 hours to give Lithium 12-(12-(10-((3R,4S)-3-((bis(4-methoxyphenyl)(phenyl)methoxy)methyl)-4-(hydroxymethyl)-3,4-dimethylpyrrolidin-1-yl)-10-oxodecanamido)dodecanamido)dodecanoate 130 quantitatively.

Step 4. Preparation of Conjugate 176

Conjugate 176 was prepared from compounds 24 and 130 using an identical procedure to that used for compound 1.

Example 13. Synthesis of Conjugate 179

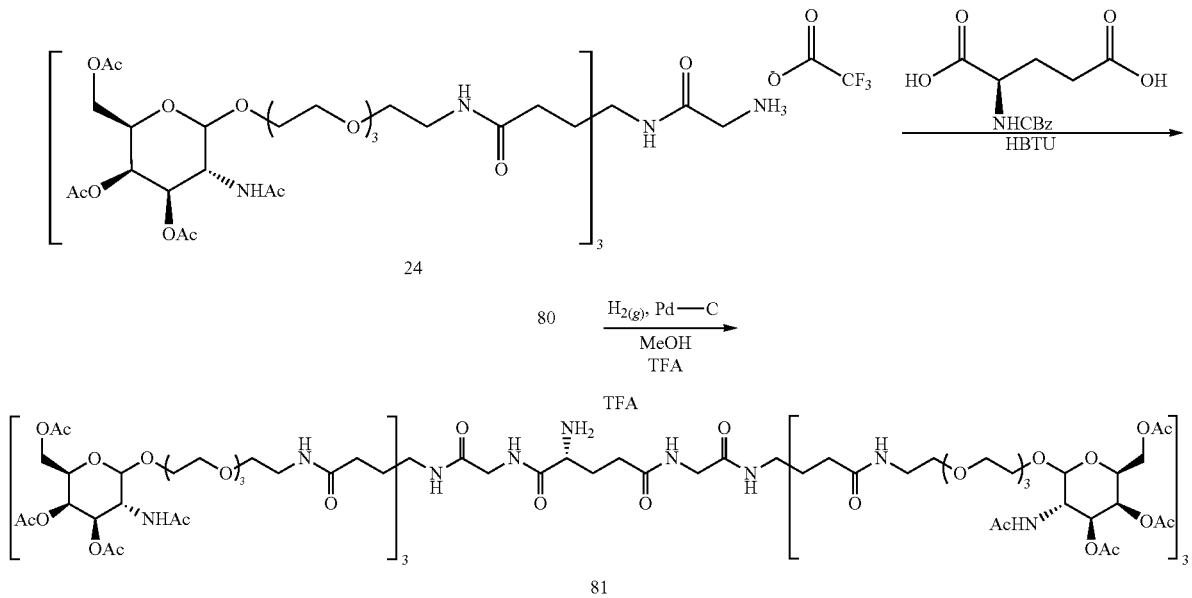

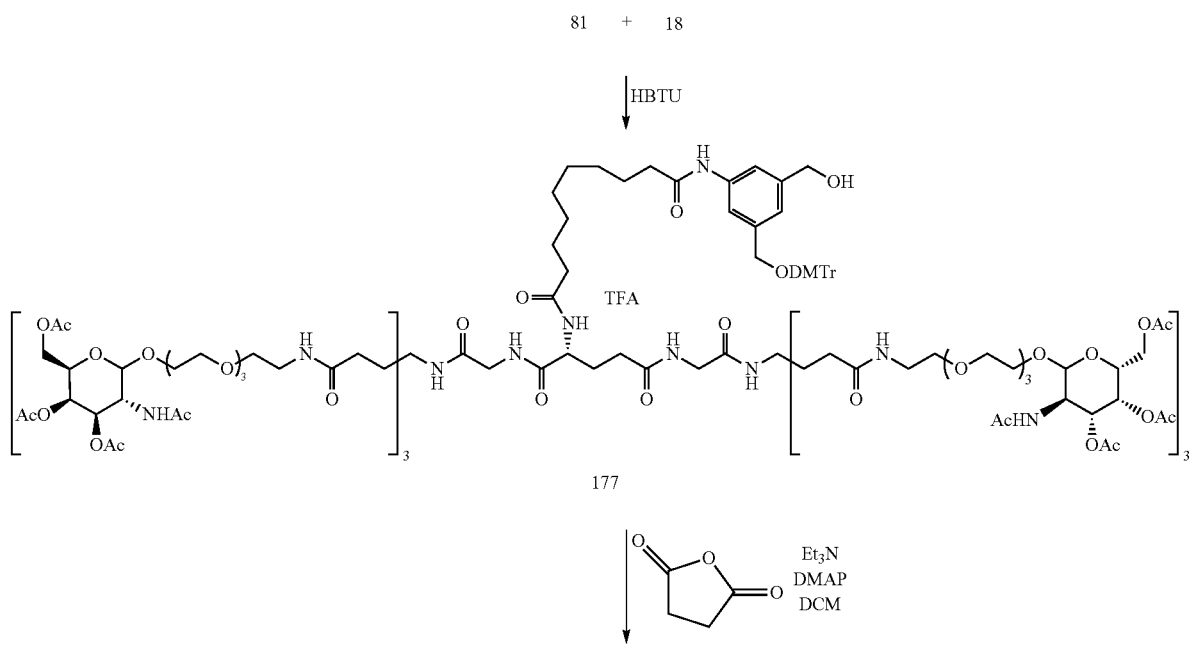

-continued

178

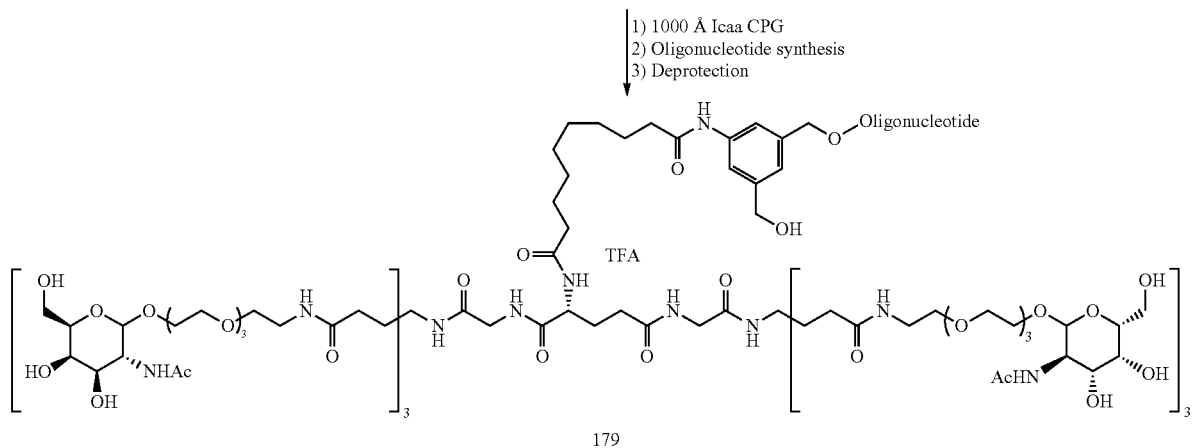

179

Step 1. Preparation of Compound 80

Compound 24 (2 g, 0.86 mmol), N-carbobenzoxy-L-glutamic acid (120 mg, 0.43 mmol), HBTU (326 mg, 0.86 mmol) and TEA (353 µL, 2.6 mmol) were stirred in DCM at RT O/N. The mixture was concentrated in-vacuo and purified by column chromatography to give compound 80 (2.88 g, 83%).

Step 2. Preparation of Compound 81

Compound 81 was prepared from compounds 80 (670 mg, 0.17 mmol) using an identical procedure to that used for compound 14. The compound was used crude in subsequent reactions and the yield taken as quantitative.

Step 3. Preparation of Conjugate 179

Conjugate 179 was prepared from compounds 18 and 81 using an identical procedure to that used for compound 1.

Example 14. Synthesis of Conjugate 182

Scheme 31.

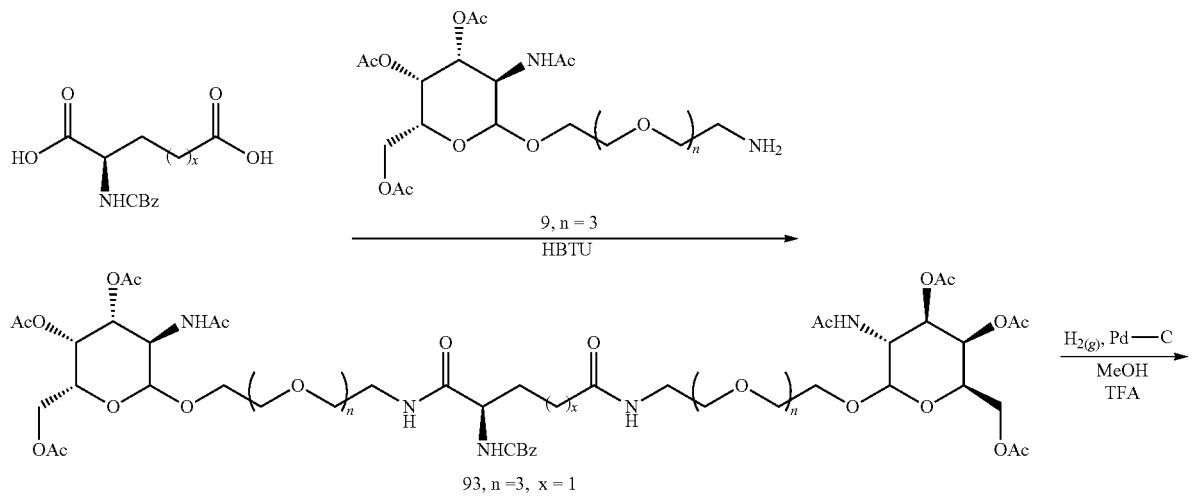

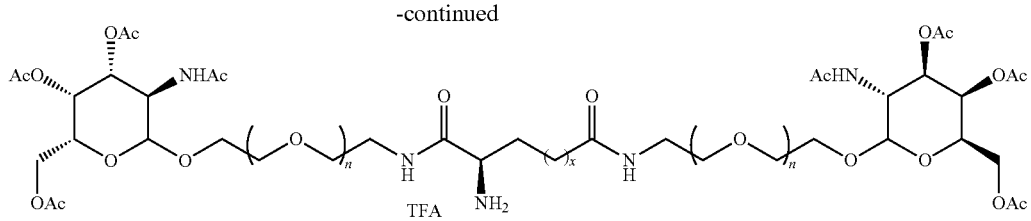
94, n = 3, x = 1
Scheme 32.
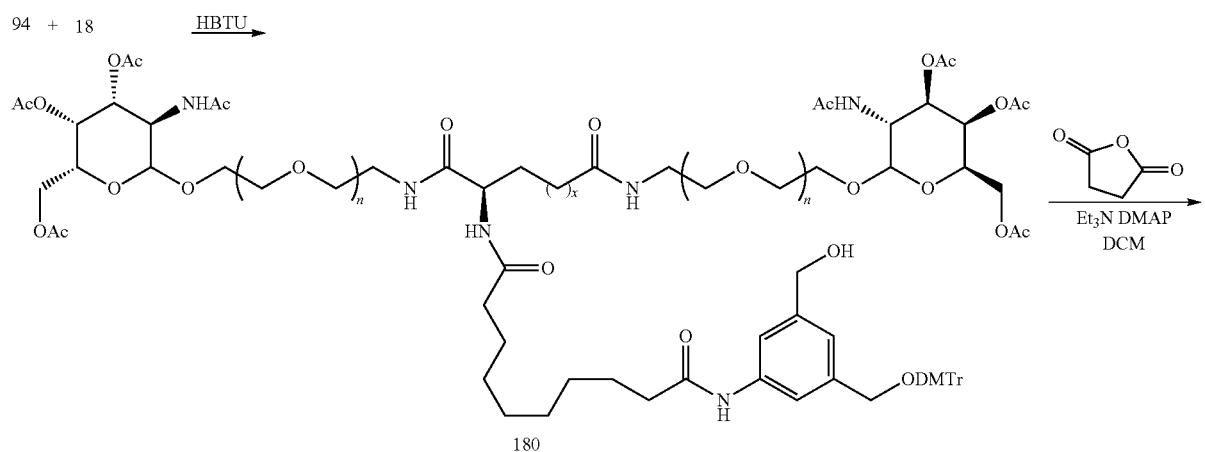
180
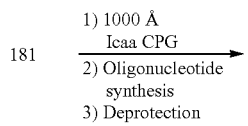
181
1) 1000 Å Icaa CPG
2) Oligonucleotide synthesis
3) Deprotection
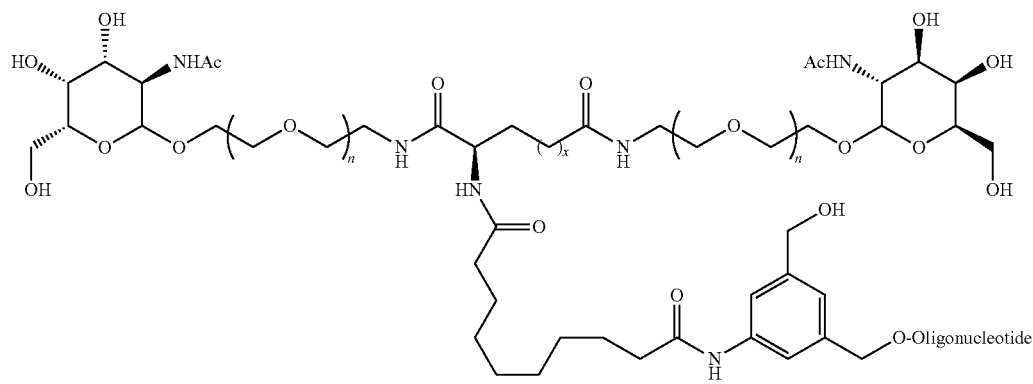
182
n = 3, x = 1

Step 1. Preparation of Compound 93

Compound 93 was prepared from (2-oxo-2-phenyl-1λ²-ethyl)-D-glutamic acid (2.25 g, 8.1 mmol) and 9 (13 g, 21 mmol) using an identical procedure to that used for compound 89. Yield: 11.2 g.

Step 2. Preparation of Compound 94

Compound 94 was prepared from compound 93 (11.1 g) using an identical procedure to that used for compound 90. Yield: 10.2 g.

Step 3. Preparation of Conjugate 182

Conjugate 182 was prepared from compounds 18 and 94 using an identical procedure to that used for compound 1.

Example 15. Synthesis of Conjugates 185 and 188

Scheme 33.

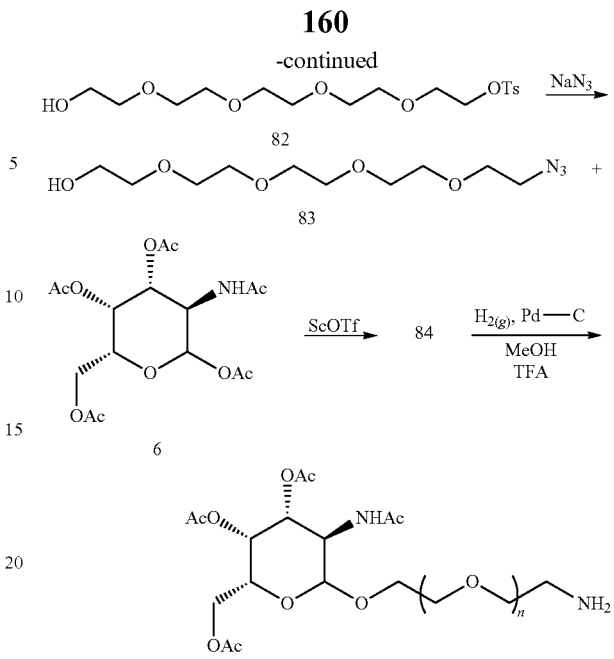

Scheme 34.

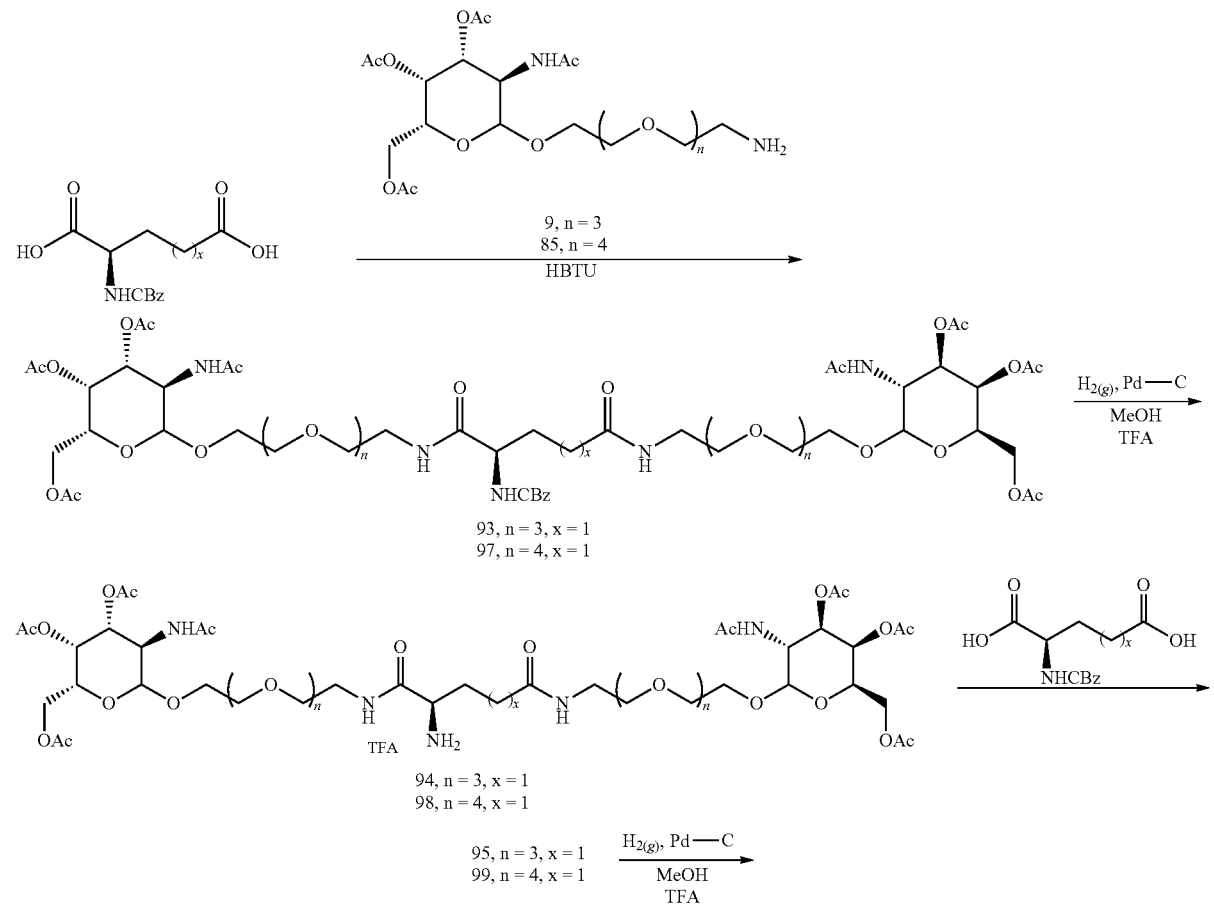

-continued
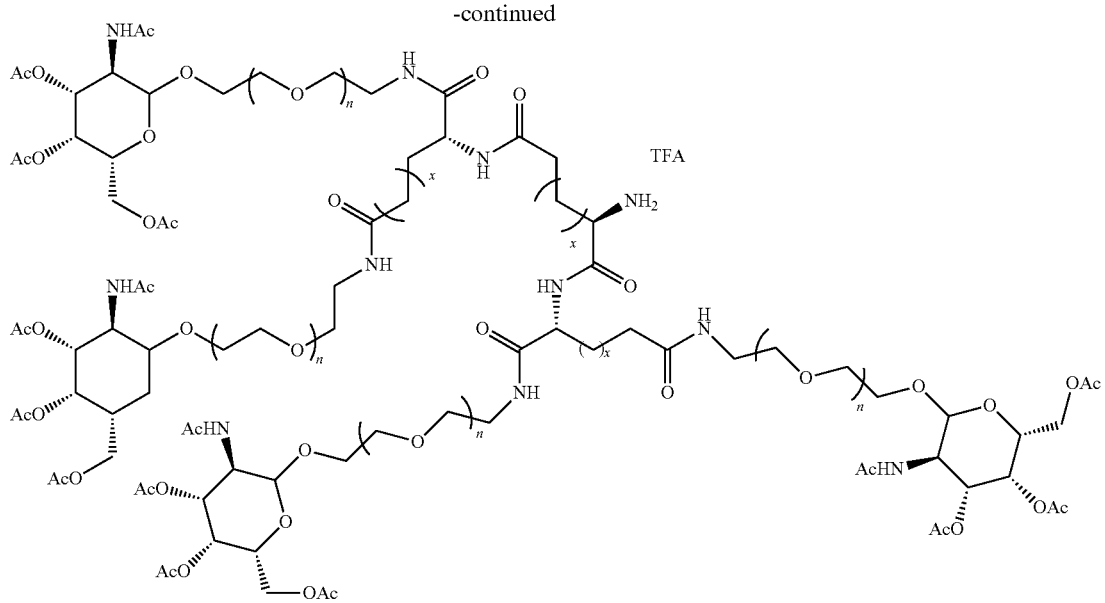
96, n = 3, x = 1
100, n = 4, x = 1
Scheme 35.
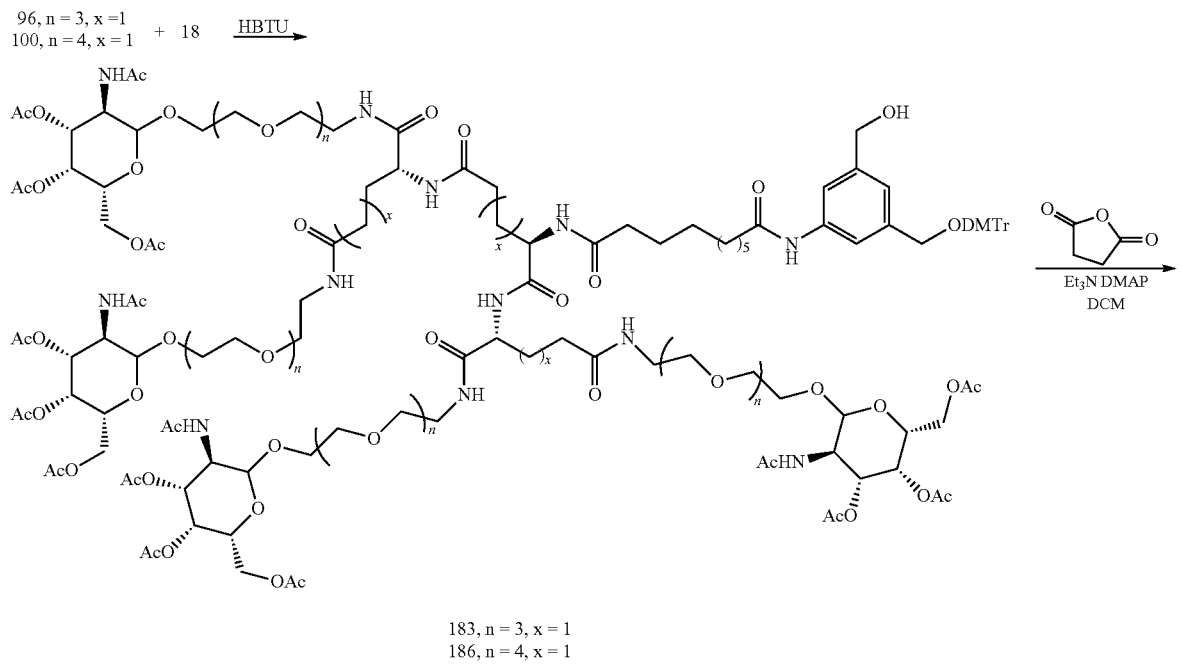
183, n = 3, x = 1
186, n = 4, x = 1
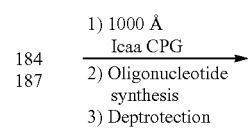

-continued

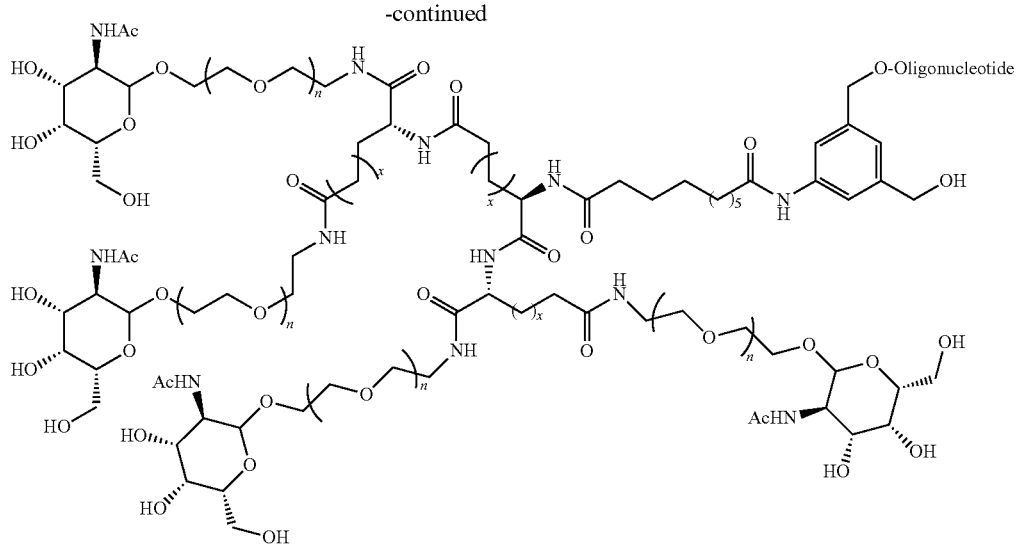

185, n = 3, x = 1
188, n = 4, x = 1

Step 1. Preparation of 14-Hydroxy-3,6,9,12-tetraoxatetradecyl 4-methylbenzenesulfonate 82

A solution of pentaethylene glycol (35 g, 147 mmol), TEA (41 mL, 294 mmol) and trimethylamine-HCl (1.4 g, 14.7 mmol) in $CH_2Cl_2$ (600 mL) was treated with tosyl chloride (29.4 g, 154 mmol). After stirring (18 h) the reaction mixture was washed with $H_2O$-brine (1:1), dried ($MgSO_4$), filtered, concentrated and subjected to chromatography to yield 82 (24.6 g, 43%) as a pale yellow oil. Rf 0.8 (10% $CH_3OH$—$CH_2Cl_2$).

Step 2. 14-azido-3,6,9,12-tetraoxatetradecan-1-ol 83

14-azido-3,6,9,12-tetraoxatetradecan-1-ol (83) was prepared from 82 (24.6 g, 62.7 mmol) and sodium azide (7.13 g, 110 mmol) using an identical procedure to that used for compound 4. Yield: 14.8 g, 90%.

Step 3. Preparation of Compound 84

A solution of GalNAc 6 (12.2 g, 31.4 mmol) and HO-PEG-$N_3$ 83 (9.2 g, 35 mmol) in 1,2-dichloroethane (150 mL) was treated with Sc(OTf)$_3$ (771 mg, 1.6 mmol). After stirring (85° C., 2 hr) the reaction was cooled (RT), quenched by the addition of TEA (40 mL) and concentrated. The crude material was subjected to chromatography to yield 84 (11.16 g, 60%) as a pale yellow foam. Rf 0.7 (10% $CH_3OH$—$CH_2Cl2$).

Step 4. Preparation of Compound 85

A solution of 84 (11.16 g, 18.8 mmol) and Pd/C (1.1 g, 10%—wet support) in EtOAc (120 mL) was treated with TFA (4.32 mL, 56.5 mmol) and purged with $H_2$. After stirring vigorously (4.5 h) the reaction was purged with $N_2$, filtered through Celite and concentrated. The crude material was subjected to chromatography to yield 85 (5.77 g, 45%) as a colorless foam. Rf 0.5 (10% $CH_3OH$—$CH_2Cl_2$).

Step 5. Preparation of Compound 95

Compound 95 was prepared from (2-oxo-2-phenyl-1)$^2$-ethyl)-D-glutamic acid (1.04 g, 3.7 mmol) and compound 94 (10.2 g) using an identical procedure to that used for compound 91. Yield: 7.2 g.

Step 6. Preparation of Compound 96

Compound 96 was prepared from compound 95 (11.1 g) using an identical procedure to that used for compound 92. Yield: 6.5 g.

Step 7. Preparation of Compound 97

Compound 97 was prepared from (2-oxo-2-phenyl-1$\lambda^2$-ethyl)-D-glutamic acid (2 g, 7.1 mmol) and 85 (12.1 g, 17.8 mmol) using an identical procedure to that used for compound 89. Yield: 10 g, quantitative.

Step 8. Preparation of Compound 98

Compound 98 was prepared from compound 97 (10 g, 7.2 mmol) using an identical procedure to that used for compound 90. Yield: 3.5 g, 36%.

Step 9. Preparation of Compound 99

Compound 99 was prepared quantitatively from (2-oxo-2-phenyl-1$\lambda^2$-ethyl)-D-glutamic acid (350 mg, 1.25 mmol) and compound 98 (2.86 mg, 2.5 mmol) using an identical procedure to that used for compound 91.

Step 10. Preparation of Compound 100

Compound 100 was prepared quantitatively from compound 99 (3.2 g, 1.25 mmol) using an identical procedure to that used for compound 92.

165
Step 11. Preparation of Conjugates 185 and 188
Conjugate 185 and 188 were prepared from compounds 18 and 96 or 18 and 100 using an identical procedure to that used for compound 1.
Example 16. Synthesis of Conjugates 191, 194, 197 and 200
Scheme 36
166
-continued
Scheme 37.
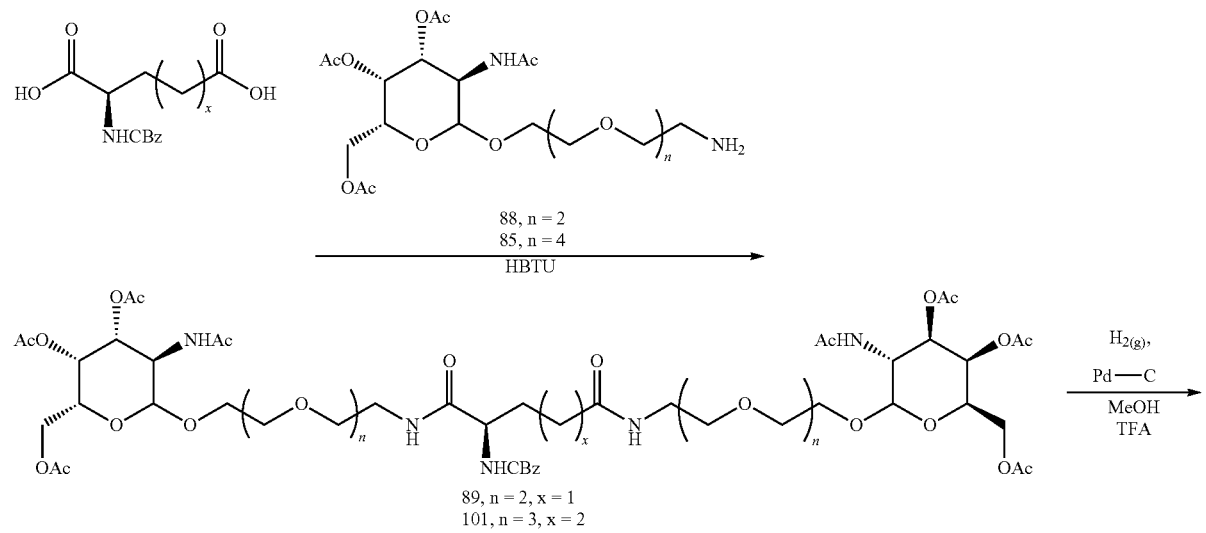
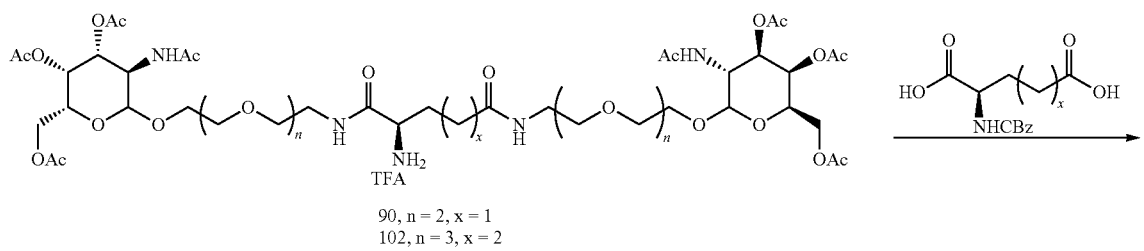
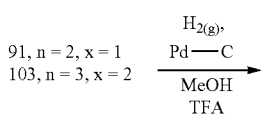

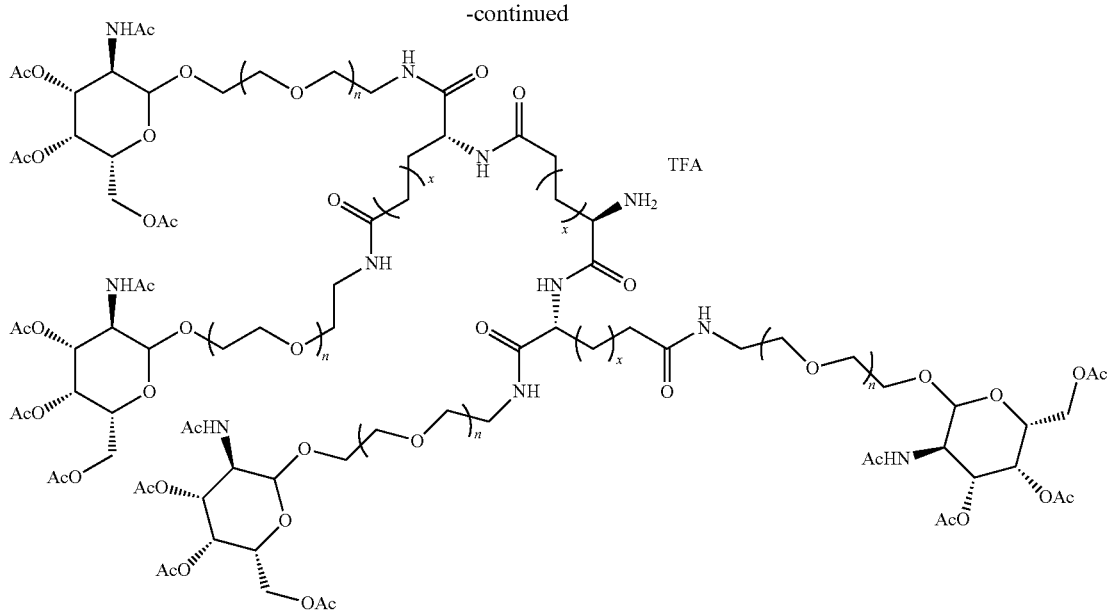
92, n = 2, x = 1
104, n = 3, x = 2
Scheme 38.
92, n = 2, x = 1
96, n = 3, x = 1
100, n = 4, x = 1
104, n = 3, x = 2
+ 128 →(HBTU)
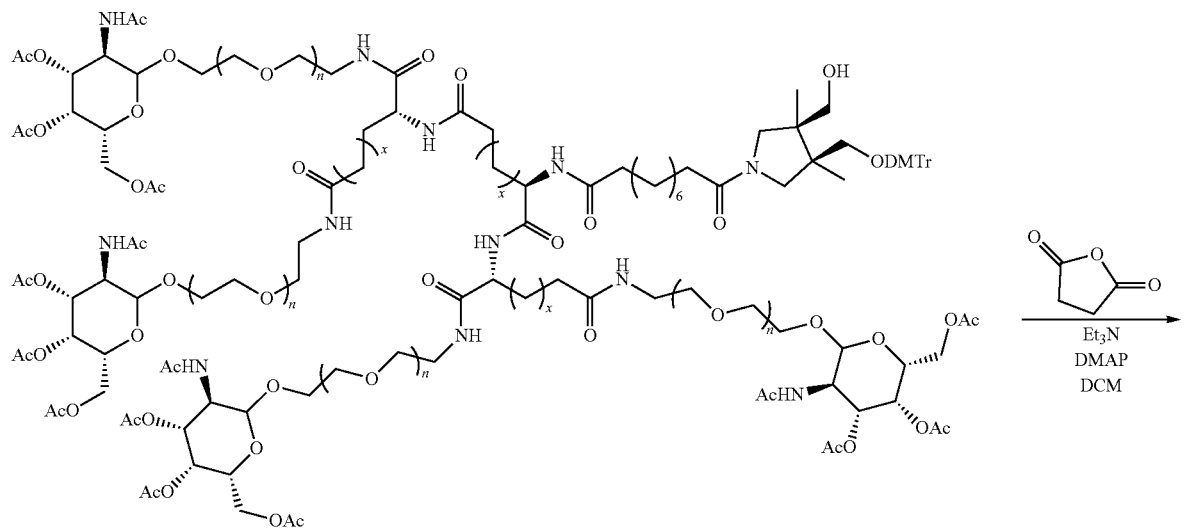
189, n = 2, x = 1
192, n = 3, x = 1
195, n = 4, x = 1
198, n = 3, x = 2

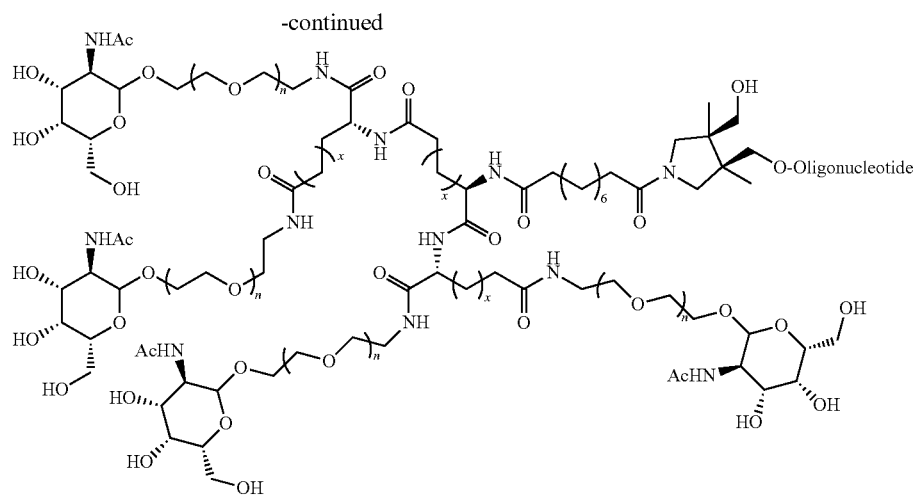

191, n = 2, x = 1
194, n = 3, x = 1
197, n = 4, x = 1
200, n = 3, x = 2

Step 1. Preparation of 2-(2-(2-azidoethoxy)ethoxy)ethan-1-ol 86

To a solution of 2-(2-(2-chloroethoxy)ethoxy)ethan-1-ol (13 g, 77 mmol) in water (200 mL) was added sodium azide (10 g, 154 mmol). The reaction was heated to 100° C. for 18 hours. The reaction was cooled to room temperature and poured into a 1 L separatory funnel and extracted with dichloromethane (3×200 mL). The combine dichloromethane extracts were dried on magnesium sulfate, filtered and concentrated to dryness to afford 2-(2-(2-azidoethoxy)ethoxy)ethan-1-ol as a colorless oil (11.7 g).

Step 2. Preparation of Compound 87

Compound 87 was prepared from 86 (4.95 g, 28.3 mmol) and 6 (10 g, 25.7 mmol) using an identical procedure to that used for compound 84. Yield: 10 g, 77%.

Step 3. Preparation of Compound 88

Compound 88 was prepared from 87 (10 g, 19.8 mmol) using an identical procedure to that used for compound 85. Yield: 7.63 g, 65%.

Step 4. Preparation of Compound 89

A solution of 88 (2 g, 3.38 mmol) and Z-glutamic acid (427 mg, 1.52 mmol) in $CH_2Cl_2$ (50 mL) was treated with HBTU (1.41 g, 3.7 mmol) and Hünig's base (1.77 mL, 10.1 mmol). After stirring (18 h) the mixture was concentrated and subjected to chromatography to yield 89 (871 mg, 48%) as a colorless foam. Rf 0.5 (10% $CH_3OH$—$CH_2C2$).

Step 5. Preparation of Compound 90

A solution of 89 (870 mg, 0.72 mmol) and Pd/C (90 mg, 10%—wet support) in EtOAc (10 mL) was treated with TFA (84 µL, 1.1 mmol) and purged with $H_2$. After stirring vigorously (2 h) the reaction was purged with $N_2$, filtered through Celite and concentrated. The crude material was used without further processing and yielded 90 (850 mg, quantitative) as a colorless foam. Rf 0.25 (10% $CH_3OH$—$CH_2Cl_2$).

Step 6. Preparation of Compound 91

A solution of 90 (850 mg, 0.72 mmol) and Z-glutamic acid (91 mg, 0.32 mmol) in $CH_2Cl_2$ (10 mL) was treated with HBTU (300 mg, 0.79 mmol) and Hünig's base (502 µL, 2.9 mmol). After stirring (1.5 h) the mixture diluted with $CH_2Cl_2$ and washed with $NaHCO_3$ (Sat. Aq.), dried ($MgSO_4$), filtered and concentrated. The crude material was subjected to chromatography to yield 91 (590 mg, 76%) as a colorless foam. Rf 0.5 (10% $CH_3OH$—$CH_2Cl_2$).

Step 7. Preparation of Compound 92

A solution of 91 (590 mg, 0.25 mmol) and Pd/C (100 mg, 10% —wet support) in $CH_3OH$ (30 mL) was treated with TFA (291 µL, 0.37 mmol) and purged with $H_2$. After stirring (3 h) the mixture was purged with $N_2$, then filtered through Celite and concentrated. The crude material was used without further processing and yielded 92 (600 mg, quantitative) as a colorless foam. Rf 0.1 (10% $CH_3OH$—$CH_2Cl_2$).

Step 8. Preparation of Compound 101

Compound 101 was prepared from (R)-2-((2-oxo-2-phenyl-112-ethyl)amino)hexanedioic acid (2.51 g, 8.6 mmol) and 9 (1 g, 17.2 mmol) using an identical procedure to that used for compound 89. Yield: 4.2 g, 37%.

Step 9. Preparation of Compound 102

Compound 102 was prepared from compound 101 (4.2 g, 3.2 mmol) using an identical procedure to that used for compound 90. Yield: 2.1 g, 47%.

Step 10. Preparation of Compound 103

Compound 103 was prepared from (R)-2-((2-oxo-2-phenyl-112-ethyl)amino)hexanedioic acid (265 mg, 0.9 mmol)

and compound 102 (2.1 g, 1.8 mmol) using an identical procedure to that used for compound 91. Yield: (560 mg, 24%).

Step 11. Preparation of Compound 104

Compound 104 was prepared quantitatively from compound 103 (560 mg) using an identical procedure to that used for compound 92. The compound was used without purification.

Step 12. Preparation of Conjugates 191, 194, 197 and 200

Conjugates 191, 194, 197 and 200 were prepared from compound 128 and 92, 96, 100 or 104 using an identical procedure to that used for compound 1.

Example 17. Synthesis of Conjugates 203 and 206

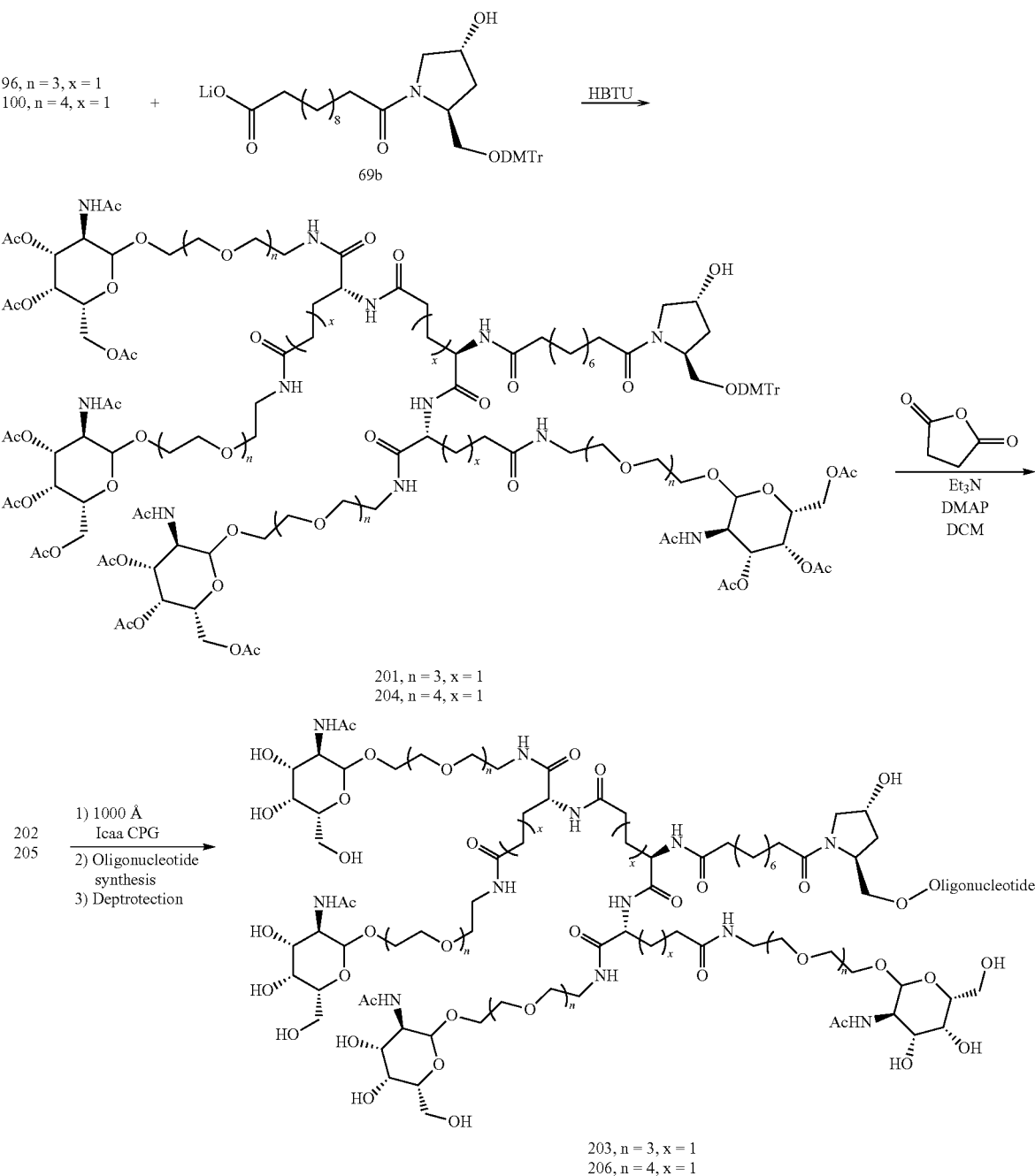

Step 1. Preparation of Compound 69b
Compound 69b was prepared from (2S,4R)-4-Hydroxy-pyrrolidine-2-carboxylic acid using an identical procedure to that used for compound 69.
Step 2. Preparation of Conjugates 203 and 206
Conjugates 203 and 206 were prepared from compound 96 and 100 using an identical procedure to that used for compound 1.
Example 18. Synthesis of Conjugate 207
Scheme 40.
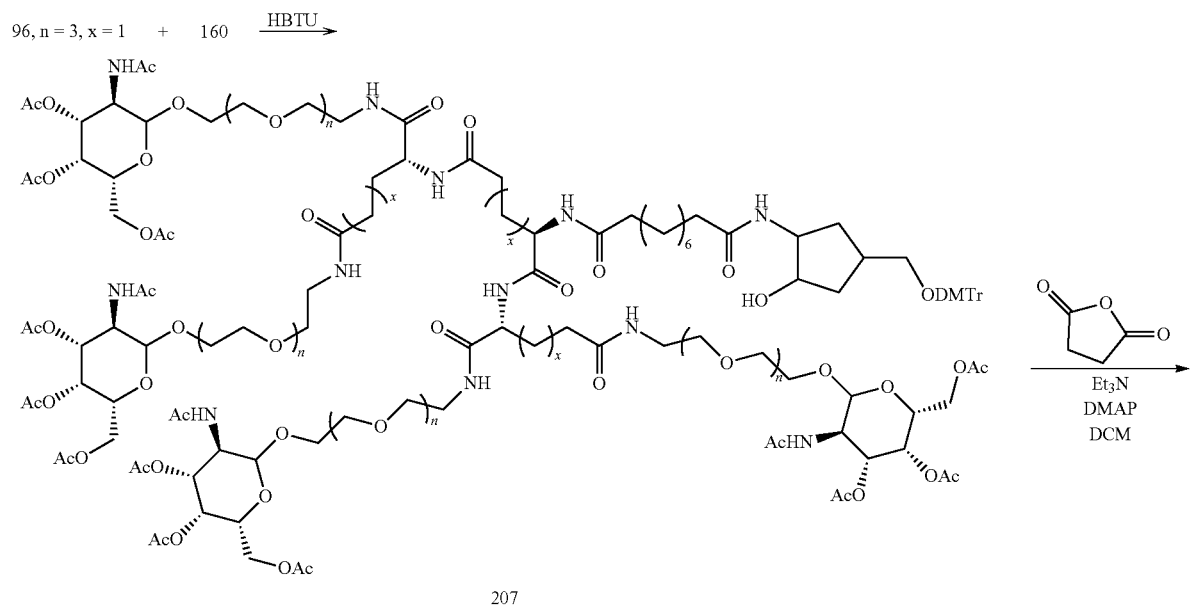
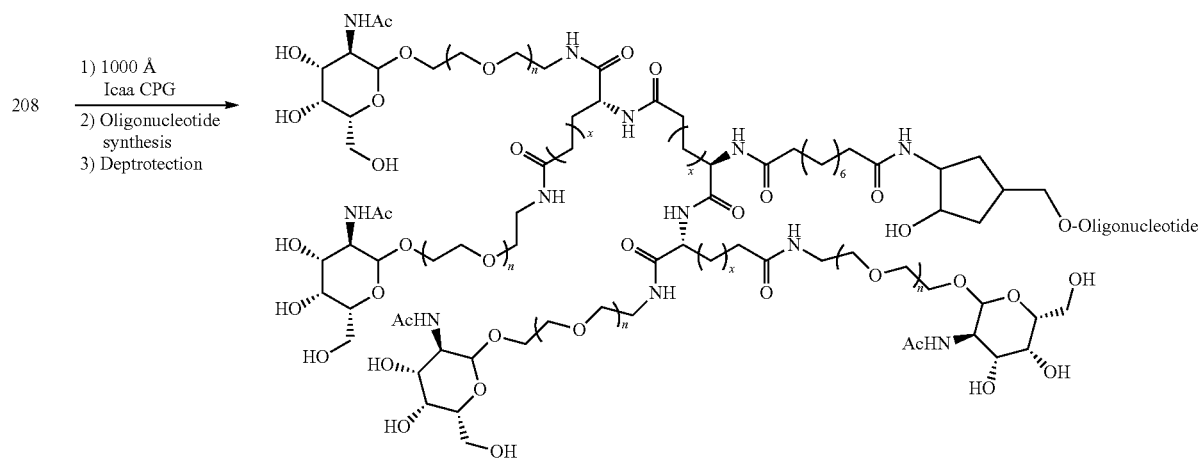

Step 1. Preparation of Conjugate 209
Conjugate 209 was prepared from compound 96 and 160 using an identical procedure to that used for compound 1.
Example 19. Synthesis of Conjugates 212 and 215
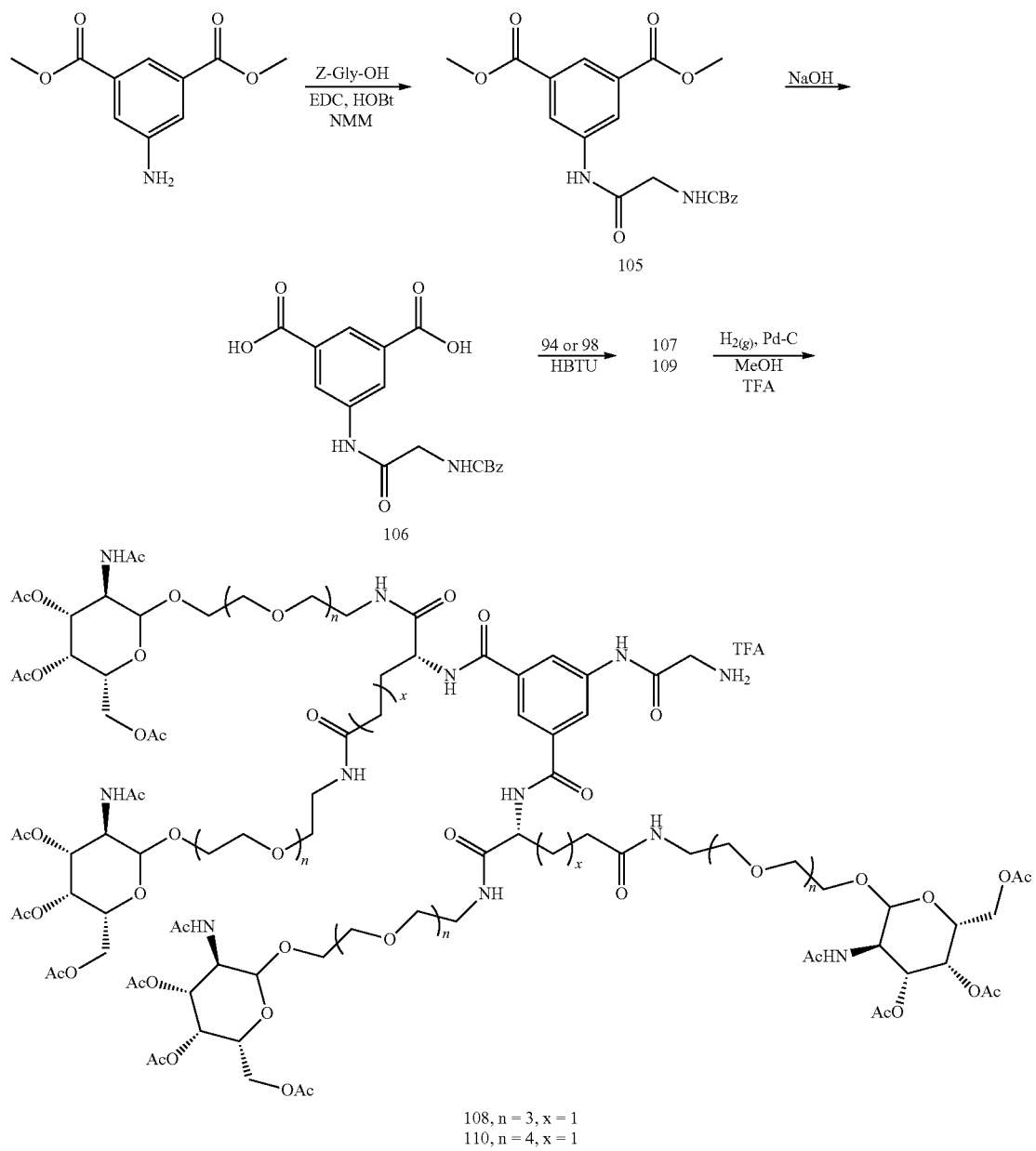
Scheme 42.

-continued

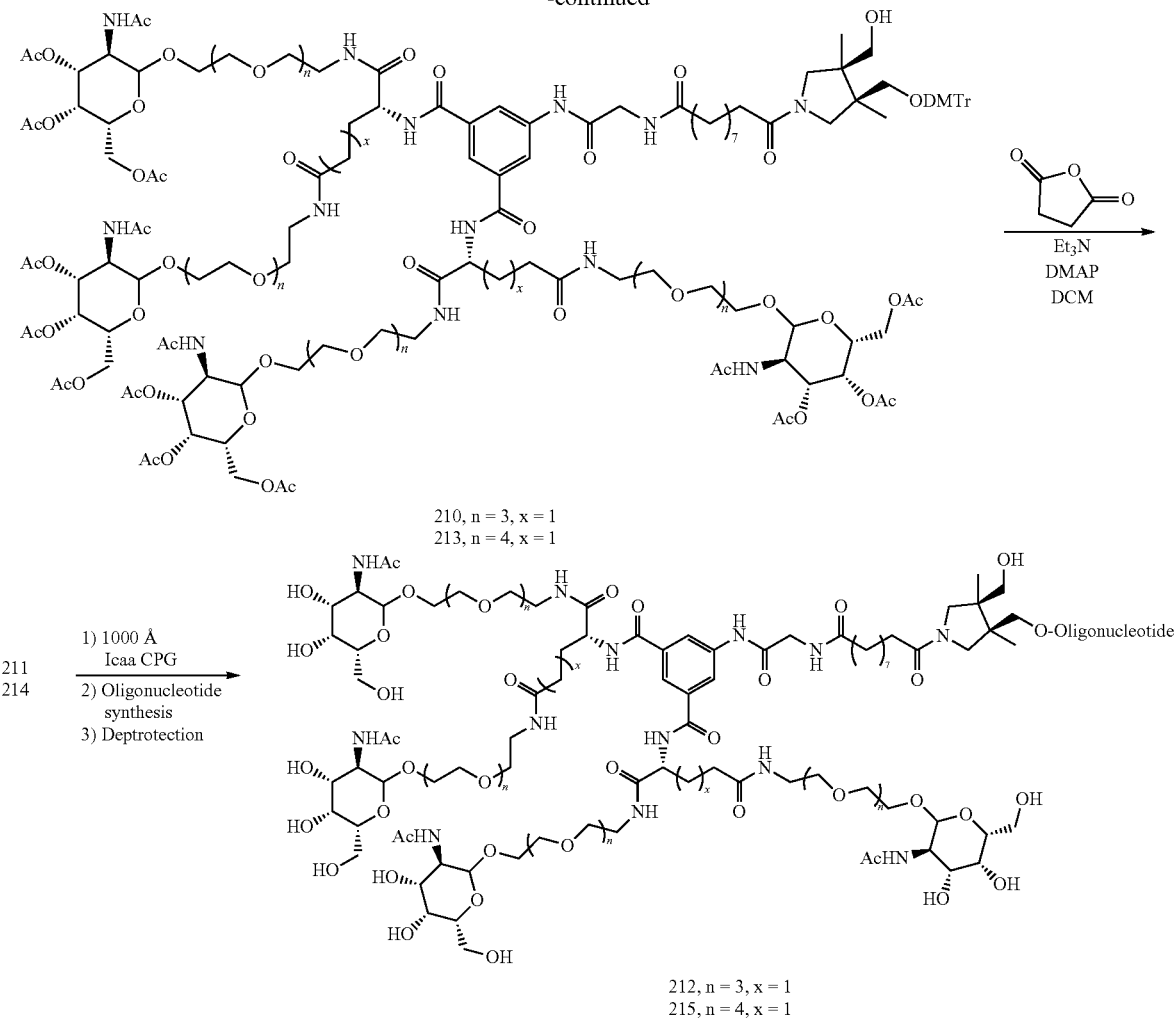

210, n = 3, x = 1
213, n = 4, x = 1

212, n = 3, x = 1
215, n = 4, x = 1

211
214

1) 1000 Å Icaa CPG
2) Oligonucleotide synthesis
3) Deptrotection

Step 1. Preparation of Dimethyl 5-(2-((2-oxo-2-phenyl-1λ²-ethyl)amino)acetamido)isophthalate 105

A solution of dimethyl 5-aminoisophthalate (5 g, 24 mmol), Z-Gly-OH (5 g, 24 mmol), EDC (5 g, 26.3 mmol), HOBt (3.6 g, 26.3 mmol), NMM (2.9 mL, 26.3 mmol) in DMF (50 mL) was stirred overnight at room temperature. Upon completion, the reaction mixture was diluted with ethyl acetate (250 mL) and washed with each 1M HCl (2×100 mL), saturated sodium bicarbonate (1×100 mL) and brine (2×100 mL). Dry on magnesium sulfate, filter and concentrate to dryness to afford Dimethyl 5-(2-((2-oxo-2-phenyl-1λ²-ethyl)amino)acetamido)isophthalate as a colorless solid (7.2 g, 79%).

Step 2. Preparation of 5-(2-((2-oxo-2-phenyl-1λ²-ethyl)amino)acetamido)isophthalic acid 106

To a solution of methyl 5-(2-((2-oxo-2-phenyl-1λ²-ethyl)amino)acetamido)isophthalate (7.2 g) in methanol (25 mL) and THF (25 mL) was added 1M NaOH (25 mL). The solution was stirred at room temperature for 2 hours then concentrated to remove THF and MeOH. The aqueous solution remaining was diluted with water (75 mL), cooled on an ice water bath and acidified to pH=1 with 6M HCl. The solid was filtered and washed with water (3×100 mL). The solid was freeze dried to afford 5-(2-((2-oxo-2-phenyl-1λ²-ethyl)amino)acetamido)-isophthalic acid (6.9 g, quantitative).

Step 3. Preparation of Compound 107

Compound 107 was prepared from 5-(2-((2-oxo-2-phenyl-1λ²-ethyl)amino)acetamido)isophthalic acid 106 (200 mg, 0.54 mmol) and 94 (1.7 g, 1.3 mmol) using an identical procedure to that used for compound 95. Yield: 600 mg.

Step 4. Preparation of Compound 108

Compound 108 was prepared from compound 107 (600 mg) using an identical procedure to that used for compound 96. Yield: 650 mg, quantitative.

Step 5. Preparation of Compound 109

Compound 109 was prepared from 5-(2-((2-oxo-2-phenyl-1λ²-ethyl)amino)acetamido)isophthalic acid 106 (180 mg, 0.48 mmol) and 98 (1.5 g, 1.1 mmol) using an identical procedure to that used for compound 99. Yield: 900 mg.

Step 6. Preparation of Compound 110
Compound 110 was prepared from compound 109 (900 mg) using an identical procedure to that used for compound 100. Yield: 920 mg, quantitative.
Step 7. Preparation of Conjugates 212 and 215
Conjugates 212 and 215 were prepared from compound 128 and 108 or 110 using an identical procedure to that used for compound 1.
Example 20. Synthesis of Conjugates 218 and 221
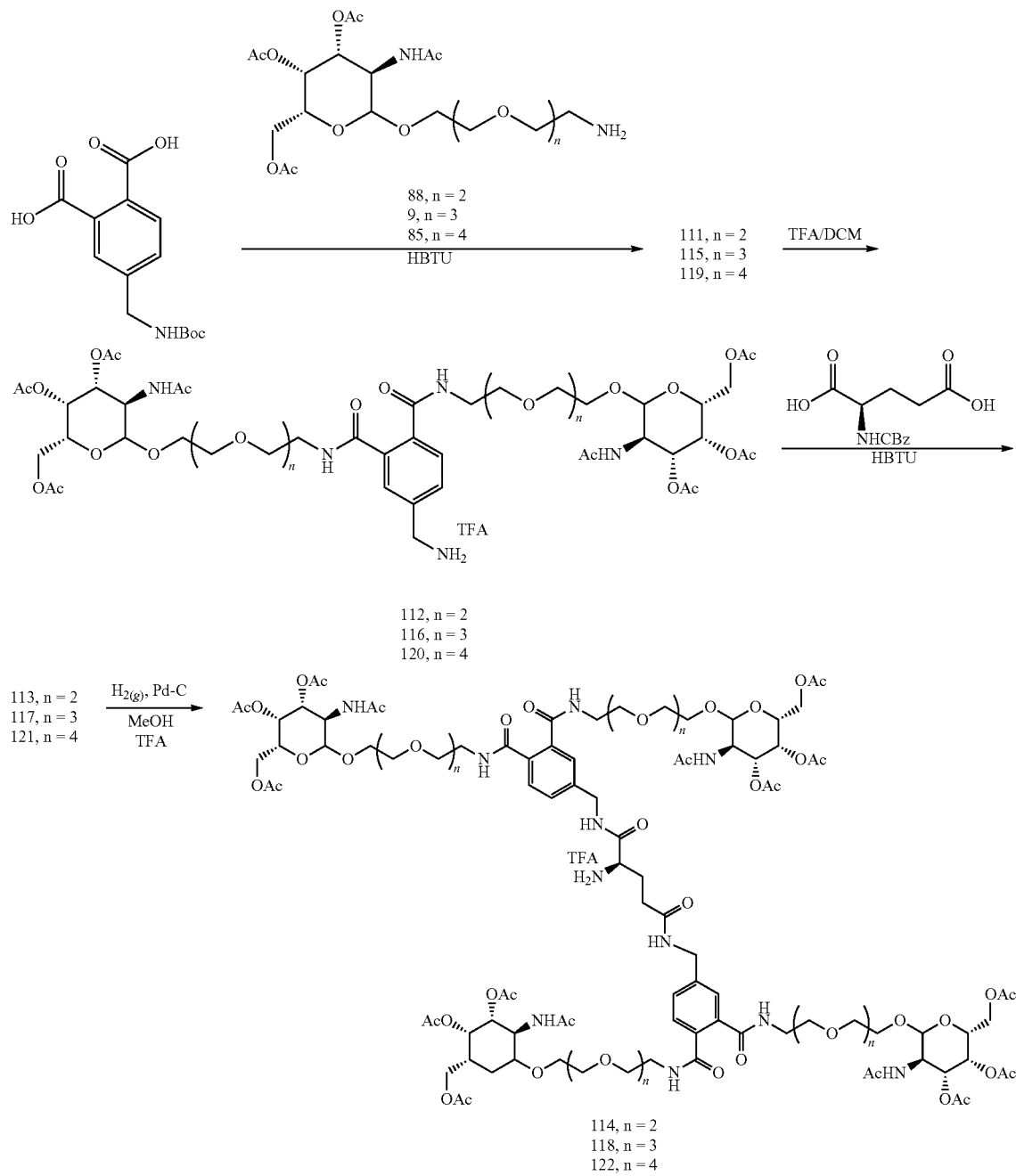

Scheme 44.

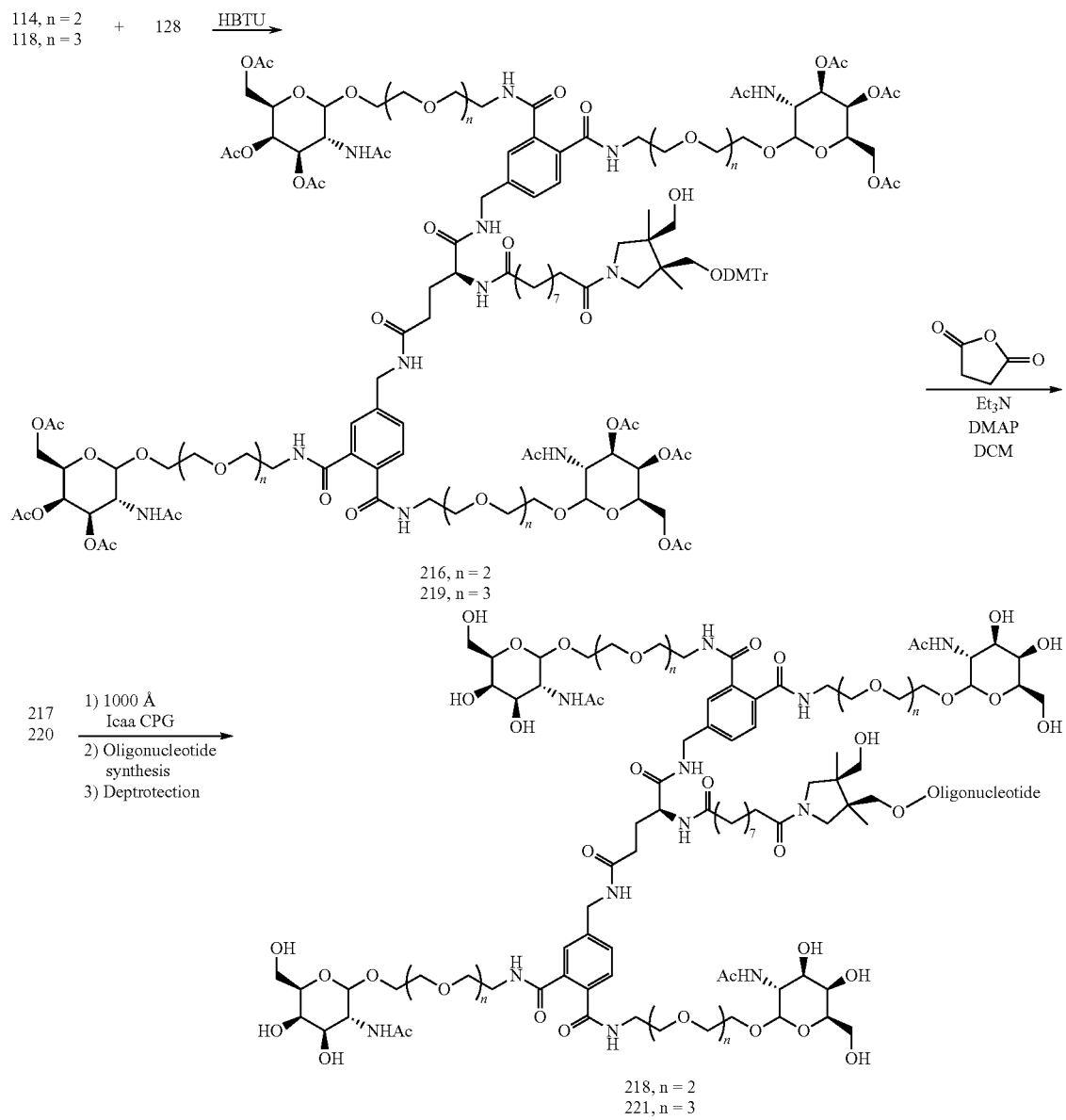

Step 1. Preparation of Compound 111

Compound 111 was prepared from 4-(((tert-butoxycarbonyl)amino)methyl)phthalic acid (1.13 g, 3.84 mmol) and 88 (5 g, 8.44 mmol) using an identical procedure to that used for compound 89. Yield: 2.21 g, 49%.

Step 2. Preparation of Compound 112

A solution of 111 (2.21 g, 1.87 mmol) in $CH_2Cl_2$ (40 mL) was slowly treated with TFA (5 mL). After stirring (2 h) the mixture was concentrated and subjected to chromatography to yield 112 (1.08 g, 47%) as a colorless foam. Rf 0.1 (10% $CH_3OH$—$CH_2Cl_2$).

Step 3. Preparation of Compound 113

Compound 113 was prepared from compound 112 (1.08 g, 0.88 mmol) and (2-oxo-2-phenyl-1$\lambda^2$-ethyl)-D-glutamic acid (112 mg, 0.39 mmol) using an identical procedure to that used for compound 91. Yield: 600 mg, 62%.

Step 4. Preparation of Compound 114

Compound 114 was prepared from compound 113 using an identical procedure to that used for compound 92.

Step 5. Preparation of Compound 115

Compound 115 was prepared from 4-(((tert-butoxycarbonyl)amino)methyl)phthalic acid (3.94 g, 13.3 mmol) and 9 (18.2 g, 29.4 mmol) using an identical procedure to that used for compound 93. Yield: 9.02 g, 53%.

Step 6. Preparation of Compound 116

Compound 116 was prepared from compound 115 (8 g, 6.3 mmol) using an identical procedure to that used for compound 112. Yield: 3.23 g, 39%.

Step 7. Preparation of Compound 117

Compound 117 was prepared from compound 116 (3.23 g, 2.45 mmol) and (2-oxo-2-phenyl-1λ²-ethyl)-D-glutamic acid (192 mg, 1.1 mmol) using an identical procedure to that used for compound 95. Yield: 2.22 g, 34%.

Step 8. Preparation of Compound 118

Compound 118 was prepared from compound 117 (2.22 g, 0.84 mmol) using an identical procedure to that used for compound 96. Yield: 2.02 g, 91%.

Step 9. Preparation of Conjugates 218 and 221

Conjugates 218 and 221 were prepared from compounds 128 and 114 or 118 using an identical procedure to that used for compound 1.

Example 21. Synthesis of Conjugate 224

Scheme 45.

96 + 130 —HBTU→

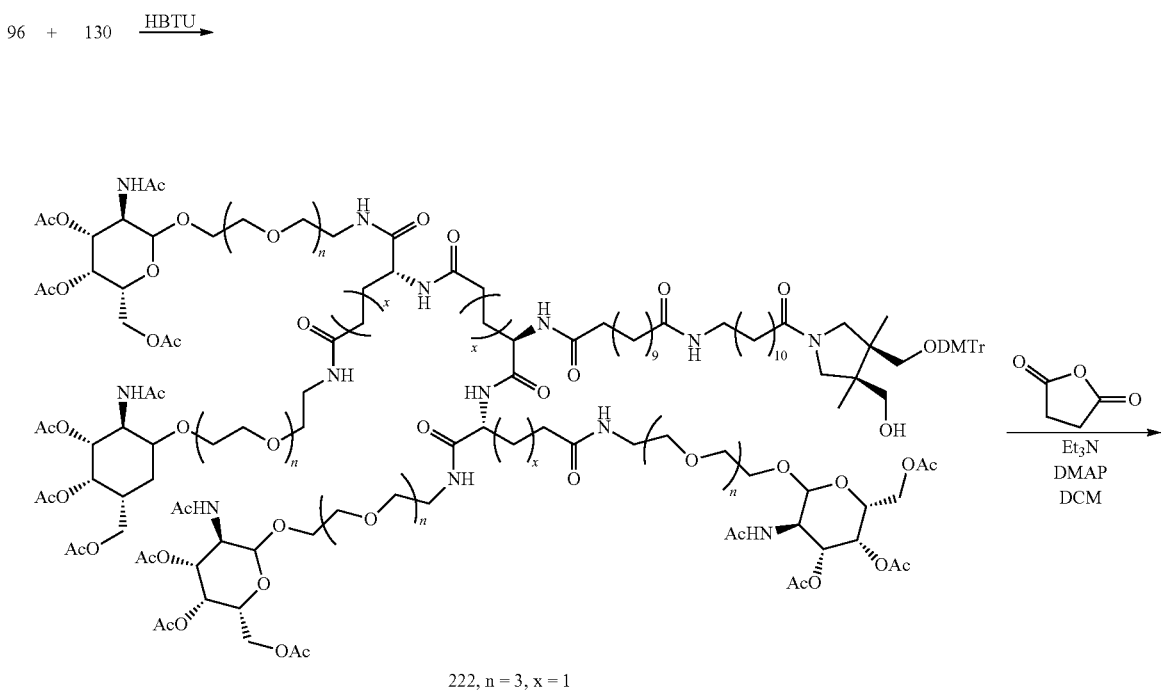

222, n = 3, x = 1

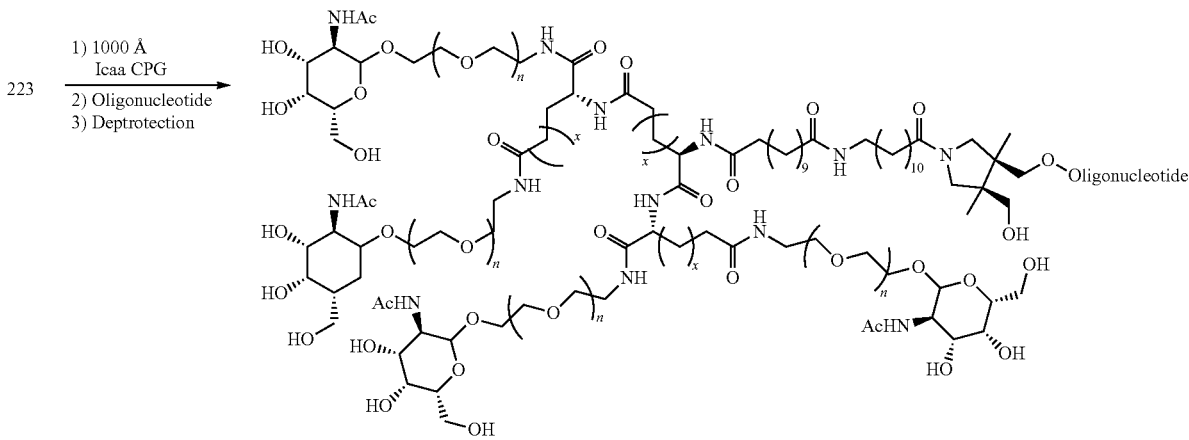

224, n = 3, x = 1

Step 1. Preparation of Compounds 224
Conjugate 224 was prepared from compounds 96 and 130 using an identical procedure to that used for compound 1.
Example 22 Synthesis of Conjugate 231
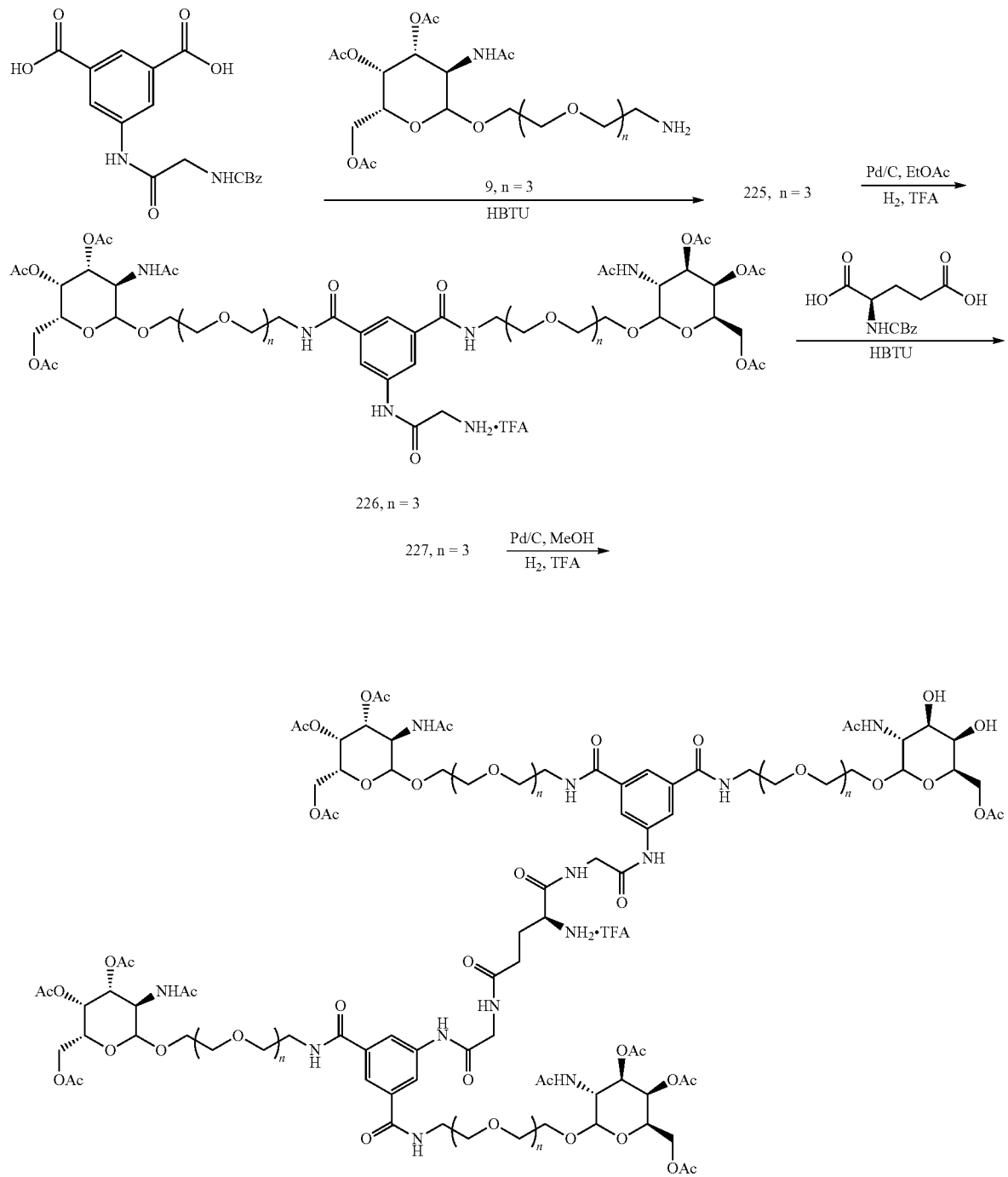
Scheme 46

Scheme 47

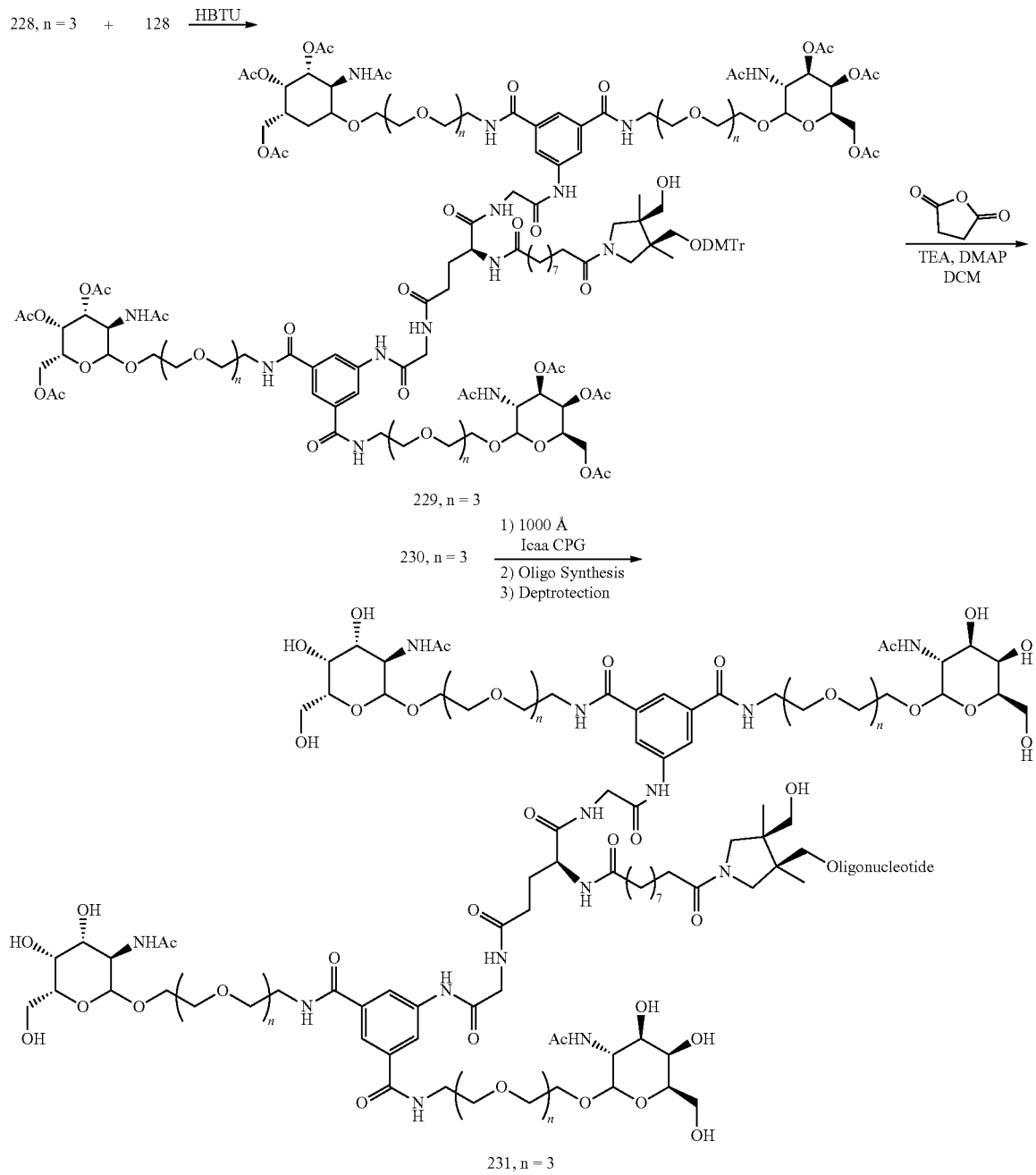

Step 1 Preparation of Compound 225

Compound 225 was prepared from 5-(2-aminoacetamido) isophthalic acid 106 (560 mg, 1.5 mmol) and 9 (2.24 g, 3.6 mmol) using an identical procedure to that used for 89. Yield 1.6 g, 80%.

Step 2 Preparation of Compound 226

Compound 226 was prepared in the same fashion as 14. Yield 1.22 g, 78%.

Step 3 Preparation of Compound 227

Compound 227 was prepared in the same fashion as 89, from Z-glutamic acid (108 mg, 0.38 mmol) and 226 (1.22 g, 0.92 mmol). Yield 471 mg, 45%.

Step 4 Preparation of Compound 228

Compound 228 was prepared in the same fashion as 14. Yield 460 mg, Quant.

Step 5 Preparation of Compound 229
Compound 229 was prepared from 228 (460 mg, 0.17 mmol) and 128 (125 mg, 0.19 mmol) in the same fashion as 89. Yield 365 mg, 66%.
Step 6 Preparation of Compound 231
Conjugate 231 was prepared using an identical procedure to that used for compound 1.
Example 23. Synthesis of Conjugate 233
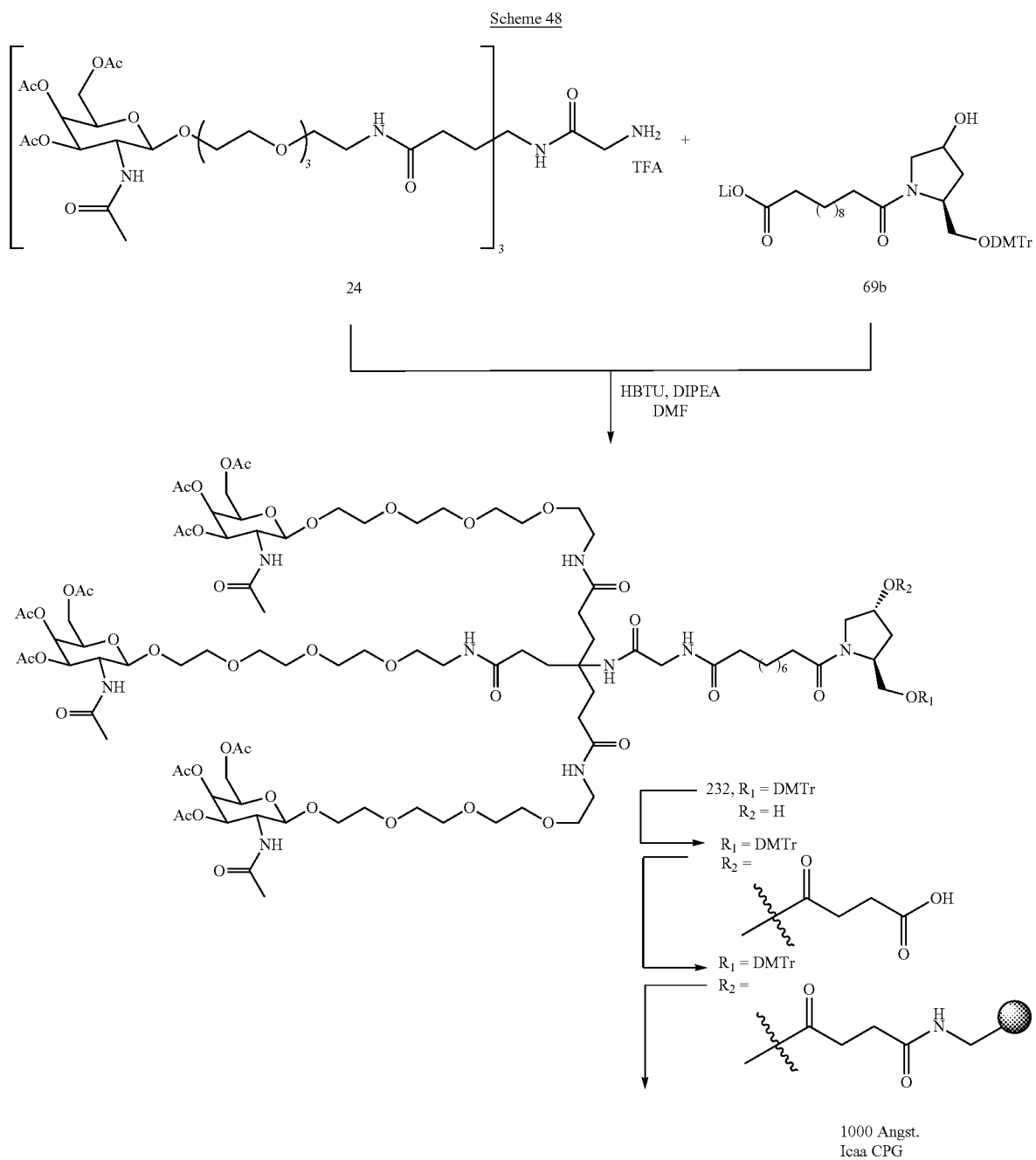

-continued
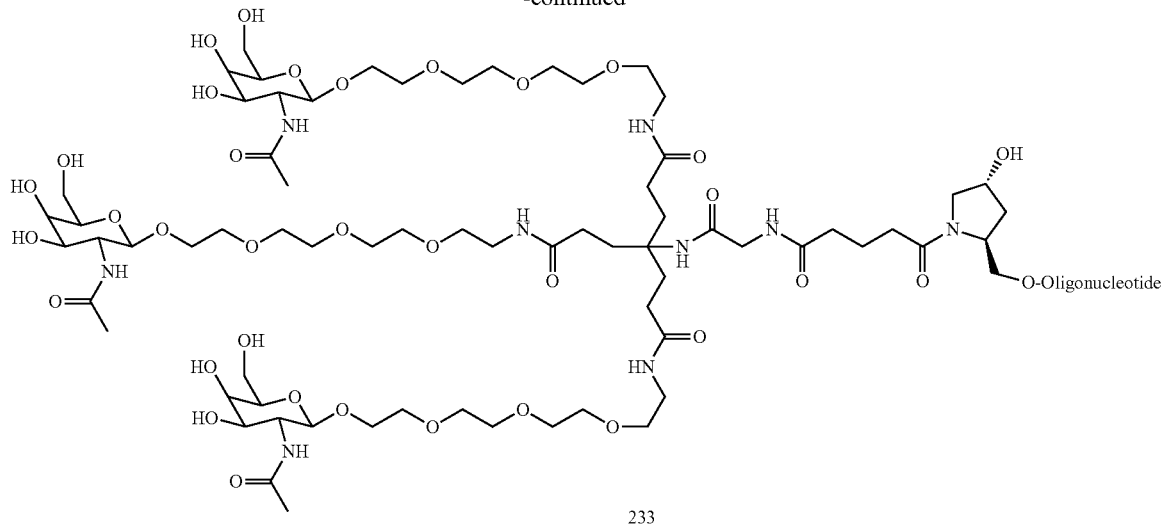
233
Step 1. Preparation of Compound 232
Compound 232 was prepared from compound 24 (650 mg, 0.33 mmol) and compound 69b (175 mg, 0.33 mmol) using an identical procedure to that used for compound 19. Yield: 380 mg, 47%.
Step 2. Preparation of Compound 233
Compound 233 was prepared from compound 232 using identical procedures to that used for compound 1.
Example 24. Synthesis of Conjugate 235
Scheme 49
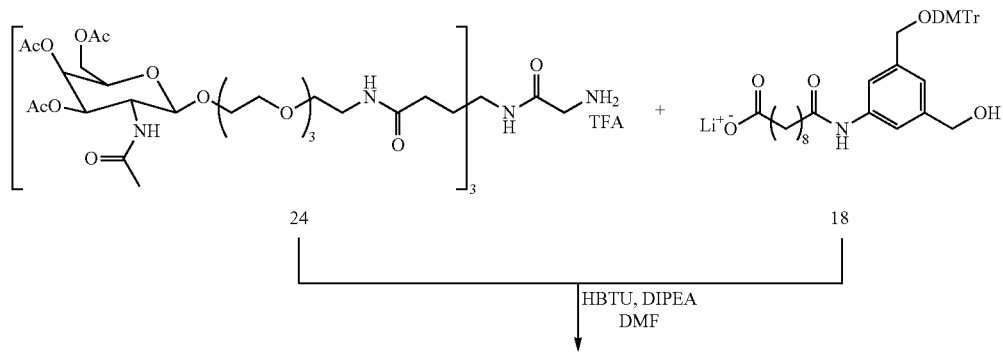

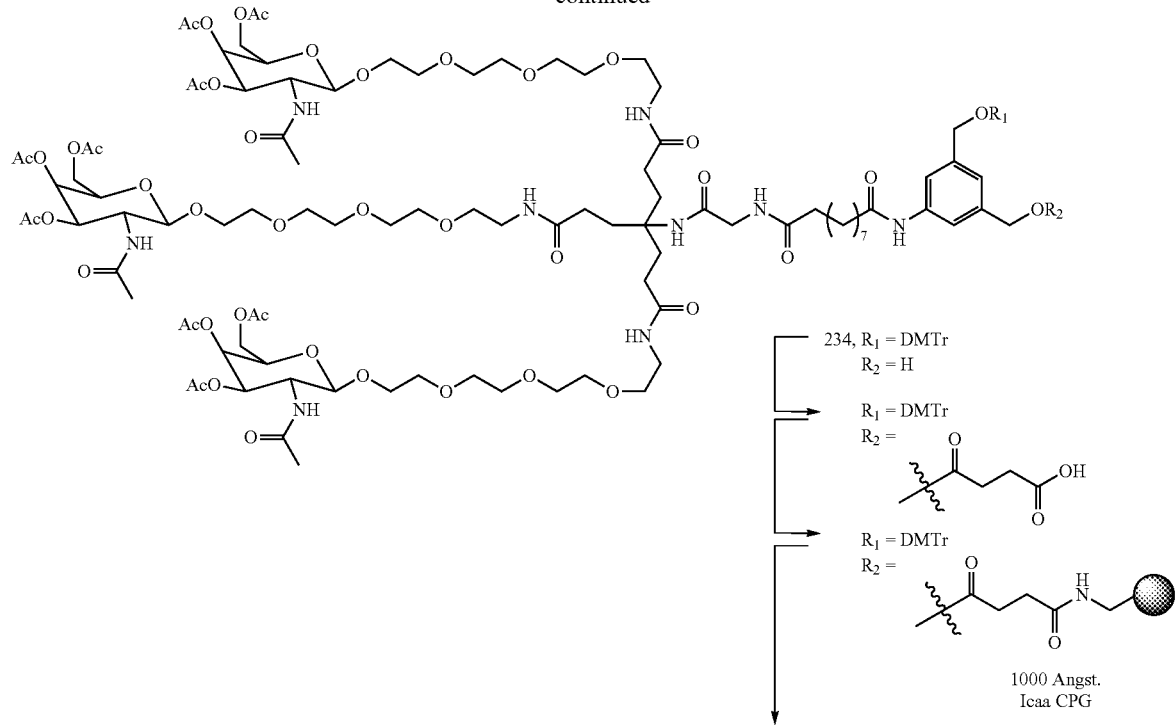

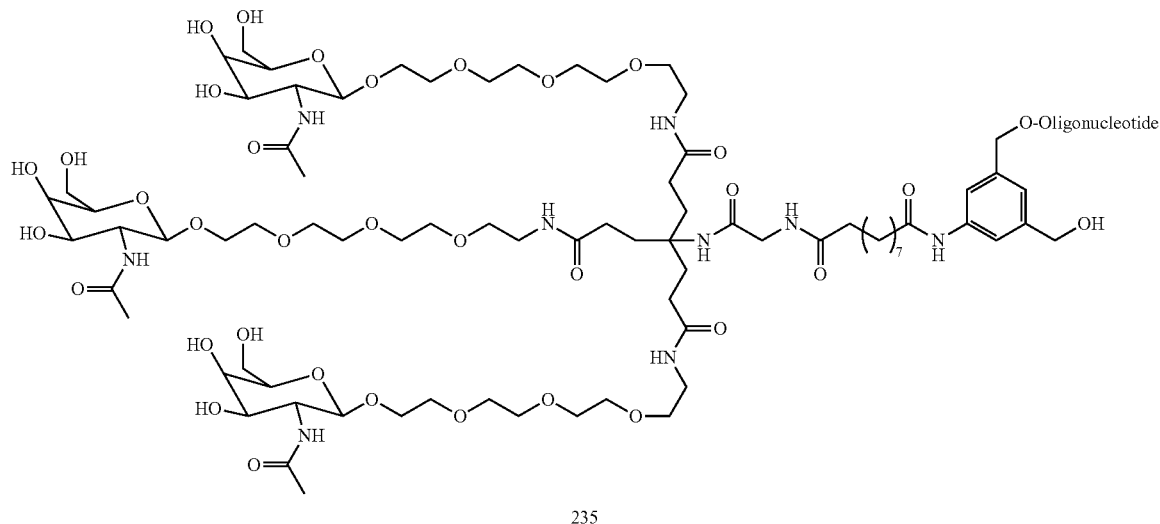

235

Step 1. Preparation of Compound 234

Compound 234 was prepared from compound 24 (1.1 g, 0.55 mmol) and compound 18 (175 mg, 0.33 mmol) using an identical procedure to that used for compound 19. Yield: 685 mg, 51%.

Step 2. Preparation of Compound 235

Compound 235 was prepared from compound 234 using identical procedures to that used for compound 1.

Example 25. In Vitro & In Vivo Evaluation of GalNAc-siTTR Conjugate

Hydration of GalNAc-siTTR Conjugates:

GalNAc-siTTR conjugates with the structure of Compound 1, employing an oligonucleotide with siRNA sequence as follows, written 5' to 3'.

Sense strand:
(SEQ ID NO: 31)
A*a*CaGuGuUCUuGcUcUaUaA(GalNAc).

-continued

Antisense strand:
(SEQ ID NO: 32)
u*U*aUaGaGcAagaAcAcUgUu*u*u.

Where upper case underlined is a 2'-OMethyl sugar modification and lower case is a 2'-fluoro sugar modification. An asterisk (*) represents a phosphorothioate (PS) linkage. Prior to use in studies the conjugates were hydrated in PBS and quantified using a NanoDrop instrument for A260 measurement.

In Vitro Comparison of GalNAc-siTTR Conjugates:

Primary hepatocytes were isolated from a C57 Bl/6 female mouse using standard procedures. Once isolated the hepatocytes were plated on 96-well Primaria plates at 2.75× $10^4$ cells/well in Williams Media E (WME) containing 10% FBS. Four hours later, and for the remainder of the experiment, media was switched to WME without FBS. The next day, 90 µL of fresh WME was applied to the cells. Stocks of siRNA conjugate were prepared in PBS at a concentration of 100 µg/mL. Serial dilution (1 in 2) into WME (50 µL of conjugate dilution+50 µL of WME) was performed. 10 JAL of each conjugate dilution was then transferred to the Primaria plate in triplicate, giving final conjugate concentrations on the hepatocytes of 5, 2.5, 1.25, 0.625, 0.312, 0156 & 0.078 µg/mL. A serial dilution of PBS in WME acted as the negative control. The cells were incubated for 24 hours at 37° C. & 5% $CO_2$. The transfection media was then removed and cells lysed by the addition of 200 µL 1×LWR (containing 0.5 mg/mL Proteinase K). The plate was freeze-thawed (60 min cycle, −80° C./52° C.) to assist in the lysis of the cells. The resulting lysates were then analyzed for mouse TTR & GAPD mRNA levels using QuantiGene 2.0 Assay according to manufacturer's instructions. Relative concentrations of TTR mRNA, normalized to GAPD mRNA, were determined and plotted. Cells treated with the conjugate exhibited a marked knockdown of target mRNA.

In Vivo Comparison of GalNAc-siTTR Conjugates:

Female C57BL/6 mice (n=4) were treated subcutaneously (scapular region) with either PBS or GalNAc-siTTR conjugate (diluted to 0.1 mg/mL or 0.2 mg/mL in PBS, such that animals received a dose of 1 mg/kg or 2 mg/kg conjugate, respectfully). Blood at Day 2, 4, 5, 7, 8, 9, 11, 14, 21 (tailnick) and Day 28 (terminal) was collected and the resulting plasma was analyzed for TTR protein by ELISA. TTR plasma protein values were relative to PBS control are tabulated (Tables 1 and 2; see FIGS. 7 and 8). Animals treated with the conjugate exhibited a marked knockdown of target mRNA and protein.

What is claimed is:

1. The compound:

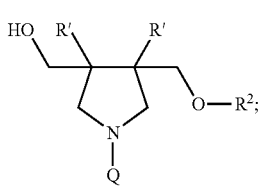

or a salt thereof, wherein Q is -$L^1$-$R^1$;

$L^1$ is a divalent, branched or unbranched, saturated or unsaturated, hydrocarbon chain, having from 1 to 14 carbon atoms, wherein one or more of the carbon atoms in the hydrocarbon chain is optionally replaced with —$NR^X$—C(=O)—, or —C(=O)—$NR^X$—, and wherein $R^X$ is hydrogen or ($C_1$-$C_6$)alkyl, and wherein the hydrocarbon chain, is optionally substituted with oxo(=O); or $L^1$ is selected from the group consisting of:

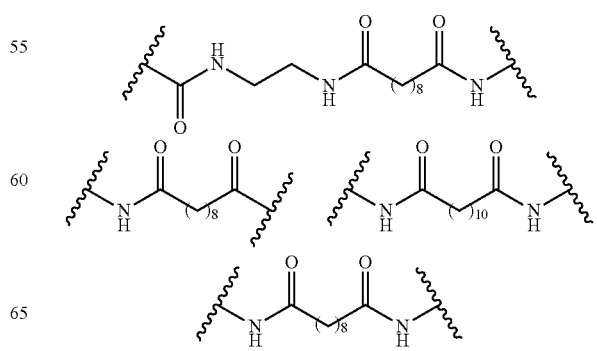

-continued

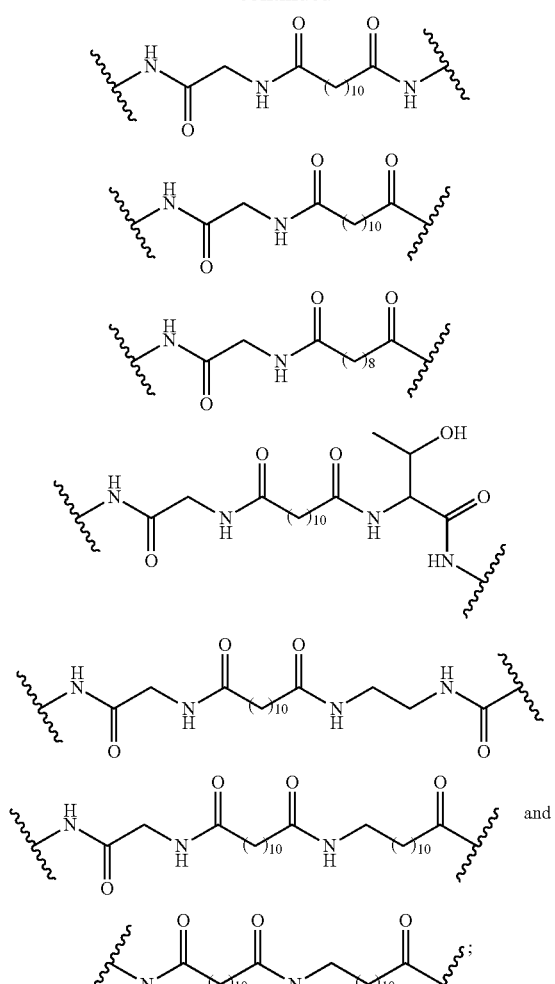

R¹ has the following formula:

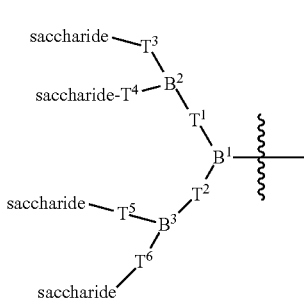

wherein:
B¹ is CH;
B² is selected from the group consisting of:

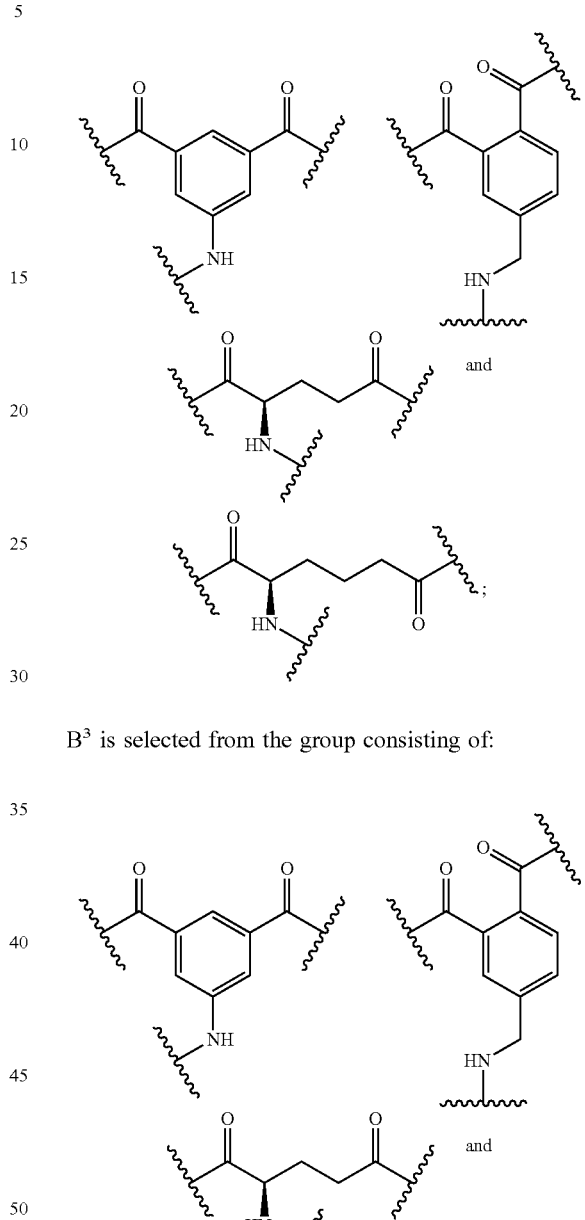

B³ is selected from the group consisting of:

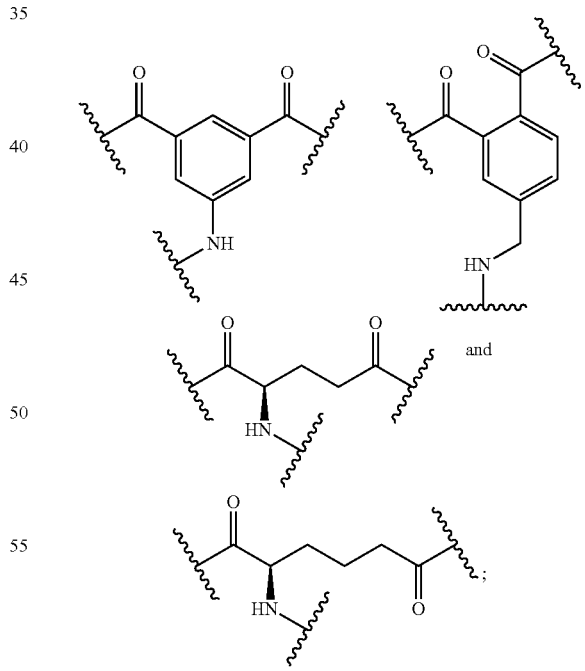

T¹ is a branched or unbranched, saturated or unsaturated, hydrocarbon chain, having from 1 to 20 carbon atoms, wherein one or more of the carbon atoms in the hydrocarbon chain is optionally replaced by —NR$^X$—C(=O)—, or —C(=O)—NR$^X$—, and wherein R$^X$ is hydrogen or (C$_1$-C$_6$)alkyl, and wherein the hydrocarbon chain, is optionally substituted with oxo (=O), that is covalently bonded to $B^1$;

$T^2$ is a branched or unbranched, saturated or unsaturated, hydrocarbon chain, having from 1 to 20 carbon atoms, wherein one or more of the carbon atoms in the hydrocarbon chain is optionally replaced by $-NR^X-C(=O)-$, or $-C(=O)-NR^X-$, and wherein $R^X$ is hydrogen or $(C_1-C_6)$alkyl, and wherein the hydrocarbon chain, is optionally substituted with oxo (=O), that is covalently bonded to $B^1$;

each of $T^3$, $T^4$, $T^5$, and $T^6$ is independently selected from the group consisting of:

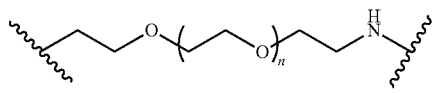

n=1, 2, or 3;

each saccharide is independently selected from the group consisting of:

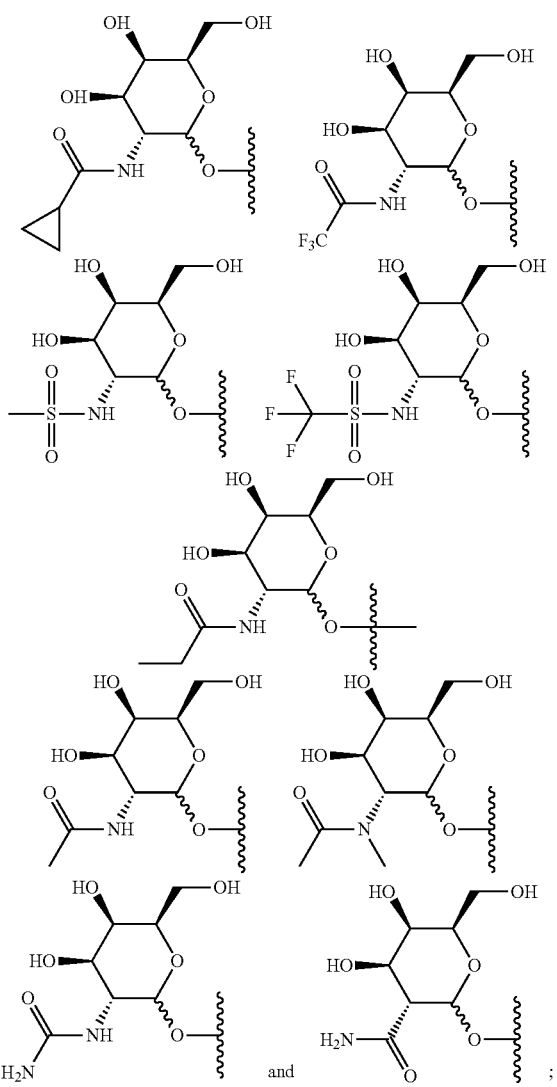

$R^2$ is a siRNA substituent; and

R' is $C_{1-9}$ alkyl, $C_{2-9}$ alkenyl or $C_{2-9}$ alkynyl; wherein the $C_{1-9}$ alkyl, $C_{2-9}$ alkenyl or $C_{2-9}$ alkynyl are optionally substituted with halo or hydroxyl.

2. The compound or salt of claim 1, wherein $L^1$ is connected to $R^1$ through $-NH-$, $-O-$, $-S-$, $-(C=O)-$, $-(C=O)-NH-$, $-NH-(C=O)-$, $-(C=O)-O-$, $-NH-(C=O)-NH-$, or $-NH-(SO_2)-$.

3. The compound of claim 1, wherein each saccharide is independently:

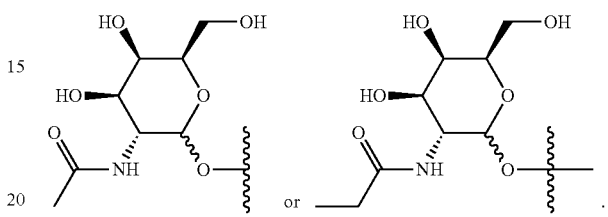

4. A pharmaceutical composition comprising a compound as described in claim 1, or a pharmaceutically acceptable salt thereof, and a pharmaceutically acceptable carrier.

5. A method to deliver siRNA to the liver of an animal in need thereof comprising administering a compound of formula I as described in claim 1, or a pharmaceutically acceptable salt thereof, to the animal in need thereof.

6. The compound of claim 1, wherein n=1.

7. The compound of claim 1, wherein n=2.

8. The compound of claim 1, wherein n=3.

9. The compound of claim 1, wherein $B^2$ is selected from the group consisting of:

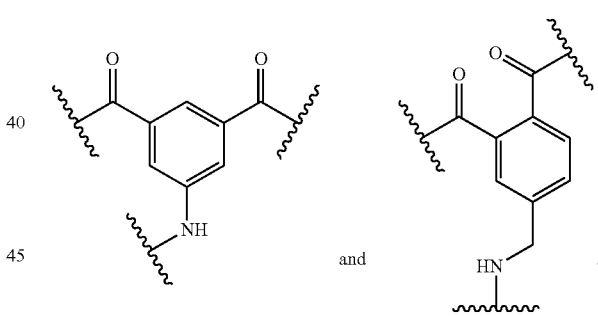

10. The compound of claim 1, wherein $B^3$ is selected from the group consisting of:

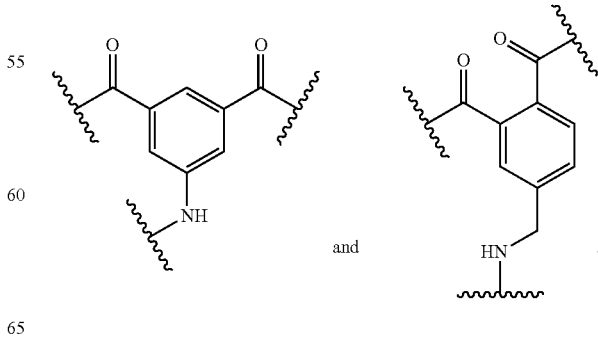

11. The compound of claim 1, wherein $L^1$ is selected from the group consisting of:

211
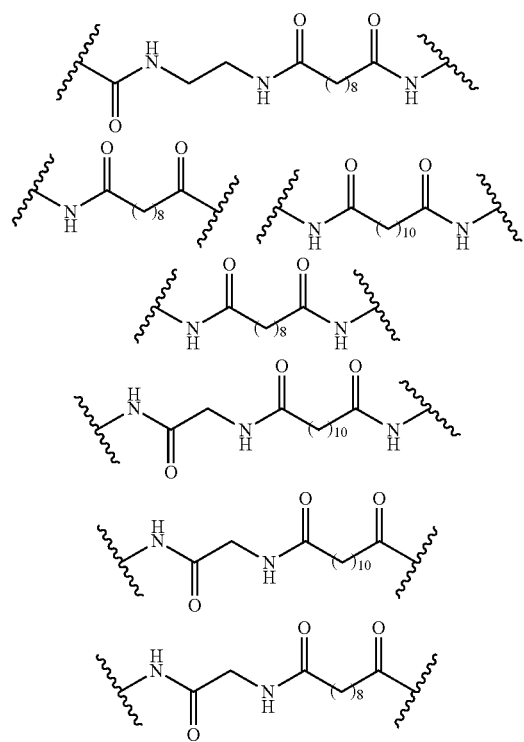
212
-continued
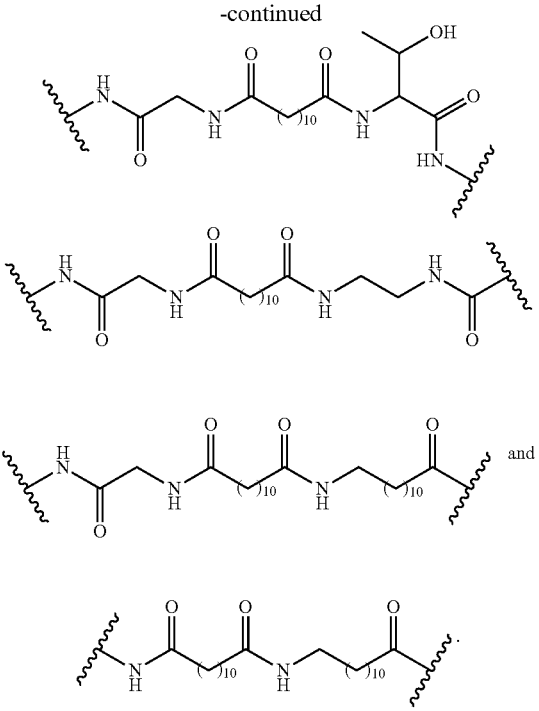
* * * * *